(12) United States Patent
Denmark et al.

(10) Patent No.: US 11,664,093 B2
(45) Date of Patent: May 30, 2023

(54) EXTRAPOLATIVE PREDICTION OF ENANTIOSELECTIVITY ENABLED BY COMPUTER-DRIVEN WORKFLOW, NEW MOLECULAR REPRESENTATIONS AND MACHINE LEARNING

(71) Applicant: The Board of Trustees of the University of Illinois, Urbana, IL (US)

(72) Inventors: Scott E. Denmark, Champaign, IL (US); Andrew F. Zahrt, Urbana, IL (US); Jeremy J. Henle, Gurnee, IL (US); Brennan T. Rose, Urbana, IL (US); Yang Wang, Cambridge, MA (US); William T. Darrow, Streator, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 719 days.

(21) Appl. No.: 16/551,007

(22) Filed: Aug. 26, 2019

(65) Prior Publication Data
US 2020/0234798 A1    Jul. 23, 2020

Related U.S. Application Data

(60) Provisional application No. 62/793,735, filed on Jan. 17, 2019.

(51) Int. Cl.
G16C 20/30     (2019.01)
G16C 20/64     (2019.01)
G16C 20/10     (2019.01)

(52) U.S. Cl.
CPC ............. *G16C 20/30* (2019.02); *G16C 20/64* (2019.02); *G16C 20/10* (2019.02)

(58) Field of Classification Search
CPC .... G16C 20/30; G16C 20/64; G16C 20/1011; G01N 33/537; G01N 33/56911; G01N 2500/00; A61P 1/02
(Continued)

(56) References Cited

U.S. PATENT DOCUMENTS

| | | | |
|---|---|---|---|
| 2008/0172216 A1* | 7/2008 | Cramer et al. ........... | G06G 7/58 703/12 |
| 2010/0267699 A1* | 10/2010 | Bradbury et al. ... | C07D 487/04 514/218 |
| 2011/0059043 A1* | 3/2011 | Barnes et al. ....... | C07D 243/24 424/85.4 |

OTHER PUBLICATIONS

Agrafiotis et al., "Recent Advances in Chemoinformatics," *J. Chem. Inf. Model*, 47 (2007) pp. 1279-1293.

(Continued)

*Primary Examiner* — Thinh T Nguyen
(74) *Attorney, Agent, or Firm* — Crowell & Moring LLP

(57) ABSTRACT

Catalyst design in asymmetric reaction development has traditionally been driven by empiricism, wherein experimentalists attempt to qualitatively recognize structural patterns to improve selectivity. Machine learning algorithms and chemoinformatics can potentially accelerate this process by recognizing otherwise inscrutable patterns in large datasets. Herein we report a computationally guided workflow for chiral catalyst selection using chemoinformatics at every stage of development. Robust molecular descriptors that are agnostic to the catalyst scaffold allow for selection of a universal training set on the basis of steric and electronic properties. This set can be used to train machine learning methods to make highly accurate predictive models over a broad range of selectivity space. Using support vector machines and deep feed-forward neural networks, we demonstrate accurate predictive modeling in the chiral phosphoric acid-catalyzed thiol addition to N-acylimines.

9 Claims, 14 Drawing Sheets

(58) Field of Classification Search
USPC .......................................................... 703/12
See application file for complete search history.

(56) References Cited

OTHER PUBLICATIONS

Akiyama, "Enantioselective Robinson-Type Annulation Reaction Catalyzed by Chiral Phosphoric Acids**," *Angew. Chem. Int. Ed.*, 48 (2009) pp. 4226-4228.

Bartók et al., "Machine-learning approach for one- and two-body corrections to density functional theory: Applications to molecular and condensed water," *Physical Review B*, 88 (2013) pp. 1-12.

Bartoszek et al., "A convenient protocol for the synthesis of axially chiral Brønsted acids," *Tetrahedron*, 64 (2008) pp. 1316-1322.

Braiuca et al., "A Three-Dimensional Quanititative Structure-Activity Relationship (3D-QSAR) Model for Predicting the Enantioselectivity of Candida antarctica Lipase B," *Adv. Synth. Catal.*, 351 (2009) pp. 1293-1302.

Cruz et al., "3D-QSAR as a Tool for Understanding and Improving Single-Site Polymerization Catalysts. A Review," *Organometallics*, 33. (2014) pp. 2944-2959.

Engel, "Basic Overview of Chemoinformatics," *J. Chem. Inf. Model.*, 46 (2006) pp. 2267-2277.

Feigenbaum et al., "Dendral and Meta-Dendral: roots of knowledge systems expert system applications and expert system applications," *Artificial Intelligence*, 59 (1993) pp. 233-240.

Harper et al., "Three-Dimensional Correlation of Steric and Electronic Free Energy Relationships Guides Asymmetric Propargylation," *Science*, 333 (2011) pp. 1875-1878.

Harper et al., "Multidimensional steric parameters in the analysis of asymmetric catalytic reactions," *Nature Chemistry*, 4 (2012) pp. 366-374.

Hatano et al., "Chiral Lithium Salts of Phosphoric Acids as Lewis Acid-Base Conjugate Catalysts for the Enantioselective Cyanosilylation of Ketones," *Adv. Synth. Catal.*, 350 (2008) pp. 1776-1780.

He, "Steroselective and hierarchical self-assembly from nanotubluar homochiral helical coordination polymers to supramolecular gels," *Chem. Commun.*, 46 (2010) pp. 5695-5697.

Hrdina, "Synthesis, Structural Analysis, and Catalytic Properties of Tetrakis(binapthyl or octahydrobinapthyl phosphate) Dirhodium(II,II) Complexes," *Organometallics*, 32 (2013) pp. 473-479.

Ingle et al., "Chiral Phosphoric Acid-Catalyzed Addition of Thiols to N-Acyl Imines:Access to Chiral N,S-Acetals," *Organic Letters*, 13:18 (2011) pp. 4822-4825.

Jolit et al., "Catalytic Enantioselective Nazarov Cyclization," *Eur. J. Org. Chem.* (2017) pp. 6067-6076.

Kaib et al., "Highly Acidic BINOL-Derived Phosphoramidimaidates and their Application in the Brønsted Acid Catalyzed Synthesis of α-Tocopherol," *Synlett*, 27 (2016) pp. 156-158.

Kennard et al., "Computer Aided Design of Experiments," *Technometrics*, 11:1 (1969) pp. 137-148.

Klussmann et al., Synthesis of TRIP and Analysis of Phosphate Salt Impurities, *Synlett* (2010) pp. 1-11.

Kozlowski et al., "Quantum Mechanical Models Correlating Structure with Selectivity: Predicting the Enantioselectivity of â-Amino Alcohol Catalysts in Aldehyde Alkylation," *J. Am. Chem. Soc.*, 125 (2003) pp. 6614-6615.

Kuno et al., "Scyllo-inositol as a convenient protecting group for aryl boronic acids in Suzuki-Miyaura cross-coupling reactions," *Tetrahedron Letters*, 55 (2014) pp. 720-724.

Lipkowitz et al., "Computational Studies of Chiral Catalysts: A Comparative Molecular Field Analysis of an Asymmetric Diels-Alder Reaction with Catalysts Containing Bisoxazoline or Phosphinooxazoline Ligands," *J. Org. Chem.*, 68 (2003), pp. 4648-4656.

Liu et al., Synthesis of Novel Chiral Phosphoric Acid-Bearing Two Acidic Phenolic Hydroxyl Groups and its Catalytic Evaluation for Enantioselective Friedel-Crafts Alkylation of Indoles and Enones, *Journal of Heterocyclic Chemistry*, 52 (2014) pp. 628-634.

Melville et al., "Computational screening of combinatorial catalyst libraries," *Royal Society of Chemistry* (2004) pp. 1410-1411.

Melville et al., "Exploring Phase-Transfer Catalysis with Molecular Dynamics and 3D/4D Quantitative Structure-Selectivity Relationships," *J. Chem. Inf. Model*, 45 (2005) pp. 971-981.

Ouyang et al., "One-dimensional (1D) helical and 2D homochiral metal-organic frameworks built from a new chiral octahydrobinaphthalene-derived dicarboxylic acid," *Inorganic Chemistry Communications*, 11 (2008) pp. 948-950.

Park et al., Quantifying Structural Effects of Amino Acid Ligands in Pd(II)-Catalyzed Enantioselective C-H Functionalization Reactions, *Organometallics*, 37 (2017) pp. 203-210.

Park et al., Synthesis and electroluminescence properties of novel deep blue emitting 6,12-dihydro-diindeno[1,2-b;1',2'-e]pyrazine derivatives, *Chem. Common.*, (2008) pp. 2143-2145.

Raccuglia et al., "Machine-learning-assisted materials discovery using failed experiments," *Nature*, 533 (2016) pp. 73-76.

Ritleng," Molybdenum Triamidoamine Complexes that Contain Hexa-tert-butylterphenyl, Hexamethylterphenyl, or p-Bromohexaisopropylterphenyl Substituents. An Examination of Some Catalyst Variations for the Catalytic Reduction of Dinitrogen," *J. Am. Chem. Soc.*, 126 (2004) pp. 6150-6163.

Romanov-Michailidis et al., "Enantioselective Halogenative Semi-Pinacol Rearrangement:Extension of Substrate Scope and Mechanistic Investigations," *Chem. Eur. J.*, 21, (2015) pp. 5561-5583.

Roy et al., "Chapter 8:Introduction to 3D-QSAR," *eBook* (2015) pp. 291-317.

Roy et al., "Understanding the basics of QSAR for applications in pharmaceutical sciences and risk assessment," *eBook* (2015) pp. 1-4.

Rueping et al., "Synthesis and Structural Aspects of N-Triflylphosphoramides and Their Calcium Salts—Highly Acidic and Effective Brønsted Acids," *Chem. Eur. J.*, 16 (2010) pp. 13116-13126.

Saha et al., "Brønsted Acid-Catalyzed, Highly Enantioselective Addition of Enamides to In Situ-Generated ortho-Quinone Methides: A Domino Approach to Complex Acetamidotetrahydroxanthenes," *Chem. Eur. J.*, 21 (2015) pp. 2348-2352.

Segler et al., "Planning chemical syntheses with deep neural networks and symbolic AI," *Nature*, 555 (Mar. 29, 2018) pp. 604-610.

Senese et al., "4D-Fingerprints, Universal QSAR and QSPR Descriptors," *J. Chem. Inf. Comput. Sci.*, 44 (2004) pp. 1526-1539.

Shao et al., "Advances in methods and algorithms in a modern quantum chemistry program package," *Phys. Chem. Chem. Phys.*, 8 (2006) pp. 3172-3191.

Sigman et al., "The Development of Multidimensional Analysis Tools for Asymmetric Catalysis and Beyond," *Acc. Chem. Res.* 49 (2016) pp. 1292-1301.

Sun et al., "Enantioselective Synthesis of Unsymmetrical Triarylmethanes by Chiral Brønsted Acids," *Eur. J. Org. Chem.* (2010) pp. 47-50.

Szymkuc' et al., "Computer-Assisted Synthetic Planning: The End of the Beginning Computer-Assisted Synthetic Planning: The End of the Beginning," *Angew. Chem. Int. Ed.*, 55 (2016) pp. 5904-5937.

Valiev et al., "NWChem: A comprehensive and scalable open-source solution for large scale molecular simulations," *Computer Physics Communications*, 181 (2010) pp. 1477-1489.

Wang et al., "Regioselective formylation of 1,3-disubstituted benzenes through in situ lithiation," *Tetrahedron Letters*, 54 (2013) pp. 6053-6056.

Wilckens et al., "Synthesis of Gold Complexes Bearing Sterically Highly Encumbered, Chiral Carbene Ligands," *Organometallics*, 30 (2011) pp. 1287-1290.

Willett, "Chemoinformatics: a history," *WIREs Computational Molecular Science*, 1 (2011) pp. 46-56.

Wipf et al., "Formal Total Synthesis of (+)-Diepoxin σ," *J. Org. Chem.* 65 (2000) pp. 6319-6337.

R. M. Fedor, G. Laure, A. Alexandre, Enantioselective Organocatalytic Fluorination-Induced Wagner-Meerwein Rearrangement. Angew. Chem. Int. Ed. 52, 9266-9270 (2013).

B. Paolo, L. Knapic, F. Valerio, E. Cynthia, G. Lucia, A Three-Dimensional Quanititative Structure-Activity Relationship (3D-

(56) References Cited

OTHER PUBLICATIONS

QSAR) Model for Predicting the Enantioselectivity of Candida antarctica Lipase B. Adv. Synth. & Catal. 351, 1293-1302 (2009).
Wei, J.N. et al., "Neural Networks for the Prediction of Organic Chemistry Reactions", ACS Cent. Sci. 2, 725-732 (2016).
Coley, C.W., et al, "Prediction of Organic Reaction Outcomes Using Machine Learning", ACS Cent. Scie. 3, 434-443 (2017).
Chen, H., et al., "The rise of deep learning in drug discovery", Drug Discov. Today, 23, 1241-1250 (2018).
Ma, J., et al. "Deep Neural Nets as a Method for Quantitative Structure-Activity Relationships", J. Chem. Inf. Mod. 55, 263-274 (2015).
Denmark, S.E., et al., "A Systemic Investigation of Quaternary Ammonium Ions as Asymmetric Phase-Transfer Catalysts", Synthesis of Catalyst Libraries and Evaluation of Catalyst Activity. J.Org. Chem. 76, 4260-4336 (2011).
Denmark, S.E., et al., A Systemtic Investigation of Quaternary Ammonium Ions as Asymmetric Phase-Transfer Catalysts. Application of Quantitative Structure Activity/Selectivity Relationships. J. Org. Chem. 76, 4337-4357 (2011).
Gómez-Bombarelli, R. et al, "Automatic Chemical Design Using a Data-Driven Continous Representation of Molecules" ACS Cent. Sci. 4, 268-276 (2018).
Zhou, Z. et al., "Optimizing Chemical Reactions with Deep Reinforcement Learning", ACS Cent. Sci. 3, 1337-1344 (2017).
Mitchell, J.B.O., "Machine learning methods in chemoinformatics", Wiley Interdisciplinary Reviews: Computational Molecular Science, 4, 468-481 (2014).
Sciabola, S., et al., "Theoretical Prediction of the Enantiomeric Excess in Asymmetric Catalysis, An Alignment-Independent Molecular Interaction Field Based Approach", J. Org. Chem. 70, 9025-9027 (2005).
Harper, K.C., "Predicting and optimizing asymmetric catalyst performance using the principles of experimental design and steric parameters" Proc. Natl. Adad. Sci. 108, 2179-2183 (2011).
Ahneman, D.T et al., "Predicting reaction performance in C-N cross-coupling using machine learning" Science 360, 186-190 (2018).
Neilsen, M.K. et al., "Deoxyfluorination with Sulfonyl Fluorides: Navigating Reaction Space with Machine Learning" J.Am. Chem. Soc. 140, 5004-5008 (2018).
Breiman, L, "Randon Forests" Machine Learning 45, 5-32 (2001).
Skoraczynski, G. et al., "Predicting the outcomes of organic reactions via machine Tearning: are current descriptors sufficient?" Sci. Rep 7, 3582 (2017).
Parmar, D., et al. "Addition and Correction to Complete Field Guide to asymmetric BINOL-Phosphate Derived Brønsted Acidity, Hydrogen Bonding, Ion Pairing, and Metal Phosphates" Chem. Rev. 117, 10608-10620 (2017).
Bellman, R.E. "Dynamic Programming", (Princeton University Press, 1957).
Pearson, K, LIII, "On lines and planes of closest fit to systems of points in space", The London, Edinburgh, and Dublin Philosophical Magazine and Journal of Science 2, 559-572 (1901).
Steinwart, I. et al., "Learning from Dependent Observations", Journal of Multivariate Analysis, 100, 175-194 (2009).
Simon, L. et al., "Theoretical Study of the Mechanism of Hantzsch Ester Hydrogenation of Imines Catalyzed by Chiral BINOL-Phosphoric Acids", J. Am. Chem. Soc., 130, 8741-8747 (2008).

Wheeler, S.E. et al., "Through-Space Effects of Substituents Dominate Molecular Electrostatic Potentials of Substituted Arenes", J. Chem. Theory Comput. 5, 2301-2312 (2009).
Hansch, C. et al., "A survey of Hammett substituent constants and resonance and field parameters", Chem. Rev. 91, 165-195 (1991).
"Seikit-learn: Machine Learning in Python", JMLR 12, pp. 2825-2830, 2011.
Denmark Lab Chemoinformatics, cchimfolib, Project ID 8113486, GitLab (2018): https://gitlab.com/SEDenmarkLab/ccheminfolib.
Wu, T.R., et al. "Asymmetric Allylboration of Aldehydes and Ketones Using 3,3'-Disubstitutedbinaphthol-Modified Boronates", Org. Lett. 6, 2701-2704 (2004).
Sattely, E.S., et al., "Design and Stereoselective Preparation of a New Class of Chiral Olefin Metathesis Catalysts and Application to Enantioselective Synthesis of Quebrachamine: Catalyst Development Inspired by Natural Product Synthesis", J.Am. Chem. Soc 131, 943-953 (2009).
Bruno, N.C., et al., "Design and preparation of new palladium precatalysts for C-C and C-N cross-coupling reaction", Chem. Scii 4, 916-920 (2013).
Wang, C., et al., "Pd-Catalyzed Direct Arylation of Nitro(pentafluorosulfanyl)benzenes with Aryl Bromodes", Org. Lett. 16, 5004-5007 (2013).
Xu, Y. et al., "Ruthenium(II) Complexes of Monodonor Ligands: Efficient Reagents for Asymmetric Ketone Hydrogenation", J. Org. Chem. 70, 8079-8087 (2005).
Yamanaka, M., et al., "Chiral Brønsted Acid Catalyzed Enantioselective Mannich-Type Reaction", J. Am. Chem. Soc. 129, 6756-5764 (2007).
Wang, L. et al., "Diastereoselective and Enantioselective Silylation of 2-Arylcyclohexanols", Org. Lett. 17, 2408-2411 (2015).
Qu, B. et al., "Ligan-Accelerated Stereoretentive Suzuki-Miyaura Coupling of Unprotected 3,3"-Dibromo-BINOL", J. Org. Chem. 81, 745-750 (2016).
Tay, J.-H, et al., "Direct Interconversion of BINOL and H8-BINOL-Based Chiral Brønsted Acids Using Single-Step Red/Ox Manipulations", Org. Lett. 17, 3774-3777 (2015).
Liu, H. et al., "Enantioselective Direct Aza Hetero-Kiels-Alder Reaction Catalyzed by Chiral Brønsted acids", Org. Lett. 8, 6023-6026 (2006).
Cai, Q., et al., "Ring-Closing Metathesis/Isomerization/Pictet-SpenglerCascade via Ruthenium/Chiral Phosphoric Acid Sequential Catalysis", Org. Lett. 14, 5022-5025 (2012).
Li, X.-Y., et al., "Chiral Calcium Phosphate Catalyzed asummetric Alkenylation Reaction of Arylglyoxals with 3-Vinylindoles", Org. Lett 19, 1120-1123 (2017).
Chen, J. et al., "Asymmetric Mannich Reaction of Isatin-Based Ketimines with α-Diazomethylphosphonates Catalyzed by Chiral Silver phosphate", Org. Lett. 18, 4336-4339 (2016).
Harb, H.Y., et al., "SmI$_2$-Mediated Radical Cyclizations Directed by a C—Si bond", Org. Lett. 12, 5446-5449 (2010).
Vamathevan, Jessica et al., "Applications of machine learning in drug discovery and development", Reviews, Apr. 11, 2019.
Durst, J. et al., "New insights into the electrochemical hydrogen oxidation and evolution reaction mechanism", Energy & Environmental Science, 2014, 7, 2255.

* cited by examiner

A) Model Reaction with Training and Test Substrate Combinations

B) Test Catalysts with Averages for All Substrate Combinations
Observed
*Predicted*

```
┌─────────────────────────────────────────────────────────────────────────┐
│ Access a library of chemical structures.                          1502  │
└─────────────────────────────────────────────────────────────────────────┘
                                    ↓
┌─────────────────────────────────────────────────────────────────────────┐
│ Determine a respective occupancy descriptor for each of the       1504  │
│ chemical structures.                                                    │
└─────────────────────────────────────────────────────────────────────────┘
                                    ↓
┌─────────────────────────────────────────────────────────────────────────┐
│ Determine a predicted behavior for a chemical metric for each of  1506  │
│ the chemical structures.                                                │
└─────────────────────────────────────────────────────────────────────────┘
                                    ↓
┌─────────────────────────────────────────────────────────────────────────┐
│ Select a sample of the chemical structures.                       1508  │
└─────────────────────────────────────────────────────────────────────────┘
                                    ↓
┌─────────────────────────────────────────────────────────────────────────┐
│ Characterize each of the chemical structures of the sample.       1510  │
└─────────────────────────────────────────────────────────────────────────┘
                                    ↓
┌─────────────────────────────────────────────────────────────────────────┐
│ Determine a difference between the predicted behavior and the     1512  │
│ measured behavior.                                                      │
└─────────────────────────────────────────────────────────────────────────┘
                                    ↓
┌─────────────────────────────────────────────────────────────────────────┐
│ Adjust the model.                                                 1514  │
└─────────────────────────────────────────────────────────────────────────┘
```

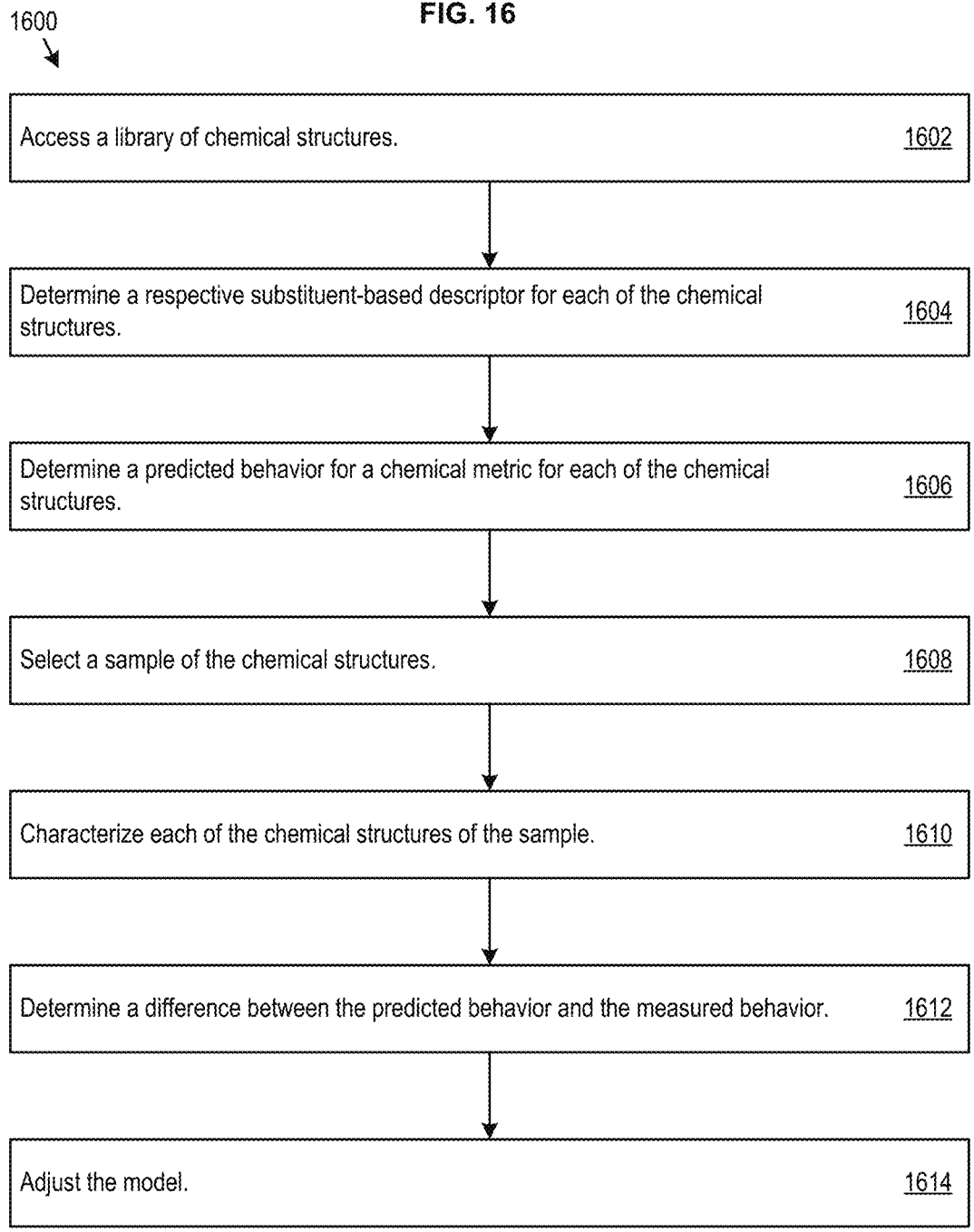

EXTRAPOLATIVE PREDICTION OF ENANTIOSELECTIVITY ENABLED BY COMPUTER-DRIVEN WORKFLOW, NEW MOLECULAR REPRESENTATIONS AND MACHINE LEARNING

CROSS-REFERENCE TO RELATED APPLICATION

The present application claims priority to and the benefit of U.S. Provisional Application No. 62/793,735, filed on Jan. 17, 2019, the entire contents of which are incorporated herein by reference.

BACKGROUND

The development of synthetic methods in organic chemistry has historically been driven by Edisonian empiricism. Catalyst design, wherein experimentalists attempt to qualitatively recognize patterns in catalyst structures to improve catalyst selectivity and efficiency, is no exception. However, this approach is hindered by a number of factors, including the lack of mechanistic understanding of a new transformation, the inherent limitations of the human brain to find patterns in large collections of data, and the lack of quantitative guidelines to aid catalyst selection. Chemoinformatics provides an attractive alternative for several reasons: No mechanistic information is needed, catalyst structures can be characterized by three-dimensional (3D) descriptors (numerical representations of molecular properties derived from the 3D structure of the molecule) that quantify the steric and electronic properties of thousands of candidate molecules, and the suitability of a given catalyst candidate can be quantified by comparing its properties with a computationally derived model on the basis of experimental data. Although artificial intelligence was applied to problems in chemistry as early as 1965, the use of machine learning methods has yet to affect the daily workflow of organic chemists. However, recent developments represent the dawn of a new era in organic chemistry, with the emergence of "big-data" methods to facilitate rapid advances in the field. Computer-assisted synthetic planning the prediction of organic reaction outcomes, assisted medicinal chemistry discovery, catalyst design, the use of continuous molecular representations for automatic generation of new chemical structures, materials discovery, the enhancement of computer simulation techniques, and the optimization of reaction conditions all provide examples in which leveraging machine learning methods facilitates advances in chemistry. The power of these methods is particularly notable for catalyst design; modern machine learning methods have the capacity to find patterns in large sets of data that are incomprehensible to experimental practitioners. Discovering these structure-activity relationships may facilitate catalyst identification, thus enabling the rapid optimization of catalytic transformations.

Lipkowitz et al. and Kozlowski et al. first reported the application of a 3D quantitative structure-activity relationship (QSAR) to asymmetric catalysis, wherein they used different molecular interaction field (MIF) approaches to study copper bis(oxazoline) complexes in enantioselective Diels-Alder reactions and enantioselective alkylations of aryl aldehydes, respectively. Although similar MIF-based approaches have since been employed, we suspect that such methods have not achieved widespread use because of the reliance on only one conformer in descriptor generation. Sigman and co-workers have employed multivariate regression techniques and catalyst-specific descriptors to glean mechanistic information. These researchers attribute some of their success to the use of Sterimol values; these substituent-based descriptors have multiple parameters designed to capture the rotation of the group of interest, thus providing a more accurate picture of how the molecule behaves in solution. Furthermore, preliminary studies in which pre-dictions are made beyond the bounds of the training data have been described; Sigman and co-workers have demonstrated the ability to predict ~10% enantiomeric excess (ee) beyond the training data. However, no examples exist wherein the prediction is far outside the selectivity regime comprising the training data. A very recent example of the utility of machine learning methods in catalysis is the prediction of reaction yields by Doyle and co-workers. These authors use many easily calculable descriptors to predict the outcomes of C—N coupling reactions and deoxyfluorination reactions with random forest models. Although this method excels in predicting the outcomes of reactions when the predicted value falls within the range of values in the training data, this method has not been used to make predictions beyond the range of observed values in the training set.

The ability to accurately predict a selective catalyst by using a set of nonoptimal data remains a primary objective of machine learning with respect to asymmetric catalysis. This feat is sometimes erroneously referred to as "extrapolation"—an understandable mistake, given that predictions are being made outside the bounds of previously observed selectivities. However, the term "extrapolation" does not refer to the selectivity space of the training data but rather to the descriptor space. Thus, a better statement of this goal is to predict high selectivity values far beyond the bounds of what is encompassed in the training data.

SUMMARY

In one aspect, the present disclosure provides a compound of Formula (I) or Formula (II):

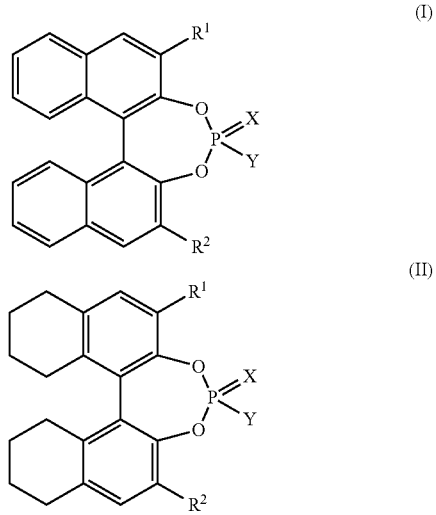

wherein:

X is O or S;

Y is OH, SH, or NHSO$_2$CF$_3$; and $R^1$ and $R^2$ are independently selected from the group consisting of:
  (i) halogen;
  (ii) unsubstituted phenyl;
  (iii) $C_1$-$C_6$ alkyl, optionally substituted with phenyl, the phenyl being optionally substituted with 1-3 substituents independently selected from $C_1$-$C_6$ alkyl and $C_1$-$C_6$ haloalkyl;
  (iv) phenyl substituted with 1-3 substituents independently selected from the group consisting of halogen, CN, $SF_5$, $CH_2OCH_3$, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_6$-$C_{10}$ aryl; and wherein each $C_1$-$C_6$ alkyl and $C_6$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy;
  (v) $C_7$-$C_{16}$ aryl optionally substituted with 1-5 substituents selected from $C_1$-$C_6$ alkyl, $C_1$-$C_6$ haloalkyl, and $C_6$-$C_{14}$ aryl; and
  (vi) $SiR^3R^4R^5$, wherein $R^3$, $R^4$, and $R^5$, are each independently selected from phenyl and $C_1$-$C_6$ alkyl.

In another aspect, the present disclosure provides a compound of Formula (I) or Formula (II):

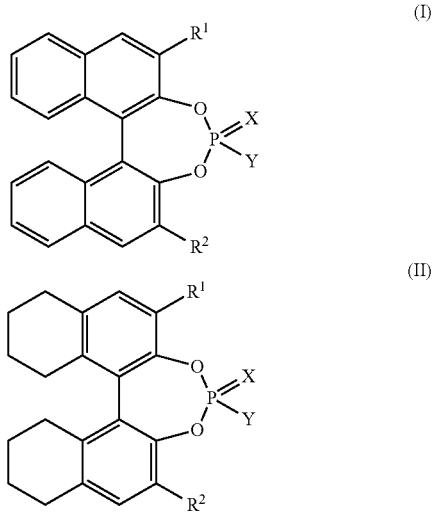

wherein:
X is O or S;
Y is OH, SH, or $NHSO_2CF_3$; and
$R^1$ and $R^2$ are independently selected from the group consisting of:
  (i) $C_1$-$C_6$ alkyl, optionally substituted with phenyl, the phenyl being optionally substituted with 1-3 substituents independently selected from $C_1$-$C_6$ alkyl and $C_1$-$C_6$ haloalkyl;
  (ii) phenyl substituted with 1-3 substituents independently selected from the group consisting of halogen, CN, $SF_5$, $CH_2OCH_3$, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_6$-$C_{10}$ aryl; and wherein each $C_1$-$C_6$ alkyl and $C_6$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy;
  (iii) $C_7$-$C_{16}$ aryl optionally substituted with 1-5 substituents selected from $C_1$-$C_6$ alkyl, $C_1$-$C_6$ haloalkyl, and $C_6$-$C_{14}$ aryl; and
  (iv) $SiR^3R^4R^5$, wherein $R^3$, $R^4$, and $R^5$, are each independently selected from phenyl and $C_1$-$C_6$ alkyl.

In another aspect, the present disclosure provides a kit including at least one compound of Formula (I) or Formula (II), or at least two such compounds, or at least three such compounds.

In another aspect, the present disclosure provides compounds 2-24 below. In another aspect, the present disclosure provides a kit including at least one compound of compounds 2-24, or at least two such compounds, or at least three such compounds.

In another aspect, the present disclosure provides compounds 52-70 below. In another aspect, the present disclosure provides a catalyst comprising at least one compound of compounds 52-70.

In another aspect, the present disclosure provides a method including accessing a library including chemical structures; via a model, determining a predicted behavior for a chemical metric for each of the chemical structures based on a level of a descriptor; selecting a sample of the chemical structures; characterizing each chemical structure of the sample to determine a measured behavior for the chemical metric; determining a difference between the predicted behavior and the measured behavior; and based on the difference, adjusting the model.

In another aspect, the present disclosure provides a method including determining a chemical descriptor by analyzing the a population of conformers for a chemical structure versus a Van der Waals radius for the chemical structure.

In another aspect, the present disclosure provides a method including determining a chemical descriptor by estimating an electrical effects of a substituent on a core molecule.

In another aspect, the present disclosure provides a method including selecting a sample from a library of chemical structures using a selection algorithm, the chemical structures characterized by a descriptor; providing physical specimens of the sample; and responsive to measured data obtained by interacting the physical specimens with a target system, determining predictive data describing interaction of the target system with a chemical structure in the library and not within the sample.

In another aspect, the present disclosure provides a product including machine-readable media other than a transitory signal; and instructions stored on the machine-readable media, the instructions configured to, when executed, cause a machine to implement any of the above methods.

DRAWINGS

In order that the disclosure may be well understood, there will now be described various forms thereof, given by way of example, reference being made to the accompanying drawings, in which:

FIG. 1 is a summary of chemoinformatics-guided workflow: (A) An in silico library of synthetically accessible catalysts is defined. For each member in the library, descriptors are calculated. (B) A representative subset is algorithmically selected on the basis of intrinsic chemical properties. (C) The representative subset is synthesized and experimentally tested. (D) The probability of identifying a highly selective catalyst in the first round of screening should be greater than by random sampling alone. (E) The data from the training set is used to train statistical learning methods. (F) The models predict selectivity values for every member of the greater in silico library. (G) If successful, the model will predict the optimal catalyst for the reaction. If unsuccessful, the new data can be used as training data to make a stronger prediction in successive rounds of modeling;

FIG. 2 pertains to the generation of average steric occupancy descriptors. (A) Pictorial description of the ASO calculation process. (B) ASO grid points away from the catalyst have values of 0 (red) whereas grid points occupied in all conformers have a value of 1 (blue, generally toward center); flexible substituents can be seen in the green/yellow region. (C) ASO discrimination of 3,3'-substituent groups; ortho-substituted arenes (red), fused ring substituents (blue), 3,5-disubstituteed arenes (yellow), and all other groups (green). (D) Bar graph representation of ASO descriptors for two different Brønsted acid catalysts;

FIG. 3 illustrates the construction of the universal training set (UTS). (A) Subset selection with the Kennard-Stone algorithm. The algorithm then selects a representative subset of points, as qualitatively depicted. (B) Locations of the catalysts selected by the Kennard-Stone algorithm in 2D chemical space (constructed from the first two principal components (18% and 12% of variance, respectively) of the full catalyst chemical space);

FIG. 4 illustrates the BPA universal training set. (A) Universal Training Set of phosphoric acid catalysts selected by the Kennard-Stone Algorithm. (B) Average selectivity of training catalysts across the 16 training reactions;

FIG. 5 illustrates a model validation on thiol addition to N-acyl imines. (A) Model reaction screened over 16 training substrate combinations and 9 test substrate combinations. (B) Test set of catalysts. Each catalyst was evaluated by the average selectivity across all 25 substrate combinations. The experimentally observed selectivity is in bold and the predicted selectivity is in italics (reported as free energy differential between the transition structures leading to each enantiomer). r.t. means room temperature;

FIG. 6 pertains to the averaged predicted selectivity values for external test sets plotted against observed enantioselectivity data. The vertical bands result from the accuracy in the analytical method, wherein the limit of detection determines enantiomeric purity to the nearest 0.5% ee. Because of the exponential relationship between ee and free energy, detectable differences in selectivity appear greater at larger free energy differentials. The mean absolute deviation (MAD) data is listed in the table for each of the ten replicate runs;

FIG. 7 pertains to the application of models from UTS. (A) The predicted vs. observed plots for the training set (purple), substrate test set (red), catalyst test set (green), and substrate/catalyst test set (orange). The Support Vector Machines ($2^{nd}$ order polynomial kernel, $q^2=0.748$ by k-fold cross validation) performs well on all external test sets, predicting reaction outcomes within 0.25 kcal/mol (MAD=0.161 kcal/mol, 0.211 kcal/mol, and 0.238 kcal/mol, respectively). The vertical bands result from the limit of accuracy in the analytical method. (B) The 3D chemical space of all catalysts (from the first three principal components of the full chemical space, 13%, 8%, and 8% of variance, respectively); the red points are unselective catalysts, the green/yellow points are more selective, and the blue points are the most selective, using average selectivity across all 25 reactions as a metric of catalyst selectivity. (C) Observed and predicted outcomes of reactions with substrate combinations that were also not included in the training data;

FIG. 8 pertains to a reaction prediction beyond the selectivity spanned by the training set. (A) A model generated using a deep feedforward neural network simulating the optimization of an unoptimized reaction by using all data below 80% ee to train the model. The vertical bands result from the limit of accuracy in the analytical method. (B) Predicted and observed average selectivities for the eight catalysts with average enantioselectivity over 80% ee. Only the common reactions (i.e. those forming the same product) that were in the test set for each of the eight catalysts were used to calculate the average selectivities;

FIG. 15 shows a flow diagram of an embodiment in the present disclosure.

FIG. 16 shows a flow diagram of another embodiment in the present disclosure.

DESCRIPTION

Herein, we describe a method to achieve this goal by proposing a more efficient alternative to traditional catalyst design.

This endeavor is challenging for a number of reasons. First, very small energy differences (~1 kcal/mol) can give rise to vastly different selectivities—even modern quantum chemical methods struggle to reproduce these energy differences in diastereomeric transition structures. Subtle changes in catalyst structure can also lead to large changes in catalyst performance, whereas descriptors capable of capturing fundamental chemical properties and the subtle features of catalyst structure responsible for enantioinduction remain imperfect. Moreover, off-cycle or background reactivity can erode enantioselectivity, and selectivity data are rarely uniformly distributed, adding the challenge of modeling on a skewed dataset. Predicting reactions that are more selective than anything in the training data (essential for machine learning to optimize a reaction) requires the model to accurately predict to a fringe case, a formidable challenge in its own right.

Perhaps the greatest impediment to accurate prediction in this manner is that no widely accepted workflow implementing chemoinformatics at all stages of development has been introduced to date. Using training set selection algorithms is essential to guarantee that the maximal breadth of feature space is covered in the training data; thus, by design, there should theoretically be no need for extrapolation. Failure to use training set selection algorithms introduces a greater level of uncertainty for predictions-if the domain of applicability is completely unknown, predictions may be outside the well-described region of feature space, and those predictions may be unfounded. If such methods are to be successful, chemical properties must be represented by robust descriptors. This aspect is especially challenging for asymmetric catalysis, as currently no mathematical representation of organic molecules exists that satisfies the following critical criteria: The descriptors must be rapidly calculable, must contain 3D information about an ensemble of conformers for each molecule, must be general for any given scaffold, and must capture the subtle features of catalyst structure responsible for enantioinduction. We describe the development of a workflow that uses chemoinformatic methods at every stage. Further, we report a molecular representation that facilitates this workflow and that enables the prediction of enantioselective reactions in a manner simulating new reaction optimization.

Figure 1:
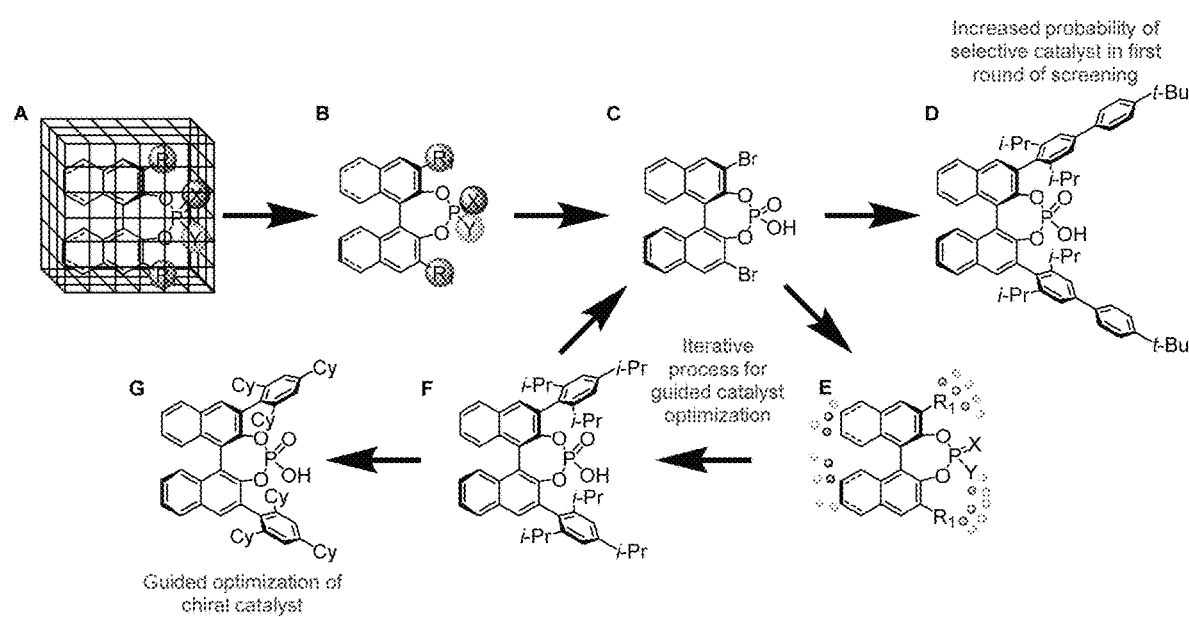

This new workflow consists of the following components (FIG. 1): (i) construction of an in silico library of a large (31) collection of conceivable, synthetically accessible catalysts of a particular scaffold; (ii) calculation of robust chemical descriptors for each scaffold, thereby creating the chemical space comprising the in silico library; and (iii) selection of a representative subset of the catalysts in this space. This subset is termed the universal training set (UTS), so named because it is agnostic to reaction or mechanism. Thus, the same set of compounds can be used to collect training data for any reaction that can be catalyzed by the common functional group and will cover the maximum breadth of feature space. The continuation of the workflow involves (iv) collection of the training data and (v) application of machine learning methods to generate models that predict the enantioselectivity of each member of the in silico library. These models are evaluated with an external test set of catalysts (predicting selectivities of catalysts outside of the training data). The validated models can then be used to select the optimal catalyst for a given reaction. At this point, either the predicted catalyst obtains the desired level of selectivity (success) or the predicted catalyst data can be recombined with the training data to make more robust models. The process can then be repeated iteratively until optimal selectivity is achieved (FIG. 1).

To develop this workflow, we chose the BINOL (1,1'-bi-2-naphthol)-derived family of chiral phosphoric acids as the catalyst scaffold. This family possesses a number of beneficial features, including synthetic accessibility and ease of diversification by installation of an array of substituents at the 3,3' positions. Additionally, the acidity of the phosphoryl group can be easily modulated, and the backbone can be unsaturated (binaphthyl backbone) or saturated (H8 backbone). These catalysts can be used for a vast number of synthetically useful reactions; thus, a UTS of this scaffold could be very powerful for method development.

Development of Average Steric Occupancy Descriptors

The plan began with the formulation of an in silico library containing 806 chiral phosphoric acid catalysts. For this class, two scaffolds were selected: catalysts with a fully aromatic binaphthyl backbone and catalysts wherein the second ring of the binaphthyl moiety is saturated (H8). Then a dataset of 403 synthetically feasible substituents (from a database of readily available commercial sources or fragments that require no more than four well-established synthetic steps) was added to the 3,3' positions of these scaffolds by using Python2 scripts (for full details see computational methods in the supplementary materials). The substituents used are found in Table 7, herein. The substituents were chosen by surveying catalogs of boronic acids, aryl halides, aldehydes, alkyl boranes, and Grignard reagents and adding all members that were compatible with the reaction conditions necessary to install that substituent (such as Suzuki coupling, use of organolithium reagents, and Kumada coupling). Thus, we are confident that our in silico library covers a large breadth of chemical space that is synthetically accessible. To construct the chemical space representing this library, chemically meaningful descriptors were calculated. However, using many types of readily available 0D, 1D, 2D, and 3D descriptors (the latter derived mostly from MIFs) led to failure because the calculated features did not adequately represent those catalyst properties responsible for enantioinduction [comparative molecular field analysis (CoMFA), grid-independent descriptors (GRIND), and all descriptors available in RDKit and MOE 2015 are some examples of previous attempts]. The likely cause of failure was that only a single conformation of each of the catalysts was included. Thus, a new set of descriptors had to be developed that included information about the entire conformer ensemble, could be used for any catalyst scaffold, and would be easily calculable for large libraries of compounds.

Figure 2:
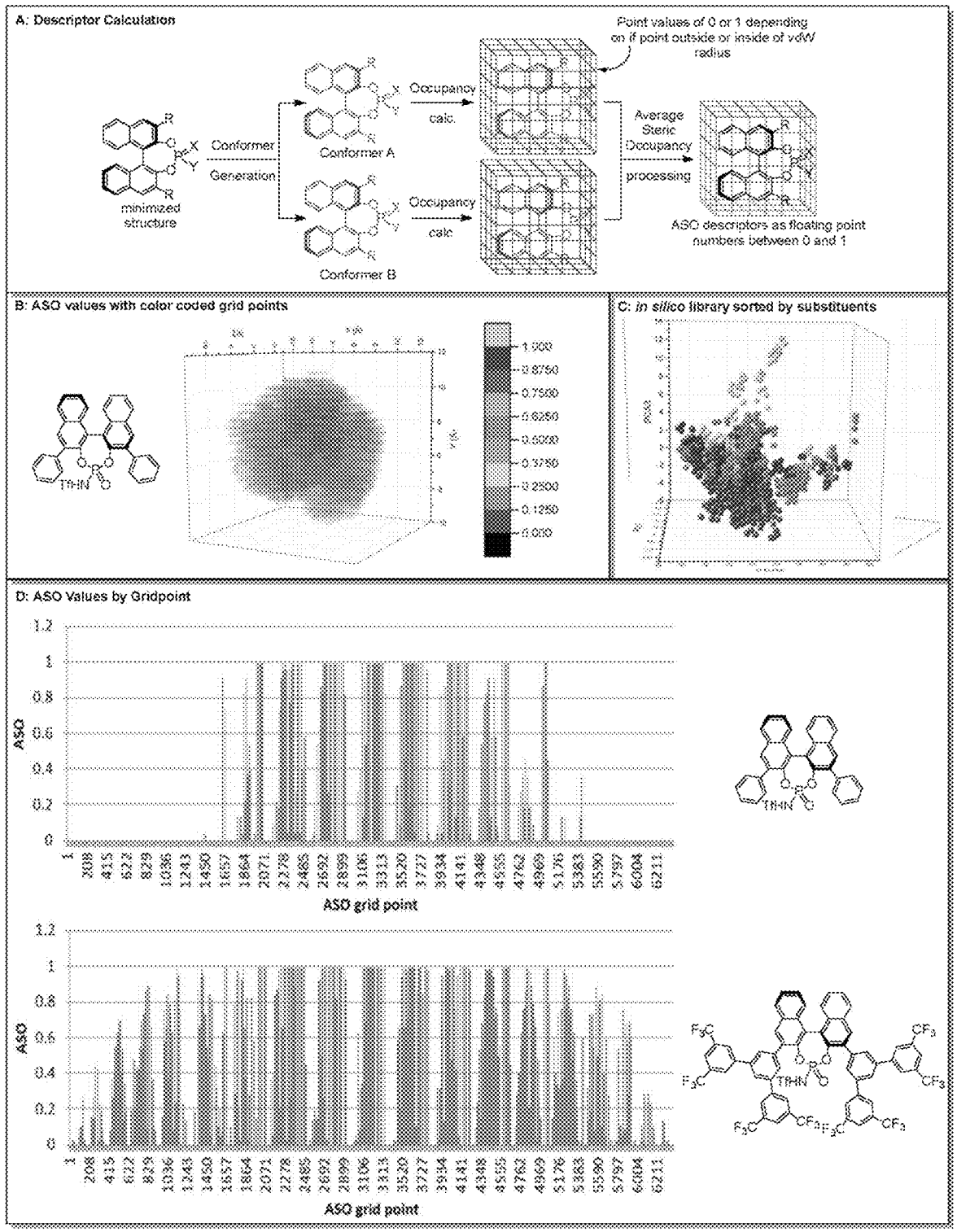

To achieve this goal, we invented a new descriptor called average steric occupancy (ASO). The ASO descriptors were inspired by 3.5D and 4D descriptors, simplifying the conformer population information into a location-specific numerical form. The protocol for ASO calculation is illustrated in FIG. 2A. First, a conformer distribution for each catalyst in the in silico library was obtained. Second, for each molecule, the conformers were aligned and individually placed in identical grids. If a grid point was within the van der Waals radius of an atom, it was assigned a value of 1; otherwise, it was assigned a value of 0. This process was repeated for n conformers, and upon completion each grid point had a cumulative value ranging from 0 to n. The values were then normalized by dividing by n, such that all grid points had a value between 0 and 1. These values constituted the steric descriptors for the structures. These features are represented in FIG. 2B, wherein the ASO values around a phosphoric acid catalyst are depicted. The red grid points mark areas away from the catalyst where ASO values are 0.000 to 0.125, whereas the blue represents grid points where the ASO values are 0.875 to 1.000. Because the catalysts are aligned to the backbone, the corresponding grid points all have a value of nearly 1, and the backbone is visible as the two overlapping blue bands. Below the blue bands are regions of green and yellow; these represent conformers that differ by the rotation of the P-NH-Tf (triflyl) moiety and the phenyl substituents at the 3,3' positions. The capacity of these descriptors to distinguish among catalysts of different classes is illustrated in FIG. 2C. The distribution of the different catalyst classes in chemical space (from the first three principal components of the ASO chemical space) demonstrates that ASO qualitatively groups like-structured catalysts.

The electronic descriptors were derived from the perturbation that a substituent exerts on the electrostatic potential map of a quaternary ammonium ion (see the computational methods in the supplementary materials for details). These substituent-based electronic descriptors were combined with the ASO descriptors. In total, this process amounted to 16,384 features per catalyst, which was later reduced upon the removal of all features with a variance of zero.

To select a representative subset of the chemical space spanned by the in silico library, the dimensionality of the chemical space must be reduced. The data were transformed with principal components analysis (PCA), which selects new dimensions such that the variance retained is maximized per dimension kept.

Figure 3:
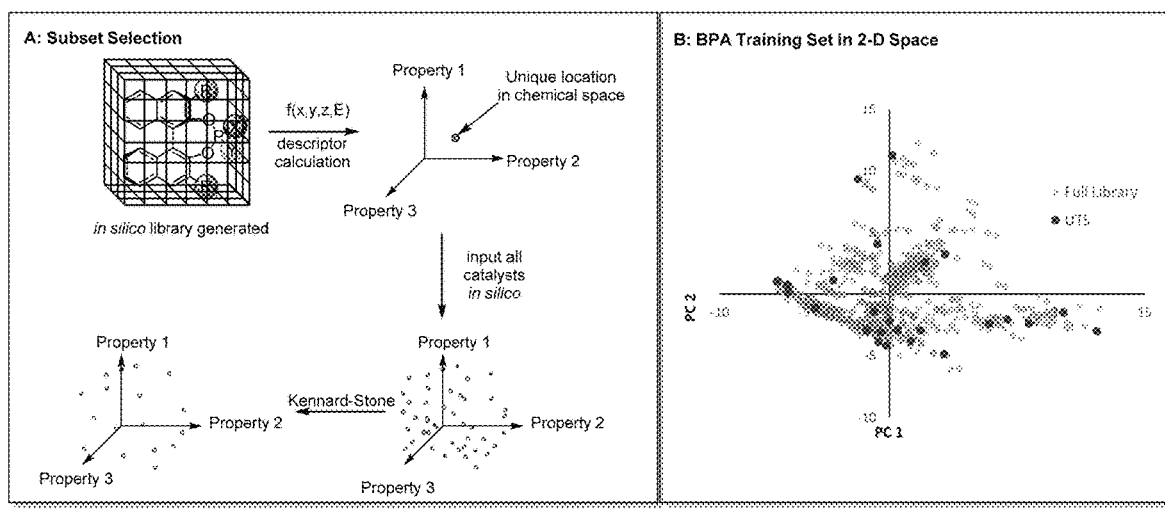

A representative subset (including boundary cases) was selected from this space by using the Kennard-Stone algorithm (FIG. 3). This sampling method is of paramount importance; it guarantees that catalysts from uniform regions of feature space are sampled. Thus, predictions made later in method development should still be in a region of feature space described by the initial training set, giving more confidence in these predictions. The subset of selected catalysts constitutes the UTS, which can then be used to optimize any reaction that can be catalyzed by that catalyst type. The 24 members of the UTS for the chiral phosphoric acid scaffold are given in FIG. 4A. To evaluate the predictions made from the UTS, a separate test set of 19 external catalysts (52 to 70) (FIG. 5B) was selected from the in silico library. These external catalysts were selected on the basis of intuitive chemical differences and synthetic accessibility.

In some implementations, an occupancy descriptor, such as the ASO (average steric occupancy) descriptor, may be determined by generating grid points and determining whether atoms (or specific atom types, such as heteroatoms) of conformers of a chemical structure occupy the grid points. In some cases, a grid point may be assigned an occupied value if it is within the Van der Waals radius of an atom of the conformer. If a grid point is not within a Van der Waals radius of an atom of the conformer, the grid point may be assigned an unoccupied value. The occupancy descriptor for a chemical structure may be determined by averaging over the values assigned to a grid point for each of the population of conformers for the chemical structure. For example, in some cases, an ASO descriptor may be determined using a fixed occupied value of 1, and a fixed unoccupied value of 0. Further, any atom of the conformers may be considered when calculating the ASO descriptor, regardless of the type of atom.

In some implementations, occupancy descriptors may be based on a constrained set of atom types. For example, some atom types may be excluded from the calculation of the occupancy descriptor. For example, heteroatoms (e.g., atoms other than hydrogen or carbon atoms) may be included in an occupancy descriptor calculation and non-heteroatoms (e.g., hydrogen and carbo atoms) may be excluded for a calculation. This heteroatom-based occupancy descriptor may serve as a heteroatom indicator field.

In some cases, specific atoms/heteroatoms may be included in the occupancy description. For example, Van der Waals radii for heteroatoms such as oxygen and nitrogen may be included in the calculation while other atoms are excluded. Additionally or alternatively, phosphorus atoms may be included (e.g., in addition to or in place of the oxygen and nitrogen heteroatoms). Other groups of atoms/heteroatoms may be selected for inclusion/exclusion within the occupancy descriptor calculation. In various implementations, the specific atoms/heteroatoms may be selected based on multiple factors including factors for selection of descriptors, the number of structure of substituents in the group of chemical structures under test, the chemical composition of the substituents in the group of chemical structures under test, or other factors.

In some implementations, the occupied value assigned to a grid point may be dependent on the atom/atoms causing occupancy of the grid point. For example, the occupied value may include that atomic charge of the atom. For grid points outside Van der Walls radii for the atoms of a conformer, the unoccupied value may remain a fixed value (for example, the 0 value used in some ASO implementations). This atomic-charge-weighted occupancy descriptor may serve as an averaged-electronic indicator field.

Figure 9:
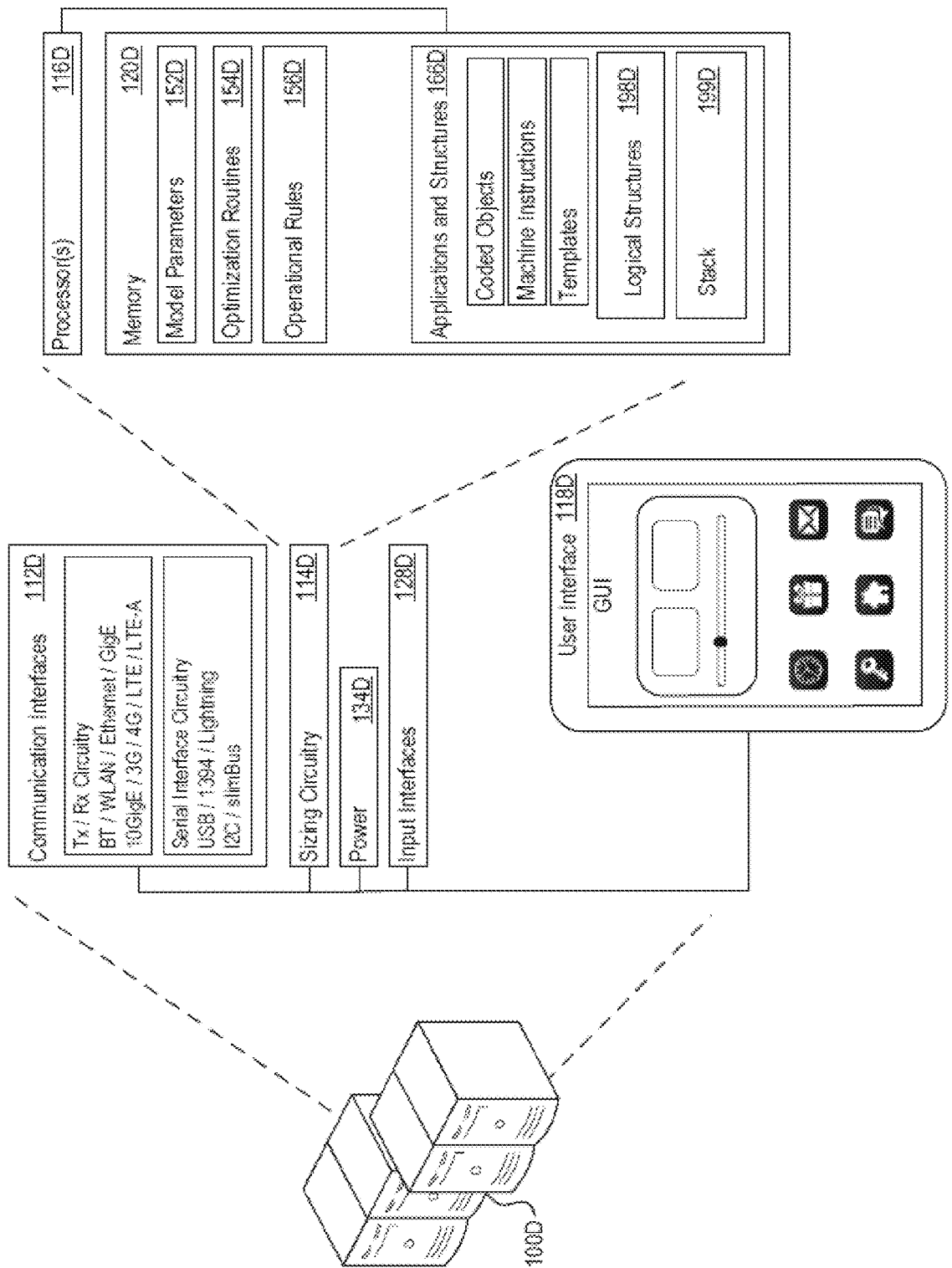
FIG. 9 is and illustration of an example execution environment for model calculation.

Referring to FIG. 15, example logic 1500 for implementing a chemoinformatics-guided workflow using an occupancy descriptor is shown. For example, the example logic 1500 may be implemented on an execution environment such as the example shown in FIG. 9, below. The example logic may access accessing a library of chemical structures (1502). The library may define a set of chemical structures for which regression of properties is desired. In some cases, the library may contain a sufficient number of structures such that individual physical characterization may be impractical or otherwise undesired. The example logic 1500 may determine a respective occupancy descriptor for each of the chemical structures (1504). The occupancy may include any of the example occupancy descriptors described above, such as an ASO descriptor, and heteroatom indicator field, an averaged-electronic indicator field, or another occupancy descriptor. Using a model (e.g., computationally rather than necessarily via individual physical characterization), the example logic 1500 may determine a predicted behavior for a chemical metric for each of the chemical structures based on their respective occupancy descriptors (1506). The chemical metric may be a chemical behavior at test among the various chemical structures in the library. The example logic 1500 may select a sample of the chemical structures (1508). The example logic 1500 may selected a sample (e.g., a subset) of the chemical structures. The sample may be selected such that it is representative of the broader library of the chemical structures. For example, the selection algorithms (e.g., Kennard-Stone or other selection algorithms) may be used to select the sample. The example logic 1500 may provide instructions to characterize (e.g., physically) each of the chemical structures in the sample (1510). The example logic 1500 may receive the measure behaviors (e.g., as input) and may determine a difference between the predicted behavior (e.g., from the model) and the measured behavior (1512). Based on this difference, the example logic may adjust the model to conform to the measured behavior (1514).

In some implementations, substituent-based descriptors are also used. Examples of this descriptor include the substituent electrostatic potential energy minimum (ESPMIN) and substituent electrostatic potential energy maximum (ESPMAX) descriptor. In some examples, a molecular subunit of interest is bound to a trimethylammonium residue. An electrostatic molecular interaction field (MIF) is calculated, in some cases it includes a single layer of grid points along the surface of the molecule. The maximum interaction energy with a positron is used to indicate the through-bond electronic character of the subunit, which is reflected by the largest electrostatic potential energy of interaction. This value is ESP-MAX. Other permutations with different probe units (a cationic copper atom, a trialkyl phosphonium reside, etc.) or other interactions (most stabilizing interaction, etc.) have also been implemented.

Referring to FIG. 16, example logic 1600 for implementing a chemoinformatics-guided workflow using a substituent-based descriptor is shown. For example, the example logic 1600 may be implemented on an execution environment such as the example shown in FIG. 9, below. The example logic 1600 may access accessing a library of chemical structures (1602). The library may define a set of chemical structures for which regression of properties is desired. In some cases, the library may contain a sufficient number of structures such that individual physical characterization may be impractical or otherwise undesired. The example logic 1600 may determine a respective substituent-based descriptor for each of the chemical structures (1604). The occupancy may include any of the example substituent-based descriptors described above, such as an ESPMIN or ESPMAX descriptor, or another substituent-based descriptor. Using a model (e.g., computationally rather than necessarily via individual physical characterization), the example logic 1600 may determine a predicted behavior for a chemical metric for each of the chemical structures based on their respective occupancy descriptors (1606). The chemical metric may be a chemical behavior at test among the various chemical structures in the library. The example logic 1600 may select a sample of the chemical structures (1608). The example logic 1600 may selected a sample (e.g., a subset) of the chemical structures. The sample may be selected such that it is representative of the broader library of the chemical structures. For example, the selection algorithms (e.g., Kennard-Stone or other selection algorithms) may be used to select the sample. The example logic 1600 may provide instructions to characterize (e.g., physically) each of the chemical structures in the sample (1610). The example logic 1600 may receive the measure behaviors (e.g., as input) and may determine a difference between the predicted behavior (e.g., from the model) and the measured behavior (1612). Based on this difference, the example logic may adjust the model to conform to the measured behavior (1614).

Application of the Catalyst Optimization Protocol to Asymmetric N,S-Acetal Formation To validate the ASO and training set selection protocol, the training set was evaluated on a previously optimized model reaction. The enantioselective formation of N,S-acetals developed by Antilla and co-workers was selected for several reasons. The reaction is high yielding and highly reproducible; it can be performed under air at room temperature, thus facilitating rapid screening; and a range of selectivities (0 to 99%) has been reported with different catalysts (six reported catalysts). Accordingly, we judged this reaction to be a good candidate for empirically evaluating the selectivity space covered in the UTS. By calculating ASO and electronic descriptors for reactants and products as well and concatenating these descriptors with catalyst descriptors, individual reaction profiles could be constructed that also took into account substrate properties. The inclusion of substrate descriptors also increased the number of data points obtained per catalyst synthesized. As a general note on the use of reactant and product descriptors, we find that it provides the following benefits: (i) More data points can be collected per catalyst synthesized, allowing for stronger models to be produced, and (ii) we can use our technology to predict the outcome of reactions with a known catalyst on new substrate combinations, thus creating another powerful tool.

Generation of Models by Using all Selectivity Data

Figure 4:
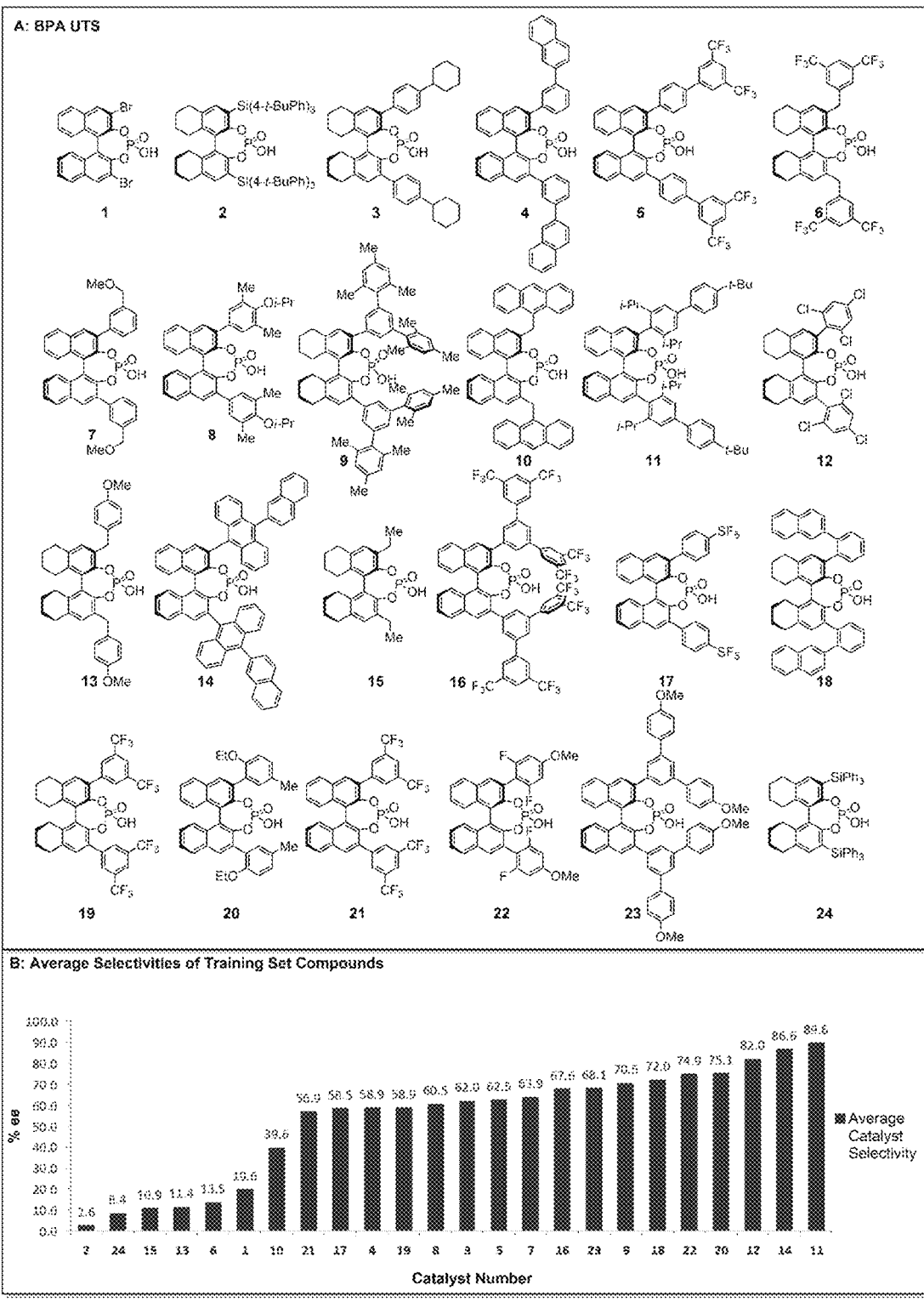
Figure 5:
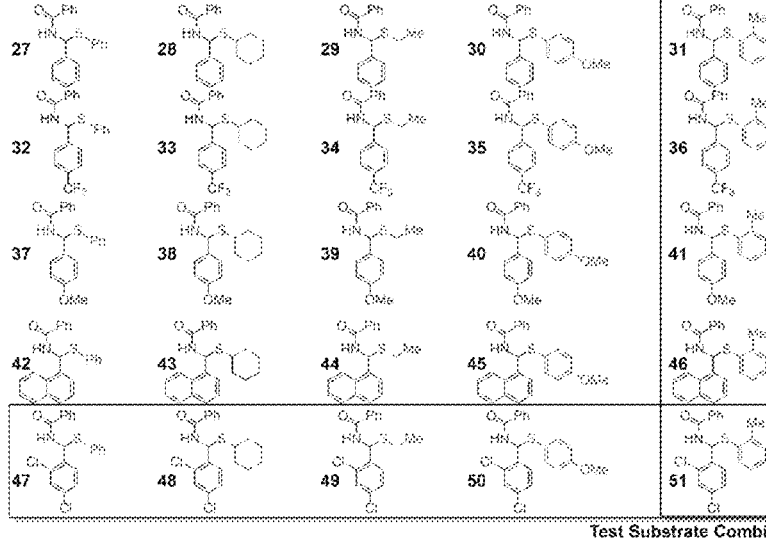
Figure 5:
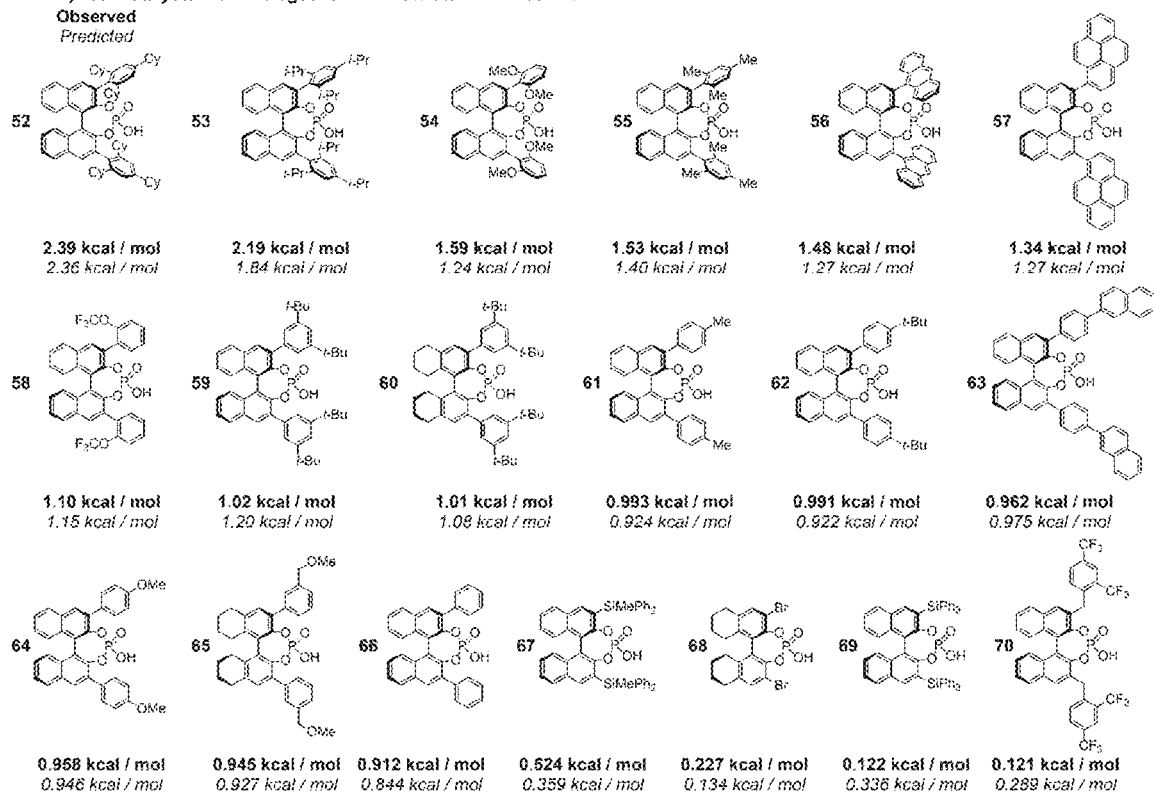
Figure 6:
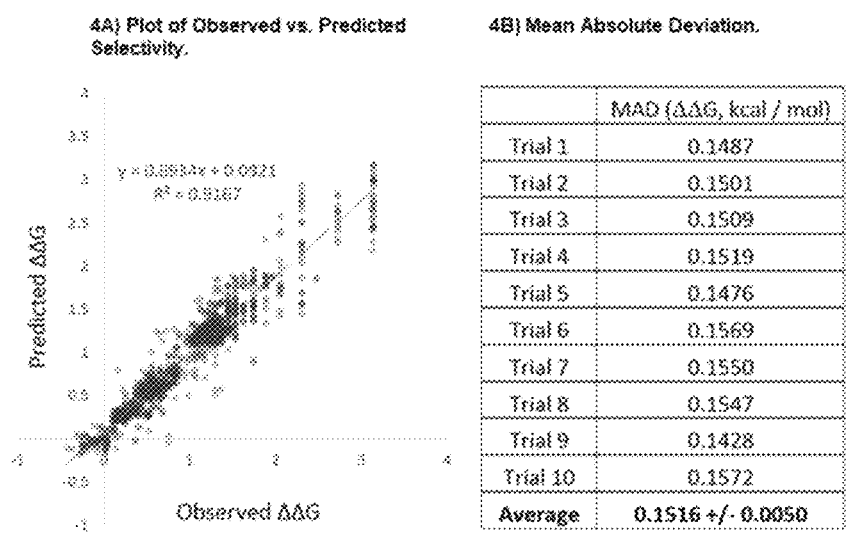

To ensure that our descriptors capture the structural information pertaining to enantioinduction and can be used to construct predictive models, 2150 separate experiments were performed, wherein the catalysts shown in FIGS. 4A and 5B (43 catalysts in total) were used in the reactions with pairwise combinations of imines and thiols, leading to the 25 different products shown in FIG. 5A. This process creates 43×25=1075 reactions, which were run in duplicate, and the average of duplicate runs was used as the experimental selectivity data. From these 1075 reactions, 475 were randomly selected as an external test set by using a Python random-number generator, and the remaining 600 reactions were used to train the model. To ensure that model efficacy and training set-test set partitioning were unbiased, this process was repeated 10 times. Models were then developed with support vector machines by using a grid-based optimization of hyperparameters with fivefold cross validation (see supplementary materials for details). The average predicted selectivities of the 475 external test set reactions (i.e., those which were not used in the model training process) reveal very good correlation when plotted against the experimental selectivity data (a high coefficient of determination R2, a y intercept very close to zero, and a slope approaching unity) (FIG. 6A). The mean absolute deviation (MAD) for each of the 10 randomized trials is listed in FIG. 6B. As is evident from the low MAD of each run, the models make highly accurate predictions of selectivity, confirming that our descriptor set is a valid, numerical representation of molecules capable of capturing the relevant features of catalysts responsible for enantioselectivity.

As experimentalists, we were interested in establishing if these tools could be used to predict the results of either new substrate combinations or new catalysts that have not previously been tested or to identify new reactions (i.e. substrates and catalysts) that are more selective than any reaction in the training data. We therefore performed two modeling studies to evaluate each hypothesis by partitioning the available data in two different ways. For the first study, the data from reactions of four imines (imines 25a-25d) and four thiols (thiols 26a-26d), i.e. 16 reactions per catalyst would be evaluated (FIG. 5A). Employing the 24-member catalyst training set (FIG. 4A) with each substrate combination then gave rise to 16×24=384 training reactions which could be used for model development. This process also generated 1075-384=691 test reactions for external validation (the test reactions were later divided into three different sets, detailed below). For the second study, we investigated if new, more selective reactions could be predicted. To investigate this possibility, the 1075 experimental selectivity data points were divided such that every catalyst/imine/thiol combination that gave product below 80% ee was included in the training set, and no reactions above 80% ee were used at any stage in model development. These remaining, highly selective reactions were instead used as an external test set. It is worth noting that both data division methods violate the iid (independent and identically distributed) assumption. Thus, we make no claims as to the generalizability of these studies and simply propose this method as a tool to facilitate experimental optimization of catalysts and exploration of substrate scope.

Generation of Models Derived from the Universal Training Set.

It was very rewarding to find a highly selective catalyst in the training set (FIG. 4A, compound 11), supporting our hypothesis that using the UTS increases the probability of finding an effective catalyst in the first round of screening (catalyst selectivity data summarized in FIG. 4B). Interestingly, 3,3'-benzyl-substituted catalysts used in reactions with aliphatic thiols as nucleophiles gave rise to the opposite stereoisomer as the major product compared to the other cases. Thus, the range of selectivities covered by the UTS in the 16 training reactions spans from −43% ee to >99% ee with the same enantiomer of catalyst, further supporting the hypothesis that the UTS covers a broad range of selectivity-space as illustrated in the full compilation of experimental results (Table 6). From this dataset, a suite of models was generated and used to predict the selectivity of three families of test sets, namely: a substrate test set of reactions generating new products (i.e. those formed from substrates not included in the training set, but using catalysts in the training set), a catalyst test set of reactions generating the same products in the training set but with catalysts not included in the training data, and a substrate-catalyst (sub-cat) test set of reactions creating new products and also using catalysts not included in the training data. For the substrate test set, nine distinct compounds (31, 36, 41, and 46 to 51) (FIG. 5A) generated from substrate combinations with unknown results in the model reaction were selected, totaling 216 re-actions (24 training catalysts×9 test substrates). For the catalyst test set, the 19 external catalysts (52 to 70) (FIG. 5B) were evaluated in reactions generating the same products as the training reactions, totaling 304 reactions (19 test catalysts from FIG. 5B×16 training substrates from FIG. 5A). For the sub-cat test set, the 19 external test set catalysts were used in reactions producing the nine new products, thus evaluating the capability to predict reaction outcomes with external substrate combinations and external catalysts, totaling 171 reactions [19 test catalysts×9 test substrates (FIG. 5B catalysts with FIG. 5A test substrate combinations)].

By using a variety of data preprocessing methods (see supplementary materials for details), we generated a suite of models. Of these, the support vector machines method gave the highest performance on the basis of the MAD from the combined external test sets (FIG. 7A). The first test set evaluated the ability of the models to predict the selectivity only of reactions forming new products. In this role, the model performed well, with an MAD of 0.161 kcal/mol. Next, the same model was used to predict the selectivity of the external test set of catalysts. The performance of the model was still highly accurate, with a MAD of 0.211 kcal/mol. Lastly, reactions forming new products with the external test catalysts were predicted with a MAD of 0.236 kcal/mol. All three test sets were predicted at a level of accuracy equal to or greater than that of most quantum chemistry methods (43). To evaluate catalyst performance, the mean selectivity (ΔΔG in kilocalories per mole) of each test catalyst across all 25 reactions was calculated (FIG. 5B). The model predicted this efficacy metric with notable accuracy, predicting all catalysts within 0.4 kcal/mol, with only two catalysts (53 and 54) predicted outside of 0.3 kcal/mol from the experimentally observed ΔΔG. Catalyst 53 gave the best selectivity in the original study (41), and our results were in good agreement with what has been previously reported. Similarly, aliphatic thiols gave diminished selectivity with respect to thiophenol derivatives. The first three principal components of catalyst space also reveal distinct regions of high, medium, and low space (FIG. 7B). Similarly, the predicted reaction outcomes for the nine test reactions with the best catalyst are illustrated in FIG. 7C. All reaction selectivities except one (49) are predicted within 2% ee of the measured value. Despite not being included at any stage of model development, compound 52 was still predicted to be the most selective catalyst in the in silico library for this transformation. A complete list of predicted selectivity values for the entire in silico library of reactions can be found in data S1.

The compounds of the training set may, in one aspect, be compounds of Formula (I) or Formula (II):

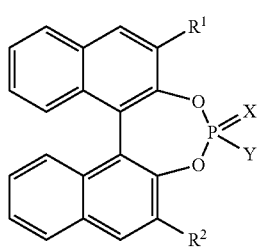

(I)

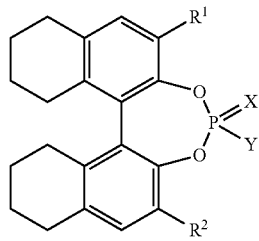

(II)

X may be O or S. In particular, X may be O.

Y may be OH, SH, or $NHSO_2CF_3$. In particular, Y may be OH.

$R^1$ and $R^2$ may be independently selected from the group consisting of (i) halogen; (ii) unsubstituted phenyl; (iii) $C_1$-$C_6$ alkyl, optionally substituted with phenyl, the phenyl being optionally substituted with 1-3 substituents independently selected from $C_1$-$C_6$ alkyl and $C_1$-$C_6$ haloalkyl; (iv) phenyl substituted with 1-3 substituents independently selected from the group consisting of halogen, CN, $SF_5$, $CH_2OCH_3$, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_6$-$C_{10}$ aryl; wherein each $C_1$-$C_6$ alkyl and $C_1$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy; (v) $C_7$-$C_{16}$ aryl optionally substituted with 1-5 substituents selected from $C_1$-$C_6$ alkyl, $C_1$-$C_6$ haloalkyl, and $C_6$-$C_{14}$ aryl; and (vi) $SiR^3R^4R^5$, wherein $R^3$, $R^4$, and $R^5$, are each independently selected from phenyl and $C_1$-$C_6$ alkyl.

$R^1$ and $R^2$ may be independently selected from the group consisting of (i) $C_1$-$C_6$ alkyl, optionally substituted with phenyl, the phenyl being optionally substituted with 1-3 substituents independently selected from $C_1$-$C_6$ alkyl and $C_1$-$C_6$ haloalkyl; (ii) phenyl substituted with 1-3 substituents independently selected from the group consisting of halogen, CN, $SF_5$, $CH_2OCH_3$, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_6$-$C_{10}$ aryl; wherein each $C_1$-$C_6$ alkyl and $C_6$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy; (iii) $C_7$-$C_{16}$ aryl optionally substituted with 1-5 substituents selected from $C_1$-$C_6$ alkyl, $C_1$-$C_6$ haloalkyl, and $C_6$-$C_{14}$ aryl; and (iv) $SiR^3R^4R^5$, wherein $R^3$, $R^4$, and $R^5$, are each independently selected from phenyl and $C_1$-$C_6$ alkyl.

$R^1$ may be the same as $R^2$. In another aspect, $R^1$ may be different from $R^2$.

When the compound is a compound of Formula (I), $R^1$ and $R^2$ may each be selected from: (i) phenyl substituted with 1-3 substituents independently selected from the group consisting of halogen, CN, $SF_5$, $C_1$-$C_6$ alkyl, $C_1$-$C_6$ haloalkyl, $C_1$-$C_6$ haloalkoxy, $C_1$-$C_6$ alkoxy, and $C_6$-$C_{10}$ aryl; wherein each $C_1$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy; (ii) $C_7$-$C_{16}$ aryl optionally substituted with $C_6$-$C_{14}$ aryl; and (iii) $SiR^3R^4R^5$, wherein $R^3$, $R^4$, and $R^5$ are each independently selected from phenyl and methyl.

In such an aspect, $R^1$ and $R^2$ may each be unsubstituted $C_{14}$ aryl, $C_{14}$ aryl substituted with $C_{10}$ aryl, or unsubstituted $C_{16}$ aryl.

When the compound is of Formula (I), and $R^1$ and $R^2$ are each phenyl, these phenyl groups may be substituted with 1-3 substituents independently selected from the group consisting of $CH_3$, F, $CF_3$, $OCF_3$, $C_1$-$C_6$ haloalkyl, $OCH_3$, $CH_2OCH_3$, isopropyl, naphthyl, and phenyl substituted with 1-3 substituents selected from the group consisting of $CF_3$, $OCH_3$, $OCH(CH_3)_2$, $CH_2OCH_3$, and tert-butyl.

When the compound the compound is of Formula (II), $R^1$ and $R^2$ may each be selected from: (i) $C_1$-$C_6$ alkyl, optionally substituted with phenyl substituted with 1-3 substituents independently selected from $C_1$-$C_6$ alkyl and $C_1$-$C_6$ haloalkyl; (ii) phenyl substituted with 1-3 substituents independently selected from the group consisting of halogen, $C_1$-$C_6$ haloalkyl, $C_1$-$C_6$ alkoxy, $CH_2OCH_3$, $C_3$-$C_6$ cycloalkyl, and $C_6$-$C_{10}$ aryl substituted with 1-3 substituents selected from the group consisting of $C_1$-$C_e$ alkyl, $C_1$-$C_6$ haloalkyl, and $C_1$-$C_6$ alkoxy; and (iii) $SiR^3R^4R^5$, wherein $R^3$, $R^4$, and $R^5$, are each independently selected from 4 tert-butylphenyl and phenyl.

When the compound the compound is of Formula (II), $R^1$ and $R^2$ may be selected from ethyl and —$CH_2$-$Ph(CF_3)_2$.

When the compound the compound is of Formula (II), $R^1$ and $R^2$ may be selected from phenyl substituted with 1-3 substituents independently selected from the group consisting of Cl, $CF_3$, $OCH_3$, cyclohexane, napthyl, and phenyl substituted with 1-3 methyl groups.

In one aspect, the compound may be a compound as found in Table 1:

TABLE 1

Compounds of training set

| 2 |
|---|
| 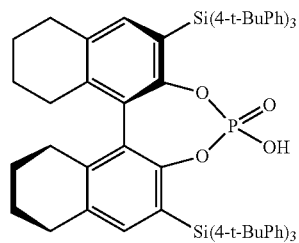 |

| 3 |
|---|
| 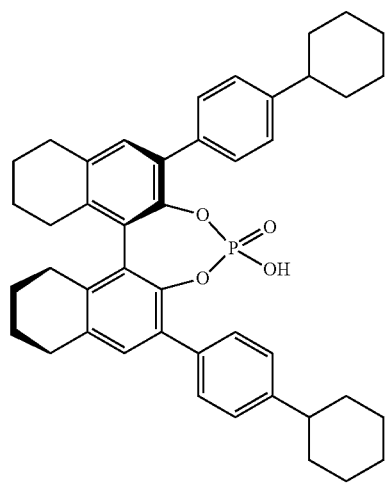 |

TABLE 1-continued

Compounds of training set

| 4 |
|---|
| 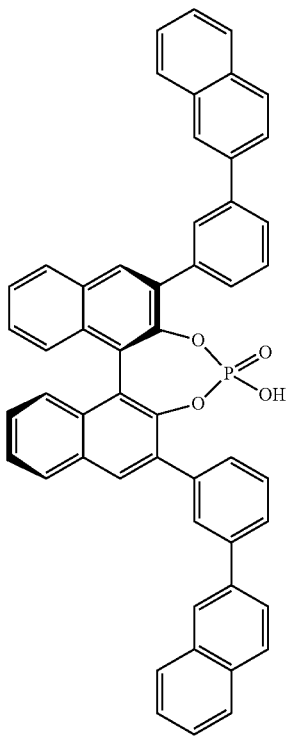 |

| 5 |
|---|
| 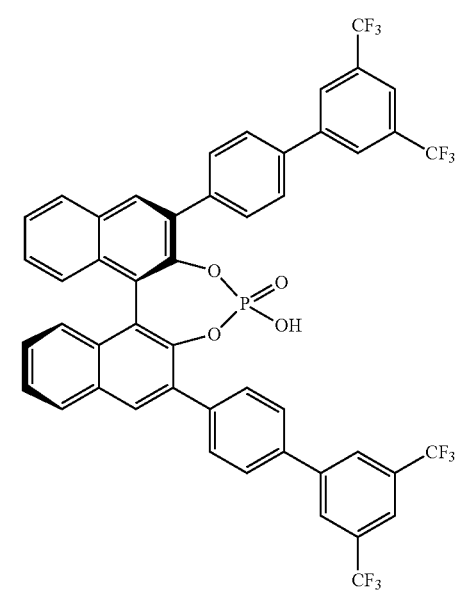 |

TABLE 1-continued
Compounds of training set
6
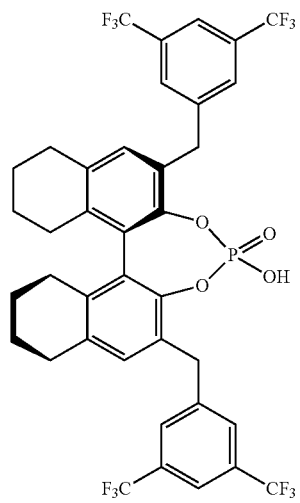
7
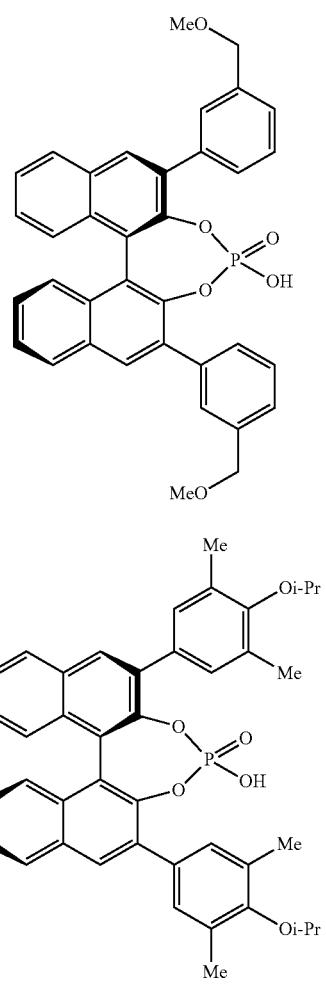
8
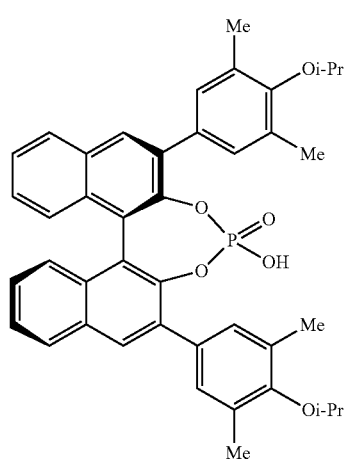
TABLE 1-continued
Compounds of training set
9
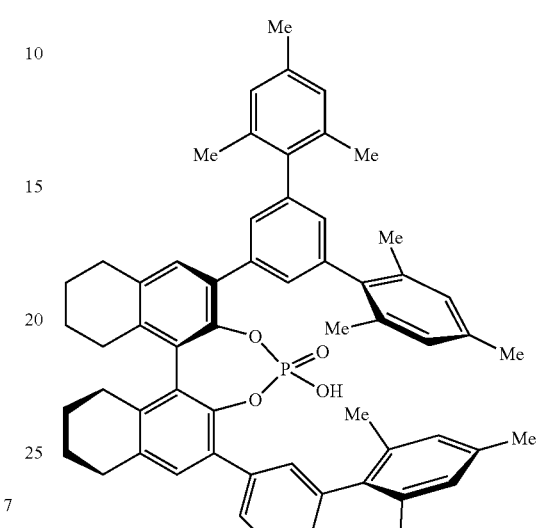
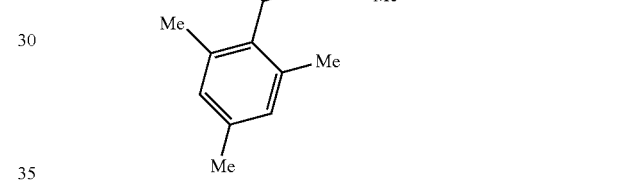
10
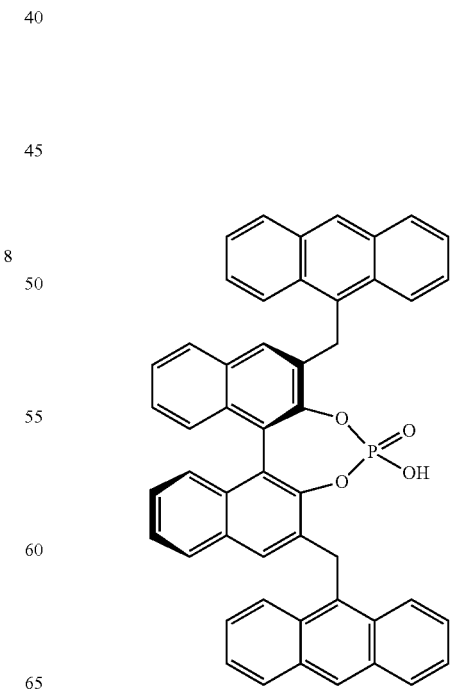

TABLE 1-continued
Compounds of training set
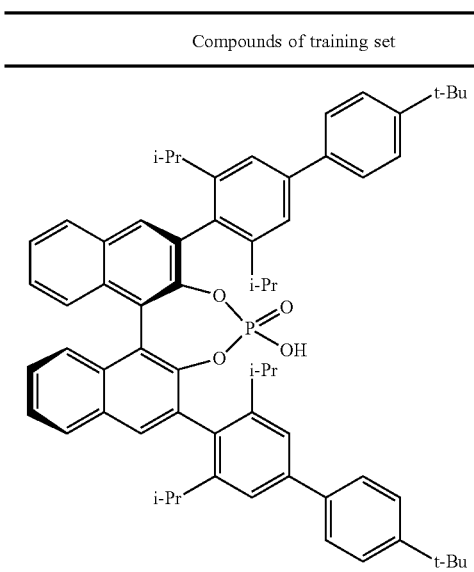
11
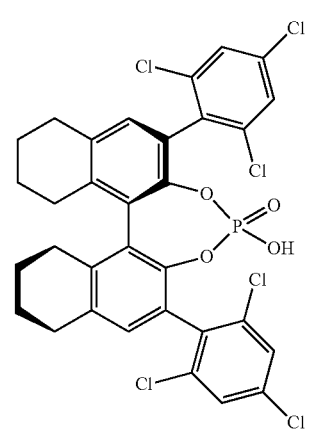
12
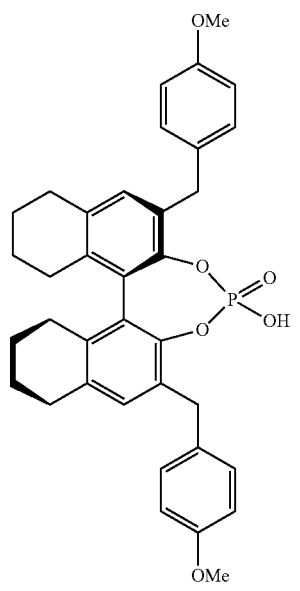
13
TABLE 1-continued
Compounds of training set
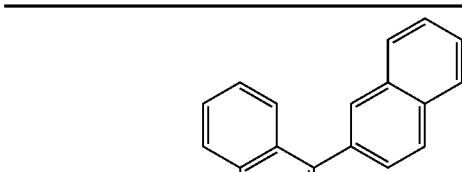
14
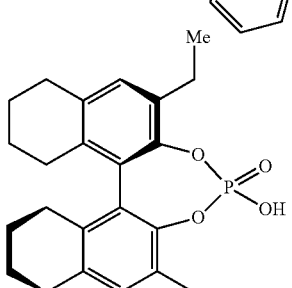
15
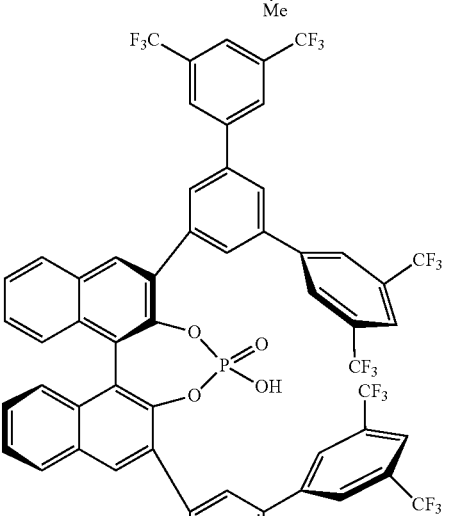
16

TABLE 1-continued
Compounds of training set
17
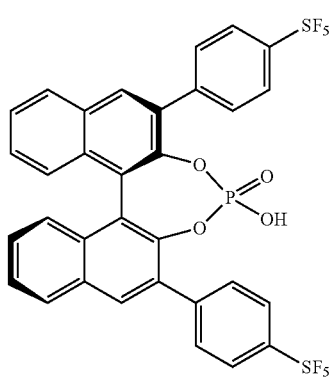
18
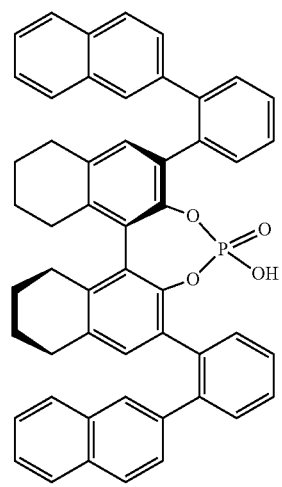
19
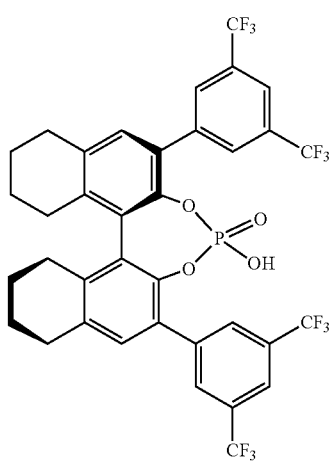
TABLE 1-continued
Compounds of training set
20
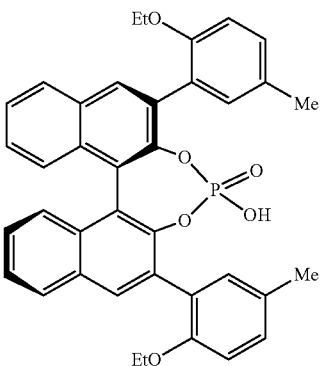
21
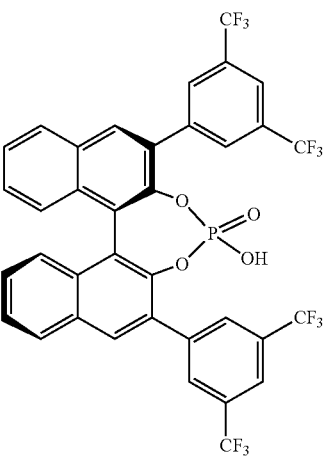
22
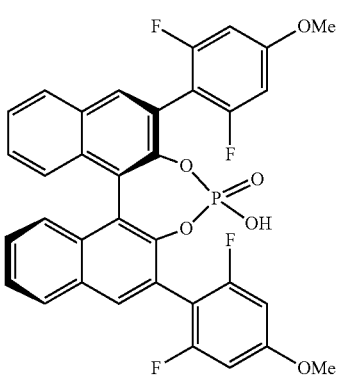

TABLE 1-continued

Compounds of training set

(23) [Structure: BINOL-phosphoric acid with 3,3'-bis(3,5-bis(4-methoxyphenyl)phenyl) substituents]

(24) [Structure: H8-BINOL phosphoric acid with 3,3'-bis(SiPh3) substituents]

The compounds of Formula (I) and Formula (II) may be packaged as a kit, such as a kit to be used for a training set for one of the methods disclosed herein. The kit may include at least one compound of Formula (I) or Formula (II), may include at least two compounds of Formula (I) or Formula (II), or may include at least three compounds of Formula (I) or Formula (II).

The compounds of Formula (I) and Formula (II) may be selected from

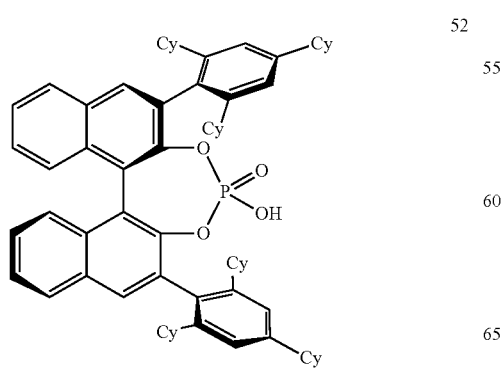

(52, 53, 54, 55)

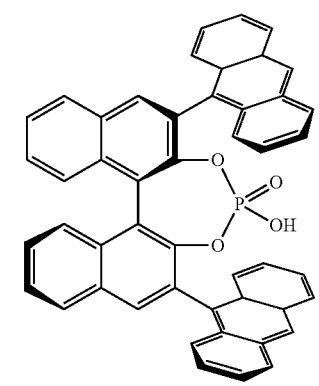

(56)

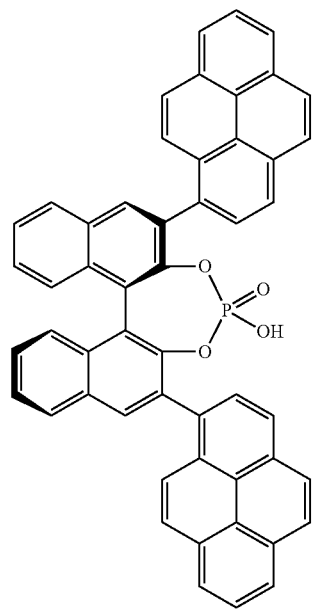
57
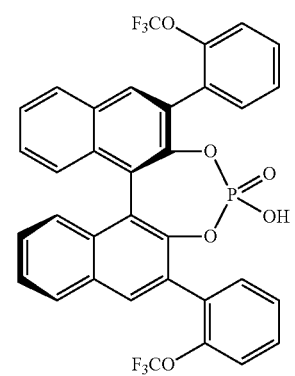
58
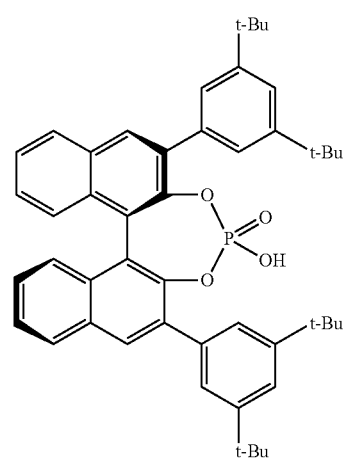
59
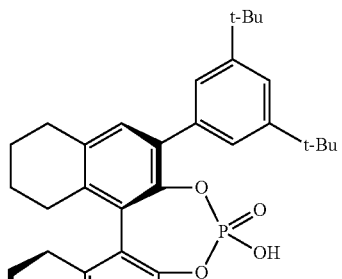
60
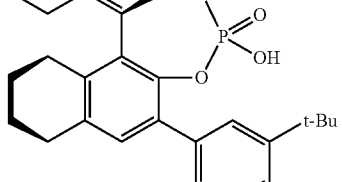
61

62
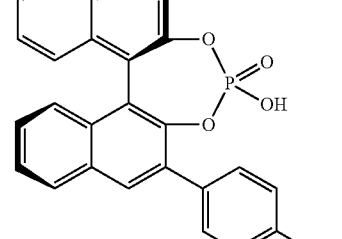
63

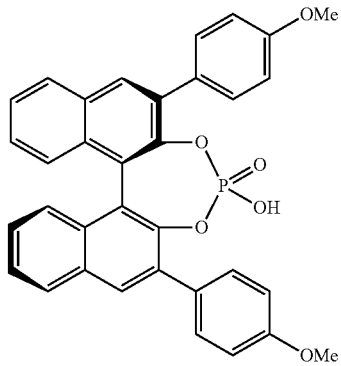

64

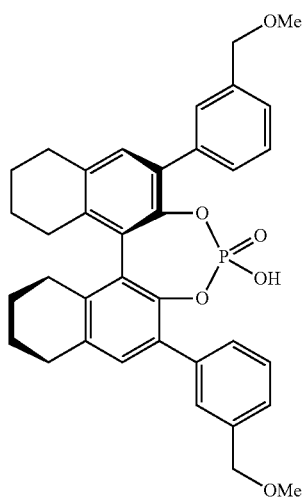

65

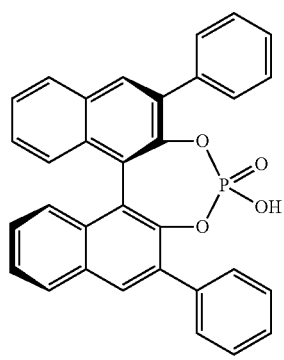

66

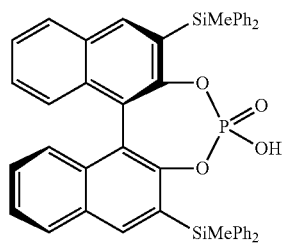

67

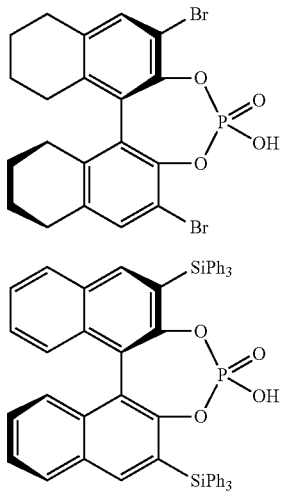

68

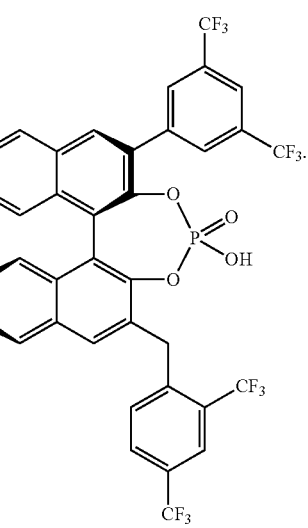

69

70

As described herein, the compounds of the invention comprise multiple variable groups (e.g., X, Y, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "substituted," refers to a group in which one or more hydrogen radicals has been replaced with a specified substituent. Unless otherwise indicated, a substituted group can have a substituent at any substitutable position of the group, and when more than one position in any given structure can be substituted with more than one substituent selected from a specified group, the substituent can be either the same or different at every position. As one of ordinary skill in the art will recognize, substituted groups envisioned by this invention are those that result in the formation of stable or chemically feasible compounds.

As used herein, the term "halo" means F, Cl, Br or I.

As used herein, the terms "CN," "cyano," and "Cy" have the same meaning.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —ORa where Ra is an alkyl group having the specified number of carbon atoms. For example, a "$C_1$-$C_6$ alkoxy" group is a radical of the formula —ORa where Ra is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond.

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers, of the compounds identified by the chemical names and chemical structures provided herein. In addition, single stereoisomers, double bond isomers, conformation isomers, and tautomers as well as mixtures of stereoisomers, double bond isomers, conformation isomers, and tautomers are within the scope of the invention.

Reaction Prediction Beyond the Training Set

Although modeling with data spanning the entire range (e.g., up to 99% ee) of interest can be valuable for predicting the outcome of new substrate combinations, modeling beyond this range can be leveraged to enhance the rate at which catalytic enantioselective reactions are optimized. To demonstrate this potential in our method, we simulated a situation in which highly selective reactions (i.e., combinations of substrates and catalysts) have not been identified. Accordingly, we partitioned all 1075 reactions as follows: All reactions below 80% ee were used as training data (718 reactions), and all reactions above 80% ee were used as test data (357 reactions). (The identities of the training and test datasets can be found in the supplementary materials.) A variety of modeling methods were tested, and although a number of methods, including support vectors, Lasso, LassoLars, ridge regression, elastic net, and random forest (by no means the state of the art in machine learning; see computational methods for a complete explanation), provided acceptable qualitative results, deep feed-forward neural networks accurately reproduced the experimental selectivities (MAD=0.33 kcal/mol) (FIG. 8A). More notably, the general trends in selectivity, on the basis of average catalyst selectivity, were correctly identified. As shown in FIG. 8B, the most selective catalyst, 52, was predicted with the highest accuracy, within 3% ee of the experimental value. Catalysts 53 and 54 were the next two to follow experimentally and computationally (the order is inverted, but they are within experimental error from each other), followed by catalyst 55. The remaining catalysts shown in FIG. 8B were predicted very accurately, likely because the experimental values are closer to the training set cutoff of 80% ee. Despite omitting about half of the experimental free energy range from the training data, we could still make accurate predictions in this region of selectivity space.

Materials and Methods

General Information

All reactions were performed in glassware that had been flame-dried under vacuum or oven-dried (140° C.) overnight. All reactions were conducted under an atmosphere of dry nitrogen or argon by using a drying tube equipped with phosphorus pentoxide and calcium sulfate. All reaction temperatures are noted as the oil bath temperature, the internal temperature as monitored by a Teflon-coated thermocouple, or the room temperature (~23° C.). Solvents used for extraction were reagent grade, and chromatography solvents were technical grade. Column chromatography was performed using ultrapure silica gel (40 to 69 mm) from Silicycle with a column mixed as a slurry, packed, and eluted at 6 to 8 psi. Retention factors, Rf, are reported for analytical thin-layer chromatography performed on Merck silica gel plates treated with F-254 indicator. Visualizations were accomplished by using ultraviolet (UV) light, aqueous KMnO4, ceric ammonium molybdate solution, or iodine. Reaction solvents tetrahydrofuran [Fischer; high-performance liquid chromatography (HPLC) grade], hexanes (Fischer; HPLC grade), diethyl ether [Fischer; butylated hydroxytoluene-stabilized American Chemical Society (ACS) grade], methylene chloride (Fischer; unstabilized HPLC grade), and N, N'-dimethylformamide (Fischer; HPLC grade) were dried by percolation through two columns packed with neutral alumina under positive pressure of argon. Toluene (Fischer; ACS grade) was dried by percolation through a column packed with neutral alumina and a column packed with Q5 reactant, a supported copper catalyst for scavenging oxygen, under a positive pressure of argon. Amines were distilled fresh before use, and pyridine (Fischer; ACS grade) used as a solvent was distilled and stored over 4-A molecular sieves before use.

Instrumentation $^1$H, $^{13}$C, $^{19}$F, and $^{31}$P nuclear magnetic resonance (NMR) spectra were recorded on a Varian Unity Inova 400 spectrometer ($^{19}$F and $^{31}$P), a Varian Unity 500 spectrometer ($^1$H and $^{13}$C), a Bruker Advance 500 spectrometer ($^1$H, $^{13}$C, $^{19}$F, $^{29}$Si, and $^{31}$P), a Varian VXR 500 spectrometer ($^1$H), or a Unity 500 NB spectrometer ($^1$H). Spectra are referenced to chloroform [d=7.26 parts per million (ppm), $^1$H; 77.0 ppm, $^{13}$C], residual benzene (d=7.15 ppm, $^1$H; 128.62 ppm, $^{13}$C), or dimethyl sulfoxide (d=2.50 ppm, $^1$H; 39.52 ppm, $_{13}$C). Chemical shifts are reported in parts per million, and multiplicities are indicated by s (singlet), d (doublet), t (triplet), q (quartet), p (pentet), h (hextet), m (multiplet), and br (broad). Coupling constants J are reported in hertz, integration is provided, and assignments are indicated. Mass spectrometry was performed by the University of Illinois Mass Spectrometry Laboratory. Mass spectrometric data were collected on a Waters Q-TOF Ultima (ESI) spectrometer, a Waters Synapt G2-Si spectrometer (ESI), a Waters Quattro Ultima spectrometer (ESI), or a Waters 70-VSE spectrometer (EI). Low-resolution spectral data are reported as (mass, intensity), and high-resolution data are reported as calculated and measured masses to 10-4 mass accuracy. Infrared spectra were recorded on a Perkin-Elmer UATR-2 FT-IR spectrophotometer. Peaks are reported as reciprocal centimeters, with relative intensities indicated as s (strong, 67 to 100%), m (medium, 34 to 66%), or w (weak, 0 to 33%). Analytical chiral stationary-phase super-critical fluid chromatography was performed on an Agilent 1100 high-performance liquid chromatograph equipped with an Aurora Systems A-5 supercritical $CO_2$ adapter for supercritical fluid chromatography and a UV detector (220 or 254 nm) by using Daicel Chiralcel OD, OJ, and OB or Chiralpak AD and AS columns.

Descriptor Calculations

To describe the steric environment around a given structure, the strategy taken in these laboratories used grid point-type descriptors. However, instead of using van der Waals potential energy values at grid point locations, this descriptor incorporates steric data from a population of conformers of a given compound. The new calculation process is as follows (see section S3 in the supplementary materials), demonstrated by using a BINOL-based phosphoric acid derivative scaffold. (i) For each base compound within an in silico library, a set of conformers within a given energy window (generally 7 to 10 kcal/mol) is generated. (ii) The full set of compounds and associated conformer libraries are aligned to a common core. (iii) A spherical grid of points is then calculated to encompass the entire set of aligned compounds to a depth of 3 Å. (iv) For each conformer, an indicator field is created by determining which grid point locations are within the van der Waals radius of an atom. Locations determined to be within atoms are given a value of 1; those outside are given a value of 0. (v) The ASO of a given catalyst is calculated as the average of the indicator fields for each conformer of that catalyst. This gives a descriptor value of 0≤ASO≤1 at each grid point. When compiled, the descriptor set acts both to describe the shape of the molecule and to weight that shape with how often the molecule occupies different regions of space. The process of calculating the ASO descriptor set is completed for every catalyst in the in silico library (FIG. S4). The same protocol is used to calculate starting material and product descriptors, and concatenation of the descriptors generates the reaction profiles.

The ASO descriptor can be used to visually compare the shapes and sizes of different compounds by plotting the descriptor values as bar charts. Shown in FIG. S5 is a comparison between 3,3'-diphenyl-substituted BINOL-phosphoramide 1_iv and the much larger catalyst 182_iv. As can be seen in the plots, the ASO descriptor values for 182_iv are much more varied, and nonzero ASO values can be seen for much more of the available descriptor range, indicating that this catalyst is much larger and covers more of the space available to the catalyst. This type of comparative analysis shows that the descriptors are capturing the shape of the molecule as well as distinguishing between catalysts of different sizes and constitutions (FIG. 2D).

To capture the electrostatic effects of substituents on the compounds of interest, a separate set of descriptors was considered. Electrostatic MIF descriptors have underperformed in the applications tested in these laboratories, and these 3D MIF-based electrostatic descriptors do not incorporate conformation-dependent information. Additionally, most descriptor calculation methods based on electrostatic field determinations fail to distinguish between through-bond and through-space effects. Although others have used 1D and 2D descriptors, such as Hammett parameters, to describe such changes, the substituent libraries used in these laboratories are too diverse to have these parameters derived for them. To that end, a new electrostatic parameter that correlates well with known 1D parameters has been devised.

This electrostatic parameter was calculated for individual substituents represented in the catalyst in silico library and is used to estimate the electronic effects of the substituents on the core molecule. The calculation was performed by attaching the substituent group to a tetramethylammonium cation, generating a benzyltrimethylammonium cation if the substituent is aryl, a homobenzyl-trimethylammonium cation if the substituent is benzyl, or an tetraalkylammonium ion if the substituent is alkyl. An electrostatic potential MIF is then calculated by using NWChem at the B3LYP/6-31G* level of theory, specifying a specific probe and range for the grid to give a single layer of grid points 0.025 Å apart. An example of the grid and calculated electrostatic potential for a 4-nitrobenzyltrimethylammonium cation is shown in FIG. S6. After the energies are calculated, the maximum and minimum energies calculated in the single-layer MIF are saved, giving the substituent electrostatic potential energy minimum (ESPMIN) and substituent electrostatic potential energy maximum (ESPMAX) descriptors. The ESPMAX descriptors correlated well with known Hammett parameters, suggesting that the descriptor was describing the electron-donating or -withdrawing nature of the given substituents (FIG. S7). These electronic parameters were also used for the nucleophiles and electrophiles, wherein the corresponding thioether and aryl moieties, respectively, were appended to the ammonium ion. Further, natural bond orbital (NBO) charges for sulfur and sulfur molecular orbital energies from the NBO calculation were used as electronic descriptors for the thiols.

Model Generation

All machine learning methods except deep neural networks were implemented with Python2 scripts by using scikit-learn, a Python machine learning package. A collection of models was generated by using a variety of feature selection methods with experimental MG as the observable. Before modeling, all data descriptors were scaled by removing the mean and scaling to unit variance. A variety of feature selection or transform methods were surveyed (variance threshold method, mutual information, f-regression, and PCA). For the feature selection methods, 100, 500, 1000, and 2000 features were selected. Additionally, by using a percentile cutoff, the 10th, 25th, and 50th percentiles were selected. By using PCA, models were generated with 10, 20, 30, 50, and 100 principal components (64, 78, 84, 89, and 94% of variance, respectively). These methods were all performed separately on the scaled descriptor data (PCA and a feature selection method were never used together). The enantioselectivity data (expressed as the free energy differential between the diastereomeric transition structures leading to the different enantiomers) were also highly skewed, so these data were transformed with the Box-Cox transformation by using SciPy before model generation. Each set of preprocessed data (meaning one of the selection methods or PCA on the features with the transformed or untransformed Y-data) were then used to make a collection of models. Models generated include partial least squares PLSn (where n=2, 4, 6, 8, 10, 14, 18 and in which n<number of principal components), random forest, LassoCV, LassoLarsCV, ElasticNetCV, RidgeCV, kernel RidgeCV [kernel=radial basis function (rbf)] [k (number of folds in k-fold cross-validation)=5], k-nearest neighbors (kNN), and support vector machines with linear, rbf, and polynomial kernels (second-, third-, and fourth-order polynomials). Grid optimization of hyperparameters was performed (example code can be found on the GitLab site). This hyperparameter optimization was performed with a fivefold train-validation split (e.g., in the case of the UTS data, the 384 "training reactions" were split). Models were evaluated via q2 (cross-validated R2), R2, and MAD from an external test set of reactions (not used in hyperparameter optimization). Three examples are given in FIG. S8. Each model used the transformed (Box-Cox) selectivity data and the top 25% of features selected by mutual information regression. SVR_poly2 (support vector regressor with second-order polynomial kernel) was the only member of the best models to accurately predict the most selective test reactions.

Whereas SVR_poly2 qualitatively selected the best reactions when attempting to predict beyond the range of selectivities in the training data, the models quantitatively underpredicted these reactions. By using Keras with the Theano backend, a Python package that can facilitate deep learning, we generated a deep feed-forward network. Grid-based hyperparameter optimization was used with linear, relu, elu, and selu activation functions; 0.05, 0.1, and 0.2 dropouts on the layers; 4, 40, 400, and 4000 nodes per layer; and 0 to 6 hidden layers. Further, all optimizers available in Keras were tested. This method of hyperparameter optimization was very time intensive, and it is strongly recommended that practitioners instead use a Bayesian optimization of hyperparameters. Attempts to use this kind of optimization and more modern machine learning methods are currently under way.

Multiple different regression models may provide suitable outputs for determining chemical behaviors of different chemical structures in a library. Regression schemes may work by identifying features in known factors between chemical structures to predict features in other factors. For example, particular features such as ratios, absolute values, or other features in selected descriptors, such as average steric occupancy or electrochemical descriptors, may be suggestive of features in chemical behaviors such as catalytic selectivity. The models identify such correlations. Table 2 show selected regression models that may be used to classify library entries, e.g., according to chemical behavior metrics.

TABLE 2

Selected Example Regression Models

| Model Name | Description |
| --- | --- |
| Support Vector Machines | Supervised learning model that generates high-dimensional plane. The system locates the plane that that may provide the largest (or relatively large compared to other calculated planes) distance between training points. Assisting in emphasizing difference to aid in point regression. In some cases, distance between points may be calculated using a Mean Absolute Difference (MAD) algorithm. |
| K-Nearest Neighbors | Points are classified based on an average (weighted average) of K-nearest neighbors. |
| K-Means Clustering | K-means clustering may partition n observations into k clusters in which each observation belongs to the cluster with the nearest mean, serving as a prototype of the cluster. |
| Logistic Regression | Probabilities for the outcome of a particular trial a modeled using a logistic function. |
| Neural Networks and Deep Neural Networks | A neural network is made up of nodes. Various "stimuli" (e.g., data inputs) activate nodes. Pathways form between nodes that often activate together or in some other correlated fashion. |

TABLE 2-continued

Selected Example Regression Models

| Model Name | Description |
| --- | --- |
| | Deep Neural networks use multiple layers of Neural Networks stacked on top of one another to tease out increasingly subtle regression differences. Regression of points may be achieved by using data observed data points as training. When points have similar features they will excite similar responses in the neural network. |
| Self-organizing maps | A self-organizing map is type of artificial (ANN) that is trained using unsupervised learning to produce a low-dimensional, discretized representation of the input space of the training samples. In some cases, the inputs may be of a higher dimensionality that the output of a self-organizing map. |

Representation of a library, class, or other grouping of chemical structures may be achieved by taking a sample (e.g., a subset) of the grouping that maintains various features of the entire grouping. For example, a sample may be selected in a descriptor space that is setup based on measureable or model-able chemical metrics (e.g., measureable or model-able values quantifying structural properties, electrical properties, chemical behaviors or other features). In some implementations, the sample may use a sampling algorithm, such as a Kennard-Stone algorithm, that may select the sample uniformly over the descriptor space volume. Other sampling algorithms may be used. For example, Table 3 shows selected example sampling algorithms.

TABLE 3

Example Selected Sampling Algorithms

| Model Name | Description |
| --- | --- |
| Kennard-Stone | Kennard-Stone selects a sample from a space of data points. For each selected pair of points to add to the sample, the algorithm selects (a previously unselected) pair that have the furthest distance from one another in the space. In some cases, Kennard-Stone leads to uniformity in distribution and higher sampling ratios for sparse areas of a space compared to populated areas of a space. |
| Random Sampling | Random sampling randomly (or pseudorandomly) selects a sample from a set. Random sampling provides no guarantees of uniformity or distribution of sampling. Repeated analyses with random sampling can avoid introduction of sampling bias into the analysis. For example, repeated overrepresentation/underpresentation of particular subsets overemphasis on spatial uniformity in sampling. Stratified random sampling may divide the set into strata from which random samples are selected. This can increase uniformity guarantees or other representation guarantees. However, the selection of strata may introduce bias and boundary artifacts. |
| Periodic Sampling | Repeated selection rules that select some subgroup irrespective of individual data point features. Provides uniformity in selection, but may be non-uniform in the dataset space due to clustering of data points according the descriptor features. |

FIG. D1 shows an example specific execution environment 100D for the calculations (e.g., descriptor calculations, execution of models representative of the chemical structure library, dimensionality reductions prior to sample selections, or other calculations) and sampling described herein. The execution environment 100D may include system logic 114D to support the calculations and sampling described herein. The system logic may include processors 116D, memory 120D, and/or other circuitry.

The memory 120D may include model parameters 152D, optimization routines 154D, and operational rules 156D. The memory 120D may further include applications and structures 166D, for example, coded objects, machine instructions, templates, or other structures to support calculations, sampling, or other tasks described herein. The applications and structures may implement logical structures 198D or hardware/software stacks 199D to support calculations, sampling, or other tasks described herein.

The execution environment 100D may also include communication interfaces 112D, which may support wireless, e.g. Bluetooth, Wi-Fi, WLAN, cellular (4G, LTE/A), and/or wired, Ethernet, Gigabit Ethernet, optical networking protocols. The communication interfaces 112D may also include serial interfaces, such as universal serial bus (USB), serial ATA, IEEE 1394, lighting port, $I^2C$, slimBus, or other serial interfaces. The communication interfaces 112D may be used to support and/or implement remote operation of the interfaces (e.g., 118D) used to support calculations, sampling, or other tasks described herein. The execution environment 100D may include power functions 134D and various input interfaces 128D. The execution environment may also include a user interface 118D that may include human-to-machine interface devices and/or graphical user interfaces (GUI). The user interface 118D may be used to support and/or implement local operation. In various implementations, the system logic 114D may be distributed over one or more physical servers, be implemented as one or more virtual machines, be implemented in container environments such as Cloud Foundry or Docker, and/or be implemented in Serverless (functions as-a-Service) environments.

General Information

All reactions were performed in glassware that had been flame-dried under vacuum or oven-dried (140° C.) overnight. All reactions were conducted under an atmosphere of dry nitrogen or argon using a drying tube equipped with phosphorus pentoxide and calcium sulfate. All reaction temperatures are noted as the oil bath temperature, the internal temperature as monitored by a Teflon-coated thermocouple), or as the room temperature (approximately 23° C.). Solvents used for extraction were reagent grade, and chromatography solvents were technical grade. Column chromatography was performed using Ultrapure Silica gel from Silicycle (40-69 µm) with a column mixed as a slurry, packed and rinsed at 6-8 psi. Column chromatography was conducted using 230-400 mesh silica gel purchased from EM Science. Retention factors, $R_f$, are reported for analytical thin layer chromatography performed on Merck silica gel plates treated with F-254 indicator. Visualizations were accomplished by UV light, aqueous $KMnO_4$, ceric ammonium molybdate (CAM) solution, or iodine powder. Reaction solvents tetrahydrofuran (Fischer, HPLC grade), hexanes (Fischer, HPLC grade), diethyl ether (Fischer, BHT stabilized ACS grade), methylene chloride (Fischer, unstabilized HPLC grade), and DMF (Fischer, HPLC grade) were dried by percolation through two columns packed with neutral alumina under positive pressure of argon. Reaction solvent toluene (Fischer, ACS grade) was dried by percolation through a column packed with neutral alumina and a column packed with Q5 reactant, a supported copper catalyst for scavenging oxygen, under a positive pressure of argon. Amines were distilled fresh prior to use, and pyridine (Fischer, ACS grade) used as a solvent was distilled and stored over 4 Å MS prior to use.

Commercial Chemical Sources

Benzamide, 98%; sodium 4-toluenesulfinate, 97%; anthracene-9-carbaldehyde, 98%; cesium carbonate, 99%; potassium carbonate, 99%; magnesium turnings, 98%; and 2,4-dichlorobenzaldehyde, 98%, were purchased from Alfa-Aesar. Ethanethiol, 97%; thiophenol, 97; triethylborane, 1.0 M in hexanes; 1,3-dimethoxybenzene, 98%; 1-naphthaldehyde, 95%; potassium tert-butoxide, 98%; tert-butyllithium, 1.7 M in pentane; n-butyllithium, 2.5 M in hexane; 4-methylmorpholine N-oxide, 97%; boron tribromide, 99%; potassium phosphate tribasic, 98%; bis(triphenylphosphine)nickel(II) dichloride, 98%; imidazole, 99%; and 4-(pentafluorosulfanyl)aniline, 95%, were purchased from Sigma-Aldrich. Cyclohexanethiol, 98%, and 2-methylthiophenol, 97%, were purchased from TCI. 4-methoxybenzenethiol, 97% was purchased from Matrix Scientific. Amberlyst-15 hydrogen form dry; 2-bromo-1,3,5-triisopropylbenzene, 97%; (2-(trifluoromethyl)phenyl)boronic acid, 97%; p-Anisaldehyde, 99%; 4-(trifluoromethyl)benzaldehyde, 98%; 3,5-bis(trifluoromethyl)benzaldehyde, 95%; tetrakis(triphenylphosphine)palladium(0), 98%; 2-naphethaleneboronic acid, 98%; 1-bromo-2-iodobenzene, 99%; and triethylsilane, 99%, were purchased from Oakwood Chemical. 4-Cyclohexylphenylboronic acid, 98%; 2-ethoxy-5-methylphenyl boronic acid, 98%; 1-bromo-2,4,6-trichlorobenzene, 97%; 4-bromo-3,5-difluoroanisole, 98%; SPhos, 98%; and 2-bromo-1,3-difluoro-5-methoxybenzene, 98%, were purchased from Combi-Blocks. Boron trifluoride etherate, ca. 48% $BF_3$, and 1-octanethiol, 97%, purchased from Acros. Sodium carbonate, 95%, was purchased from Fisher. Palladium(II) acetate, 98%, was purchased from Strem.

Instrumentation $^1H$, $^{13}C$, $^{19}F$, and $^{31}P$ NMR spectra were recorded on a Varian Unity Inova 400 spectrometer ($^{19}F$ and $^{31}P$), a Varian Unity 500 spectrometer ($^1H$ and $^{13}C$), a Bruker Avance 500 spectrometer ($^1H$, $^{13}C$, $^{19}F$, $^{29}Si$, and $^{31}P$), a Varian VXR 500 spectrometer ($^1H$), or a Unity 500 NB spectrometer ($^1H$). Spectra are referenced to chloroform ($\delta$=7.26 ppm, $^1H$; 77.0 ppm, $^{13}C$), residual benzene ($\delta$=7.15 ppm, $^1H$; 128.62 ppm, $^{13}C$), or DMSO ($\delta$=2.50 ppm $^1H$, 39.52 ppm $^{13}C$). Chemical shifts are reported in ppm, and multiplicities are indicated by s (singlet), d (doublet), t (triplet), q (quartet), p (pentet), h (hextet), m (multiplet) and br (broad). Coupling constants, J, are reported in Hertz, and integration is provided and assignments are indicated. Mass spectrometry was performed by the University of Illinois Mass Spectrometry Laboratory. Mass spectrometric data was collected on a Waters Q-TOF Ultima (ESI) spectrometer, a Waters Synapt G2-Si spectrometer (ESI), a Waters Quattro Ultima spectrometer (ESI), or a Waters 70-VSE spectrometer (EI). Low resolution spectral data are reported as (mass, intensity), and high resolution data are reported as calculated and measured masses to 10-4 mass accuracy. Infrared spectra were recorded on a Perkin-Elmer UATR-2 FT-IR spectrophotometer. Peaks are reported in cm-1 with relative intensities indicated: s (strong, 67-100%); m (medium, 34-66%), w (weak, 0-33%).

Preparation of Known Compounds

The following compounds were prepared according to a literature procedure. The 1H NMR spectra were identical to previously published spectra: (S)-3,3'-dibromo-2,2'-dimethoxy-1,1'-binaphthalene, (S)-(2,2'-dimethoxy-[1,1'-binaphthalene]-3,3'-diyl)diboronic acid(51), (S)-2,2'-(2,2'-dimethoxy-[1,1'-binaphthalene]-3,3'-diyl)bis(4,4,5,5- tetramethyl-1,3,2-dioxaborolane), (R)-3,3'-dibromo-2,2'-bis (methoxymethoxy)-1,1'-binaphthalene, (R)-3,3'-dibromo-5, 5',6,6',7,7',8,8'-octahydro-[1,1'-binaphthalene]-2,2'-diol, (R)-3,3'-dibromo-2,2'-dimethoxy-5,5',6,6',7,7',8,8'-octahydro-1,1'-binaphthalene, (R)-3,3'-dibromo-2,2'-bis (methoxymethoxy)-5,5',6,6',7,7',8,8'-octahydro-1,1'-binaphthalene, (R)-2,2'-(2,2'-Bis(methoxymethoxy)-5,5',6,6',7,7',8, 8'-octahydro-1,1'-binaphthyl-3,3'-diyl)bis(4,4,5,5-tetramethyl-1,3,2-dioxaborolane), 5'-bromo-4,4''-dimethoxy-1,1':3',1''-terphenyl, 5'-bromo-2,2'',4,4'',6,6''-hexamethyl-1,1':3',1''-terphenyl, Tri-tert-butylphosphine palladium precatalyst, 4-bromophenyl)pentafluoro-A6-sulfane, (R)-3,3'-dibromo-[1,1'-binaphthalene]-2,2'-diol, 9-bromo-10-(naphthalen-2-yl)anthracene, (R)-3,3'-dimesityl-[1,1'-binaphthalene]-2,2'-diol, Tris(4-(tert-butyl)phenyl) chlorosilane, (R)-3,3'-bis(triphenylsilyl)-5,5',6,6',7,7',8,8'-octahydro-[1,1'-binaphthalene]-2,2'-diol, (R)-3,3'-bis(3,5-di-tert-butylphenyl)-[1,1'-binaphthalene]-2,2'-diol, (R)-3,3'-bis(4-methoxyphenyl)-[1,1'-binaphthalene]-2,2'-diol, (R)-3, 3'-bis(2,4,6-triisopropylphenyl)-[1,1'-binaphthalene]-2,2'-diol, (R)-3,3'-di(pyren-1-yl)-[1,1'-binaphthalene]-2,2'-diol, (R)-3,3'-bis(3,3'',5,5''-tetrakis(trifluoromethyl)-[1,1':3',1''-terphenyl]-5'-yl)-[1,1'-binaphthalene]-2,2'-diol, 5'-bromo-4, 4''-dimethoxy-1,1':3',1''-terphenyl, (R)-3,3'-di-p-tolyl-[1,1'-binaphthalene]-2,2'-diol, (R)-3,3'-bis(3,5-bis (trifluoromethyl)phenyl)-5,5',6,6',7,7',8,8'-octahydro-[1,1'-binaphthalene]-2,2'-ciiol, (3-(naphthalen-2-yl)phenyl) boronic acid, T1, T2, T3, T4, T5, T6, T7, T8, T9, T10, T11, T12, T13, T14, T15, T16, T17, T18, T19, and T20.

Preparation of 2-(2-Bromophenyl)naphthalene (S1)

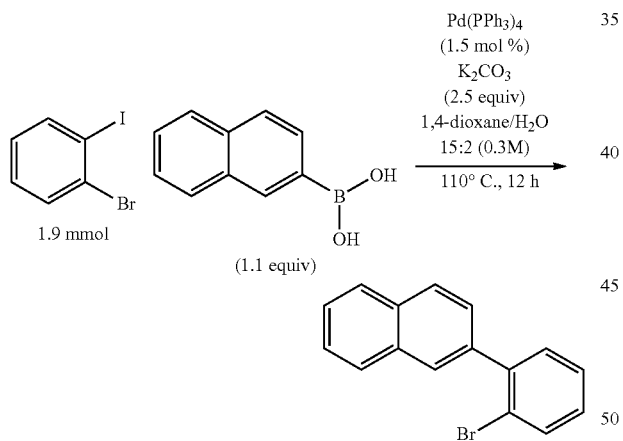

An oven-dried, 25-mL, round-bottomed flask equipped with a reflux condenser, gas adaptor, and septum was charged with potassium carbonate (0.611 g, 4.42 mmol, 2.5 equiv), napthalen-2-ylboronic acid (0.334 g, 1.94 mmol, 1.1 equiv), 1-bromo-2-iodobenzene (227 µL, 1.77 mmol), and tetrakis(triphenylphosphine)palladium(0) (30.6 mg, 26.5 µmol, 0.015 equiv). The vessel was evacuated and refilled with nitrogen 5 times. A mixture of 1,4-dioxane/water, 4:1 (5 mL, sparged 2 h with nitrogen) was added via syringe. The reaction was then heated at reflux in an oil bath at 110° C. for 12 h. Full conversion was assessed by TLC ($R_f$=0.47 (hexanes) [UV]). The reaction was cooled to room temperature and diluted with diethyl ether (50 mL) and water (20 mL); the phases were separated and the aqueous layer was extracted with diethyl ether (3×30 mL). The combined organic layers were washed with sat. aq. ammonium chloride (30 mL), brine (30 mL), dried over sodium sulfate (5 g), and concentrated (30° C., 15 mm Hg). The product was purified by chromatography (silica gel, 89 g, 3 cm×18 cm, dry loaded on Celite, 25 mL fractions, hexanes isocratic elution) to afford 483 mg (96%) of the title compound as a white solid. The proton NMR matched literature reported values.

Preparation of 2,4-Bis(trifluoromethyl)benzaldehyde (S2)

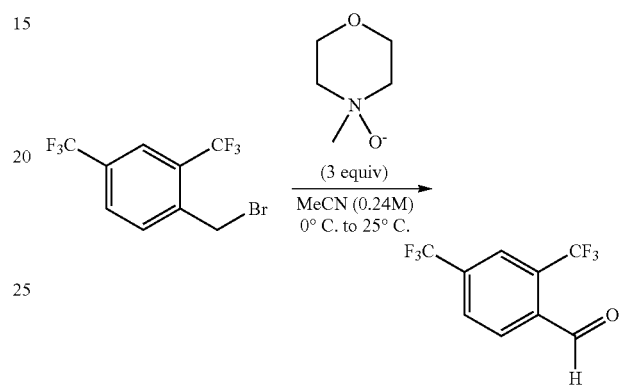

An oven-dried, 50-mL, round-bottomed flask equipped with a 2.5-cm×1.5-cm stir bar was charged with N-methylmorpholine N-oxide (4.58 g, 39.1 mmol, 3 equiv) and acetonitrile (27 mL, 0.24 M), the reaction was placed in an ice bath and stirred for 0.5 h. Next, 2,4-bis(trifluoromethyl) benzyl bromide (2.44 mL, 13.0 mmol, 1 equiv) was added dropwise by syringe over 8 min. Once the addition was complete, the reaction was allowed to warm to room temperature and stirred for 8 h. The reaction mixture was filtered through a 6 cm×5 cm plug of silica gel and the silica plug was rinsed with pentane (500 mL), and carefully concentrated (24° C., 300 mm Hg, the product is volatile). The crude oil was purified by Kugelrohr distillation; an impurity distilled at (80° C., 150 mm Hg) and the desired product distilled at (120° C., 150 mm Hg) to afford 2.3 g (73%) of the title compound as a colorless oil. The proton NMR matched the literature reported values.

Preparation of the Universal Training Set

Synthesis of 1,1'-Binaphthyl-2,2'-diols

Preparation of (R)-3,3'-Diethyl-5,5',6,6',7,7',8,8'-octahydro-[1,1'-binaphthalene]-2,2'-diol (S3)

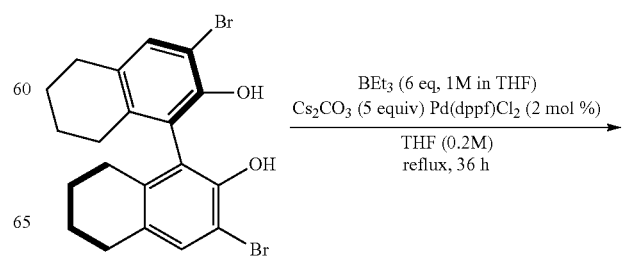

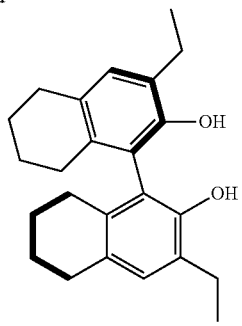

An oven-dried, 100-mL, round-bottomed flask equipped with a 3.0-cm×0.5-cm rod-shaped stir bar, reflux condenser and gas adaptor was charged with (R)-3,3'-dibromo-[1,1'-binaphthalene]-2,2'-diol (0.88 g, 2.0 mmol), cesium carbonate (3.9 g, 1.2 mmol, 0.6 equiv), Pd(dppf)Cl$_2$ (14 mg, 0.20 mmol, 0.1 equiv) and THF (20 mL, 0.1 M) was added via syringe. Triethylborane (1 M, 12 mL, 6 equiv) was added slowly over 1 min by syringe. The reaction was heated at reflux in an 80° C. oil bath for 36 h. Conversion was assessed by TLC (R$_f$=0.60 (hexanes/EtOAc, 10:1) [UV]). The reaction mixture was cooled to room temperature, poured into sat. aq. ammonium chloride (100 mL) and transferred to a 250-mL, separatory funnel. The phases were separated and the aqueous layer was extracted with dichloromethane (3×100 mL). Next the combined organic layers were washed with brine (100 mL), dried over sodium sulfate (10 g), filtered, rinsed with dichloromethane (30 mL) and concentrated (30° C., 75 mm Hg). The product was purified by chromatography (silica gel, 1.5 cm×20 cm, dry load on Celite, 15 mL fractions, hexanes/EtOAc gradient elution: 20:1 (1 L) to 10:1 (1 L)) to afford 0.36 g (52%) of the title compound as a white solid.

Data for S3: $^1$H NMR: (500 MHz, CDCl$_3$) 6.95 (s, 2H), 4.60 (s, 2H), 2.73 (t, J=6.2 Hz, 4H), 2.63 (q, J=7.5 Hz, 4H), 2.30-2.17 (m, 2H), 2.17-2.06 (m, 2H), 1.79-1.59 (m, 8H), 1.23 (t, J=7.5 Hz, 6H). $^{13}$C NMR: (126 MHz, CDCl$_3$) 149.19, 134.16, 130.40, 129.54, 127.92, 118.61, 29.26, 26.92, 23.16, 23.14, 23.04, 14.13. HRMS: (ESI$^+$, TOF) calcd for C$_{24}$H$_{31}$O$_2$ (M$^{+1}$) 351.2324, found: 351.2334 TLC: R$_f$=0.60 (hexanes/EtOAc, 10:1) [UV]

Preparation of (R)-3,3'-Bis(2,4,6-trichlorophenyl)-5,5',6,6',7,7',8,8'-octahydro-[1,1'-binaphthalene]-2,2'-diol (S4)

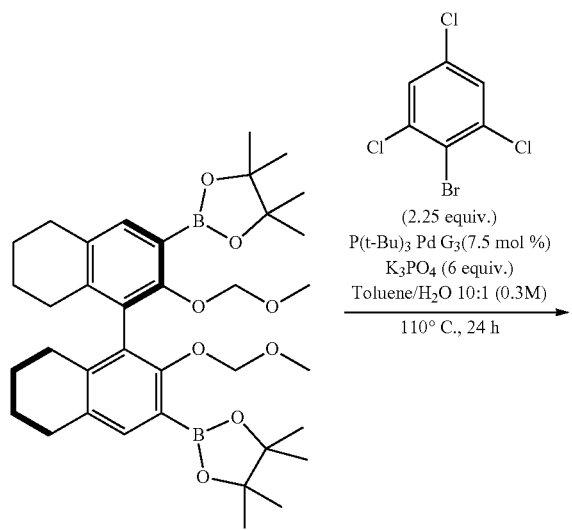

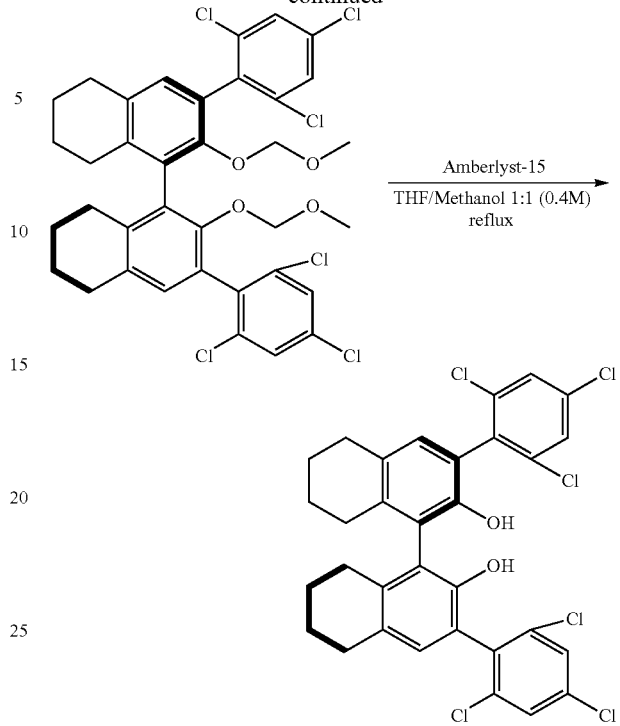

A 5-mL, round-bottomed flask equipped with a 1.5-cm×1.0-cm football-shaped stir bar, reflux condenser, and a gas adaptor was charged with potassium phosphate (0.800 g, 3.78 mmol, 6 equiv), 2-bromo-1,3,5-trichlorobenzene (0.369 g, 1.42 mmol, 2.25 equiv), (R)-2,2'-(2,2'-bis(methoxymethoxy)-5,5',6,6',7,7',8,8'-octahydro-[1,1'-binaphthalene]-3,3'-diyl)bis(4,4,5,5-tetramethyl-1,3,2-dioxaborolane) (0.400 g, 0.630 mmol), and Pd-P(t-Bu)$_3$-G3 (25 mg, 44 μmol, 0.07 equiv). The vessel was evacuated and the atmosphere was replaced with argon 5 times. Toluene (2.5 mL, sparged for 1 h with argon) and water (0.25 mL, sparged 1 h with argon) were added via syringe and the reaction was placed in a 110° C. oil bath for 24 h. The vessel was cooled to room temperature, diluted with water (15 mL) and EtOAc (15 mL); the phases were separated, and the aqueous layer was extracted with EtOAc (3×30 mL). Next the organic layers were combined, dried over sodium sulfate (5 g), filtered, rinsed with EtOAc (30 mL), and concentrated (30° C., 15 mm Hg) to afford the crude protected intermediate as a yellow solid. The product was purified by chromatography (silica gel, 3 cm×12 cm, dry load on Celite, 25 mL fractions, hexanes/dichloromethane gradient elution: 80:20 (250 mL) to 75:25 (500 mL)) to afford 0.265 g of the protected intermediate as a white solid.

A 5-mL, round-bottomed flask equipped with a 1.5-cm×1.0-cm football-shaped stir bar, reflux condenser, and gas adaptor was charged with the protected intermediate (0.265 g, 0.32 mmol), a mixture of 1:1 THF/methanol (0.8 mL), and Amberlyst-15 dry resin (0.200 mg). The reaction mixture was heated at reflux in an 80° C. oil bath for 12 h. Full conversion was assessed by TLC(R$_f$=0.29 (hexanes/dichloromethane, 6:4) [UV]). The reaction was cooled to room temperature, filtered through Celite (5 g), the filter cake washed with dichloromethane (30 mL), and the filtrate concentrated via rotary evaporation (30° C., 15 mm Hg) to afford the crude product. Next the product was purified by chromatography (silica gel, 3 cm×12 cm, dry load on Celite, 25 mL fractions, hexanes/dichloromethane gradient elution: 70:30 (250 mL) to 65:35 (250 mL) to 60:40 (500 mL)) then recrystallized from boiling methanol (3 mL) with dropwise addition of boiling TBME (0.6 mL) until a homogeneous solution. The solution was concentrated to ~1.5 mL and allowed to cool to room temperature over 3 h. The flask was capped and placed in a −20° C. freezer for 24 h. The resulting white crystals were collected by vacuum filtration, rinsing with ice cold methanol (5 mL) to afford 0.161 g (39%) of the title compound as a white solid.

Data for S4: $^1$H NMR: (500 MHz, CDCl$_3$) 7.42 (d, J=2.5 Hz, 4H), 6.94 (s, 2H), 4.68 (s, 2H), 2.83-2.78 (m, 4H), 2.49-2.21 (m, 4H), 1.85-1.71 (m, 8H). $^{13}$C NMR: (126 MHz, CDCl$_3$) 148.47, 138.42, 136.38, 136.31, 134.86, 134.07, 132.12, 130.46, 128.06, 127.94, 120.91, 118.97, 29.24, 27.26, 23.02, 22.95. HRMS: (ESI$^+$, TOF) calcd for C$_{32}$H$_{25}$O$_2$Cl$_6$ (M$^{+1}$) 650.9986, found: 651.0005 TLC: R$_f$=0.29 (hexanes/dichloromethane, 6:4) [UV]

Preparation of (R)-3,3'-Bis(4-(pentafluoro-λ$^6$-sulfaneyl)phenyl)-[1,1'-binaphthalene]-2,2'-diol (S5)

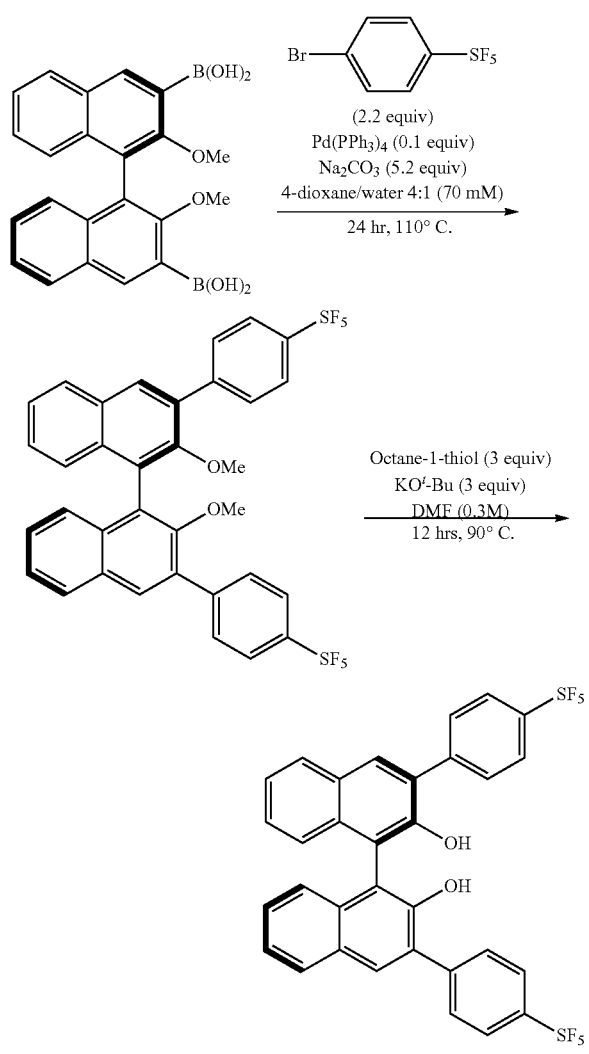

A flame-dried, 50-mL, round-bottomed flask equipped with a 2.0-cm×1.0-cm football-shaped stir bar, under a nitrogen atmosphere, was charged with tetrakis(triphenylphosphine)palladium(0) (450 mg, 0.390 mmol, 0.10 equiv), 4-bromophenyl)pentafluoro-λ$^6$-sulfane (2.43 g, 8.57 mmol, 2.2 equiv), (2,2'-dimethoxy-[1,1'-binaphthalene]-3,3'-diyl)diboronic acid (2.80 g, 3.90 mmol), sodium carbonate (2.15 g, 20.3 mmol, 5.2 equiv), and a mixture of 4:1 1,4-dioxane/water (40 mL, sparged 0.5 h with nitrogen) added by syringe. The reaction was heated at reflux in an 110° C. oil bath for 24 h and full conversion was assessed by TLC (R$_f$=0.10 (hexanes/dichloromethane, 9:1) [UV]). The reaction was cooled to room temperature, filtered, rinsed with dichloromethane (50 mL), and concentrated (30° C., 15 mm Hg). Next the crude residue was diluted with dichloromethane (50 mL), washed with sat. aq. ammonium chloride (50 mL), water (50 mL), brine (50 mL), dried over sodium sulfate (18 g), filtered, rinsed with dichloromethane (50 mL), and concentrated (30° C., 15 mm Hg) to afford the crude intermediate. The product was purified by chromatography (silica gel (100 g), 4 cm×18 cm, dry load on Celite, 25 mL fractions, hexanes/dichloromethane isocratic elution: 9:1 (1 L)) to afford 2.50 g of the protected intermediate.

A flame-dried, 25-mL, round-bottomed flask equipped with a 2.0-cm×1.0-cm football-shaped stir bar, Teflon sleeve, and gas inlet was charged potassium t-butoxide (593 mg, 5.28 mmol, 3 equiv), DMF (3 mL), and octane-1-thiol (387 mg, 2.64 mmol, 3 equiv). The mixture formed a white suspension upon addition of the octane-1-thiol, and was allowed to stir for 10 min. Addition of the protected intermediate (633 mg, 0.881 mmol), in one portion, turned the white suspension to an orange color. The solution was heated to 90° C. in an oil bath for 12 h, over which time the solution turned a deep red color. Full conversion was assessed by TLC (R$_f$=0.12 (hexanes/dichloromethane, 3:1) [UV]). The reaction was cooled to room temperature and aq. 6 M HCl (1.5 mL) was added until the reaction mixture was a pH of 1. Next the reaction was diluted with EtOAc (20 mL), forming a yellow/orange solution, the layers separated, and the aqueous layer was extracted with EtOAc (3×15 mL). The combined organic layers were washed with a 10% w/v aq. lithium chloride (10×25 mL) to remove residual DMF, brine (20 mL), dried over sodium sulfate, filtered, rinsed with dichloromethane (50 mL), and concentrated (30° C., 15 mm Hg) to afford the crude title compound. The product was purified by chromatography (silica gel (101 g), 4 cm×15 cm, dry loaded on Celite, 25 mL fractions, hexanes/dichloromethane isocratic elution: 4:3 1 L)) to afford 314 mg (52%) of the title compound as a white, crystalline solid.

Data for S5: $^1$H NMR: (500 MHz, CDCl$_3$) 8.06 (d, J=1.6 Hz, 2H), 7.96 (dd, J=8.3, 1.5 Hz, 2H), 7.86 (t, J=2.1 Hz, 8H), 7.49-7.41 (m, 2H), 7.38 (ddd, J=8.3, 6.8, 1.5 Hz, 2H), 7.21 (d, J=8.4 Hz, 2H), 5.31 (d, J=1.2 Hz, 2H). $^{13}$C NMR: (126 MHz, CDCl$_3$) 150.25 (s, 2C), 141.21 (s, 2C), 133.33 (s, 2C), 132.48 (s, 2C), 130.12 (s, 4C), 129.67 (s, 2C), 129.03 (s, 2C), 128.87 (s, 2C), 128.50 (s, 2C), 126.18 (m, 2C), 125.17 (s, 2C), 124.27 (s, 2C), 112.06 (s, 2C). HRMS:(EI$^+$, TOF) calcd for C$_{32}$H$_{20}$O$_2$S$_2$F$_{10}$ (M$^{+\cdot}$) 690.07448, found: 690.07340 TLC: R$_f$=0.120 (hexanes/dichloromethane, 3:1) [UV]

Preparation of (R)-3,3'-Bis(10-(naphthalen-2-yl)anthracen-9-yl)-[1,1'-binaphthalene]-2,2'-diol (S6)

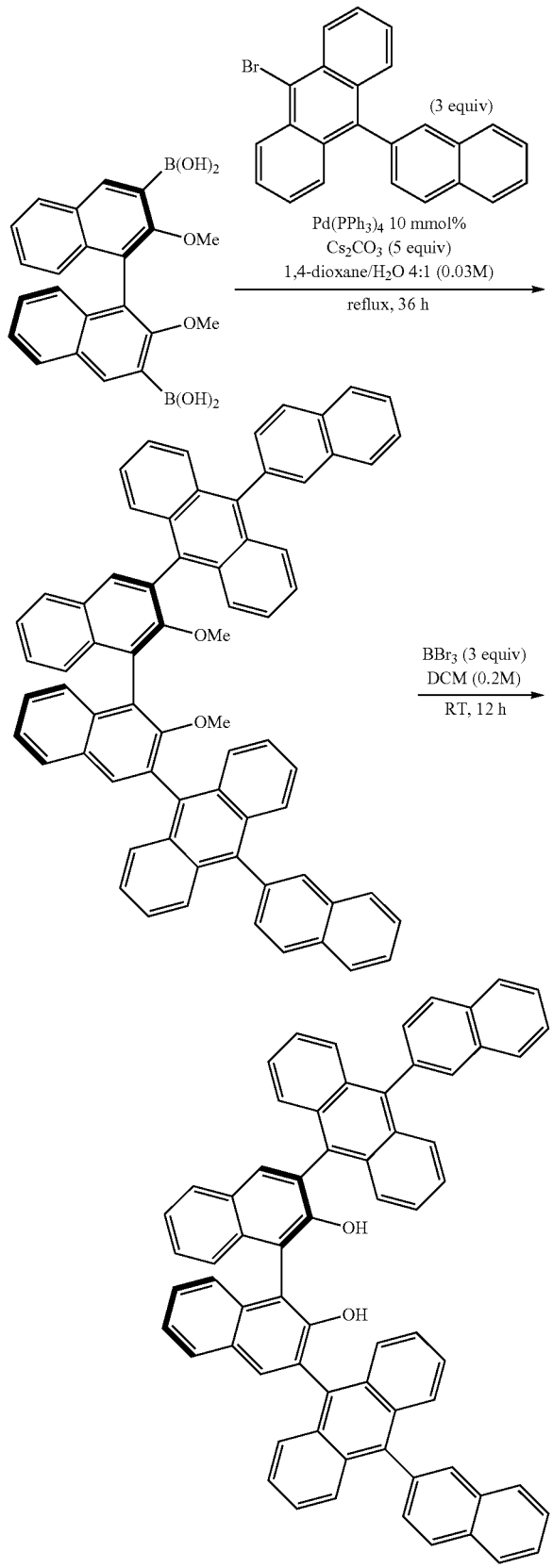

An oven-dried, 100-mL, round-bottomed flask equipped with a 3.0-cm×0.5-cm rod-shaped stir bar, reflux condenser and gas adaptor was charged with (R)-(2,2'-dimethoxy-[1,1'-binaphthalene]-3,3'-diyl)diboronic acid (0.60 g, 1.5 mmol), 9-bromo-10-(naphthalen-2-yl)anthracene (1.7 g, 4.5 mmol, 3 equiv), Tetrakis(triphenylphosphine)palladium(0) (0.17 g, 0.15 mmol, 0.10 equiv), and cesium carbonate (2.4 g, 7.5 mmol, 5 equiv). The system was evacuated and replaced with argon 5 times. A mixture of 4:1 1,4-dioxane/water (20 mL, sparged 1 h with argon) was added via syringe. The reaction was heated at reflux in a 110° C. oil bath for 36 h. The reaction was cooled to room temperature, poured into sat. aq. ammonium chloride (100 mL), and transferred into a 1000-mL, separatory funnel. Next the phases were separated and the aqueous layer was extracted with dichloromethane (3×200 mL). The combined organic layers were washed with brine (200 mL), dried over sodium sulfate (20 g), filtered, rinsed with dichloromethane (30 mL) and concentrated (30° C., 75 mm Hg) to afford 1.2 g of the crude intermediate as a yellow solid. The resulting crude mixture was triturated in dichloromethane (20 mL) with stirring for 12 h. The precipitate was collected by vacuum filtration to afford 0.85 g of (R)-10,10'-(2,2'-dimethoxy-[1,1'-binaphthalene]-3,3'-diyl)bis(9-(naphthalen-2-yl)anthracene) as a light yellow solid.

A flame-dried, 50-mL, Schlenk flask equipped with a 3.0-cm×0.5-cm rod-shaped stir bar was charged with (R)-10,10'-(2,2'-dimethoxy-[1,1'-binaphthalene]-3,3'-diyl)bis(9-(naphthalen-2-yl)anthracene) (0.74 g, 0.80 mmol), the flask was evacuated and backfilled 3 times with argon. Dichloromethane (15 mL) was added to the flask and the solution was cooled in an ice bath for 30 min. A separate flame-dried, 10-mL, Schlenk flask equipped with a stir bar was charged with dichloromethane (3 mL), cooled in a dry ice/isopropyl alcohol bath for 30 min, and boron tribromide (0.60 g, 2.4 mmol, 3 equiv) was added dropwise over 5 min. Once the addition was complete, the solution was allowed to warm to room temperature over 1 h. Next the resulting solution of boron tribromide was added dropwise to the solution of (R)-10,10'-(2,2'-dimethoxy-[1,1'-binaphthalene]-3,3'-diyl)bis(9-(naphthalen-2-yl)anthracene) at 0° C. by syringe. Once the addition was complete, the ice bath was removed and the reaction was allowed to warm to room temperature over 11 h. Conversion was assessed by TLC ($R_f$=0.40 (hexanes/EtOAc, 10:1) [UV]). The reaction was quenched by the addition of water (20 mL) over 1 min, and followed by 0.5 h of stirring. The mixture was poured into water (100 mL), and transferred into a 1000-mL, separatory funnel. The phases were separated and the aqueous layer extracted with dichloromethane (3×200 mL). The combined organic layers were washed with brine (200 mL), dried over sodium sulfate (20 g), filtered, rinsed with $CH_2Cl_2$ (100 mL), and concentrated (30° C., 75 mm Hg). The resulting solid was triturated in dichloromethane (20 mL) with stirring for 12 h. The precipitate was collected by vacuum filtration to afford 0.65 g crude product as a light yellow solid. Next the product was recrystallized by dissolving in boiling chloroform (30 mL), allowed to cool to room temperature for 4 h, and moved to a −20° C. freezer for 12 h. The product was collected by vacuum filtration, followed by drying under vacuum to afford 0.36 g (26% over two steps) of the title compound as a pale yellow solid.

Data for S6: $^1$H NMR: (500 MHz, CDCl$_3$) 8.16-8.08 (m, 4H), 8.01 (m, Hz, 10H), 7.83-7.73 (m, 6H), 7.70-7.59 (m, 8H), 7.59-7.46 (m, 6H), 7.39 (m, 2H), 7.31 (m, 4H), 5.25 (dd, J=4.8, 1.2 Hz, 2H). $^{13}$C NMR: (126 MHz, CDCl$_3$) 151.12, 138.15, 136.37, 136.30, 133.96, 133.36, 133.30, 132.79, 131.01, 130.97, 130.95, 130.54, 130.49, 130.28, 130.23, 130.20, 129.45, 129.39, 128.56, 128.17, 128.11, 128.01, 127.95, 127.91, 127.51, 127.46, 127.36, 126.50, 126.33, 126.31, 126.27, 125.98, 125.94, 125.38, 124.98, 124.38, 113.49, 113.44. HRMS: (ESI+, TOF) calcd for $C_{68}H_{42}O_2Na$ $(M^{+1})$ 913.3083, found: 913.3093. TLC: $R_f$ =0.40 (hexanes/EtOAc, 10:1) [UV].

Preparation of (R)-3,3'-Bis(2,4-bis(trifluoromethyl)benzyl)-[1,1'-binaphthalene]-2,2'-diol (S7)

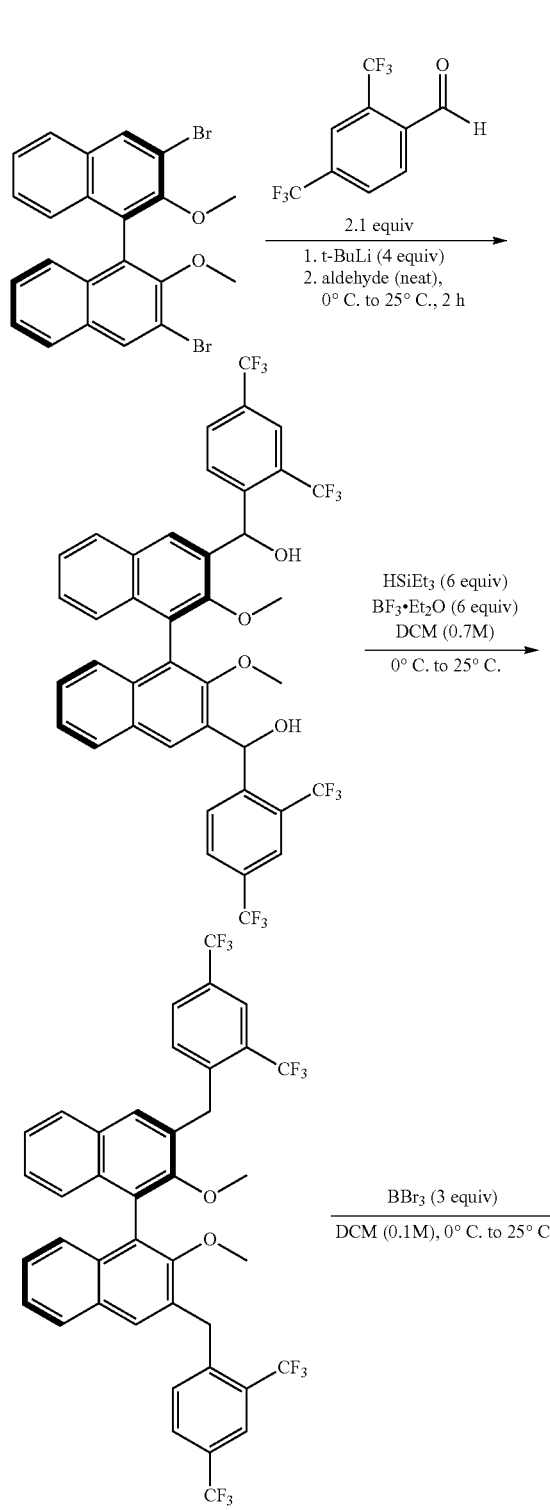

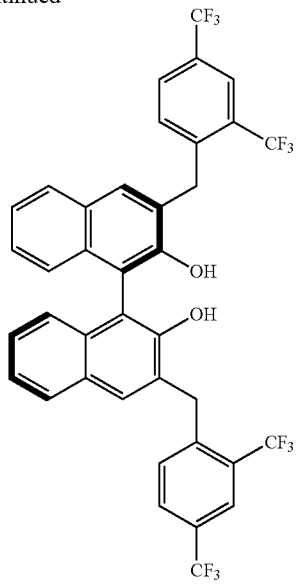

An oven dried, 100-mL, Schlenk flask equipped with a 3.0-cm×0.5-cm rod-shaped stir bar was charged with (R)-3,3'-dibromo-2,2'-dimethoxy-1,1'-binaphthalene (0.94 g, 2.0 mmol) and diethyl ether (18 mL) under argon. The solution was cooled in an ice bath for 30 min and t-butyllithium (1.7 M in hexanes, 4.9 mL, 4 equiv) was added dropwise over 5 min by syringe. The reaction mixture was stirred for 30 min, at 0° C., and 2,4-bis(trifluoromethyl)benzaldehyde (1.1 g, 4.4 mmol, 2.1 equiv) was added dropwise over 5 min by syringe. Upon complete addition, the ice bath was removed and the reaction mixture was allowed to warm to room temperature over 2 h. The reaction mixture was poured into sat. aq. ammonium chloride (50 mL) and stirred for 30 min. Next the resulting mixture was transferred to a 250-mL, separatory funnel and extracted with EtOAc (3×50 mL). The combined organic layers were washed with brine (50 mL), dried over sodium sulfate (10 g), filtered, rinsed with EtOAc (50 mL) and concentrated (30° C., 100 mbar) to afford the crude of (R)-(2,2'-dimethoxy-[1,1'-binaphthalene]-3,3'-diyl)bis((2,4-bis(trifluoromethyl)phenyl)methanol) (1.6 g) as viscous yellow oil (as a mixture of diastereomers).

An oven-dried 100-mL, Schlenk flask with a 2.0-cm×0.5-cm rod-shaped stir bar was charged with the crude (R)-(2,2'-dimethoxy-[1,1'-binaphthalene]-3,3'-diyl)bis((2,4-bis(trifluoromethyl)phenyl)methanol) (1.6 g, 1.8 mmol) as a solution in THF (20 mL). The solution was stirred in an ice bath for 10 min, followed by the addition of triethylsilane (1.4 g, 10 mmol, 1.3 mL, 5.56 equiv) over 5 min by syringe. The solution was stirred in an ice bath for 10 min before boron trifluoride diethyl etherate (1.2 g, 10 mmol, 1.5 mL, 5.56 equiv) was added slowly over 5 min by syringe. Upon complete addition, the ice bath was removed and the reaction was allowed to warm to room temperature over 2 h. The reaction mixture was diluted with sat. aq. sodium bicarbonate (60 mL) and stirred for 10 min and the aqueous layer was extracted with dichloromethane (3×50 mL). The combined organic layers were washed with brine (100 mL), dried over sodium sulfate (10 g), filtered, rinsed by dichloromethane (50 mL), and concentrated by rotary evaporation (30° C., 100 mbar) to afford crude (R)-3,3'-bis(2,4-bis(trifluoromethyl)benzyl)-2,2'-dimethoxy-1,1'-binaphthalene (1.5 g) as a yellow oil.

An oven-dried 100-mL Schlenk flask equipped with a 3.0-cm×0.5-cm rod-shaped stir bar was charged with (R)-3,3'-bis(2,4-bis(trifluoromethyl)benzyl)-2,2'-dimethoxy-1,1'-binaphthalene (1.5 g, 1.7 mmol), and the flask was evacuated and backfilled 3 times with argon. Dichloromethane (30 mL) was added to the flask, and the solution was cooled in an ice bath for 30 min. A separate flame-dried 10-mL, Schlenk flask equipped with a 2.0-cm×0.5-cm rod-shaped stir bar was charged with dichloromethane (5 mL) and cooled in a dry ice-isopropyl alcohol bath for 30 min. To this flask was added boron tribromide (1.3 g, 5.1 mmol, 0.50 mL, 3 equiv), dropwise over 5 min. Upon complete addition, the bath was removed, and the solution was allowed to warm to room temperature over 1 h, and added dropwise to the solution of the substrate by syringe. Once the addition was complete, the ice bath was removed, and the reaction was allowed to warm to room temperature over 11 h. Full conversion was assessed by TLC($R_f$=0.30 (hexanes/dichloromethane, 10:1) [UV]). The reaction mixture was quenched with water (30 mL) over 1 min and stirred for 30 min, transferred to a 250-mL, separatory funnel, and extracted with dichloromethane (3×50 mL). The combined organic layers were washed with brine (50 mL), dried over sodium sulfate (10 g), filtered, and rinsed with dichloromethane (50 mL) and concentrated (30° C., 100 mbar). The crude residue was subjected to flash chromatography (silica gel, 1.5 cm×20 cm, dry loaded on celite, 10-mL fractions, dichloromethane/hexanes gradient elution: 1:10 (500 mL) to 1:5 (1 L) to 1:3 (500 mL)) to afford 1.2 g (80% over three steps) of the title compound as white solid.

Data for S7: $^1$H NMR: (500 MHz, CDCl$_3$) 8.02 (s, 2H), 7.83 (d, J=8.2 Hz, 2H), 7.75 (d, J=8.2 Hz, 2H), 7.64 (s, 2H), 7.47 (d, J=8.1 Hz, 2H), 7.43-7.37 (m, 2H), 7.34 (ddd, J=8.1, 7.0, 1.2 Hz, 2H), 7.16 (d, J=8.3 Hz, 2H), 5.18 (s, 2H), 4.53 (q, J=16.8 Hz, 4H). $^{13}$C NMR: (126 MHz, CDCl$_3$) 151.23, 143.19, 132.44, 131.71, 131.66, 129.75 (q, J=31.5, 2 C), 129.37, 129.12 (q, J=31.5, 2 C), 128.98, 128.58 (m, 2C), 128.21, 127.71, 127.46, 123.81 (q, J=275 Hz, 2C), 123.51 (q, J=275 Hz, 2C), 124.52, 123.83, 123.36 (m, 2C), 111.00, 77.25, 77.00, 76.75, 32.91. $^{19}$F NMR: (471 MHz, CDCl$_3$) −60.50 (s, 6F), −62.70 (s, 6F) HRMS: (EI$^+$, TOF) C$_{38}$H$_{21}$O$_2$F$_{12}$ (M$^{+1}$) 737.1350, found: 737.1357. TLC: $R_f$=0.30 (hexanes/dichloromethane, 10:1) [UV].

Preparation of (R)-3,3'-Bis(tris(4-(tert-butyl)phenyl)silyl)-5,5',6,6',7,7',8,8'-octahydro-[1,1'-binaphthalene]-2,2'-diol (S8)

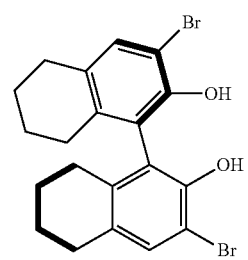

(4-t-BuPh)$_3$SiCl (2.4 equiv)
imidazole (3 equiv)
⟶
DMF (0.2M)
25° C., 12 h

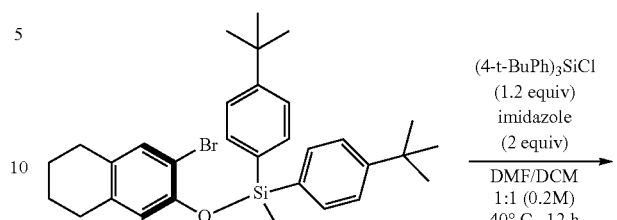

(4-t-BuPh)$_3$SiCl (1.2 equiv)
imidazole (2 equiv)
⟶
DMF/DCM 1:1 (0.2M)
40° C., 12 h

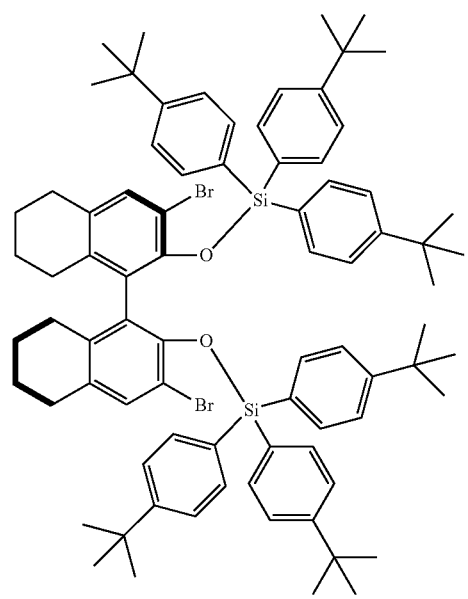

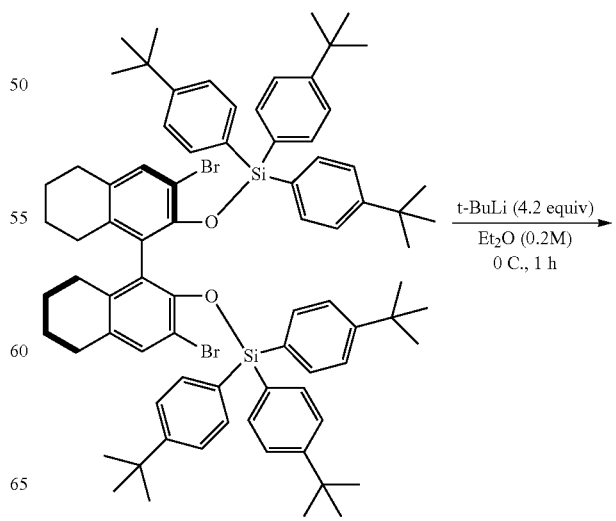

t-BuLi (4.2 equiv)
⟶
Et$_2$O (0.2M)
0 C., 1 h

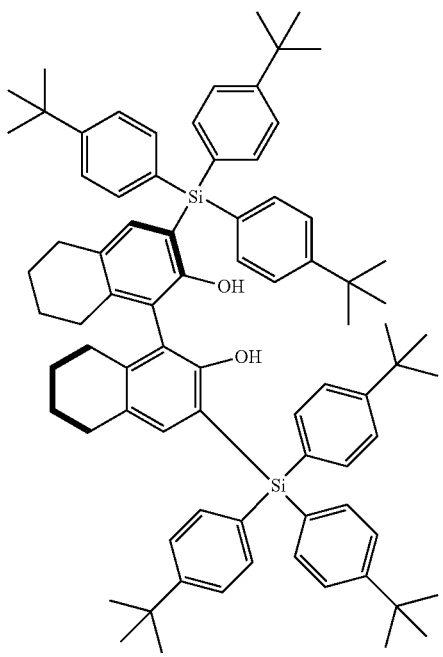

An oven-dried, 25-mL, round-bottomed flask equipped with a 2.0-cm×0.5-cm rod-shaped stir bar, gas adaptor, and septum, was charged with (R)-3,3'-dibromo-5,5',6,6',7,7',8,8'-octahydro-[1,1'-binaphthalene]-2,2'-diol (180 mg, 0.5 mmol), imidazole (80 mg, 1.5 mmol, 3 equiv), tris(4-(tert-butyl)phenyl)chlorosilane (0.46 g, 1.5 mmol, 2.4 equiv) and DMF (5.0 mL) under argon. The reaction was stirred at room temperature for 12 h. The reaction mixture was poured into sat. aq. sodium bicarbonate (50 mL). The mixture was transferred to a 250-mL, separatory funnel, the phases separated and the aqueous phase was extracted with dichloromethane (3×50 mL). The combined organic layers were washed with brine (50 mL), dried over sodium sulfate (10 g), filtered, rinsed with dichloromethane (25 mL) and concentrated via rotary evaporation (30° C., 75 mm Hg) to afford crude mono-protected product. The product was purified by chromatography (silica gel, 1.5 cm×20 cm, dry load on Celite, 10 mL fractions, hexanes/EtOAc gradient elution: 20:1 (400 mL) to 10:1 (500 mL)) to afford 0.40 g of (R)-3,3'-dibromo-2'-((tris(4-(tert-butyl)phenyl)silyl)oxy)-5,5',6,6',7,7',8,8'-octahydro-[1,1'-binaphthalen]-2-ol as a white solid.

An oven-dried, 10-mL, round-bottomed flask equipped with a 3.0-cm×0.5-cm rod-shaped stir bar and a reflux condenser was charged with (R)-3,3'-dibromo-2'-((tris(4-(tert-butyl)phenyl)silyl)oxy)-5,5',6,6',7,7',8,8'-octahydro-[1,1'-binaphthalen]-2-ol (0.40 g, 0.46 mmol), imidazole (80 mg, 1.5 mmol, 3 equiv), tris(4-(tert-butyl)phenyl)chlorosilane (0.23 g, 0.75 mmol, 1.2 equiv), dichloromethane (2.0 mL), DMF (2.0 mL), and heated to 40° C. (oil bath temperature) for 12 h. The reaction was cooled to room temperature and poured into sat. aq. sodium bicarbonate (30 mL), transferred to a 250-mL, separatory funnel, phases separated, and the aqueous layers was extracted with dichloromethane (3×30 mL). The combined organic layers were washed with brine (50 mL), dried over sodium sulfate (10 g), filtered, and concentrated (30° C., 75 mm Hg) to afford crude (R)-((3,3'-dibromo-5,5',6,6',7,7',8,8'-octahydro-[1,1'-binaphthalene]-2,2'-diyl)bis(oxy))bis(tris(4-(tert-butyl)phenyl)silane). The product was purified by chromatography (silica gel, 1.5 cm×20 cm, dry load on Celite, 10 mL fractions, hexanes/EtOAc gradient elution: 20:1 (400 mL) to 10:1 (500 mL)) to afford 0.38 g of (R)-((3,3'-dibromo-5,5',6,6',7,7',8,8'-octahydro-[1,1'-binaphthalene]-2,2'-diyl)bis(oxy))bis(tris(4-(tert-butyl)phenyl)silane) as a white solid. The solid contained an impurity of silanol which was not removed.

A 50-mL, Schlenk flask equipped with a 3.0-cm×0.5-cm rod-shaped stir bar was charged with (R)-((3,3'-dibromo-5,5',6,6',7,7',8,8'-octahydro-[1,1'-binaphthalene]-2,2'-diyl)bis(oxy))bis(tris(4-(tert-butyl)phenyl)silane) (0.38 g, 0.19 mmol), evacuated and replaced with argon, charged with THF (15 mL), and cooled to 0° C. in an ice bath. Next, t-butyllithium (1.7 M, 0.49 mL, 4.2 equiv) was added dropwise over 5 min. Upon complete addition, the ice bath was removed and the mixture was allowed to warm to room temperature over 12 h. Full conversion was assessed by TLC ($R_f$=0.25 (hexanes/dichloromethane, 10:1) [CAM]). The reaction was poured into sat. aq. ammonium chloride (50 mL) and stirred for 30 min, transferred to a 250-mL, separatory funnel, the phases separated, and the aqueous layer was extracted with dichloromethane (3×50 mL). The combined organic layers were washed with brine (50 mL), dried over sodium sulfate (10 g), filtered, rinsed with dichloromethane (25 mL), and concentrated (30° C., 75 mm Hg) to afford the crude title compound. The product was purified by chromatography (silica gel, 1.5 cm×20 cm, dry load on Celite, 10 mL fractions, hexanes/dichloromethane gradient elution: 10:1 (400 mL) to 5:1 (500 mL)) to afford 0.21 g (12% over three steps) of the title compound as a white solid.

Data for S8: $^1$H NMR: (500 MHz, CDCl$_3$) 7.53 (d, J=8.3 Hz, 12H), 7.34 (d, J=8.4 Hz, 12H), 6.96 (s, 2H), 4.94 (s, 2H), 2.58 (d, J=4.2 Hz, 4H), 2.44-2.32 (m, 2H), 2.22 (m, 2H), 1.67 (t, J=8.2 Hz, 8H), 1.31 (s, 54H). $^{13}$C NMR: (126 MHz, CDCl$_3$) 156.29, 151.97, 139.64, 139.48, 136.13, 131.35, 129.59, 124.61, 119.39, 117.40, 34.67, 31.29, 29.23, 27.28, 23.04, 22.98. HRMS:(ESI$^+$, TOF) calcd for C$_{80}$H$_{98}$O$_2$Na (M$^{+Na}$) 1169.7003, found: 1169.6979 TLC: R, =0.25 (hexanes/dichloromethane, 10:1) [CAM]

Preparation of (R)-3,3'-Bis(3,5-bis(trifluoromethyl)benzyl)-5,5',6,6',7,7',8,8'-octahydro-[1,1'-binaphthalene]-2,2'-diol (S9)

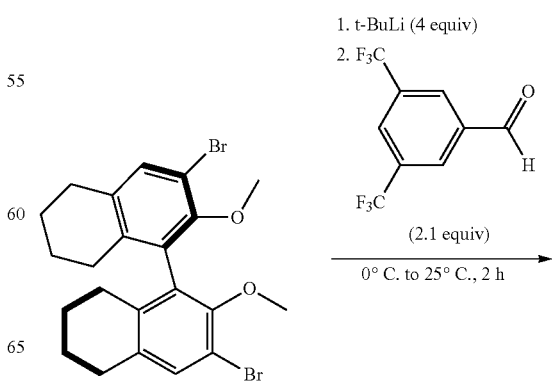

-continued

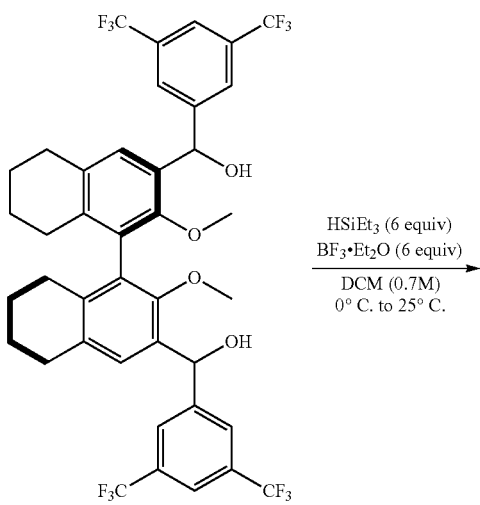

HSiEt₃ (6 equiv)
BF₃·Et₂O (6 equiv)
―――――――――→
DCM (0.7M)
0° C. to 25° C.

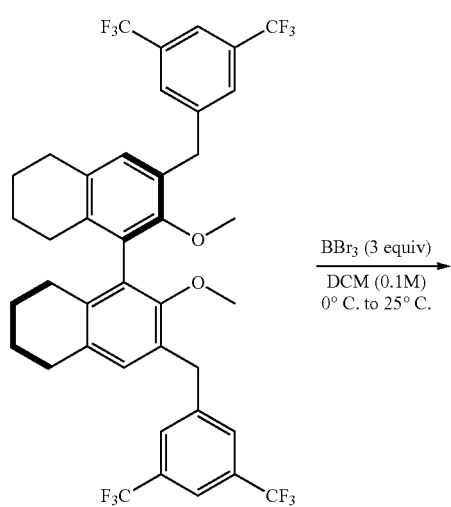

BBr₃ (3 equiv)
―――――――→
DCM (0.1M)
0° C. to 25° C.

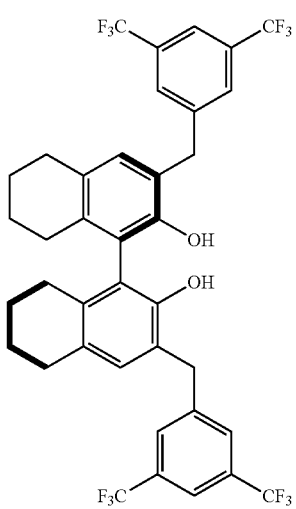

An oven-dried, 100-mL, Schlenk flask equipped with a 3.0-cm×0.5-cm rod-shaped stir bar was charged with (R)-3,3'-dibromo-2,2'-dimethoxy-5,5',6,6',7,7',8,8'-octahydro-1, 1'-binaphthalene (1.9 g, 4.0 mmol), and diethyl ether (36 mL, 0.11 M) under argon. The solution was cooled to 0° C. (internal temperature) using an ice bath and t-butyllithium (1.7 M, 9.8 mL, 4 equiv) was added dropwise over 5 min. The reaction was stirred at 0° C. in an ice bath for 30 min, and then 3,5-bis(trifluoromethyl)benzaldehyde (2.1 g, 8.8 mmol, 2.1 equiv) was added dropwise. Once the addition was complete, the ice bath was removed and the mixture was allowed to warm to room temperature over 2 h. The reaction mixture was poured into sat. aq. ammonium chloride (50 mL) and stirred for 30 min, transferred to a 250-mL, separatory funnel, and extracted with EtOAc (3×50 mL). The combined organic layers were washed with brine (50 mL), dried over sodium sulfate (10 g), filtered and concentrated (30° C., 75 mm Hg) to afford the crude product 3.1 g of (R)-(2,2'-dimethoxy-5,5',6,6',7,7',8,8'-octahydro-[1,1'-bi-naphthalene]-3,3'-diyl)bis((3,5-bis(trifluoromethyl)phenyl) methanol) as a viscous yellow oil.

A 50-mL, Schlenk flask with a 3.0-cm×0.5-cm rod-shaped stir bar was charged with the (R)-(2,2'-dimethoxy-5,5',6,6', 7,7',8,8'-octahydro-[1,1'-binaphthalene]-3,3'-diyl)bis((3,5-bis(trifluoromethyl)phenyl)methanol) (0.80 g, 1.0 mmol) and THF (10 mL) under argon. The resulting solution was cooled to 0° C. in an ice bath for 10 min, and triethylsilane (0.71 g, 0.63 mL, 6 equiv) was added dropwise over 5 min by syringe. The solution was stirred at 0° C. for 10 min and boron trifluoride diethyl etherate (0.58 g, 0.73 mL, 6 equiv) was added dropwise over 5 min by syringe. The resulting solution was stirred at room temperature for 2 h. The reaction was diluted with sat. aq. sodium bicarbonate (30 mL), stirred for 10 min, transferred to a 250-mL separatory funnel, and extracted with dichloromethane (3×50 mL). Next the combined organic layers were washed with brine (100 mL), dried over sodium sulfate (10 g), filtered and concentrated (30° C., 75 mm Hg) to afford 0.75 g (96%) (R)-3,3'-bis(3,5-bis(trifluoromethyl)benzyl)-2,2'-dime-thoxy-5,5',6,6',7,7',8,8'-octahydro-1,1'-binaphthalene as a yellow oil.

A 50-mL, Schlenk flask with a 2.0-cm×0.5-cm rod-shaped stir bar was charged with the (R)-3,3'-bis(3,5-bis(trifluorom-ethyl)benzyl)-2,2'-dimethoxy-5,5',6,6',7,7',8,8'-octahydro-1, 1'-binaphthalene (0.28 g, 0.36 mmol), and the flask evacuated and replaced with argon three times. Dichloromethane (15 mL) was added to the flask, and the solution was cooled to 0° C. using an ice bath. A flame-dried, 10-mL, Schlenk flask equipped with a 2.0-cm×0.5-cm rod-shaped stir bar was charged with dichloromethane (1 mL) and cooled to −78° C. using a dry ice/isopropyl alcohol bath and added boron tribromide (0.27 g, 1.0 mmol, 3 equiv) dropwise over 5 min. Once addition was complete, the solution was warmed to room temperature over 1 h. The boron tribromide solution was added dropwise to the reaction flask via syringe. Once addition was complete, the ice bath was removed and the solution was allowed to warm to room temperature over 11 h. Full conversion was assessed by TLC ($R_f$=0.30 (hexanes/dichloromethane, 10:1) [UV]). The reaction was diluted with water (20 mL), stirred for 30 min, transferred to a 250-mL, separatory funnel, and extracted with dichloromethane (3×20 mL). The combined organic layers were washed with brine (30 mL), dried over sodium sulfate (10 g), filtered and concentrated by rotary evaporation (30° C., 75 mm Hg) to afford the crude product. The crude product was purified by chromatography (silica gel, 1.5 cm×20 cm, dry load on Celite, 10 mL fractions, hexanes/

EtOAc gradient elution: 20:1 (500 mL) to 10:1 (1 L)) to afford a light-yellow oil, which was triturated in pentane (1 mL) for 1 h and collected by vacuum filtration to afford 0.19 g (71%) of the title compound as a white solid.

Data for S9: $^1$H NMR: (500 MHz, CDCl$_3$) 7.71 (s, 6H), 6.95 (s, 2H), 4.68 (s, 2H), 4.17 (d, J=15.2 Hz, 2H), 4.01 (d, J=15.2 Hz, 2H), 2.74 (t, J=6.2 Hz, 4H), 2.39-1.98 (m, 4H), 1.83-1.66 (m, 8H). $^{13}$C NMR: (126 MHz, CDCl$_3$) 149.19, 149.10, 143.67, 136.05, 132.14, 131.34 (q, J=33.0 Hz, 4C), 130.59, 128.74, 123.46 (q, J=273 Hz, 4C), 123.13, 119.96 (m), 118.84, 36.05, 29.11, 26.96, 22.84, 22.81. $^{19}$F NMR: (471 MHz, CDCl$_3$) −62.66 (s, 12F) HRMS:(ESI$^+$, TOF) calcd for C$_{80}$H$_{98}$O$_2$Na (M$^{+Na}$): 1169.7003, found: 1169.6979. TLC: R$_f$=0.30 (hexanes/dichloromethane, 10:1) [UV].

Preparation of (R)-3,3'-Bis(methyldiphenylsilyl)-[1,1'-binaphthalene]-2,2'-diol (S10)

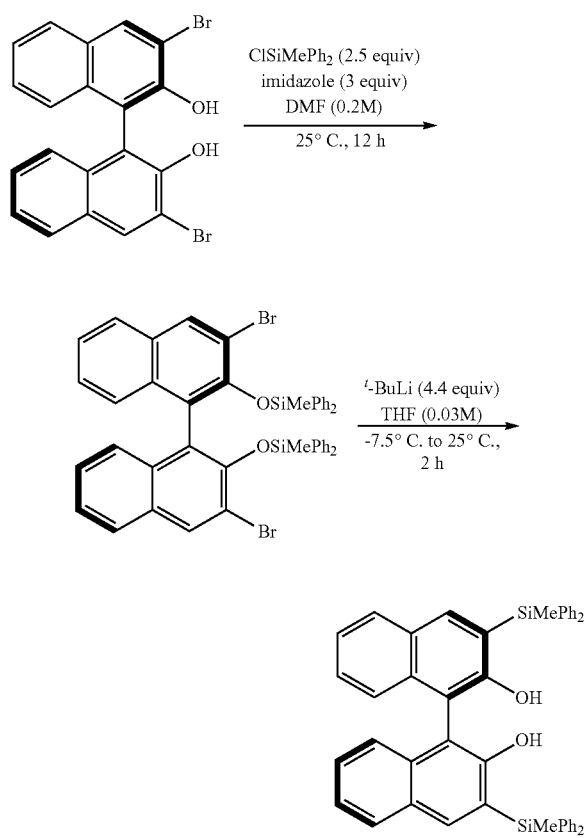

A flame-dried, 100-mL, Schlenk flask equipped with a 2.0-cm×1.0-cm football-shaped stir bar was charged with (R)-3,3'-dibromo-[1,1'-binaphthalene]-2,2'-diol (2.65 g, 5.97 mmol) in DMF (35 mL), imidazole (1.22 g, 17.9 mmol, 3 equiv), and chloromethyldiphenylsilane (3.47 g, 14.9 mmol, 2.5 equiv). The reaction was stirred overnight, at room temperature, with conversion assessed by TLC (R$_f$=0.64 (hexanes/EtOAc, 4:1) [UV]). The solution was diluted with sat. aq. sodium bicarbonate (100 mL), and the aqueous layer was extracted with dichloromethane (3×100 mL). The combined organic layers were washed with sat. aq. sodium bicarbonate (150 mL), dried over sodium sulfate (17 g), filtered, rinsed with dichloromethane (50 mL), and concentrated to afford a yellow oil. Next the crude product was taken up in hexanes (10 mL), forming a suspension, and filtered through a Celite plug (7 g) affording a clear solution (the solid was discarded). The clear solution was concentrated (30° C., 15 mm Hg) to afford a yellow oil. The oil was taken up in hexanes (10 mL), EtOAc (1 mL), and dichloromethane (0.5 mL) in a 20-mL, scintillation vial and the solution was heated at reflux until ca. 4 mL of the solvent remained, and cooled to room temperature. The resulting crystals were collected by vacuum filtration to afford 3.1794 g (64%) of (R)-((3,3'-dibromo-[1,1'-binaphthalene]-2,2'-diyl)bis(oxy))bis(methyldiphenylsilane) as a crystalline solid.

A 250-mL, Schlenk flask equipped with a septum and 2.0-cm×1.0-cm football-shaped stir bar was charged with (R)-((3,3'-dibromo-[1,1'-binaphthalene]-2,2'-diyl)bis(oxy)) bis(methyldiphenylsilane) (1.8322 g, 2.1896 mmol) and THF (74 mL). The vessel was cooled to −7.5° C. (internal temperature) in an ice/salt bath. t-BuLi (1.7 M, 9.6 mL, 4.4 equiv) was added dropwise over 3 min, maintaining an internal temperature of under 0° C. The solution turned a lime green color during the addition. Once the addition was completed, the ice/salt bath was removed and the reaction was allowed to warm to room temperature over 2 h. Full conversion was assessed by TLC(R$_f$=0.54 (hexanes/EtOAc, 4:1) [UV]). The reaction was quenched by pouring the reaction mixture into sat. aq. ammonium chloride (200 mL), the reaction vessel was rinsed with dichloromethane (50 mL), and the biphasic mixture was stirred vigorously for 15 min. Next the phases were separated and the aqueous layer extracted with dichloromethane (3×100 mL). The combined organic layers were dried over sodium sulfate (7 g), filtered, rinsed with dichloromethane (50 mL), and concentrated (34° C., 22 mm Hg) to afford a colorless oil. The resulting oil was placed under reduced pressure (22° C., 0.1 mm Hg) for 12 h to afford a white solid. The product was purified by recrystallization from refluxing TBME/hexanes (17 mL:22 mL), refluxed for 5 min in an oil bath temperature of 130° C., followed by cooling to room temperature. The compound was allowed to crystallize at room temperature for 40 h, and upon crystal formation was placed in a−20° C. freezer for ca. 16 h. The crystals were removed by vacuum filtration and washed with TBME/hexanes (17:22, ca. 10 mL, chilled). A second crop was collected and recrystallized from a mixture of 1:1 TBME/hexanes (10 mL). The two different crops of white solid were combined and triturated with pentane (3×40 mL) to afford 995.8 mg (67%) of the title compound as a white, crystalline solid.

Data for S10: $^1$H NMR: (500 MHz, CDCl$_3$) 7.86 (s, 2H), 7.76-7.70 (m, 2H), 7.62-7.54 (m, 8H), 7.45-7.33 (m, 12H), 7.33-7.28 (m, 4H), 7.19-7.13 (m, 2H), 5.21 (s, 2H), 0.96 (s, 6H). $^{13}$C NMR: (126 MHz, CDCl$_3$) 156.78 (s), 140.77 (s), 136.16 (s), 135.15 (d, J=6.8 Hz), 134.47 (s), 129.33 (d, J=4.2 Hz), 129.14 (s), 128.85 (s), 127.98 (s), 127.81 (d, J=7.6 Hz), 125.14 (s), 123.82 (d, J=13.1 Hz), 110.00 (s), −3.01 (s). $^{29}$Si NMR: (126 MHz, CDCl$_3$) −3.93 (s). HRMS:(ESI$^+$, TOF) calcd for C$_{46}$H$_{38}$O$_2$Si$_2$ (M$^{+1}$) 701.2308, found: 701.2295. TLC: R$_f$=0.54 (hexanes/EtOAc, 4:1) [UV].

Preparation of (R)-3,3'-Bis(4-methoxybenzyl)-5,5',6,6',7,7',8,8'-octahydro-[1,1'-binaphthalene]-2,2'-diol (S11)

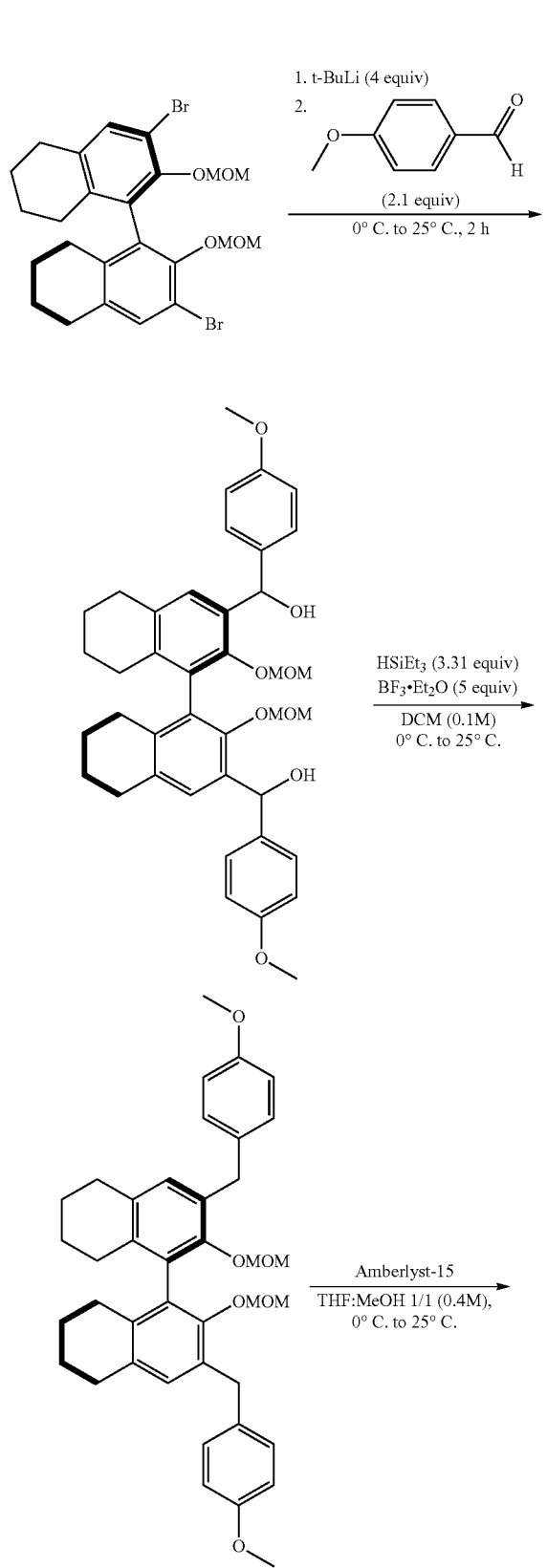

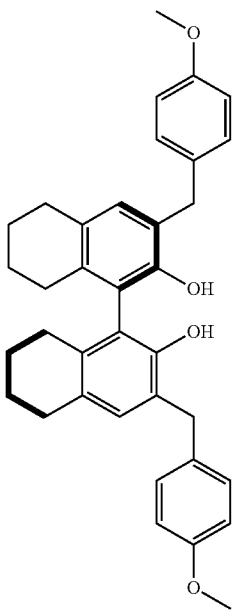

A flame-dried, 25-mL, Schlenk flask equipped with a 2.0-cm×1.0-cm football-shaped stir bar was charged with (R)-3,3'-dibromo-2,2'-bis(methoxymethoxy)-5,5',6,6',7,7',8,8'-octahydro-1,1'-binaphthalene (0.532 g, 0.9847 mmol), diethyl ether (9 mL), and the vessel was cooled to 0° C. using an ice bath (internal temp). After cooling, t-butyl-lithium (1.7 M, 2.5 mL, 4 equiv) was added dropwise, forming a white suspension, which was allowed to stir at 0° C. for 0.5 h. Next, p-anisaldehyde (0.402 g, 2.954 mmol, 4 equiv) was added in one aliquot. Upon completion of the addition, the ice bath was removed and the reaction was allowed to warm to room temperature and stirred for 2 h. The reaction was quenched by pouring into sat. aq ammonium chloride (ca. 50 mL), and the aqueous layer was extracted with EtOAc (4×20 mL). The combined organic layers were washed with brine (20 mL), dried over sodium sulfate, filtered, washed with EtOAc (40 mL), and concentrated (30° C., 15 mm Hg) to afford a viscous yellow oil.

The yellow oil was dissolved in dichloromethane (10 mL) and charged into a flame-dried, 25-mL, round-bottomed flask equipped with a gas inlet, 2.0-cm×1.0-cm football-shaped stir bar, internal temperature probe, and septum. The flask was cooled to 0° C. with an ice bath and Triethylsilane (390.2 mg, 3.355 mmol, 3.31 equiv) was added in one portion by syringe, and stirred for 5 min maintaining an internal temperature below 0° C. Boron trifluoride etherate (1.5 g, 4.920 mmol, 5 equiv) was added dropwise over 5 min, maintaining an internal temperature below 0° C. Upon complete addition, the ice bath was removed and the reaction was allowed to warm to room temperature and stirred for 5 h. The reaction was quenched by pouring the reaction mixture into sat. aq. sodium bicarbonate (100 mL). The phases were separated and the aqueous layer was extracted with dichloromethane (3×20 mL). The combined organic layers were washed with brine (80 mL), dried over sodium sulfate, filtered, and concentrated (30° C., 15 mm Hg) to afford crude (R)-3,3'-bis(4-methoxybenzyl)-2,2'-bis(methoxymethoxy)-5,5',6,6',7,7',8,8'-octahydro-1,1'-binaphthalene.

A 50-mL, round-bottomed flask equipped with a stir bar, Teflon sleeve, and reflux condenser was charged with the crude (R)-3,3'-bis(4-methoxybenzyl)-2,2'-bis(methoxymethoxy)-5,5',6,6',7,7',8,8'-octahydro-1,1'-binaphthalene and a mixture of 1:1 THF/methanol (25 mL), and Amberlyst 15 (750 mg). The reaction was placed under a nitrogen atmosphere and heated at reflux in an 80° C. oil bath for 12 h. Full conversion was assessed by TLC ($R_f$=0.26 (pentane/diethyl ether, 4:1) [UV]) The reaction was cooled to room temperature, filtered through Celite (8 g), the filter cake washed with EtOAc (75 mL), and the filtrate concentrated (30° C., 15 mm Hg) affording a green-grey residue. The product was purified by chromatography (silica gel, 4 cm×18 cm, 25 mL fractions, pentane/diethyl ether isocratic elution: 9:1 (1 L)) to afford 199 mg (39%) of the title compound as a white crystalline solid.

Data for S11: $^1$H NMR: (500 MHz, CDCl$_3$) 7.17 (d, J=8.3 Hz, 4H), 6.89-6.75 (m, 6H), 4.63 (s, 2H), 3.90 (s, 4H), 3.79 (s, J=1.2 Hz, 6H), 2.66 (t, J=7.4 Hz, 4H), 2.30-2.03 (m, 4H), 1.82-1.59 (m, 8H). $^{13}$C NMR: (126 MHz, CDCl$_3$) 158.05 (s, 2C), 149.40 (s, 2C), 135.05 (s, 2C), 133.25 (s, 2C), 131.91 (s, 2C), 130.02 (s, 4C), 125.73 (s, 2C), 119.11 (s, 2C), 114.04 (s, 4C), 55.50 (s, 2C), 35.18 (s, 2C), 29.43 (s, 2C), 27.19 (s, 2C), 23.32 (s, 2C), 23.27 (s, 2C). HRMS: (ESI$^+$, TOF) calcd for C$_{36}$H$_{38}$O$_4$Na (M$^{+Na}$) 557.2668, found: 557.2687. TLC: $R_f$=0.26 (pentane/diethyl ether, 4:1) [UV].

Preparation of (R)-3,3'-Bis(2,6-dimethoxyphenyl)-[1,1'-binaphthalene]-2,2'-diol (S12)

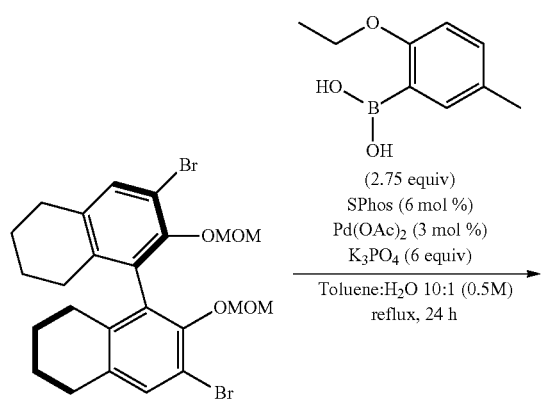

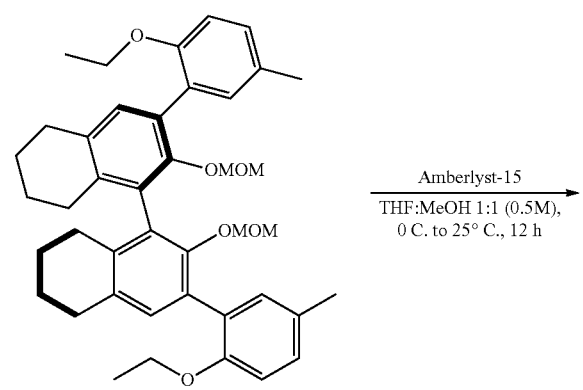

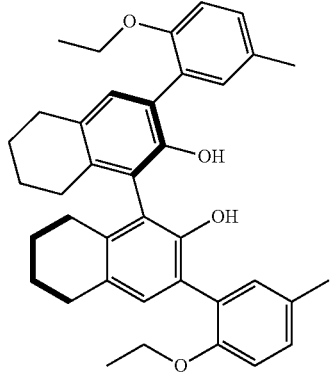

An oven-dried, 35-mL, pressure tube equipped with a 1.5-cm×1.0-cm football-shaped stir bar, and a septum was charged with potassium phosphate (7.07 g, 33.3 mmol, 6.0 equiv), (R)-3,3'-dibromo-2,2'-bis(methoxymethoxy)-5,5',6,6',7,7',8,8'-octahydro-1,1'-binaphthalene (3.00 g, 5.55 mmol), (2-ethoxy-5-methylphenyl)boronic acid (2.75 g, 15.3 mmol, 2.75 equiv), SPhos (140 mg, 0.333 mmol, 0.06 equiv), and palladium(II) acetate (38 mg, 0.167 mmol, 0.03 equiv). The flask was evacuated and placed under argon 5 times. Toluene (10 mL, sparged for 1 h with argon) and water (1 mL, sparged for 1 h with argon) were added via syringe. The septum was quickly replaced with a Teflon screw threaded cap, and the reaction was heated in a 110° C. oil bath for 24 h. Full conversion was assessed by TLC ($R_f$=0.64 (hexanes/EtOAc, 8:2) UV). The reaction was cooled to room temperature, filtered through Celite (10 g), the filter cake was washed with of EtOAc (150 mL), diluted with water (50 mL), and the aqueous layer was extracted EtOAc (2×50 mL). The combined organic layers were washed with brine (50 mL), dried over sodium sulfate (22 g) for 40 min, filtered, and concentrated (30° C., 15 mm Hg) to afford a yellow oil. The product was purified by chromatography (silica gel, 6 cm×15 cm, 50 mL fractions, dry load on Celite, hexanes/EtOAc gradient elution: 99:1 (500 mL) to 98:2 (500 mL) to 97:3 (500 mL) to 96:4 (2 L)) to afford 3.11 g of (R)-3,3'-bis(2-ethoxy-5-methylphenyl)-2,2'-bis(methoxymethoxy)-5,5',6,6',7,7',8,8'-octahydro-1,1'-binaphthaleneas as a yellow solid.

A 250-mL, round-bottomed flask equipped with a 2.5-cm×1.5-cm football-shaped stir bar, reflux condenser, and a gas adaptor was charged with (R)-3,3'-bis(2-ethoxy-5-methylphenyl)-2,2'-bis(methoxymethoxy)-5,5',6,6',7,7',8,8'-octahydro-1,1'-binaphthalene (3.11 g, 4.77 mmol), a mixture of 1:1 THF/methanol (100 mL), and Amberlyst-15 dry resin (350 mg). The reaction was placed under nitrogen and heated at reflux in an 80° C. oil bath for 36 h. Full conversion was assessed by $^1$H NMR. The reaction was cooled to room temperature, filtered through Celite, the filter cake washed with EtOAc (50 mL). The filtrate was concentrated (30° C., 15 mm Hg) to afford a yellow solid. The product was purified by chromatography (silica gel, 6.5 cm×15 cm, dry load on Celite, 50 mL fractions, hexanes/EtOAc isocratic: 95:5 (2 L)) which was further purified by trituration with pentane to afford 2.2 g (71% yield) of the title compound as a white solid.

Data for S12: $^1$H NMR: (500 MHz, CDCl$_3$) 7.23 (s, 2H), 7.11 (d, J=8.2 Hz, 2H), 7.03 (s, 2H), 6.88 (d, J=8.3 Hz, 2H), 6.11 (s, 2H), 4.03 (m, 4H), 2.82 (m, 4H), 2.52 (dt, J=17.2, 6.1 Hz, 2H), 2.34 (s, 6H), 2.22 (m, 2H), 1.74 (m, 8H), 1.32 (t, J=7.0 Hz, 6H). $^{13}$C NMR: (126 MHz, CDCl$_3$) 153.35 (s, 2C), 149.14 (s, 2C), 136.77 (s, 2C), 133.47 (s, 2C), 131.56 (s, 2C), 131.52 (s, 2C), 129.67 (s, 2C), 129.30 (s, 2C), 128.74 (s, 2C), 125.00 (s, 2C), 124.40 (s, 2C), 113.31 (s, 2C), 65.45 (s, 2C), 29.82 (s, 2C), 27.48 (s, 2C), 23.68 (s, 2C), 23.63 (s, 2C), 20.98 (s, 2C), 15.18 (s, 2C) HRMS: (ESI+, TOF) calcd for $C_{38}H_{43}O_4$ ($M^{+1}$): 563.3161, found: 563.3160. TLC: $R_f$=0.19 (hexanes/EtOAc, 9:1) [UV]

Preparation of (R)-3,3'-Bis(4-isopropoxy-3,5-dimethylphenyl)-[1,1'-binaphthalene]-2,2'-diol (S13)

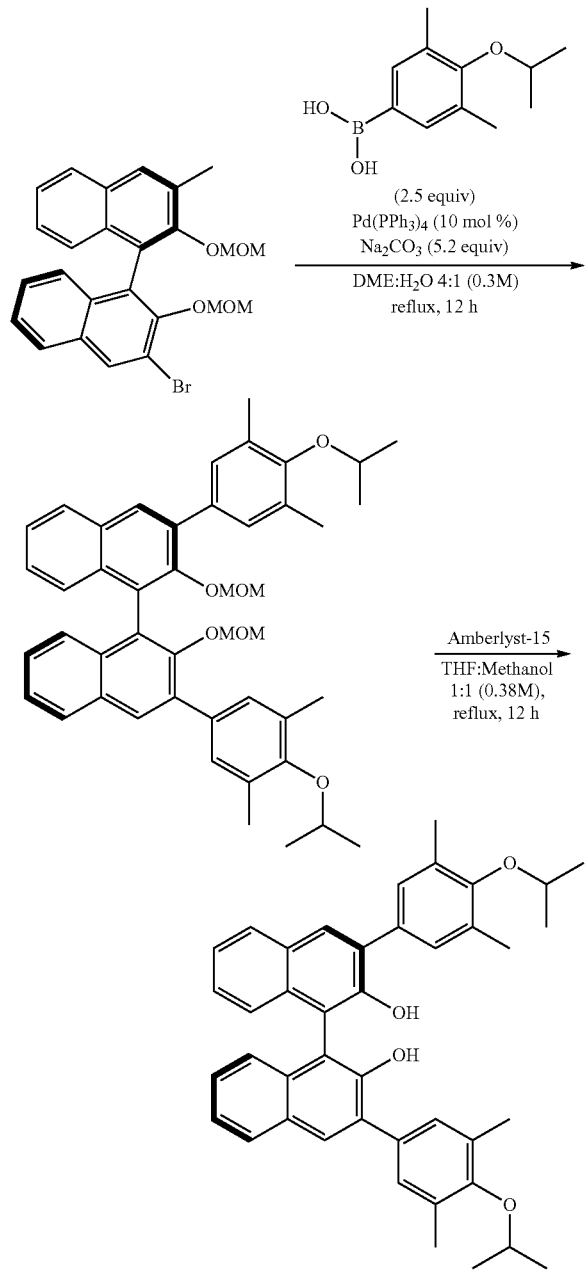

An oven-dried, 100-mL, round-bottomed flask equipped with a 3.0-cm×1.0-cm football-shaped stir bar, reflux condenser and gas adaptor was charged with sodium carbonate (2 M, 4.9 mL, 5.2 equiv), (4-isopropoxy-3,5-dimethylphenyl)boronic acid (1.20 g, 5.64 mmol, 3 equiv), (R)-3,3'-dibromo-2,2'-bis(methoxymethoxy)-1,1'-binaphthalene (1.00 g, 1.88 mmol), tetrakis(triphenylphosphine)palladium (0) (0.241 g, 0.188 mmol, 0.10 equiv). The system was evacuated and backfilled with argon 5 times. Glyme (19.5 mL, sparged for 1 h with an argon) was added via syringe. The reaction was heated at reflux in a 110° C. oil bath for 12 h. Full conversion was assessed by TLC ($R_f$=0.26 (hexanes/dichloromethane, 1:1) [UV]). The reaction was cooled to room temperature, filtered through Celite (8 g), and concentrated (30° C., 15 mm Hg). The residue was taken up in dichloromethane (50 mL), washed with sat. aq. ammonium chloride (30 mL), brine (30 mL), dried over sodium sulfate (11 g), filtered, and concentrated (30° C., 15 mm Hg). The product was purified by chromatography (silica gel, 5 cm×16 cm, dry load on Celite, hexanes/EtOAc gradient elution: 96:4 (500 mL) to 94:6 (500 mL) to 92:8 (500 mL) to 9:1 (500 mL)) to afford 1.18 g of (R)-3,3'-bis(4-isopropoxy-3,5-dimethylphenyl)-2,2'-bis(methoxymethoxy)-1,1'-binaphthalene as a white solid.

A 250-mL, round-bottomed flask equipped with a 4.0-cm×1.0-cm rod-shaped stir bar, gas inlet adapter, reflux condenser and septum was charged with (R)-3,3'-bis(4-isopropoxy-3,5-dimethylphenyl)-2,2'-bis(methoxymethoxy)-1,1'-binaphthalene (1.18 g, 2.22 mmol), a mixture of 1:1 THF/methanol (50 mL), and Amberlyst-15 dry resin (1.00 g). The mixture was heated at reflux in an 80° C. oil bath for 12 h. Full conversion was assessed by TLC ($R_f$=0.31 (hexane/EtOAc, 9:1) [UV]). The reaction was cooled to room temperature, filtered through Celite (11 g), and concentrated (30° C., 15 mm Hg). The product was purified by chromatography (silica gel, 5 cm×18 cm, dry load on Celite, 50 mL fractions, hexanes/EtOAc gradient elution: 95:5 (500 mL) to 90:10 (500 mL) to 85:15 (500 mL) to 80:20 (500 mL)) to afford 0.883 g (77%) of the title compound as a white solid.

Data for S13: $^1$H NMR: (500 MHz, CDCl$_3$) 7.98 (s, 2H), 7.90 (d, J=8.0 Hz, 2H), 7.37 (s, 6H), 7.29 (s, 2H), 7.21 (d, J=8.1 Hz, 2H), 5.40 (s, 2H), 4.24 (hept, J=6.1 Hz, 2H), 2.34 (s, 12H), 1.34 (d, J=6.1 Hz, 12H). $^{13}$C NMR: (126 MHz, CDCl$_3$) 154.92 (s, 2C), 150.09 (s, 2C), 133.03 (s, 2C), 132.14 (s, 2C), 131.69 (s, 4C), 130.90 (s, 2C), 130.53 (s, 2C), 130.10 (s, 4C), 129.54 (s, 2C), 128.54 (s, 2C), 127.72 (s, 2C), 124.52 (s, 2C), 124.26 (s, 2C), 112.89 (s, 2C), 74.92 (s, 2C), 22.81 (s, 4C), 17.44 (s, 4C). HRMS: (ESI+, TOF) calcd for $C_{42}H_{43}O_4$($M^{+1}$): 611.3161, found: 611.3143. TLC: $R_f$=0.31 (hexane/EtOAc, 9:1) [UV].

Preparation of (R)-3,3'-Bis(2,2'',4,4'',6,6''-hexamethyl-[1,1':3',1''-terphenyl]-5'-yl)-5,5',6,6',7,7',8,8'-octahydro-[1,1'-binaphthalene]-2,2'-diol (S14)

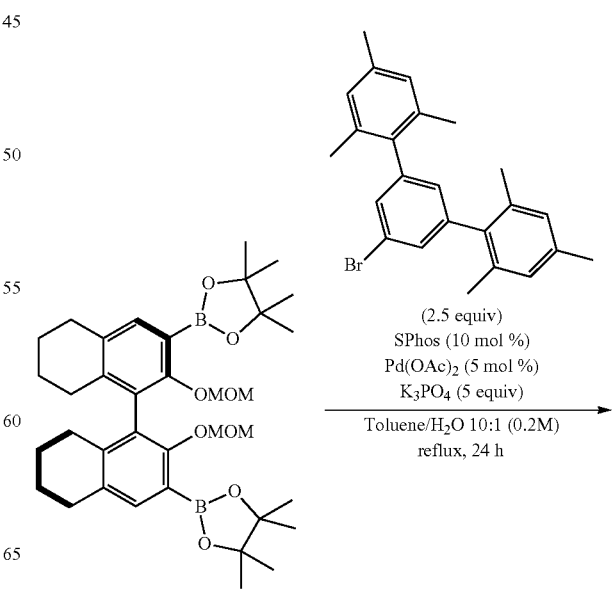

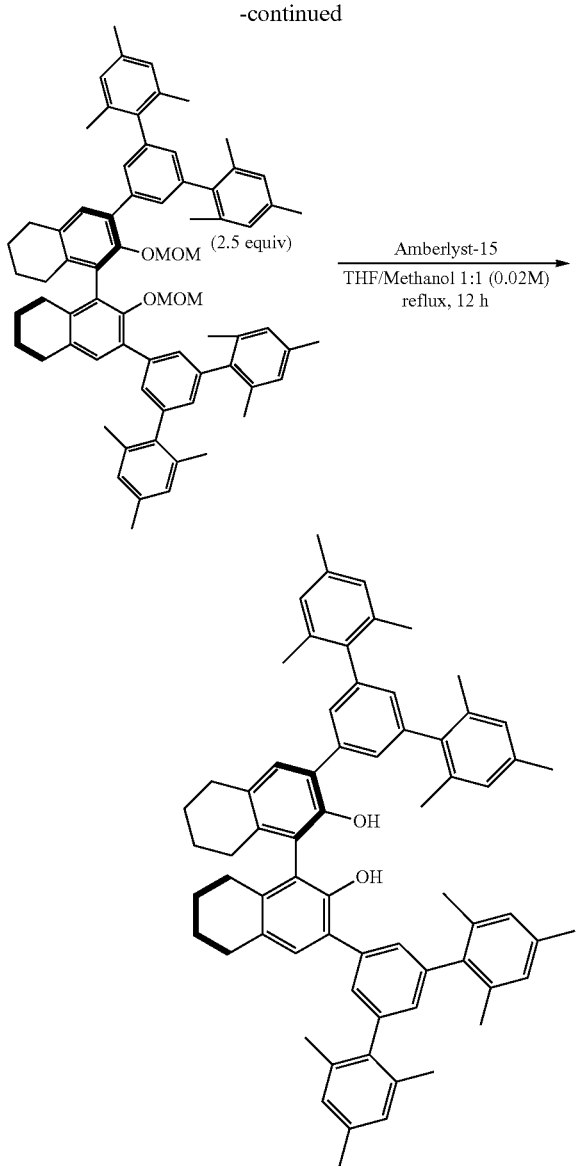

An oven-dried, 35-mL, pressure tube equipped with a 1.5-cm×1.0-cm football-shaped stir bar and septum was charged with potassium phosphate (836 mg, 3.94 mmol, 5 equiv), (R)-2-(2,2'-bis(methoxymethoxy)-3'-(4,4,5,5-tetramethyl-1,3-dioxolan-2-yl)-5,5',6,6',7,7',8,8'-octahydro-[1,1'-binaphthalen]-3-yl)-4,4,5,5-tetramethyl-1,3,2-dioxaborolane (0.500 g, 0.788 mmol), 5'-bromo-2,2'',4,4'',6,6''-hexamethyl-1,1':3',1''-terphenyl (0.775 g, 1.97 mmol, 2.5 equiv), SPhos (32.4 mg, 0.078 mmol, 0.10 equv) and palladium(II) acetate (8.85 mg, 0.039 mmol, 0.05 equiv). The vessel was evacuated and backfilled with argon 5 times. Toluene (3.6 mL, sparged for 1 h with an nitrogen) and water (0.36 mL, sparged for 1 h with an nitrogen) was added via syringe. The septum was quickly replaced with a threaded, Teflon screw cap and the pressure tube heated in a 110° C. oil bath for 24 h. Full conversion was assessed by TLC ($R_f$=0.53 (hexanes/EtOAc, 9:1) [UV]). The reaction was cooled to room temperature and diluted with EtOAc (8 mL) and sat. aq. ammonium chloride (5 mL), allowed to stir in the sealed tube for 15 min, and further diluted with EtOAc (50 mL) and water (30 mL). The phases were separated and the aqueous layer was further extracted with EtOAc (3×50 mL). The combined organic layers were washed with brine (50 mL), dried over sodium sulfate for 40 min, filtered, rinsed with EtOAc (50 mL) and concentrated (30° C., 15 mm Hg). The product was purified by chromatography (silica gel, 5 cm×4 cm, dry load on Celite, 50 mL fractions, hexanes/EtOAc gradient elution: 100:0 (500 mL) to 50:50 (500 mL)) to afford 0.732 g of (R)-3,3'-bis(2,2'',4,4'',6,6''-hexamethyl-[1,1':3',1''-terphenyl]-5'-yl)-2,2'-bis (methoxymethoxy)-5,5',6,6',7,7',8,8'-octahydro-1,1'-binaphthalene as a yellow solid.

A 100-mL, round-bottomed flask equipped with a 3.0-cm×1.0-cm rod-shaped stir bar, reflux condenser, and gas adaptor was charged with (R)-3,3'-bis(2,2'',4,4'',6,6''-hexamethyl-[1,1':3',1''-terphenyl]-5'-yl)-2,2'-bis (methoxymethoxy)-5,5',6,6',7,7',8,8'-octahydro-1,1'-binaphthalene (0.732 g, 0.73 mmol) a mixture of 1:1 THF/methanol (40 mL), and Amberlyst-15 dry resin (650 mg). The reaction was placed under nitrogen and heated at reflux in an 80° C. oil bath for 12 h. Full conversion was assessed by NMR ($R_f$=0.53, (hexanes/EtOAc, 9:1) $R_f$ of starting material and product is the same as the product). The reaction was cooled to room temperature, diluted with EtOAc (25 mL) and filtered through Celite (8 g), the filter cake was washed with EtOAc (50 mL) and the reaction mixture was concentrated (30° C., 15 mm Hg) to afford a yellow solid. The product was purified by chromatography (silica gel, 4 cm×15 cm, dry load on Celite, 25 mL fractions, hexanes/EtOAc gradient elution: 92.5:7.5 (500 mL) to 90:10 (500 mL) to 85:15 (1 L)) to afford 0.650 g the title compound a white solid. The title compound was further purified by recrystallization from a mixture of 40:1 boiling hexanes/diethyl ether to afford 330 mg (46%) as a white solid.

Data for S13: $^1$H NMR: (500 MHz, CDCl$_3$) 7.39 (d, J=1.5 Hz, 4H), 7.21 (s, 2H), 6.95 (s, 8H), 6.89 (s, 2H), 4.92 (s, 2H), 2.83-2.75 (m, 4H), 2.49-2.36 (m, 2H), 2.33 (s, 12H), 2.30-2.19 (m, 2H), 2.10 (d, J=3.0 Hz, 24H), 1.83-1.66 (m, 8H). $^{13}$C NMR: (126 MHz, CDCl$_3$) 154.92 (s, 2C), 150.09 (s, 2C), 133.03 (s, 2C), 132.14 (s, 2C), 131.69 (s, 4C), 130.90 (s, 2C), 130.53 (s, 2C), 130.10 (s, 4C), 129.54 (s, 2C), 128.54 (s, 2C), 127.72 (s, 2C), 124.52 (s, 2C), 124.26 (s, 2C), 112.89 (s, 2C), 74.92 (s, 2C), 22.81 (s, 4C), 17.44 (s, 4C) HRMS: (ESI$^+$, TOF) calcd for $C_{68}H_{71}O_2(M^{+1})$ 919.5454, found: 919.5483. TLC: $R_f$=0.53 (hexanes/EtOAc, 9:1) [UV].

Preparation of (R)-3,3'-Bis(4,4''-dimethoxy-[1,1':3',1''-terphenyl]-5'-yl)-[1,1'-binaphthalene]-2,2'-diol (S15)

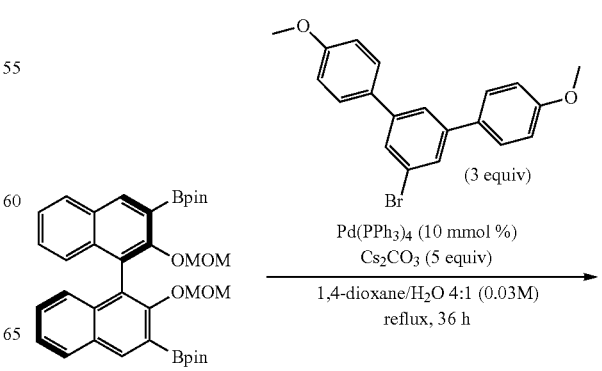

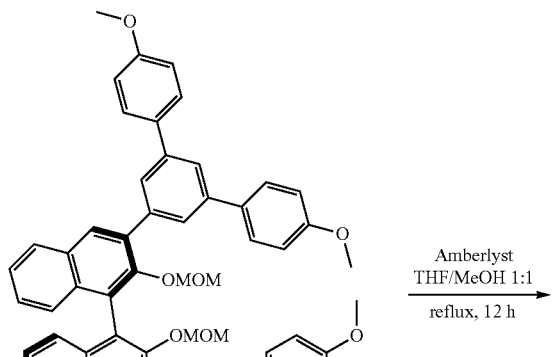

assessed by TLC ($R_f$=0.10 (hexanes/EtOAc, 5:1) [UV]). The mixture was cooled to room temperature, poured into sat. aq. ammonium chloride (50 mL), transferred to a 250-mL, separatory funnel, and the aqueous layer was extracted by dichloromethane (3×30 mL). The combined organic layers were washed with brine (200 mL), dried over sodium sulfate (20 g), filtered and concentrated (30° C., 75 mm Hg). The product was purified by chromatography (silica gel, 3 cm×20 cm, dry load on Celite, hexanes/EtOAc gradient elution: 10:1 (1 L) to 8:1 (1 L) to 6:1 (1 L)) to afford 0.15 g (85%) of (R)-3,3'-bis(4,4"-dimethoxy-[1,1':3',1"-terphenyl]-5'-yl)-2,2'-bis(methoxymethoxy)-1,1'-binaphthalene as a white solid.

An oven-dried, 50 mL, Schlenk flask equipped with a 3.0-cm×0.5-cm rod-shaped stir bar was charged with the protected intermediate (0.15 g, 0.17 mol) Amberlyst-15 dry resin (100 mg), and a mixture of 1:1 THF/methanol (4.0 mL). The mixture was heated at reflux in an 80° C. oil bath for 12 h. Full conversion was assessed by TLC ($R_f$=0.35 (hexanes/EtOAc, 2:1) [UV]). The mixture was cooled to room temperature, filtered through Celite (2 g), the filter cake was washed with EtOAc (20 mL) and concentrated to afford the crude title compound. The product was purified by chromatography (silica gel, 2 cm×18 cm, dry load on Celite, 10 mL Fractions, hexanes/EtOAc gradient elution: 10:1 (500 mL) to 5:1 (500 mL) to 3:1 (500 mL)) to afford 0.14 g (81% over two steps) of the title compound as a white solid.

Data for S15: $^1$H NMR: (500 MHz, CDCl$_3$) δ 8.17 (s, 2H), 7.98 (d, J=8.0 Hz, 2H), 7.90 (d, J=1.7 Hz, 4H), 7.80 (t, J=1.7 Hz, 2H), 7.68 (d, J=8.8 Hz, 8H), 7.44 (ddd, J=8.1, 6.9, 1.2 Hz, 2H), 7.38 (ddd, J=8.1, 6.8, 1.2 Hz, 2H), 7.31 (d, J=8.4 Hz, 2H), 7.03 (d, J=8.8 Hz, 8H), 5.54 (s, 2H), 3.88 (s, 12H). $^{13}$C NMR: (126 MHz, CDCl$_3$) δ 159.30, 150.22, 141.64, 138.26, 133.60, 133.07, 131.50, 130.62, 129.50, 128.52, 128.43, 127.49, 126.55, 124.81, 124.45, 124.37, 114.25, 112.48, 55.41. HRMS: (ESI, TOF) calcd for $C_{60}H_{47}O_6$ ($M^{+1}$): 863.3373, found: 863.3359. TLC: $R_f$=0.35 (hexanes/EtOAc, 2:1) [UV]

Preparation of (R)-3,3'-Bis(2,6-difluoro-4-methoxyphenyl)-[1,1'-binaphthalene]-2,2'-diol (S16)

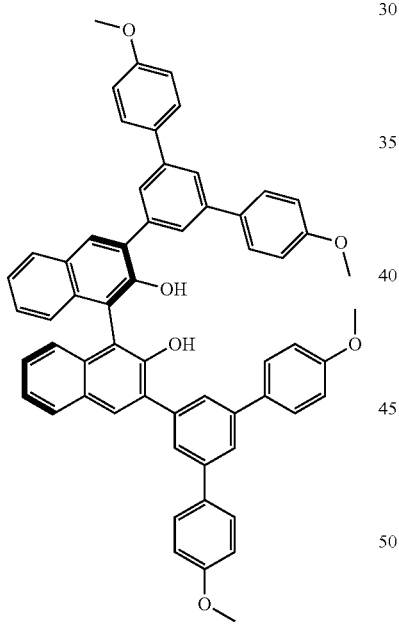

An oven-dried, 100-mL, round-bottomed flask equipped with a 3.0-cm×0.5-cm rod-shaped stir bar, reflux condenser, and gas adaptor was charged with (R)-2,2'-(2,2'-bis(methoxymethoxy)-[1,1'-binaphthalene]-3,3'-diyl)bis(4,4,5,5-tetramethyl-1,3,2-dioxaborolane) (0.12 g, 0.20 mmol), 5'-bromo-4,4"-dimethoxy-1,1':3',1"-terphenyl (0.22 g, 0.60 mmol, 3 equiv), tetrakis(triphenylphosphine)palladium(0) (23 mg, 0.020 mmol, 0.10 equiv) and cesium carbonate (0.33 g, 1.0 mmol, 5 equiv) under argon. A mixture of 4:1 1,4-dioxane/water (5 mL, sparged for 1 h with an inert gas) was added to the flask via syringe. The reaction was heated at reflux in a 110° C. oil bath for 36 h. Full conversion was

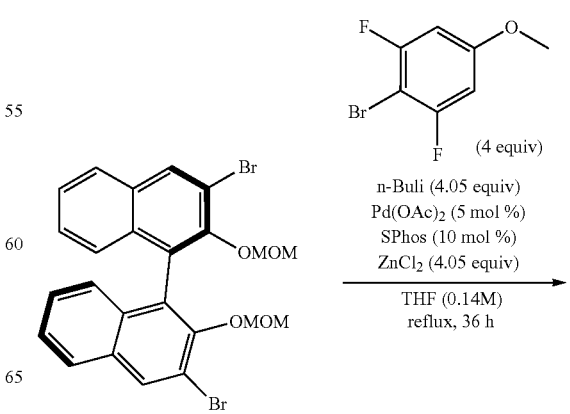

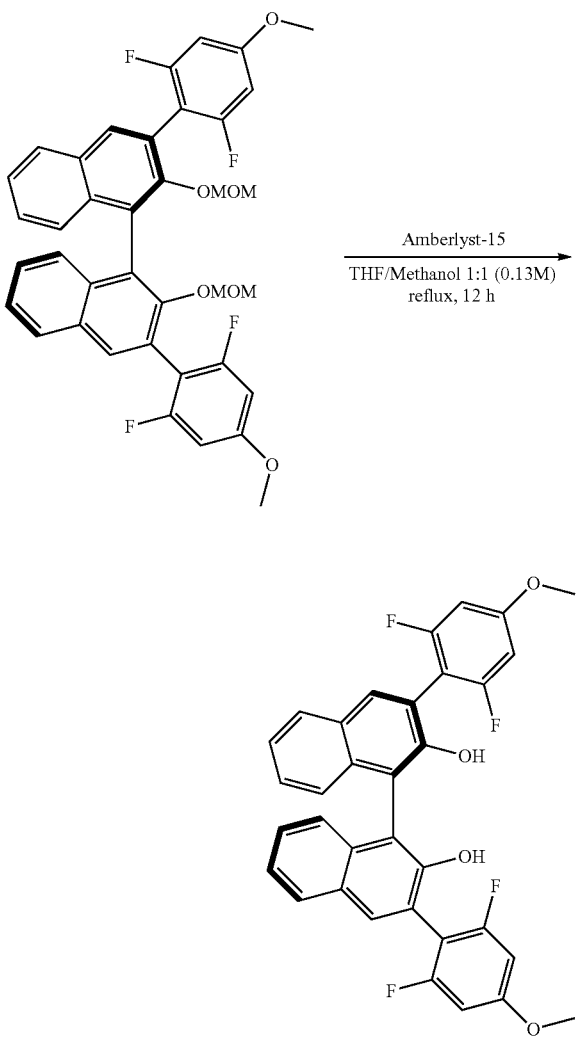

An oven-dried, 50-mL, Schlenk flask equipped with a 2-cm×1-cm football-shaped stir bar was charged with 2-bromo-1,3-difluoro-5-methoxybenzene (3.7 g, 17 mmol, 4 equiv), and THF (30 mL). The solution was cooled to an internal temperature of −78° C., with a dry ice/isopropyl alcohol bath and n-butyllithium (2.0 M, 8.72 mL, 4.05 equiv) was added dropwise over 15 min, keeping the internal temperature below −75° C. Once the addition was complete, the mixture was stirred at −78° C. for 1 h, before fused zinc chloride (2.3 g, 17 mmol, 4 equiv) was added quickly in one portion. The Schlenk flask was purged with argon. To the Schlenk flask was quickly added (R)-3,3'-dibromo-2,2'-dimethoxy-1,1'-binaphthalene (2.2 g, 4.1 mmol), palladium (II) acetate (46 mg, 0.21 mmol, 0.05 equiv), SPhos (170 mg, 0.041 mmol, 0.10 equiv), and the reaction flask was fitted with a reflux condenser and the vessel was purged with argon. The mixture was heated at reflux in a 90° C. oil bath for 36 h. The mixture was cooled to room temperature, and diluted with EtOAc (50 mL) and water (50 mL). The phases were separate and the aqueous phase was extracted with EtOAc (3×50 mL) and the combined organics layers were washed with brine (100 mL), filtered through Celite (5 g), and the filter cake washed with EtOAc (50 mL). The filtrate was dried over sodium sulfate (15 g) for 45 min, filtered and concentrated (30° C., 15 mm Hg). The product was purified by chromatography (silica gel, 5 cm×5 cm, dry load on Celite, hexanes/EtOAc isocratic elution: 60:40 (2 L)) to afford 3.5 g of (R)-3,3'-bis(2,6-difluoro-4-methoxyphenyl)-2,2'-bis(methoxymethoxy)-1,1'-binaphthalene as a yellow solid.

A 100-mL, round-bottomed flask equipped with a reflux condenser, gas adaptor, septum, and a 3.0-cm×1.0-cm rod-shaped stir bar was charged with (R)-3,3'-bis(2,6-difluoro-4-methoxyphenyl)-2,2'-bis(methoxymethoxy)-1,1'-binaphthalene (3.5 g, 5.3 mmol), Amberlyst-15 dry resin (1.00 g), and a mixture of 1:1 THF/methanol (40 mL). The mixture was heated at reflux in an 80° C. oil bath for 9 h. Full conversion was assessed by TLC ($R_f$=0.43 (hexanes/EtOAc, 7:3) [UV]). The mixture was cooled to room temperature, diluted with EtOAc (25 mL) and filtered through Celite (5 g), the filter cake was washed with EtOAc (50 mL), and concentrated (30° C., 15 mm Hg). The product was purified by chromatography (silica gel, 5 cm×22 cm, dry load on Celite, 50 mL fractions, hexanes/EtOAc gradient elution: 85:15 (250 mL) to 80:20 (500 mL) to 75:25 (500 mL) to 70:30 (1 L)) to afford 2.2 g of the title compound as a yellow solid which was further purified by precipitation from a mixture of 20:1 pentane/dichloromethane 3 times, collected by vacuum filtration and washed with ice cold pentane. The solid was then recrystallized form a mixture of 5:1 boiling hexanes/diethyl ether (10 mL) to afford 1.54 g (66%) of the title compound as a white solid.

Data for S16: $^1$H NMR: (500 MHz, CDCl$_3$) 7.99 (s, 2H), 7.90 (d, J=7.4 Hz, 2H), 7.45-7.32 (m, 4H), 7.24 (s, 2H), 6.59 (d, J=9.3 Hz, 4H), 5.23 (s, 2H), 3.84 (s, 6H). $^{13}$C NMR: (126 MHz, CDCl$_3$) 162.60 (dd, J=10.4, 3.9 Hz), 160.98 (t, J=13.9 Hz), 160.64 (dd, J=10.4, 3.9 Hz), 151.69, 134.04, 133.90, 129.47, 128.75, 124.51, 124.35, 119.18, 111.88, 107.38 (t, J=21.3 Hz), 98.06 (dt, J=25.4, 4.6 Hz), 55.05. $^{19}$F NMR: (376.5 MHz, CDCl3) −111.15−−111.27 (m), −111.33−−111.44 (m). HRMS: (ESI+, TOF) calcd for C34H23O4F4 (M+1) 571.1532, found: 571.1550. TLC: $R_f$=0.43 (hexanes/EtOAc, 7:3) [UV].

Preparation of (R)-3,3'-Bis(4-cyclohexylphenyl)-5,5',6,6',7,7',8,8'-octahydro-[1,1'-binaphthalene]-2,2'-diol (S17)

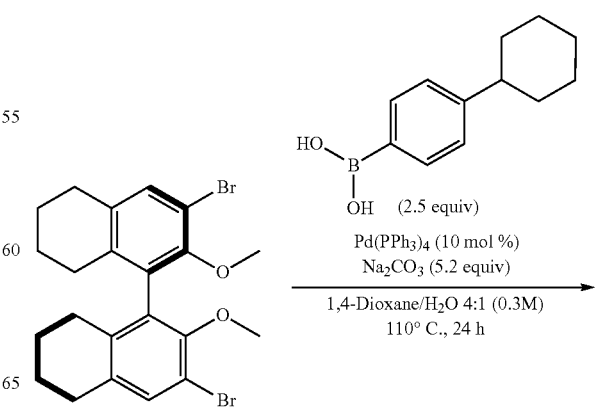

-continued

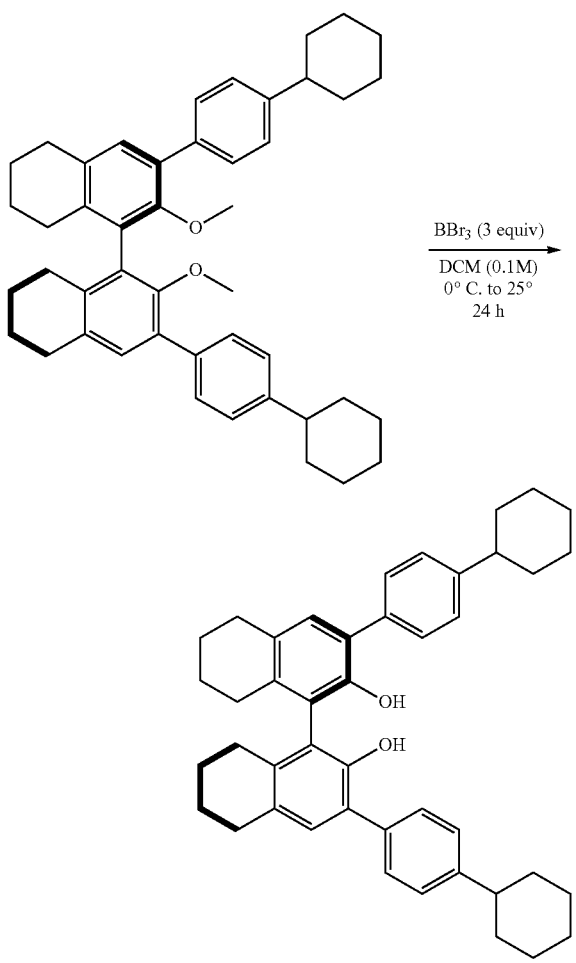

A 25-mL, round-bottomed flask equipped with a 2.0×1.0 cm football shaped stir bar, reflux condenser and gas adaptor was charged with sodium carbonate (1.15 g, 10.8 mmol, 5.2 equiv), 4-cyclohexylphenyl boronic acid (1.06 g, 5.21 mmol, 2.5 equiv), (R)-3,3'-dibromo-2,2'-dimethoxy-5,5',6,6',7,7',8,8'-octahydro-1,1'-binaphthalene (1.00 g, 2.08 mmol), and Pd(PPh$_3$)$_4$ (0.241 g, 0.208 mmol, 10 mol %). The atmosphere was evacuated and refilled with nitrogen 5 times. Next a 4:1 mixture of 1,4-dioxane/H$_2$O (8.75 mL, 0.3 M, sparged with inert atmosphere 1 h) was added via syringe. The mixture was heated at reflux in a 110° C. oil bath for 24 h. Full conversion was assessed by TLC (R$_f$=0.82 (hexanes/EtOAc, 8:2) [UV]). The reaction mixture was cooled to room temperature and dissolved in EtOAc (50 mL) and a sat. aq. solution of ammonium chloride (30 mL) was added forming a suspension which was filtered through Celite (8 g), and the filter cake was washed with EtOAc (30 mL), The phases were separated and the aqueous phase was further extracted with EtOAc (2×50 mL). The combined organic layers were washed with H$_2$O (35 mL), brine (35 mL), and dried over sodium sulfate for 35 min, filtered, rinsed with EtOAc (30 mL), and concentrated under reduced pressure (30° C., 15 mm Hg). The product was purified by chromatography (silica gel, 5 cm×15 cm, dry load on Celite, 50 mL fractions, hexanes/EtOAc gradient elution: 100:0 (500 mL), 99:1 (250 mL), 98:2 (750 mL), 97:3 (750)) to afford 1.052 g of the title compound as a pale yellow solid.

The resulting solid was transferred to an oven dried 25-mL, round-bottomed flask equipped with a 2.0×1.0 cm football shaped stir bar, gas inlet, and septum. The flask was evacuated and backfilled three times with argon. Dichloromethane (25 mL) was added to the flask, and the solution was cooled to 0° C. using an ice bath. A separate flame-dried 10 mL round-bottomed flask equipped with a 2.0×1.0 cm football shaped stir bar, gas inlet, and septum was charged with dichloromethane (5.0 mL) and cooled to −78° C. using a dry ice-isopropyl alcohol bath. To the flask containing only dichloromethane, boron tribromide (0.466 mL, 4.93 mmol, 3 equiv) added dropwise. Upon complete addition, this solution was allowed to warm to room temperature for 1 h and was added dropwise to the solution of substrate, maintaining an internal temperature below 1° C. The reaction mixture was allowed to warm to room temperature and stirred for 12 h. Full conversion was assessed by TLC (R$_f$=0.44 (hexanes/EtOAc, 9:1) [UV]). The reaction mixture was cooled to 0° C. quenched by slow dropwise addition of ice cold water (10 mL). The phases were separated and the aqueous layer was extracted with dichloromethane (3×25 mL), the combined organic layers were washed with brine (25 mL), dried over sodium sulfate for 20 min, filtered, rinsed with dichloromethane (30 mL), and concentrated under reduced pressure (30° C., 15 mm Hg). The product was purified by chromatography (silica gel, 4 cm×15 cm, dry load on Celite, 50 mL fractions, hexanes/EtOAc gradient elution: 97:3 (250 mL), 95:5 (1 L)) to afford 0.911 g (72% yield) of the title compound as a white solid.

Data for S17: $^1$H NMR: (500 MHz, CDCl$_3$) 7.35 (d, J=8.4 Hz, 4H), 7.28 (d, J=7.9 Hz, 4H), 7.15 (s, 2H), 4.92 (s, 2H), 2.80 (t, J=6.3 Hz, 4H), 2.55 (tt, J=11.5, 3.4 Hz, 2H), 2.41 (dt, J=17.3, 6.3 Hz, 2H), 2.25 (dt, J=17.3, 6.3 Hz, 2H), 1.99-1.82 (m, 8H), 1.82-1.67 (m, 10H), 1.52-1.36 (m, 8H), 1.33-1.22 (m, 2H). $^{13}$C NMR: (126 MHz, CDCl$_3$) 147.89 (s, 2C), 146.81 (s, 2C), 136.14 (s, 2C), 135.17 (s, 2C), 131.46 (s, 2C), 129.94 (s, 2C), 128.93 (s, 4C), 126.78 (s, 4C), 126.78 (s, 2C), 125.86 (s, 2C), 120.77 (s, 2C), 44.23 (s, 2C), 34.34 (s, 4C), 29.16 (s, 2C), 27.04 (s, 2C), 26.83 (s, 4C), 26.10 (s, 2C), 23.00 (s, 2C), 23.98 (s, 2C). HRMS: (ESI$^+$, TOF) calcd for C$_{44}$H$_{51}$O$_2$(M$^{+1}$): 611.3889, found: 611.3892. TLC: R$_f$=0.44 (hexanes:EtOAc, 9:1) [UV].

Preparation of (R)-3,3'-Bis(2,6-dimethoxyphenyl)-[1,1'-binaphthalene]-2,2'-diol (S18)

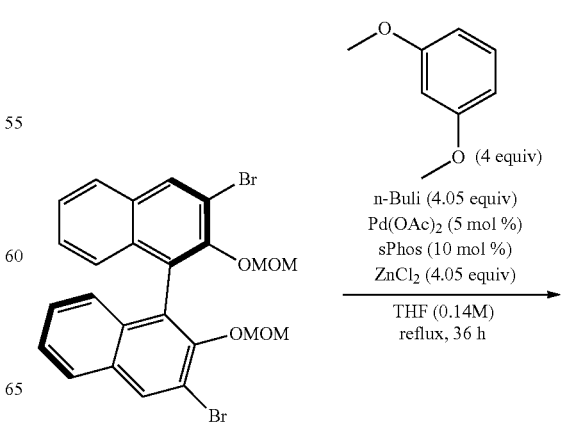

-continued

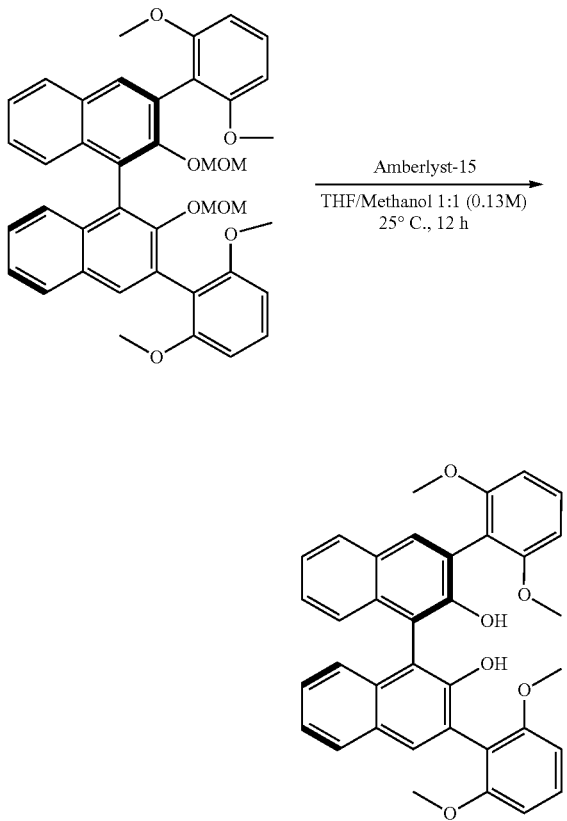

An oven-dried, 50-mL, Schlenk flask equipped with a 2-cm×1-cm football-shaped stir bar was charged with 1,3-dimethoxybenzene (1.04 g, 7.52 mmol, 4 equiv) and THF (13.7 mL). The flask was evacuated and placed under argon 3 times. The solution was cooled to an internal temperature of −78° C., with a dry ice/isopropyl alcohol bath n-butyllithium (2 M, 4 mL, 4.05 equiv) was added dropwise over 5 min. Once the addition was complete, the mixture was stirred for 35 min before fused zinc chloride (1.02 g, 7.52 mmol, 4 equiv) was added quickly in one portion. The Schlenk flask was purged with argon, and the reaction mixture was allowed to warm to room temperature over 1 h. To the Schlenk flask was quickly added (R)-3,3′-dibromo-2,2′-dimethoxy-1,1′-binaphthalene (1.00 g, 1.88 mmol), palladium(II) acetate (22 mg, 0.094 mmol, 0.05 equiv), SPhos (77 mg, 0.188 mmol, 0.10 equiv), and the reaction flask was fitted with a reflux condenser and gas adaptor, then the reaction vessel was purged with argon. The mixture was heated at reflux in a 90° C. oil bath for 36 h. Full conversion was assessed by TLC($R_f$=0.32, (hexanes/EtOAc, 7:3) [UV]). The mixture was cooled to room temperature, diluted with sat. aq. ammonium chloride (25 mL), dichloromethane (50 mL) and water (50 mL). The phases were separated and the aqueous phase was extracted with dichloromethane (3×50 mL) and the combined organics were washed with brine (100 mL), dried over sodium sulfate (10 g) for 45 min, filtered, rinsed with dichloromethane (50 mL) and concentrated (30° C., 15 mm Hg) to afford 1.52 g of crude (R)-3,3′-bis(2,6-dimethoxyphenyl)-2,2′-bis(methoxymethoxy)-1,1′-binaphthalene. The product was purified by chromatography (silica gel, 4 cm×22 cm, dry load on Celite, 50 mL fractions, hexanes/EtOAc gradient elution: 85:15 (250 mL) to 82.5:17.5 (500 mL) to 80:20 (1 L)) to afford 1.047 g of (R)-3,3′-bis(2,6-dimethoxyphenyl)-2,2′-bis(methoxymethoxy)-1,1′-binaphthalene as a white solid.

A flame-dried, 100-mL, round-bottomed flask equipped with a reflux condenser, gas adaptor, septum, and a 3-cm×1-cm rod-shaped stir bar was charged with the protected intermediate (1.047 g), Amberlyst-15 dry resin (650 mg), and a mixture of THF/methanol, 1:1 (40 mL). The mixture was heated at reflux in an 80° C. oil bath for 9 h. Full conversion was assessed by TLC($R_f$=0.11, (hexanes/EtOAc, 7:3) [UV]). The mixture was cooled to room temperature, diluted with EtOAc (25 mL), filtered through Celite (5 g), the filter cake was washed with EtOAc (50 mL), and the filtrate concentrated under reduced pressure (30° C., 15 mm Hg). The product was purified by chromatography (silica gel, 5 cm×27 cm, dry load on Celite, 50 mL fractions, hexanes/EtOAc gradient elution: 85:15 (250 mL, discarded) to 80:20 (500 mL) to 75:25 (500 mL) to 70:30 (1 L)) to afford 0.732 g of the title compound as a white solid, which was further purified by recrystallization by hot/cold crystallization from a mixture of 7:1 ethanol/chloroform (4 mL) to afford 0.697 g (64%) of the title compound as a white solid.

Data for S18: $^1$H NMR: (500 MHz, CDCl$_3$) 7.86 (d, J=7.9 Hz, 4H), 7.38-7.27 (m, 8H), 6.70 (dd, J=8.4, 1.3 Hz, 4H), 5.29 (s, 2H), 3.76 (d, J=21.5 Hz, 12H). $^{13}$C NMR: (126 MHz, CDCl$_3$) 158.52 (s, 2C), 158.39 (s, 2C), 151.35 (s, 2C), 133.88 (s, 2C), 132.61 (s, 2C), 129.64 (s, 2C), 129.37 (s, 2C), 128.46 (s, 2C), 126.60 (s, 2C), 124.85 (s, 2C), 123.81 (s, 2C), 123.54 (s, 2C), 115.07 (s, 2C), 112.73 (s, 2C), 104.52 (s, 4C), 56,30 (s, 2C), 56.14 (s, 2C). HRMS: (ESI+, TOF) calcd for C36H31O6 (M+1) 559.2121, found: 559.2131. TLC: $R_f$=0.11 (hexanes/EtOAc, 7:3) [UV].

Preparation of (R)-3,3′-Bis(3-(naphthalen-2-yl)phenyl)-[1,1′-binaphthalene]-2,2′-diol (S19)

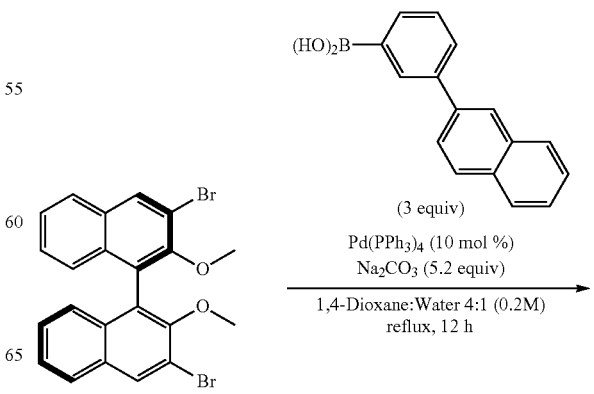

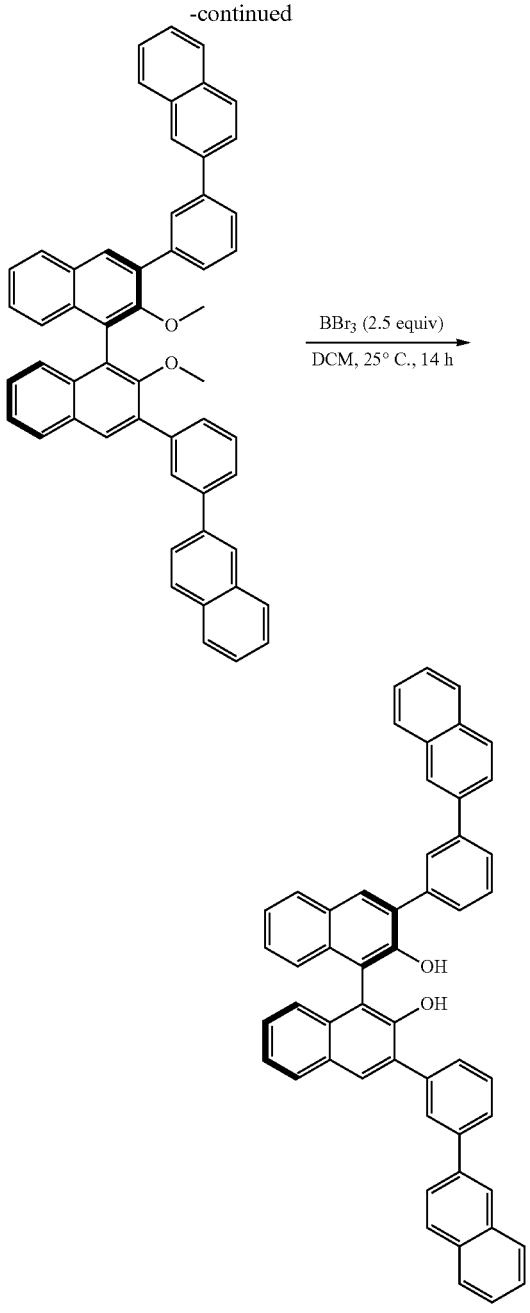

A flame-dried, 25-mL, round-bottomed flask equipped with a reflux condenser, 0.75-cm×1.5-cm stir bar, and a gas adapter was charged with (R)-3,3'-dibromo-2,2'-dimethoxy-1,1'-binaphthalene (944 mg, 2 mmol), sodium carbonate (1.1 g, 10.4 mmol, 5.2 equiv), (3-(naphthalen-2-yl)phenyl)boronic acid (1.5 g, 3 equiv, 6 mmol), and the flask was evacuated and backfilled with argon 3 times. A mixture of 4:1 1,4-dioxane/water (5 mL, sparged for 0.5 h with argon) and tetrakis(triphenylphosphine)palladium(0) (231 mg, 0.2 mmol, 0.10 equiv) were added to the flask, which was rinsed with 5 mL additional 4:1 1,4-dioxane/water. The mixture was heated at reflux in an 80° C. oil bath for 12 h, monitoring the progress by 1 H NMR. The mixture was cooled to room temperature, diluted with dichloromethane (30 mL) and water, (30 mL), and transferred to a 125-mL, separatory funnel. The aqueous layer was extracted with dichloromethane (3×20 mL), the combined organic layers were dried over sodium sulfate (10 g), filtered, and concentrated (30° C., 15 mm Hg). The concentrate was then dissolved dichloromethane (10 mL) and filtered through a plug silica gel (15 g), rinsing with dichloromethane (300 mL), and concentrated (30° C., 15 mm Hg) to afford 1.2 g of crude (R)-2,2'-dimethoxy-3,3'-bis(3-(naphthalen-2-yl)phenyl)-1,1'-binaphthalene. A flame-dried, 250-mL, round-bottomed flask equipped with a side-arm gas adapter was charged with crude (R)-2,2'-dimethoxy-3,3'-bis(3-(naphthalen-2-yl)phenyl)-1,1'-binaphthalene (1.2 g, 1.67 mmol), and dichloromethane (40 mL).

A flame-dried, 25-mL, Schlenk flask equipped with a 0.75-cm×1.5-cm stir bar was charged with dichloromethane (7 mL) and cooled to an internal temperature of −77° C., in a dry ice/isopropyl alcohol bath for 30 min. Boron tribromide (1.75 g, 7 mmol, 2.5 equiv) was added dropwise over 5 min. Once the addition was complete, the solution was allowed to warm to room temperature. The 250-mL, round-bottomed flask was then cooled to an internal temperature of 0° C., in brine/ice bath and the 1 M boron tribromide solution was added dropwise over 10 min. The mixture was allowed to warm to room temperature over 14 h. Full conversion was assessed by $^1$H NMR. The mixture was cooled to an internal temperature of 0° C., in an ice bath and quenched with addition of water (40 mL). The phases were separated and the aqueous layer was extracted with dichloromethane (3×40 mL). The combined organic layers were dried over sodium sulfate (10 g), filtered, rinsed with dichloromethane (40 mL), and concentrated under reduced pressure (30° C., 15 mm Hg) to afford a yellow foam. The product was purified by recrystallization from refluxing chloroform (20 mL), which was allowed to cool to room temperature over 16 h, and then placed in a −20° C. freezer for 16 h. The resulting crystals were collected by vacuum filtration, and washed with cold chloroform (10 mL) to afford 1.08 g (78%) of the title compound as a white solid.

Data for S19: $^1$H NMR: (500 MHz, CDCl$_3$) δ 8.19-8.11 (m, 6H), 7.99-7.75 (m, 14H), 7.62 (t, J=7.7 Hz, 2H), 7.50 (tt, J=6.9, 5.1 Hz, 4H), 7.43 (ddd, J=8.1, 6.7, 1.3 Hz, 2H), 7.36 (ddd, J=8.2, 6.7, 1.3 Hz, 2H), 7.29 (dd, J=8.4, 1.2 Hz, 2H), 5.48 (s, 2H). $^{13}$C NMR: (126 MHz, CDCl$_3$) δ 150.47, 141.67, 138.59, 138.30, 133.92, 133.30, 132.93, 131.80, 130.83, 129.76, 129.25, 129.05, 128.86, 128.77, 128.73, 128.48, 127.89, 127.75, 127.11, 126.56, 126.24, 126.22, 125.90, 124.70, 124.57, 112.66. HRMS: (ESI$^+$, TOF) calcd for $C_{52}H_{35}O_2(M^{+1})$: 691.2637, found: 691.2635.

Preparation of (R)-3,3'-Bis(4'-(tert-butyl)-3,5-diisopropyl-[1,1'-biphenyl]-4-yl)-[1,1'-binaphthalene]-2,2'-diol (S20)

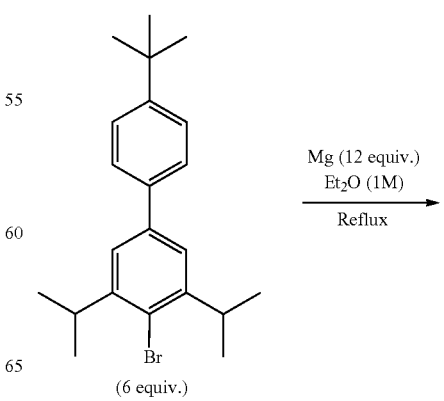

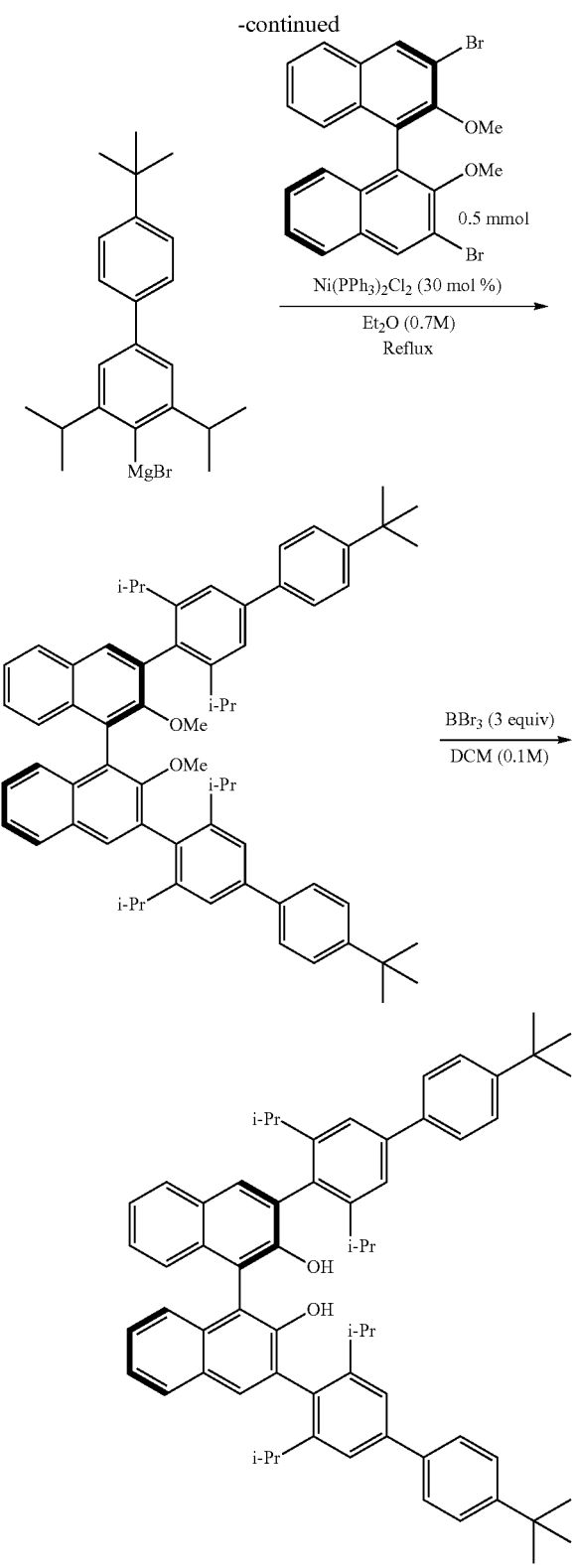

A flame-dried, 25-mL, round-bottomed flask equipped with a 3.0-cm×1.0-cm rod-shaped stir bar, reflux condenser, gas adaptor, and septum was charged with mechanically activated magnesium turnings (161 mg, 6.61 mmol, 12 equiv) ground with a mortar and pestle for 10 min and the turnings were covered by minimal diethyl ether (1.5 mL). A 100-mL, round-bottomed flask was charged with (R)-4-bromo-4'-(tert-butyl)-3,5-diisopropyl-1,1'-biphenyl (1.23 g, 3.30 mmol, 6 equiv) and diethyl ether (8 mL) to form a homogeneous solution. A small portion of the resulting bromide solution (2 mL) was added dropwise to the magnesium turnings by cannula transfer. One drop of 1,2-dibromoethane was added to the mixture containing the magnesium and was gently heated with an oil bath at 35° C. for 5 min to allow for initiation of the grignard. The remaining bromide solution (6 mL) was added dropwise by cannula transfer to the 35° C. reaction mixture. The transfer flask was washed with diethyl ether (3×2 mL) and transferred by cannula. The reaction mixture was brought to reflux for 24 h and the consumption of the bromide starting material was monitored by GCMS to confirm complete formation of the consumption of starting bromide.

A 100-mL, two-necked, round-bottomed flask was equipped with a 1.5-cm×1.0-cm football-shaped stir bar, a reflux condenser, gas adaptor, and a septum was charged with (R)-3,3'-dibromo-2,2'-dimethoxy-1,1'-binaphthalene (0.260 g, 0.551 mmol), bis(triphenylphosphine)nickel(II) dichloride (108 mg, 0.30 equiv), and diethyl ether (15 mL), forming a suspension. The Grignard solution was added dropwise to this suspension over 10 min at room temperature. The resulting brown solution was heated at reflux in a 40° C. oil bath for 6 h. The reaction mixture was poured into a vigorously stirred 0° C. solution of 1 N aq. HCl (15 mL) and stirred for 3 min before being transferred to a 250-mL separatory funnel and diluted with water (20 mL) and diethyl ether (30 mL). The aqueous phase was extracted with diethyl ether (3×30 mL). The combined organic layers were washed with brine (50 mL), dried over sodium sulfate (5 g), filtered, rinsed with diethyl ether (30 mL), and concentrated (30° C., 15 mm Hg). The product was purified by chromatography (silica gel, 5 cm×15 cm, dry load on Celite, 50 mL fractions, hexanes/diethyl ether gradient elution: 90:10 (200 mL) to 85:15 (200 mL) to 80:20 (200 mL) to 75:25 (300 mL)) to afford 0.994 g of (R)-3,3'-bis(4'-(tert-butyl)-3,5-diisopropyl-[1,1'-biphenyl]-4-yl)-2,2'-dimethoxy-1,1'-binaphthalene as a yellow solid. A flame-dried, 100-mL, round-bottomed flask equipped with a 1.5-cm×1.0-cm stir bar, gas adaptor, and septum was charged with (R)-3,3'-bis(4'-(tert-butyl)-3,5-diisopropyl-[1,1'-biphenyl]-4-yl)-2,2'-dimethoxy-1,1'-binaphthalene (0.994 g, 1.1 mmol), and dichloromethane (20 mL).

A flame-dried, 10-mL, Schlenk flask equipped with a 0.75-cm×1.5-cm stir bar was charged with dichloromethane (3.3 mL) and cooled to an internal temperature of −77° C., in a dry ice/isopropyl alcohol bath for 0.5 h. Boron tribromide (0.31 mL, 3.3 mmol, 3 equiv) was added dropwise over 5 min. Once the addition was complete, the solution was allowed to warm to room temperature. The solution of (R)-3,3'-bis(4'-(tert-butyl)-3,5-diisopropyl-[1,1'-biphenyl]-4-yl)-2,2'-dimethoxy-1,1'-binaphthalene was cooled to an internal temperature of 0° C., in an ice bath. The 1 M boron tribromide solution was added dropwise at 0° C. over 5 min. Once the addition was complete, the mixture was allowed to warm to room temperature over 12 h. Full conversion was assessed by TLC($R_f$=0.63 (hexanes/Et$_2$O, 9:1) [UV]). The mixture was quenched by the slow dropwise addition of water (20 mL) over 5 min, phases were separated, and the aqueous layer was extracted with dichloromethane (3×25 mL). The combined organic layers were washed with brine (30 mL), dried over sodium sulfate (5 g) for 30 min, filtered, rinsed with dichloromethane (30 mL) and concentrated (30° C., 15 mm Hg) to afford a yellow solid. The product was purified by chromatography (silica gel, 4 cm×15 cm, dry load on Celite, 25 mL fractions, hexanes/diethyl ether isocratic elution: 99:1 (1 L)) to afford 620 mg of the title compound as a white solid, which was further purified by recrystallization from hot methanol to afford 281 mg (58%) of the title compound as a white solid.

Data for S20: $^1$H NMR: (500 MHz, CDCl$_3$) 7.91 (d, J=8.0 Hz, 2H), 7.81 (s, 2H), 7.60 (d, J=8.4 Hz, 4H), 7.52-7.46 (m, 8H), 7.43-7.39 (m, 2H), 7.37-7.28 (m, 4H), 4.97 (s, 2H), 2.91 (hept, J=7.0 Hz, 2H), 2.76 (hept, J=6.8 Hz, 2H), 1.38 (s, 18H), 1.25 (d, J=6.7 Hz, 6H), 1.17 (d, J=6.9 Hz, 6H), 1.14 (d, J=6.8 Hz, 6H), 1.09 (d, J=6.9 Hz, 6H). 13C NMR: (126 MHz, CDCl$_3$) 150.64 (s, 2C), 150.24 (s, 2C), 148.37 (s, 2C), 148.30 (s, 2C), 141.62 (s, 2C), 138.98 (s, 4C), 133.48 (s, 2C), 132.05 (s, 2C), 130.82 (s, 2C), 129.13 (s, 2C), 128.86 (s, 2C), 128.35 (s, 2C), 126.99 (s, 4C), 126.87 (s, 2C), 125.66 (s, 2C), 124.50 (s, 2C), 123.98 (s, 2C), 122.14 (s, 2C), 122.09 (s, 2C), 112.95 (s, 2C), 34.58 (s, 2C), 31.43 (s, 2C), 31.03 (s, 6C), 31.00 (s, 2C), 24.35 (s, 2C), 24.29 (s, 2C), 23.92 (s, 2C), 23.75 (s, 2C). HRMS: (ESI$^+$, TOF) calcd for C$_{64}$H$_{71}$O$_2$(M$^{+1}$): 871.5454, found: 871.5481. TLC: R$_f$=0.63 (hexanes/Et$_2$O, 9:1)[UV].

Preparation of (R)-3,3'-Bis(2-(naphthalen-2-yl)phenyl)-5,5',6,6',7,7',8,8'-octahydro-[1,1'-binaphthalene]-2,2'-diol (S21)

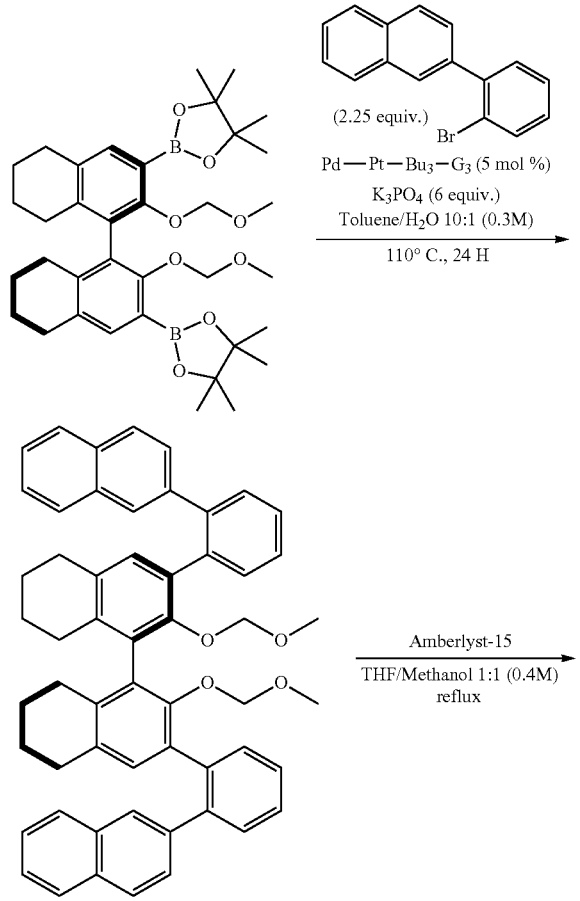

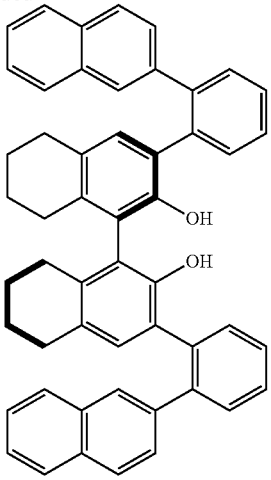

A 10-mL, round-bottomed flask equipped with a 1.5-cm× 1.0-cm rod-shaped stir bar, reflux condenser, gas adaptor, and septum was charged with tribasic potassium phosphate (1.61 g, 7.56 mmol, 6 equiv), 2-(2-bromophenyl)naphthalene (0.800 g, 2.8 mmol, 1.26 equiv), Pd-P(t-Bus)-G3 (50.5 mg, 0.088 mmol, 0.07 equiv), 2,2'-(2,2'-bis(methoxymethoxy)-5,5',6,6',7,7',8,8'-octahydro-[1,1'-binaphthalene]-3,3'-diyl)bis(4,4,5,5-tetramethyl-1,3,2-dioxaborolane) (0.800, 1.22 mmol), and the flask was evacuated and backfilled with argon 3 times. Toluene (5 mL, sparged 1 h with argon gas) and water (0.05 mL, sparged 1 h with an inert gas) were added via syringe. The mixture was heated at reflux in a 110° C. oil bath for 24 h. The mixture was cooled to room temperature, diluted with water (35 mL) and EtOAc (30 mL); the aqueous layer extracted with EtOAc (3×5 mL). The combined organic layers were dried over sodium sulfate (5 g), filtered, rinsed with EtOAc (30 mL) and concentrated under reduced pressure (30° C., 15 mm Hg) to afford an orange solid. The product was purified by chromatography (silica gel, 5 cm×12 cm, dry load on Celite, 25 mL fractions, hexanes/EtOAc gradient elution: 95:5 (250 mL) to 92.5:7.5 (250 mL) to 90:10 (500 mL)) to afford 0.932 g of (R)-2,2'-bis(methoxymethoxy)-3,3'-bis(2-(naphthalen-2-yl)phenyl)-5,5',6,6',7,7',8,8'-octahydro-1,1'-binaphthalene as a yellow solid.

A 50-mL, round-bottomed flask equipped with a 3.0-cm× 1.0-cm rod-shaped stir bar, reflux condenser, and a gas adaptor was charged with (R)-2,2'-bis(methoxymethoxy)-3,3'-bis(2-(naphthalen-2-yl)phenyl)-5,5',6,6',7,7',8,8'-octahydro-1,1'-binaphthalene (0.932 g, 1.18 mmol), a mixture of 1:1 THF/methanol (20 mL), and Amberlyst-15 dry resin (1.00 g). The mixture was heated at reflux in a 67° C. oil bath for 13 h. The mixture was diluted with EtOAc (50 mL), filtered through Celite (5 g), the filter cake was washed with EtOAc (50 mL), and concentrated to afford a yellow solid. The product was purified by chromatography (silica gel, 5 cm×10 cm, dry load on Celite, 50 mL fractions, hexanes/EtOAc isocratic elution: 92.5:7.5 (2 L)) to afford 0.699 g (79%) of the title compound as a beige solid.

Data for S21: $^1$H NMR: (500 MHz, CDCl$_3$) 7.80-7.71 (m, 2H), 7.68 (d, J=6.7 Hz, 4H), 7.61 (d, J=8.5 Hz, 2H), 7.51 (d, J=7.3 Hz, 2H), 7.48-7.33 (m, 10H), 7.28 (s, 2H), 6.91 (s, 2H), 4.14 (s, 4H), 2.55 (t, J=5.9 Hz, 4H), 1.73-1.49 (m, 4H), 1.45-1.00 (m, 8H). $^{13}$C NMR: (126 MHz, CDCl$_3$) 147.94 (s, 2C), 141.89 (s, 2C), 139.77 (s, 2C), 137.07 (s, 2C), 136.60 (s, 2C), 133.49 (s, 2C), 132.37 (s, 2C), 132.21 (s, 2C), 131.38 (s, 2C), 130.39 (s, 2C), 129.59 (s, 2C), 128.16 (s, 2C), 128.08 (s, 2C), 128.00 (s, 2C), 127.89 (s, 2C), 127.69 (s, 2C), 127.56 (s, 2C), 127.08 (s, 2C), 126.22 (s, 2C), 125.91 (s, 2C), 125.70 (s, 2C), 120.09 (s, 2C), 29.23 (s, 2C), 26.77 (s, 2C), 23.06 (s, 2C), 22.91 (s, 2C). HRMS: (ESI+, TOF) calcd for C52H43O2 (M+1): 699.3263, found: 699.3259. TLC: R$_f$=0.021 (hexanes/EtOAc, 9:1) [UV].

Preparation of (R)-3,3'-Bis(3-(methoxymethyl)phenyl)-4a,5,5',6,6',7,7',8,8'-octahydro-[1,1'-binaphthalene]-2,2'-diol (S22)

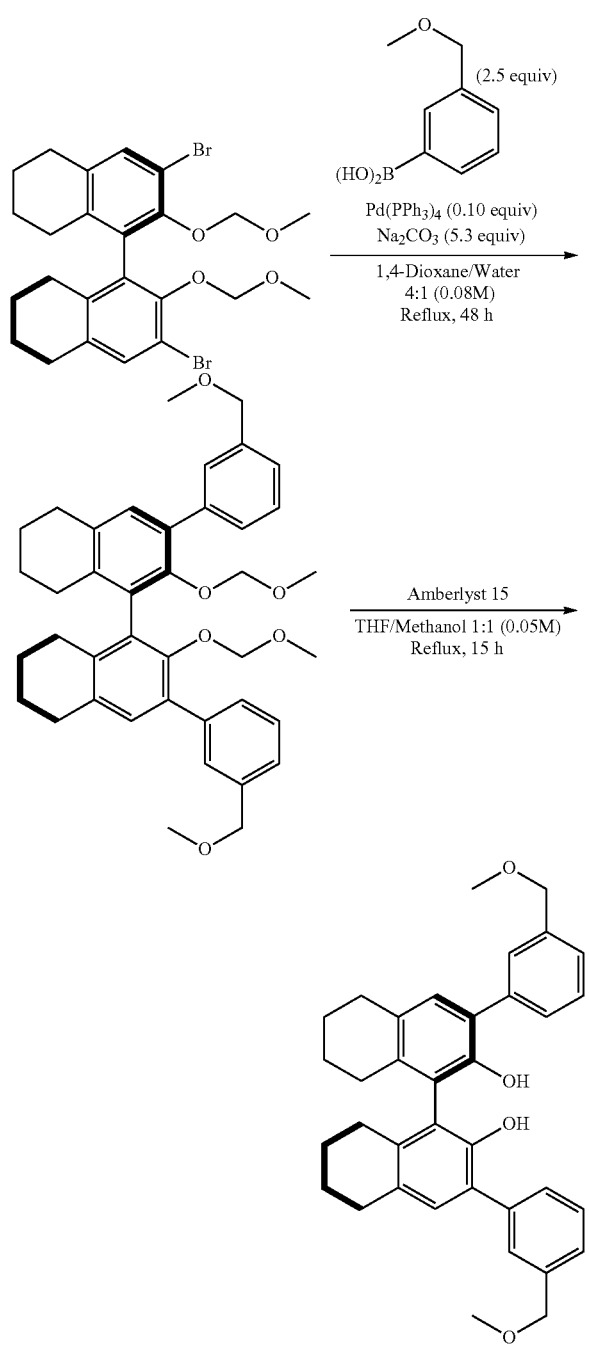

An oven-dried, 100-mL, round bottomed flask equipped with a 2.0-cm×1.0-cm football-shaped stir bar, reflux condenser and gas inlet adapter was added (R)-3,3'-dibromo-2,2'-bis(methoxymethoxy)-5,5',6,6',7,7',8,8'-octahydro-1,1'-dinaphthalene (2.30 g, 4.26 mmol), sodium carbonate (2.43 g, 22.6 mmol, 5.3 equiv) and (3-(methoxymethyl)phenyl)boronic acid (1.77 g, 10.6 mmol, 2.5 equiv) tetrakis(triphenylphosphine)palladium(0) (0.492 g, 0.426 mmol, 0.10 equiv), and the flask was evacuated and backfilled with argon 3 times. A mixture of 4:1 1,4-dioxane/water (56 mL) (sparged for 1 h with inert atmosphere) was added via syringe. The mixture was heated at reflux in a 110° C. oil bath for 48 h. Full conversion was assessed by TLC (R$_f$=0.18 (hexanes/EtOAc, 9:1) [UV]). The mixture was cooled to room temperature, diluted with EtOAc (20 mL) and sat. aq. ammonium chloride (20 mL). The phases were partitioned, and the aqueous phase was extracted with EtOAc (3×20 mL). The combined organic layers were washed with brine (20 mL), dried over sodium sulfate (15 g), filtered and concentrated (34° C., 15 mm Hg) to afford 3.9462 g of the crude protected intermediate as a viscous orange oil. The product was purified by chromatography (silica gel, 5 cm×18 cm, dry load on Celite, 50 mL fractions, hexanes/EtOAc gradient elution: 95:5 (500 mL) to 90:10 (500 mL) to 85:15 (500 mL) to 80:20 (1 L)) to afford 2.383 g of (R)-2,2'-bis(methoxymethoxy)-3,3'-bis(3-(methoxymethyl)phenyl)-5,5',6,6',7,7'8,8'-octahydro-1,1'-binaphthalene.

An oven-dried, 250-mL, round-bottomed flask equipped with a 2.5-cm×1.5-cm football-shaped stir bar, reflux condenser, and gas inlet adapter was charged with (R)-2,2'-bis(methoxymethoxy)-3,3'-bis(3-(methoxymethyl)phenyl)-5,5',6,6',7,7'8,8'-octahydro-1,1'-binaphthalene (2.383 g, 3.82 mmol), Amberlyst-15 dry resin (400 mg), and a mixture of 1:1 THF/methanol (70 mL). The mixture was heated at reflux in an 80° C. oil bath for 15 h. Full conversion was assessed by TLC (R$_f$=0.21 (hexanes/EtOAc 4:1) [UV]). The mixture was cooled to room temperature and filtered through Celite (9 g). The filter cake was washed with EtOAc (100 mL), and concentrated under reduced pressure (34° C., 15 mm Hg) to afford 1.963 g of crude (R)-3,3'-bis(3-(methoxymethyl)phenyl)-4a,5,5',6,6',7,7',8,8'-octahydro-[1,1'-binaphthalene]-2,2'-diol. The product was purified by chromatography (silica gel, 5 cm×20 cm, dry load on Celite, 50 mL fractions, hexanes/EtOAc gradient elution: 95:5 (500 mL) to 90:10 (500 mL) to 80:20 (500 mL) to 70:30 (500 mL) to 60:40 (500 mL) to 50:50 (500 mL)) to afford 1.631 g (72% yield over two steps) of the title compound as an off-white solid.

Data for S22: $^1$H NMR: (500 MHz, CDCl$_3$) 7.58 (d, J=1.8 Hz, 2H), 7.53 (dt, J=7.8, 1.5 Hz, 2H), 7.41 (t, J=7.6 Hz, 2H), 7.30 (d, J=7.6 Hz, 2H), 7.16 (s, 2H), 4.91 (s, 2H), 4.51 (s, 4H), 3.41 (s, 6H), 2.80 (t, J=6.3 Hz, 4H), 2.40 (dt, J=17.5, 6.3 Hz, 2H), 2.25 (dt, J=17.4, 6.3 Hz, 2H), 1.82-1.67 (m, 8H). $^{13}$C NMR: (126 MHz, CDCl$_3$) 148.22 (s, 2C), 138.40 (s, 2C), 138.17 (s, 2C), 136.75 (s, 2C), 131.83 (s, 2C), 130.83 (s, 2C), 128.74 (s, 2C), 128.64 (s, 2C), 128.55 (s, 2C), 126.57 (s, 2C), 125.97 (s, 2C), 120.22 (s, 2C), 74.85 (s, 2C), 58.21 (s, 2C), 29.38 (s, 2C), 27.30 (s, 2C), 23.20 (s, 2C), 23.17 (s, 2C). HRMS: (ESI+, TOF) calcd for C36H38O4Na (M+Na): 557.2668, found: 557.2693. TLC: R$_f$=0.21 (hexanes/EtOAc, 4:1) [UV].

Preparation of (R)-3,3'-Bis(3-(methoxymethyl)phenyl)-[1,1'-binaphthalene]-2,2'-diol (S23)

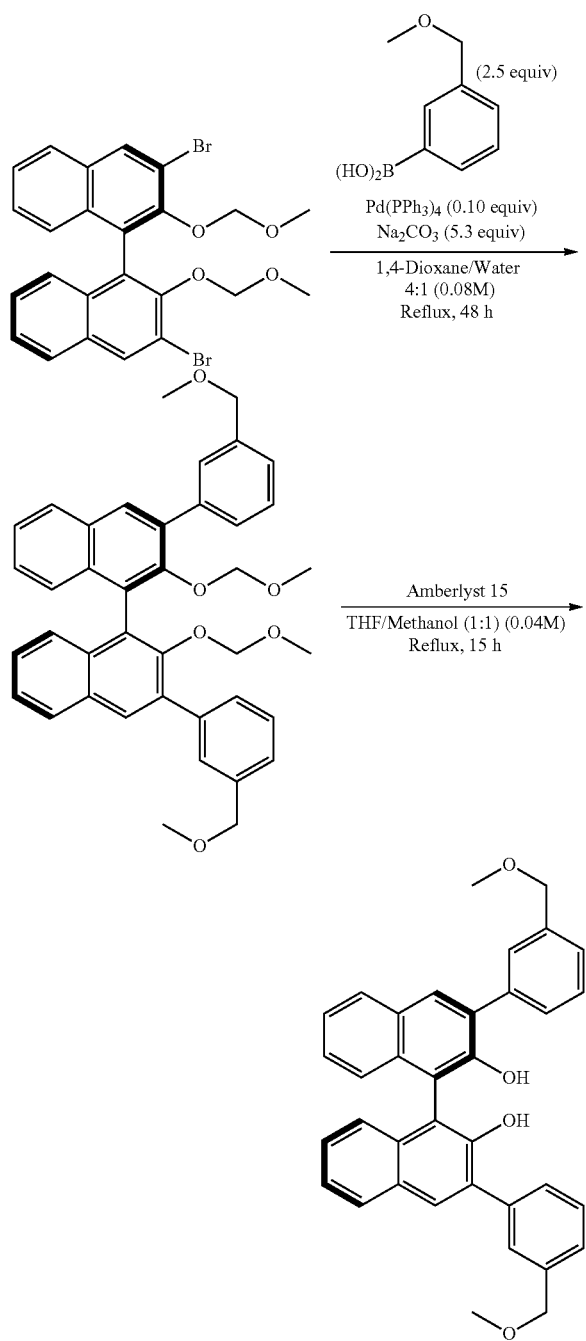

An oven-dried, 100-mL, round-bottomed flask equipped with a 2.0-cm×1.0-cm football-shaped stir bar, reflux condenser and gas inlet adapter was charged with (R)-3,3'-dibromo-2,2'-bis(methoxymethoxy)-1,1'-binaphthalene (2.30 g, 4.32 mmol), sodium carbonate (2.43 g, 22.9 mmol, 5.3 equiv), (3-(methoxymethyl)phenyl) boronic acid (1.79 g, 10.8 mmol, 2.5 equiv), and tetrakis(triphenylphosphine) palladium(0) (0.499 g, 0.43 mmol, 0.10 equiv). The flask was evacuated and backfilled with argon 3 times. A mixture of 1,4-dioxane/water, 4:1 (57 mL) (sparged for 1 h with argon) was added via syringe. The mixture was heated at reflux in a 110° C. oil bath for 48 h. Full conversion was assessed by TLC ($R_f$=0.07 (hexanes/EtOAc, 9:1) [UV]). The mixture was cooled to room temperature, diluted with EtOAc (20 mL) and sat. aq. ammonium chloride (20 mL), and the aqueous phase was extracted with EtOAc (3×20 mL). The combined organic layers were washed with brine (20 mL), dried over sodium sulfate (10 g), filtered, rinsed with EtOAc (10 mL), and concentrated (34° C., 15 mm Hg) to afford 3.599 g of (R)-2,2'-bis(methoxymethoxy)-3,3'-bis(3-(methoxymethyl)phenyl)-1,1'-binaphthalene as a viscous orange oil. The product was purified by chromatography (silica gel, 5 cm×18 cm, dry load on Celite, 50 mL fractions, hexanes/EtOAc gradient elution: 95:5 (500 mL) to 90:10 (500 mL), 85:15 (500 mL) to 80:20 (1 L) to afford 1.592 g of (R)-2,2'-bis(methoxymethyl)-3,3'-bis(3-(methoxymethyl)phenyl-[1,1'-binaphthalene].

An oven-dried, 250-mL, round-bottomed flask equipped with a 3.5-cm×1.5-cm football-shaped stir bar, reflux condenser, and gas inlet adapter was charged with (R)-2,2'-bis(methoxymethyl)-3,3'-bis(3-(methoxymethyl)phenyl-[1,1'-binaphthalene] (1.592 g, 2.59 mmol), Amberlyst-15 dry resin (400 mg), and a mixture of 1:1 THF:methanol (70 mL). The mixture was heated at reflux in an 80° C. oil bath for 15 h. Full conversion was assessed by TLC ($R_f$=0.15 (hexanes/EtOAc, 4:1) [UV]). The reaction mixture was cooled to room temperature and filtered through Celite. The filter cake was washed with EtOAc (100 mL), and concentrated under reduce pressure (34° C., 15 mm Hg) to afford 1.363 g of crude (R)-3,3'-bis(3-(methoxymethyl)phenyl)-[1,1'-binaphthalene]-2,2'-diol. The product was purified by chromatography (silica gel, 5 cm×20 cm, dry load on Celite, 50 mL fractions, hexanes/EtOAc gradient elution: 95:5 (500 mL) to 90:10 (500 mL) to 80:20 (500 mL) to 70:30 (500 mL) to 60:40 (500 mL) to 50:50 (500 mL)) to afford 0.524 g (24%, yield over 2 steps) of the title compound as a light brown solid.

Data for S23: $^1$H NMR: (500 MHz, CDCl$_3$) 8.04 (s, 2H), 7.93 (d, J=8.1 Hz, 2H), 7.72 (s, 2H), 7.67 (d, J=7.7 Hz, 2H), 7.48 (t, J=7.6 Hz, 2H), 7.39 (d, J=7.7 Hz, 4H), 7.33 (t, J=7.7 Hz, 2H), 7.23 (d, J=8.5 Hz, 2H), 5.36 (s, 2H), 4.55 (s, 4H), 3.43 (s, 6H). $^{13}$C NMR: (126 MHz, CDCl$_3$) 150.25 (s, 2C), 138.55 (s, 2C), 137.73 (s, 2C), 133.11 (s, 2C), 131.51 (s, 2C), 130.62 (s, 2C), 129.54 (s, 2C), 129.03 (s, 2C), 129.03 (s, 2C), 128.65 (s, 2C), 128.56 (s, 2C), 127.47 (s, 2C), 127.20 (s, 2C), 124.44 (s, 2C), 124.40 (s, 2C), 112.52 (s, 2C), 74.76 (s, 2C), 58.34 (s, 2C). HRMS:(ESI$^+$, TOF) calcd for C$_{36}$H$_{30}$O$_4$Na (M$^{+Na}$) 549.2042, found: 549.2048. TLC: $R_f$=0.15 (hexanes/EtOAc, 4:1) [UV].

Preparation of (R)-3,3'-Bis(anthracen-9-ylmethyl)-[1,1'-binaphthalene]-2,2'-diol (S24)

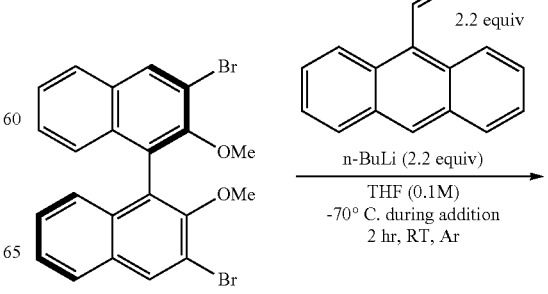

-continued

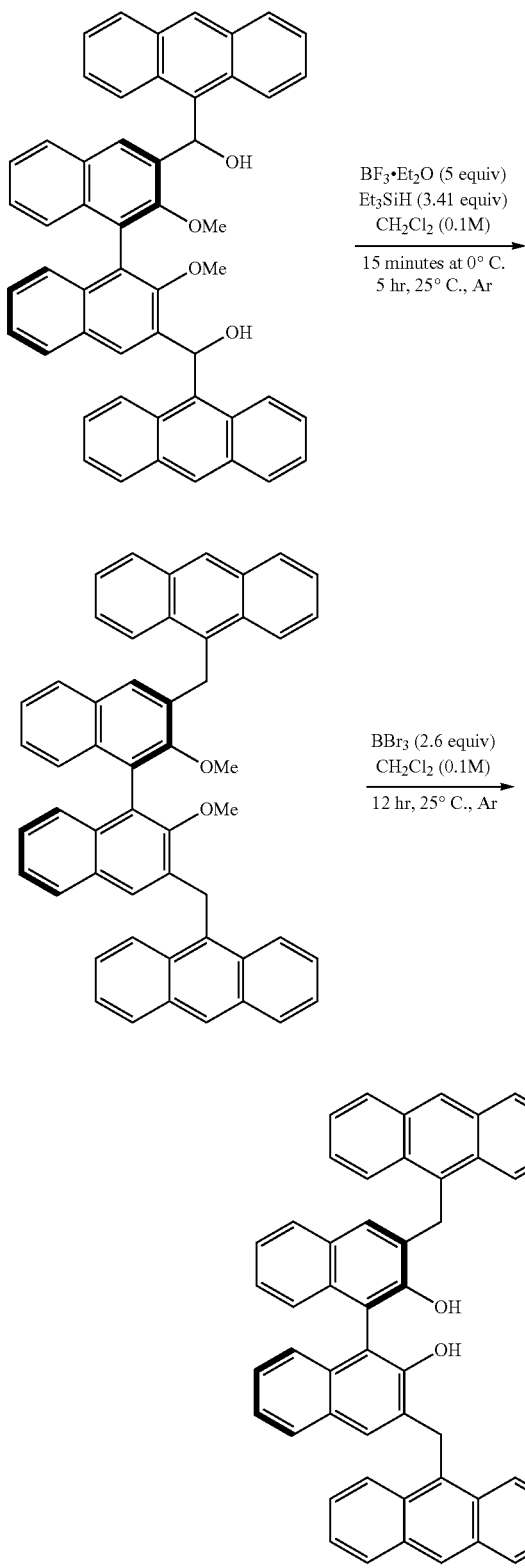

The following procedure were run in the dark, as the products and intermediates are extremely light-sensitive: A flame-dried, 250-mL, round-bottomed flask was charged with (R)-3,3'-dibromo-2,2'-dimethoxy-1,1'-binaphthalene (6.5 g, 14 mmol), and THF (100 mL) to give a light-yellow solution, which was cooled to an internal temperature of −78° C. using a dry ice/isopropyl alcohol bath. After cooling, n-butyllithium (1.92 M, 16 mL, 2.2 equiv) was added dropwise over 20 min, maintaining a temperature below-69° C. and generating a deep red solution. Upon complete addition, the mixture was stirred at −78° C. for 15 min. After the 15 min stir period, 9-anthraldehyde (6.2 g, 30 mmol, 2.2 equiv) was added dropwise, maintaining a temperature below −70° C. Once the addition was complete, the dry ice/isopropyl alcohol bath was removed, and the mixture was allowed to warm to room temperature over 20 h. The mixture turned a dark brown color after 20 h. The mixture was quenched with sat. aq. ammonium chloride (50 mL), and the aqueous layer was extracted with EtOAc (3×30 mL). The combined organic layers were washed with brine (40 mL), dried over sodium sulfate (27 g), filtered, rised with EtOAc (30 mL), and concentrated (53 mm Hg, 34° C.) to afford 12.53 g of crude (R)-(2,2'-dimethoxy-[1,1'-binaphthalene]-3,3'-diyl)bis(anthracen-9-ylmethanol) as a mixture of diastereomers.

A flame-dried, 250-mL, round-bottomed flask equipped with a 2.0-cm×1.0-cm football-shaped stir bar was charged with the crude protected intermediate (12.53 g), dichloromethane (100 mL), and the solution was cooled to 0° C., using an ice bath. Triethylsilane (5.3 g, 47 mmol, 3.4 equiv) was added in one portion, then boron trifluoride etherate (9.8 g, 69 mmol, 5 equiv) was added dropwise over 10 min, forming a dark red color. Upon complete addition, the mixture was stirred for at 0° C. in an ice bath for 3 h. Full conversion was assessed by TLC ($R_f$=0.608 (hexanes/EtOAc, 8:2) [UV]). The mixture was quenched by pouring into a sat. aq. sodium bicarbonate (500 mL), stirred for 1.3 h, and the aqueous layer was extracted with dichloromethane (4×50 mL). The combined, ruby red, organic layers were washed with brine (75 mL), dried over sodium sulfate (22 g), filtered, rinsed with dichloromethane (45 mL) and concentrated under reduced pressure (22 mm Hg, 34° C.) to afford 11.8 g of crude (R)-9,9'-((2,2'-dimethoxy-[1,1'-binaphthalene]-3,3'-diyl)bis(methylene))dianthracene as a red solid. The product was purified by chromatography (silica gel (148.5 g), 5 cm×19 cm, dry load on Celite, 50 mL fractions, hexanes/toluene isocratic elution: 2:3 (1500 mL)) to afford 3.6 g of (R)-9,9'-((2,2'-dimethoxy-[1,1'-binaphthalene]-3,3'-diyl)bis(methylene))dianthracene as a yellow solid.

A flame-dried, 25-mL, round-bottomed flask equipped with a 2.0-cm×1.0-cm, football-shaped stir bar, gas inlet, internal temperature probe, and septum was charged with (R)-9,9'-((2,2'-dimethoxy-[1,1'-binaphthalene]-3,3'-diyl)bis(methylene))dianthracene (0.70 g, 1.01 mmol). The flask was evacuated and backfilled with argon 3 times, and charged with dichloromethane (5.0 mL). The solution was cooled to an internal temperature of 0° C., using a brine/ice bath. A flame-dried, 10-mL, round-bottomed flask equipped with a 2.0-cm×1.0-cm football-shaped stir bar, gas inlet adapter, internal temperature probe, and septum was charged with dichloromethane (5.0 mL) and cooled to an internal temperature of −78° C. using a dry ice/isopropyl alcohol bath. Boron tribromide (656 mg, 2.6 mmol, 2.6 equiv) was added dropwise, maintaining an internal temperature of below −75° C. Once the addition was complete, the dry ice/isopropyl alcohol bath was removed, the solution was allowed to warm to room temperature, and was added dropwise to the solution of substrate, maintaining an internal temperature below 1° C. Once the addition was complete, the mixture was allowed to warm to room temperature over 11 h. Full conversion was assessed by TLC(R$_f$=0.175 (hexanes/EtOAc, 94:6) [UV]). The rest of the procedure was performed in the dark due to the light and heat sensitivity of the title compound. The mixture was quenched by addition of water (50 mL), stirred for 30 min, and the aqueous layer was extracted with dichloromethane (3×5 mL). The combined organic layers were washed with brine (100 mL), dried over sodium sulfate (9 g), filtered, rinsed with dichloromethane (25 mL) and concentrated to afford 1.002 g of red solid. The product was purified by chromatography (silica gel, 4 cm×18 cm, dry load on Celite, 25 mL fractions, hexanes/EtOAc isocratic elution: 94:6 (2 L)) to afford 531.5 mg (79%), after sonicating with pentane (10×25 mL), of the title compound as a pale yellow solid.

Data for S24: $^1$H NMR: (500 MHz, CDCl$_3$) 8.60 (s, 2H), 8.35 (dt, J=6.8, 3.7 Hz, 4H), 8.23-8.09 (m, 4H), 7.64-7.53 (m, 8H), 7.44 (d, J=8.1 Hz, 2H), 7.36-7.19 (m, 6H), 7.11 (s, 2H), 5.67 (s, 2H), 5.29 (s, 4H). $^{13}$C NMR: (126 MHz, CDCl$_3$) 151.36 (s, 2C), 131.98 (s, 2C), 131.77 (s, 2C), 131.24 (s, 2C), 130.88 (s, 2C), 130.04 (s, 2C), 129.72 (s, 2C), 129.44 (s, 2C), 129.22 (s, 2C), 128.13 (s, 2C), 126.77 (s, 4C), 126.07 (2C), 125.09 (s, 2C), 124.87 (s, 2C), 123.90 (s, 2C), 110.56 (s, 2C), 27.91 (s, 2C). HRMS: (ESI$^+$, TOF) calcd for C$_{50}$H$_{35}$O$_2$(M$^{+1}$) 667.2637, found: 667.2634. TLC: R$_f$=0.18 (hexanes/EtOAc, 94:6) [UV].

Preparation of (R)-3,3'-Bis(2-(trifluoromethoxy) phenyl)-[1,1'-binaphthalene]-2,2'-diol (S25)

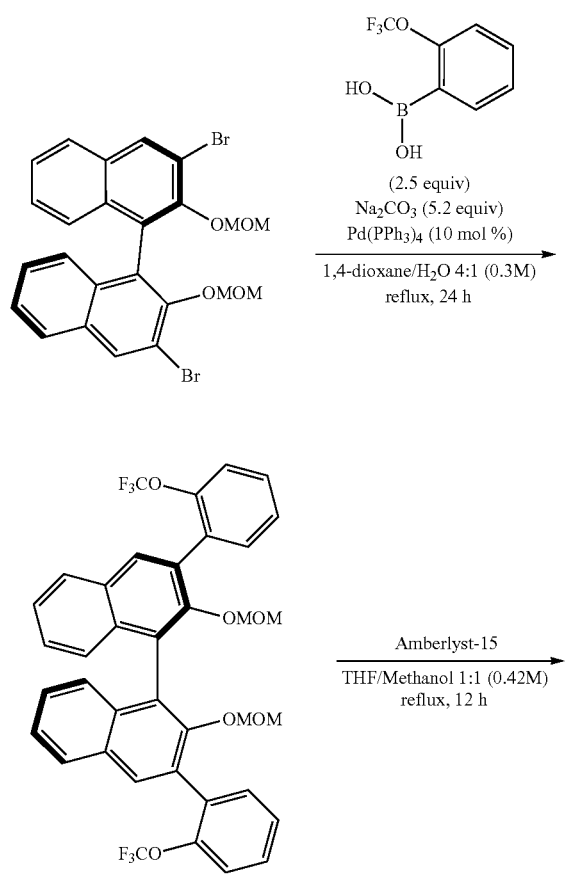

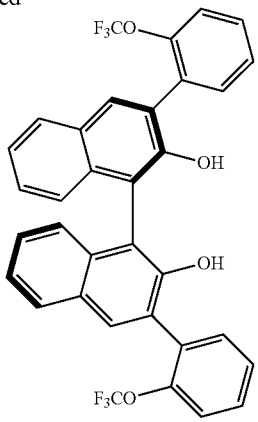

An oven-dried, 35-mL, round-bottomed flask equipped with a 2.0-cm×1.0-cm football-shaped stir bar, reflux condenser, and gas adaptor was charged with sodium carbonate (1.05 g, 9.77 mmol, 5.2 equiv), 2-trifluoromethoxy boronic acid (0.892 g, 4.70 mmol, 2.5 equiv), (R)-3,3'-dibromo-2,2'-dimethoxy-1,1'-binaphthalene (1.00 g, 1.88 mmol), and tetrakis(triphenylphosphine)palladium(0) (0.217 g, 0.188 mmol, 0.10 equiv). The system was evacuated and backfilled with nitrogen 5 times. A mixture of 4:1 1,4-dioxane:water (18.8 mL, sparged for 1 h with argon) was added via syringe. The mixture was heated at reflux in a 110° C. oil bath for 24 h. The mixture was cooled to room temperature then diluted with EtOAc (50 mL) and sat. aq. ammonium chloride (30 mL). A suspension formed, which was filtered through Celite (7 g), and the filter cake was washed with EtOAc (30 mL). The phases were separated and the aqueous phase was extracted with EtOAc (2×50 mL). The combined organic layers were washed with water (35 mL), brine (35 mL), dried over sodium sulfate (12 g) for 40 min, filtered, and rinsed with EtOAc (25 mL), and concentrated (30° C., 15 mm Hg) to afford an orange oil. The product was purified by chromatography (silica gel, 5 cm×5 cm, dry load on Celite, 50 mL fractions, hexanes/EtOAc isocratic elution: 75:25 (500 mL)) to afford 1.19 g of (R)-2,2'-bis(methoxymethoxy)-3,3'-bis(2-(trifluoromethoxy)phenyl)-1,1'-binaphthalene as an orange solid.

A 25-mL, round-bottomed flask equipped with a 2.0-cm×1.0-cm football-shaped stir bar, reflux condenser and gas adaptor was charged with (R)-2,2'-bis(methoxymethoxy)-3,3'-bis(2-(trifluoromethoxy)phenyl)-1,1'-binaphthalene (1.19 g, 1.7 mmol), a mixture of 1:1 THF/methanol (40 mL), and Amberlyst-15 dry resin (1.00 g). The mixture was heated at reflux in an 80° C. oil bath for 12 h. Full conversion was assessed by TLC (R$_f$=0.34 (hexanes/EtOAc, 8:2) [UV]). The mixture was cooled to room temperature and filtered through Celite (4 g), the filter cake was washed with EtOAc (50 mL), and the filtrate was concentrated (30° C., 15 mm Hg) to afford a yellow solid. The product was purified by chromatography (silica gel, 5 cm×15 cm, dry load on Celite, 25 mL fractions, hexanes/EtOAc isocratic: 90:10 (1 L)) affording 0.825 g (74%) of the title compound as a white solid.

Data for S25: $^1$H NMR: (500 MHz, CDCl$_3$) 7.99 (s, 2H), 7.90 (d, J=7.4 Hz, 2H), 7.45-7.32 (m, 4H), 7.24 (s, 2H), 6.59 (d, J=9.3 Hz, 4H), 5.23 (s, 2H), 3.84 (s, 6H). 13C NMR:(126 MHz, CDCl$_3$) 162.60 (dd, J=10.4, 3.9 Hz), 160.98 (t, J=13.9 Hz), 160.64 (dd, J=10.4, 3.9 Hz), 151.69, 134.04, 133.90, 129.47, 128.75, 124.51, 124.35, 119.18, 111.88, 107.38 (t, J=21.3 Hz), 98.06 (dt, J=25.4, 4.6 Hz), 55.05. $^{19}$F NMR:

(376.5 MHz, CDCl$_3$) −57.33, (s, 6F). HRMS: (ESI$^+$, TOF) calcd for C$_{34}$H$_{21}$F$_6$O$_4$ (M$^{+1}$) 607.1344, found: 607.1357 TLC: R$_f$=0.34 (hexanes/EtOAc, 8:2) [UV].

Synthesis of Chiral Phosphoric Acids: General Procedures.

General Procedure 1: In an oven-dried, 20-mL scintillation vial was placed an oven-dried 0.75-cm×1.5-cm stir bar. To the vial was added the corresponding diol, followed by pyridine (0.1 M solution of substrate in pyridine, distilled from CaH$_2$ then dried over 4 Å molecular sieves). The mixture was stirred, and to the mixture was added POCl$_3$ (10 equiv). The mixture was the capped, and the cap secured with electrical tape. The mixture was then placed in a preheated oil bath at 60° C. for 16 h. After 16 h, the reaction mixture was allowed to cool to room temperature then was placed in an ice bath and 200 equiv water was added dropwise (anything other than a slow, dropwise addition of water before complete consumption of POCl$_3$ causes a violent exothermic reaction). This mixture was then recapped and stirred for an additional 6 h at 60° C. The mixture was then cooled to room temperature and was poured into a separatory funnel and the vial was rinsed with dichloromethane (3×double the original volume of pyridine) which was also added to the separatory funnel. The mixture was then washed with aq. 6 N HCl (7×30 mL). The organic layer was then dried over sodium sulfate (ca. 4 g) and was filtered. The filtrate was rinsed with an additional 20 mL of dichloromethane, and the combined organic layers were concentrated on a rotary evaporator (30° C., 15 mm Hg). The final products were then purified by silica gel chromatography. After chromatography, most compounds were isolated as a mixture of different salt states. Therefore, the chromatographed compounds were taken up in dichloromethane (10 mL) and washed with 6 N aq. HCl (5×10 mL). The combined aqueous layers were then extracted with dichloromethane (30 mL) and the combined organic layers concentrated (30° C., 15 mm Hg) without drying. The concentrate was then dried on high vacuum (24 h, 60° C., 0.5 mm Hg) to remove water. To be absolutely certain the compound obtained was not complexed with HCl, the dried concentrate was then crystallized to afford the final products. Specific details from chromatography and crystallization are given with each compound.

General Procedure 2: To an oven-dried, 20-mL, scintillation vial was added an oven-dried 0.75-cm×1.5-cm stir bar. To the vial was added the diol (amounts given individually below), followed pyridine (0.1 M, distilled from CaH$_2$). The mixture was stirred, and to the mixture was added POCl$_3$ (10 equiv). The mixture was the capped, and the cap secured with electrical tape. The mixture was then placed in a preheated oil bath at 80° C. for 16 h. After 16 h, the reaction mixture was allowed to cool to room temperature, placed in an ice bath and 200 equiv of water was added dropwise (anything other than a slow, dropwise addition of water before complete consumption of POCl$_3$ causes a violent exothermic reaction). This mixture was then heated for an additional 3 h at 80° C. The mixture was then cooled to room temperature and was diluted with dichloromethane (10 mL) which and washed with aq. 6 N HCl (7×5 mL). The organic layer was then filtered through silica gel (0.5-1.0 g), which was rinsed with dichloromethane (5 mL). This layer was washed again with aq. 6 N HCl (3×5 mL) and concentrated (30° C., 15 mm Hg). The concentrate was then dried on high vacuum (24 h, 60° C. at 0.5 mm Hg) to remove water. To be certain the compound obtained was not complexed with HCl, the dried concentrate was then crystallized to afford the final products (crystallization conditions given individually later).

Purification of (11bR)-2,6-Diethyl-4-hydroxy-8,9,10,11,12,13,14,15-octahydrodinaphtho[2,1-d:1',2'-][1,3,2]dioxaphosphepine 4-Oxide (15)

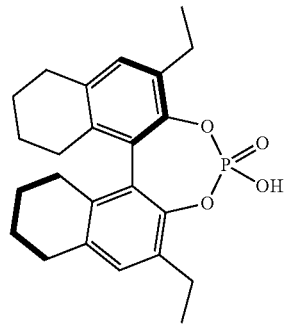

Synthesized on a 0.3 mmol scale (100 mg) following General Procedure 2. Compound 15 (130 mg crude mass) was recrystallized from methanol (0.5 mL) by dissolving the compound in the refluxing solvent mixture followed by cooling to room temperature. The product was allowed to crystallize (formed white needles) overnight at room temperature, then was filtered, and washed with cold methanol (1 mL). The product was dried under high vacuum (23° C., 0.1 mm Hg) for 24 h to afford 81 mg (70%) of 15 as a white solid.

Data for 15: $^1$H NMR: (500 MHz, DMSO-d$_6$) 7.03 (s, 2H), 2.73 (m, 6H), 2.58 (tt, J=13.8, 6.6 Hz, 4H), 2.06 (dt, J=16.4, 5.7 Hz, 2H), 1.79-1.64 (m, 6H), 1.48 (td, J=8.0, 4.7 Hz, 2H), 1.19 (t, J=7.5 Hz, 6H). $^{13}$C NMR: (126 MHz, DMSO-d$_6$) 145.15, 145.08, 135.23, 134.68, 132.98, 132.95, 129.75, 126.98, 29.21, 27.81, 22.88, 22.81, 14.74. $^{31}$P NMR: (161.97 MHz, DMSO-d$_6$) 0.76 (s, 1P). HRMS: (ESI$^+$, TOF) calcd for C$_{24}$H$_{30}$O$_4$P (M$^{+1}$) 413.1882, found: 413.1880.

Purification of (11bR)-2,6-Bis(2,4,6-trichlorophenyl)-4-hydroxy-8,9,10,11,12,13,14,15-octahydrodinaphtho[2,1-d:1',2'-f][1,3,2]dioxaphosphepine 4-Oxide (12)

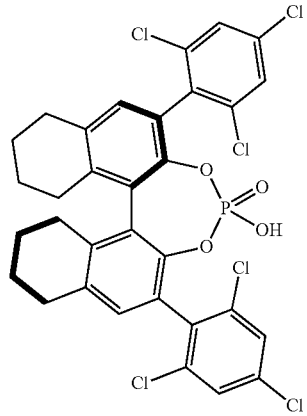

Synthesized on a 0.2 mmol scale (130 mg) following General Procedure 2. Compound 12 (151 mg crude mass) was recrystallized from EtOAc (1 mL) by dissolving the compound in the refluxing solvent mixture followed by cooling to room temperature. The product was allowed to crystallize overnight in a −20° C. freezer, then was filtered, and washed with cold 1:1 EtOAc/hexanes (1 mL). The product was dried under high vacuum (23° C., 0.1 mm Hg) for 24 h to afford 74 mg (52%) of 12 as a white solid.

Data for 12: $^1$H NMR: (500 MHz, DMSO-d$_6$) 7.76 (d, J=2.1 Hz, 2H), 7.74 (d, J=2.0 Hz, 2H), 7.10 (s, 2H), 2.97-2.67 (m, 6H), 2.24 (dt, J=16.9, 5.8 Hz, 2H), 1.88-1.74 (m, 6H), 1.62 (tq, J=12.5, 7.2, 6.3 Hz, 2H). 13C NMR: (126 MHz, DMSO-d$_6$) 144.58, 144.51, 138.73, 136.64, 136.33, 135.03, 134.50, 134.09, 131.68, 128.89, 128.09, 127.18, 125.82, 125.79, 29.21, 28.07, 22.70, 22.61. $^{31}$P NMR: (161.97 MHz, DMSO-d$_6$) −0.20 (s, 1P). HRMS: (ESI$^+$, TOF) calcd for $C_{32}H_{24}O_4PCl_6$ (M$^{+1}$) 712.9543, found: 712.9543.

Purification of (11bR)-2,6-bis(4-(pentafluorothio) phenyl)-4-hydroxy-dinaphtho[2,1-d:1',2'-f][1,3,2] dioxaphosphepine 4-Oxide (17)

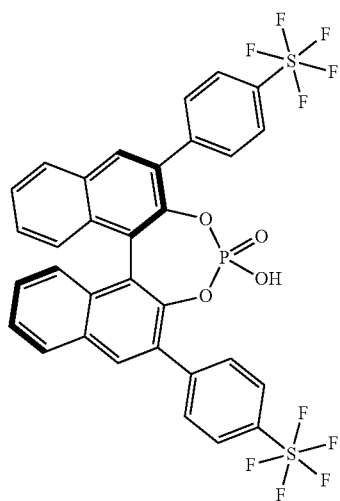

Compound 17 (60 mg) was recrystallized from EtOAc (1 mL) and hexane (5 mL) by dissolving the compound in the refluxing solvent mixture followed by cooling to room temperature. The product was allowed to crystallize overnight in a −20° C. freezer, then was filtered, and washed with cold hexane (1 mL). The product was dried under high vacuum (23° C., 0.1 mm Hg) for 24 h to afford 41 mg (63%) of 17 as a white solid.

Data for 17: $^1$H NMR: (500 MHz, DMSO-d$_6$) 8.26 (d, J=1.7 Hz, 2H), 8.14 (dd, J=8.4, 4.8 Hz, 6H), 8.09-7.97 (m, 4H), 7.54 (t, J=7.5 Hz, 2H), 7.47-7.30 (m, 2H), 7.17 (d, J=8.6 Hz, 2H). $^{13}$C NMR: (126 MHz, DMSO-d$_6$) 151.94, 146.03 (d, J=9.2 Hz), 141.68, 131.99, 131.91, 131.31, 130.92, 130.34, 128.82, 128.34, 127.10, 126.02, 125.56, 122.54. $^{31}$P NMR: (161.97 MHz, DMSO-d$_6$) 3.56 (s, 1P).

$^{19}$F NMR: (161.97 MHz, DMSO-d$_6$) −177.31—180.99 (m, 1F), −201.88 (d, J=150.4 Hz, 4F). HRMS: (ESI$^+$, TOF) calcd for $C_{32}H_{19}O_4S_2PF_{10}Na$ (M$^{+1}$): 775.0200, found: 775.0216.

Purification of (11bR)-2,6-bis(10-(naphthalen-2-yl) anthracen-9-yl)-4-hydroxy-dinaphtho[2,1-d:1',2'-f] [1,3,2]dioxaphosphepine 4-Oxide (14)

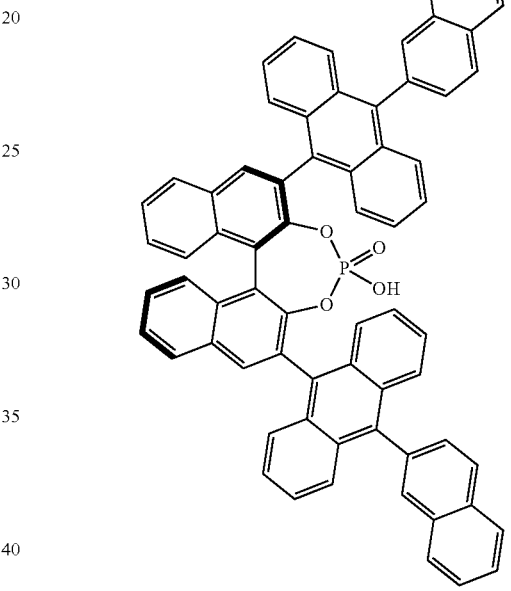

Synthesized on a 0.25 mmol scale (222 mg) following General Procedure 2, with the exception that the scintillation vial was wrapped in aluminum foil to exclude light and the entirety of the procedure was carried out in the dark. Compound 14 (275 mg crude mass) was recrystallized from ethanol (3 mL) by dissolving the compound in the refluxing solvent mixture followed by cooling to room temperature. The product was allowed to crystallize (formed plate-like crystals) overnight in a −20° C. freezer, then was filtered, and washed with cold ethanol (2 mL). The product was dried under high vacuum (23° C., 0.1 mm Hg) for 24 h to afford 114 mg (48%) of 14 as a light yellow-green solid.

Data for 14: $^1$H NMR: (500 MHz, DMSO-d$_6$) 8.30-8.07 (m, 6H), 8.06-7.95 (m, 2H), 7.90-7.84 (m, 1H), 7.74-7.53 (m, 12H), 7.46-7.26 (m, 5H). $^{13}$C NMR: (126 MHz, CDCl$_3$) 146.98, 137.89, 136.77, 136.49, 134.40, 133.60, 133.52, 133.01, 132.94, 132.86, 131.73, 131.65, 131.38, 130.66, 130.30, 130.22, 130.16, 129.93, 129.61, 128.79, 128.44, 128.25, 128.13, 128.05, 127.87, 127.74, 127.33, 127.22, 126.72, 126.51, 126.35, 126.30, 125.87, 125.26, 125.20, 125.06, 124.69, 122.81. $^{31}$P NMR: (161.97 MHz, DMSO-$d_6$) 2.41 (s, 1P). HRMS: (ESI$^+$, TOF) calcd for $C_{68}H_{42}O_4P^+$: 953.2821, found: 953.2780.

Purification of (11bR)-2,6-Bis(2,4-bis(trifluoromethyl)benzyl)-4-hydroxydinaphtho[2,1-d:1',2'-f][1,3,2]dioxaphosphepine 4-Oxide (70)

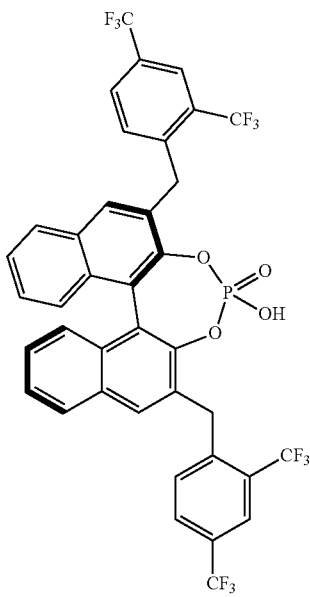

Synthesized on a 0.31 mmol scale (234 mg) following General Procedure 2. Compound 70 (235 mg crude mass) was recrystallized from 1:10 EtOAc/hexanes (3 mL) by dissolving the compound in the refluxing solvent mixture followed by cooling to room temperature. The product was allowed to crystallize overnight in a –20° C. freezer, then was filtered, and washed with hexanes (2 mL). The product was dried under high vacuum (23° C., 0.1 mm Hg) for 24 h to afford 114 mg (45%) of 70 as a light yellow solid.

Data for 70: $^1$H NMR: (500 MHz, DMSO-d) 8.06 (s, 2H), 7.97 (t, J=8.0 Hz, 4H), 7.76 (s, 2H), 7.58 (d, J=8.2 Hz, 2H), 7.47 (t, J=7.5 Hz, 2H), 7.33 (t, J=7.7 Hz, 2H), 7.22 (d, J=8.6 Hz, 2H), 4.74 (d, J=16.8 Hz, 2H), 4.51 (d, J=16.8 Hz, 2H). $^{13}$C NMR: (126 MHz, DMSO-$d_6$) 147.37, 147.29, 143.78, 133.53, 131.66, 131.53, 131.40, 131.28, 130.24, 129.55, 129.31, 129.07, 128.94, 128.52, 128.25, 127.15, 126.70, 126.30, 125.44, 125.26, 123.49, 123.25, 123.09, 122.50, 121.07, 33.20. $^{31}$P NMR: (161.97 MHz, DMSO-$d_6$) 3.73 (s, 1P). $^{19}$F NMR: (376.5 MHz, DMSO-$d_6$) –59.76 (s, 3F), –61.69 (s, 3F). HRMS: (ESI$^+$, TOF) calcd for $C_{38}H_{22}O_4PF_{12}^+$: 801.1064, found: 801.1061.

Purification of (11bR)-2,6-Bis(tris(4-(tert-butyl)phenyl)silyl)-4-hydroxy-8,9,10,11,12,13,14,15-octahydrodinaphtho[2,1-d:1',2'-f][1,3,2]dioxaphosphepine 4-Oxide (2)

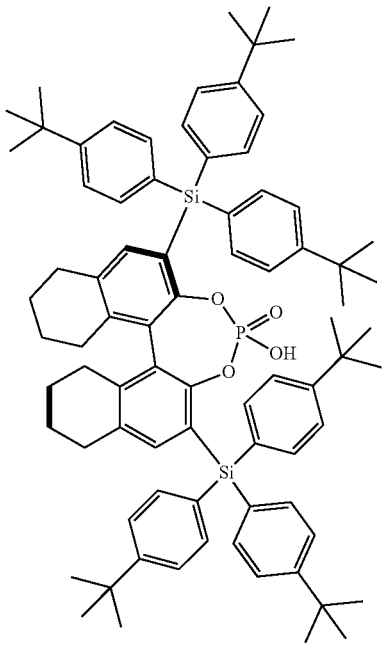

Compound 2 (0.10 mmol, 108 mg) was added to a 20-mL scintillation vial. To the vial was added pyridine (2 mL) and POCl$_3$ (3 mmol, 0.56 mL, 60 equiv). The vessel was then capped, sealed with electrical tape, and heated in a 100° C. oil bath for 48 h. The vial was then removed from the oil bath cooled to room temperature, and placed in an ice bath. Upon cooling, water (1.5 mL) was added to the bath followed by an additional of pyridine (1 mL) to help solubilize the mixture. This mixture was then resealed and headed for an additional 7 h at 60° C. The mixture was cooled again, poured into a separatory funnel, and diluted with dichloromethane (10 mL). The organic layer was then washed with aq. 6 N HCl (2×10 mL), and concentrated (30° C., 15 mm Hg). The crude residue was then taken up in dichloromethane (ca. 1 mL), filtered through silica gel (1 g), and the silica gel rinsed with an additional dichloromethane (10 mL). The combined organic layers were concentrated to afford a yellow solid. This solid was crystallized from hexanes (crude mass 147 mg, 1 mL of hexanes) by dissolving in hot hexanes and cooling to room temperature. The mixture was allowed to crystallize overnight in a –20° C. freezer, then filtered, and washed with cold hexanes (1 mL). The product was dried under high vacuum (23° C., 0.1 mm Hg) for 24 h to afford 94 mg (78%) of 2 as a white solid.

Data for 2: $^1$H NMR: (500 MHz, DMSO-$d_6$) 8.06 (s, 2H), 7.97 (t, J=8.0 Hz, 4H), 7.76 (s, 2H), 7.58 (d, J=8.2 Hz, 2H), 7.47 (t, J=7.5 Hz, 2H), 7.33 (t, J=7.7 Hz, 2H), 7.22 (d, J=8.6 Hz, 2H), 4.74 (d, J=16.8 Hz, 2H), 4.51 (d, J=16.8 Hz, 2H).

$^{13}$C NMR: (126 MHz, CDCl$_3$) 152.43, 152.10, 140.67, 139.81, 139.76, 136.82, 136.74, 136.69, 136.55, 131.49, 130.83, 125.10, 124.88, 124.83, 124.74, 124.60, 34.91, 34.85, 31.52, 31.49, 29.96, 29.48, 29.36, 28.29, 28.17, 22.87, 22.85, 22.64. $^{31}$P NMR: (161.97 MHz, DMSO-d$_6$) 3.73 (s, 1P). $^{19}$F NMR: (376.5 MHz, DMSO-d$_6$) −59.76 (s, 3F), −61.69 (s, 3F). HRMS: (ESI$^+$, TOF) calcd for C$_{80}$H$_{98}$O$_4$Si$_2$P$^+$: 1209.6741, found: 1209.6726.

Purification of (11bR)-2,6-Bis(methyldiphenylsilyl)-4-hydroxy-dinaphtho[2,1-d:1',2'-f][1,3,2]dioxaphosphepine 4-Oxide (67)

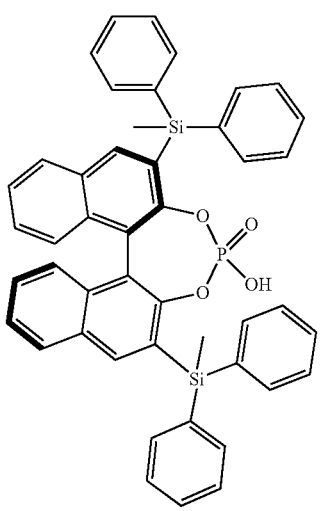

Synthesized on a 0.29 mmol scale (200 mg) following General Procedure 1. Compound 67 (212 mg crude mass) was recrystallized from TBME (1 mL) by dissolving the compound in the refluxing solvent mixture followed by cooling to room temperature. The product was allowed to crystallize overnight in a −20° C. freezer, then was filtered, and washed with hexanes (2 mL). The product was dried under high vacuum (23° C., 0.1 mm Hg) for 24 h to afford 127 mg (59%) of 67 as a white solid.

Data for 67: $^1$H NMR: (500 MHz, DMSO-d$_6$) 7.92-7.83 (m, 4H), 7.61-7.57 (m, 4H), 7.45 (m 13H), 7.33 (m, 9H), 7.04 (d, J=8.5 Hz, 2H), 1.08 (s, 6H). $^{13}$C NMR: (126 MHz, DMSO-d$_6$). 152.20, 152.12, 140.66, 136.76, 136.60, 135.81, 135.25, 134.27, 134.15, 133.85, 130.73, 130.22, 130.02, 129.58, 129.34, 128.88, 128.67, 128.60, 128.57, 128.37, 126.48, 126.19, 125.99, 121.43, −1.27. $^{31}$P NMR: (161.97 MHz, DMSO-d$_6$) 1.29 (s, 1P). HRMS: (ESI$^+$, TOF) calcd for C$_{46}$H$_{37}$O$_4$NaPSi$_2$$^+$: 763.1866, found: 763.1869.

Purification of (11bR)-2,6-Bis(4-methoxybenzyl)-4-hydroxy-8,9,10,11,12,13,14,15-octahydrodinaphtho[2,1-d:1',2'-f][1,3,2]dioxaphosphepine 4-Oxide (13)

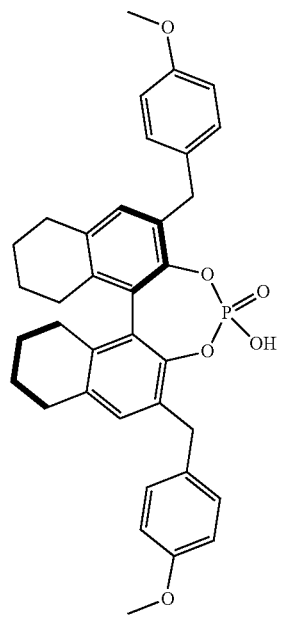

Synthesized on a 0.11 mmol scale (60 mg) following General Procedure 2. Compound 13 was recrystallized from EtOAc (1 mL) and hexane (5 mL) by dissolving the compound in the refluxing solvent mixture followed by cooling to room temperature. The product was allowed to crystallize overnight at room temperature, then was filtered, and washed with cold hexane (1 mL). The product was dried under high vacuum (23° C., 0.1 mm Hg) for 24 h to afford 44 mg (66%) of 13 as a white solid.

Data for 13: $^1$H NMR: (500 MHz, DMSO-d$_6$) 7.14 (d, J=8.6 Hz, 4H), 6.96-6.73 (m, 6H), 4.08 (d, J=15.1 Hz, 2H), 3.82 (d, J=15.1 Hz, 2H), 3.71 (s, 6H), 2.68 (dt, J=24.0, 6.9 Hz, 4H), 2.60-2.54 (m, 2H), 2.04 (dd, J=16.4, 6.6 Hz, 2H), 1.54-1.33 (m, 2H). $^{13}$C NMR: (126 MHz, DMSO-d$_6$) 152.20, 152.12, 140.66, 136.76, 136.60, 135.81, 135.25, 134.27, 134.15, 133.85, 130.73, 130.22, 130.02, 129.58, 129.34, 128.88, 128.67, 128.60, 128.57, 128.37, 126.48, 126.19, 125.99, 121.43, −1.27. $^{31}$P NMR: (161.97 MHz, DMSO-d$_6$) 1.29 (s, 1P). HRMS: (ESI$^+$, TOF) calcd for C$_{36}$H$_{38}$O$_6$P$^+$: 597.2406, found: 597.2392.

93

Purification of (11bR)-2,6-Bis(2-ethoxy-5-methylphenyl)-4-hydroxy-8,9,10,11,12,13,14,15-octahydrodinaphtho[2,1-d:1',2'-t][1,3,2]dioxaphosphepine 4-Oxide (20)

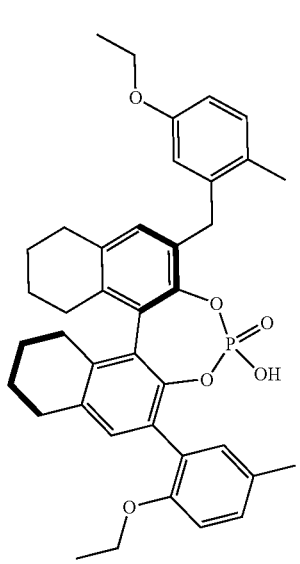

Synthesized on a 0.3 mmol scale (168 mg) following General Procedure 1. Compound 20 (217 mg crude mass) was recrystallized from ethanol (1 mL) by dissolving the compound in the refluxing solvent mixture followed by cooling to room temperature. The product was allowed to crystallize overnight in a −20° C. freezer, then was filtered, and washed with cold ethanol (1 mL). The product was dried under high vacuum (23° C., 0.1 mm Hg) for 24 h to afford 140 mg (75%) of 20 as a light yellow solid.

Data for 20: $^1$H NMR: (500 MHz, DMSO-d$_6$) 7.11 (d, J=2.2 Hz, 2H), 7.07 (dd, J=8.4, 2.3 Hz, 2H), 7.02 (s, 2H), 6.90 (d, J=8.3 Hz, 2H), 3.93 (dq, J=9.5, 6.9 Hz, 2H), 3.83 (dq, J=9.4, 6.9 Hz, 2H), 2.91-2.71 (m, 4H), 2.66 (ddd, J=16.7, 8.0, 4.7 Hz, 2H), 2.24 (s, 8H), 1.78 (tt, J=12.0, 5.8 Hz, 6H), 1.55 (tt, J=8.1, 5.2 Hz, 2H), 1.07 (t, J=6.9 Hz, 6H). $^{13}$C NMR: (126 MHz, DMSO-d$_6$) 154.60, 144.59, 144.51, 136.47, 133.99, 132.45, 131.90, 129.70, 129.40, 128.98, 128.95, 127.44, 127.26, 113.69, 64.57, 29.13, 27.91, 22.93, 22.88, 20.88, 15.32. $^{31}$P NMR:(161.97 MHz, DMSO-d$_6$) −0.67 (s, 1P) HRMS: (ESI$^+$, TOF) calcd for C$_{38}$H$_{42}$O$_6$P$^+$: 625.2719, found: 625.2724.

94

Purification of (11bR)-2,6-Bis(4-isopropoxy-3,5-dimethylphenyl)-4-hydroxy-dinaphtho[2,1-d:1',2'-f][1,3,2]dioxaphosphepine 4-Oxide (8)

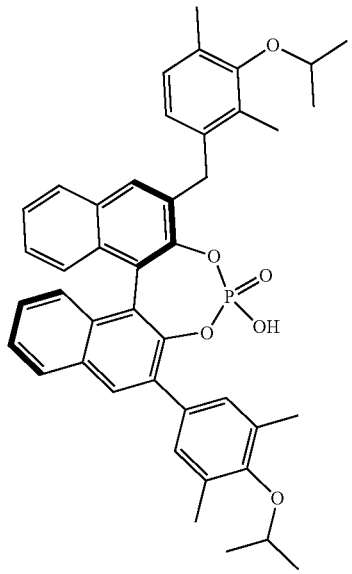

Synthesized on a 0.25 mmol scale (150 mg) following General Procedure 2. Compound 8 (142 mg crude mass) was purified by chromatography (silica gel, 2 cm×8 cm, dry load on Celite, 10 mL fractions, dichloromethane/methanol gradient eluent: 100:0 (200 mL) to 99:1 (100 mL) to 98:2 (100 mL) to 97:3 (100 mL) to 95:5 (300 mL)) (R$_f$=0.57 (dichloromethane/methanol 8:2) [UV]). The purified compound was taken up in dichloromethane (10 mL) and washed with aq. 6 N HCl (5×10 mL). The combined aqueous layers were then extracted with dichloromethane (30 mL) and the combined organic layers concentrated (30° C., 15 mm Hg) without drying. The concentrate was then dried under high vacuum (24 h, 80° C. at 0.5 mm Hg) to remove water and HCl to afford 0.111 g (67%) of 8 as a white solid.

Data for 8: $^1$H NMR: (500 MHz, DMSO-d$_6$) 8.17 (s, 2H), 8.11 (d, J=8.3 Hz, 2H), 7.51 (s, 6H), 7.33 (t, J=7.9 Hz, 2H), 7.11 (d, J=8.5 Hz, 2H), 4.29-4.18 (m, 2H), 2.50 (s, 12H), 2.28 (s, 12H), 1.28 (d, J=5.9 Hz, 12H). $^{13}$C NMR: (126 MHz, DMSO-d$_6$) 154.84, 145.76, 145.69, 134.03, 132.35, 131.87, 131.52, 131.49, 130.97, 129.25, 127.28, 126.66, 126.35, 122.76, 74.81, 23.20, 17.71. $^{31}$P NMR: (161.97 MHz, DMSO-d$_6$) 2.00 (s, 1P). HRMS: (ESI$^+$, TOF) calcd for C$_{42}$H$_{42}$O$_6$P (M$^{+1}$) 673.2719, found: 673.2737. TLC: R$_f$=0.57 (dichloromethane/methanol. 8:2) [UV].

Purification of (11bR)-2,6-Bis(3,5-bis(trifluoromethyl)benzyl)-4-hydroxy-8,9,10,11,12,13,14,15-octahydrodinaphtho[2,1-d:1',2'-f][1,3,2]dioxaphosphepine 4-Oxide (6)

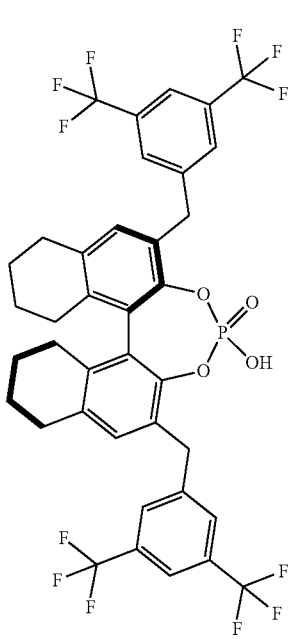

Synthesized on a 0.15 mmol scale (110 mg) following General Procedure 2. Compound 6 (142 mg crude mass) was recrystallized from hexanes (0.5 mL) by dissolving the compound in the refluxing solvent mixture followed by cooling to room temperature. The product was allowed to crystallize overnight in a −20° C. freezer, then was filtered, and washed with cold hexanes (1 mL). The product was dried under high vacuum (23° C., 0.1 mm Hg) for 24 h to afford 83 mg (68%) of 6 as a white solid.

Data for 6: $^1$H NMR: (500 MHz, DMSO-$d_6$) 7.93 (d, J=7.5 Hz, 6H), 7.01 (s, 2H), 4.32 (d, J=15.3 Hz, 2H), 4.15 (d, J=15.3 Hz, 2H), 2.80-2.63 (m, 4H), 2.59 (ddd, J=16.5, 8.5, 4.3 Hz, 2H), 2.05 (dt, J=16.6, 5.4 Hz, 2H), 1.78-1.62 (m, 6H), 1.45 (ddt, J=12.8, 9.2, 3.7 Hz, 2H). $^{13}$C NMR: (126 MHz, DMSO-$d_6$) 145.58 (d, J=9.1 Hz), 144.74, 136.58, 135.03, 131.16, 130.74, 130.48, 130.19, 129.16 (d, J=3.0 Hz), 127.59, 125.14, 122.97, 120.63, 35.07, 29.07, 27.85, 22.68, 22.57. $^{31}$P NMR: (161.97 MHz, DMSO-$d_6$) 1.07 (s, 1P). $^{19}$F NMR: (376.5 MHz, DMSO-$d_6$) −61.70 (s, 6F). HRMS: (ESI$^+$, TOF) calcd for $C_{38}H_{30}O_4F_{12}P^+$: 809.1690, found: 809.1686.

Purification of (11bR)-2,6-Bis(2,2'',4,4'',6,6''-hexamethyl-[1,1':3',1''-terphenyl]-5'-yl)-4-hydroxy-8,9,10,11,12,13,14,15-octahydrodinaphtho[2,1-d:1',2'-f][1,3,2]dioxaphosphepine 4-Oxide (9)

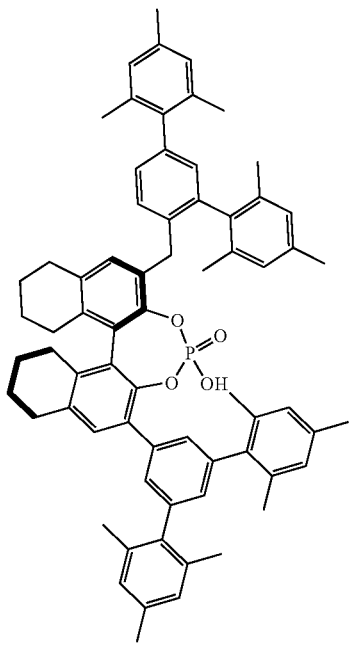

Synthesized on a 0.13 mmol scale (120 mg) following General Procedure 2. Compound 9 (163 mg crude mass) was recrystallized from 1:30 DCE/ethanol (2 mL) by dissolving the compound in the refluxing solvent mixture followed by cooling to room temperature. The product was allowed to crystallize overnight in a −20° C. freezer, then was filtered, and washed with ethanol (2 mL). The product was dried under high vacuum (23° C., 0.1 mm Hg) for 24 h to afford 102 mg (79%) of 9 as a white solid.

Data for 9: $^1$H NMR: (500 MHz, DMSO-$d_6$) 7.32 (d, J=1.5 Hz, 4H), 7.29 (s, 2H), 6.91 (s, 8H), 6.74 (s, 2H), 2.91-2.75 (m, 4H), 2.62 (dt, J=23.2, 4.7 Hz, 2H), 2.25 (s, 12H), 2.19 (dd, J=16.8, 6.5 Hz, 2H), 2.02 (d, J=11.8 Hz, 24H), 1.79-1.66 (m, 6H), 1.52 (qd, J=10.1, 9.3, 5.6 Hz, 2H). $^{13}$C NMR: (126 MHz, CDCl$_3$) 143.43, 143.36, 140.94, 139.12, 137.57, 136.64, 136.46, 136.36, 136.24, 136.15, 135.37, 135.35, 131.76, 131.73, 131.44, 129.35, 129.12, 128.28, 128.20, 127.70, 29.51, 28.05, 22.96, 22.84, 21.28, 21.20, 21.09, 21.02. $^{31}$P NMR: (161.97 MHz, DMSO-$d_6$) 0.68 (s, 1P). HRMS: (ESI$^+$, TOF) calcd $C_{68}H_{70}O_4P^+$: 981.5012, found: 981.4979.

Purification of (11bR)-2,6-Bis(3,3",5,5"-tetrakis(trifluoromethyl)-[1,1':3',1"-terphenyl]-5'-yl)-4-hydroxy-dinaphtho[2,1-d:1',2'-t][1,3,2]dioxaphosphepine 4-Oxide (16)

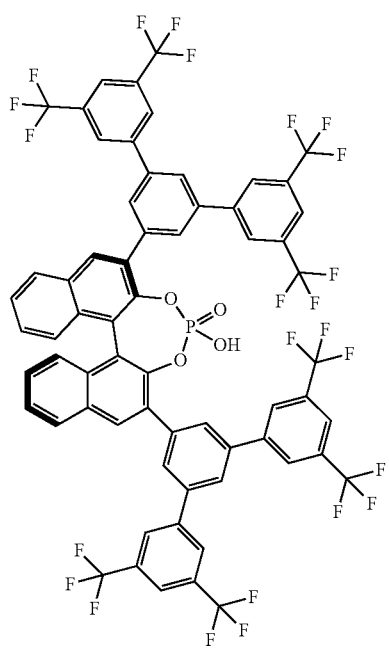

Synthesized on a 0.19 mmol scale (250 mg) following General Procedure 2. Compound 16 (312 mg crude mass) was recrystallized from a mixture of 1:15 DCE/ethanol (4 mL) by dissolving the compound in the refluxing solvent mixture followed by cooling to room temperature. The product was allowed to crystallize overnight in a −20° C. freezer, then was filtered, and washed with ethanol (5 mL). The product was dried under high vacuum (23° C., 0.1 mm Hg) for 24 h to afford 163 mg (64%) of 16 as a white solid.

Data for 16: $^1$H NMR: (500 MHz, DMSO-$d_6$) 8.67 (d, J=1.6 Hz, 8H), 8.56 (d, J=1.7 Hz, 4H), 8.39 (s, 2H), 8.36 (t, J=1.8 Hz, 2H), 8.14 (d, J=9.5 Hz, 6H), 7.58-7.49 (m, 2H), 7.37 (ddd, J=8.3, 6.8, 1.3 Hz, 2H), 7.18 (d, J=8.6 Hz, 2H). 13C NMR: (126 MHz, DMSO-$d_6$) 146.81, 143.16, 139.92, 138.59, 133.83, 132.47, 132.19, 132.00, 131.73, 131.47, 131.15, 130.43, 129.40, 128.91, 127.39, 126.89, 126.45, 125.18, 123.01, 122.87, 121.83. $^{31}$P NMR: (161.97 MHz, DMSO-$d_6$) 3.85 (s, 1P). $^{19}$F NMR: (376.5 MHz, DMSO-$d_6$) −61.42 (s, 24F) HRMS:(ESI$^+$, TOF) calcd for $C_{84}H_{30}O_4F_{24}P^+$: 1349.1498, found: 1349.1469.

Purification of (11bR)-2,6-Bis(4,4"-dimethoxy-[1,1':3',1"-terphenyl]-5'-yl)-4-hydroxydinaphtho[2,1-d:1',2'-t][1,3,2]dioxaphosphepine 4-Oxide (23)

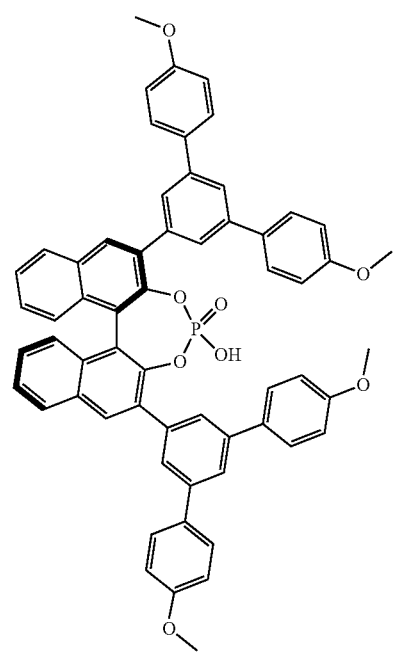

Synthesized on a 0.31 mmol scale (234 mg) following General Procedure 2. Compound 23 (235 mg crude mass) was recrystallized from a mixture of 8:2 hexanes/EtOAc (2 mL) by dissolving the compound in the refluxing solvent mixture followed by cooling to room temperature. The product was allowed to crystallize for Ca. 168 h in a −20° C. freezer, then was filtered, and washed with hexanes (2 mL). The product was dried under high vacuum (23° C., 0.1 mm Hg) for 24 h to afford 114 mg (45%) of 23 as a light yellow.

Data for 23: $^1$H NMR: (500 MHz, DMSO-$d_6$) 8.37 (s, 2H), 8.15 (d, J=8.2 Hz, 2H), 8.10 (t, J=1.4 Hz, 4H), 7.89-7.81 (m, 9H), 7.57-7.50 (m, 2H), 7.37 (ddd, J=8.3, 6.8, 1.4 Hz, 2H), 7.19 (d, J=8.7 Hz, 2H), 7.04 (d, J=8.7 Hz, 8H), 3.80 (d, J=1.2 Hz, 14H). $^{13}$C NMR: (126 MHz, DMSO-$d_6$) 159.67, 140.89, 139.17, 134.64, 133.27, 132.33, 131.71, 131.29, 129.36, 128.90, 127.26, 127.13, 126.78, 126.06, 123.75, 123.03, 114.99, 55.86. $^{31}$P NMR: (161.97 MHz, DMSO-$d_6$) 3.19 (s, 1P). HRMS: (ESI$^+$, TOF) calcd for $C_{60}H_{46}O_8P^+$: 925.2930, found: 925.2903.

Purification of (11bR)-2,6-Bis(2,6-difluoro-4-methoxyphenyl)-4-hydroxy-dinaphtho[2,1-d:1',2'-f][1,3,2]dioxaphosphepine 4-Oxide (22)

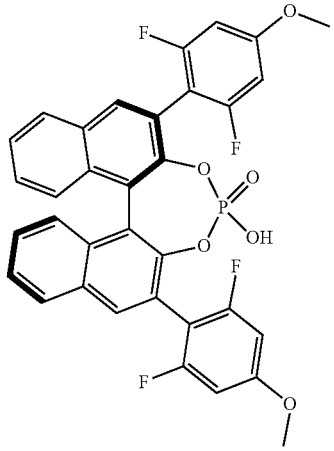

Synthesized on a 0.56 mmol scale (320 mg) following General Procedure 2. Compound 22 (361 mg crude mass) was recrystallized from chloroform (5 mL) by dissolving the compound in the refluxing solvent mixture followed by cooling to room temperature. The product was allowed to crystallize 96 h in a –20° C. freezer, then was filtered, and washed with chloroform (3 mL). The product was dried under high vacuum (23° C., 0.1 mm Hg) for 24 h to afford 260 mg (73%) of 22 as a white solid.

Data for 22: $^1$H NMR: (500 MHz, DMSO-d$_6$) 8.22 (s, 2H), 8.17-8.12 (m, 2H), 7.59 (ddd, J=8.0, 6.8, 1.1 Hz, 2H), 7.46 (ddd, J=8.3, 6.8, 1.3 Hz, 2H), 7.30 (d, J=8.5 Hz, 2H), 6.90 (dt, J=11.2, 1.9 Hz, 2H), 6.85 (dt, J=11.3, 1.8 Hz, 2H), 3.85 (s, 6H). $^{13}$C NMR: (126 MHz, DMSO-de) 161.53 (dd, J=17.2, 10.2 Hz), 160.77 (t, J=14.2 Hz), 159.58 (dd, J=17.1, 10.4 Hz), 145.75 (d, J=9.7 Hz), 132.99, 131.72, 130.56, 128.74, 127.55, 126.00 (d, J=9.2 Hz), 121.67 (dd, J=17.3, 2.4 Hz), 105.97 (t, J=21.3 Hz), 98.55 (d, J=26.7 Hz), 97.80 (d, J=25.8 Hz), 56.14. $^{31}$P NMR:(161.97 MHz, DMSO-d$_6$) 2.43 (s, 1P). $^{19}$F NMR: (376.5 MHz, DMSO-d$_6$) –110.59 (s, 1F), –112.36 (s, 1F). HRMS: (ESI$^+$, TOF) calcd for C$_{34}$H$_{22}$O$_6$F$_4$P$^+$: 633.1090, found: 633.1094

Purification of (11bR)-2,6-Bis(4-cyclohexylphenyl)-4-hydroxy-8,9,10,11,12,13,14,15-octahydrodinaphtho[2,1-d:1',2'-f][1,3,2]dioxaphosphepine 4-Oxide

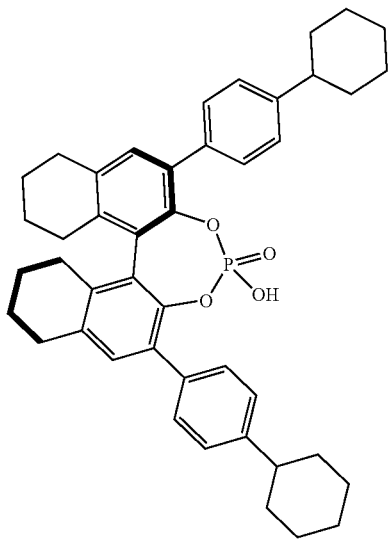

Synthesized on a 0.33 mmol scale (200 mg) following General Procedure 2. Compound 3 (209 mg crude mass) was recrystallized from hexanes (2 mL) by dissolving the compound in the refluxing solvent mixture followed by cooling to room temperature. The product was allowed to crystallize overnight in a –20° C. freezer, then was filtered, and washed with hexanes (1 mL). The product was dried under high vacuum (23° C., 0.1 mm Hg) for 24 h to afford 144 mg (66%) of 3 as a white solid.

Data for 3: $^1$H NMR: (500 MHz, DMSO-d$_6$) 7.55 (d, J=8.2 Hz, 4H), 7.26 (d, J=8.3 Hz, 4H), 7.18 (s, 2H), 2.82 (tq, J=16.1, 8.5, 6.4 Hz, 4H), 2.63 (ddd, J=16.9, 9.2, 4.6 Hz, 2H), 2.56-2.51 (m, 2H), 2.18 (dt, J=17.0, 5.8 Hz, 2H), 1.87-1.64 (m, 16H), 1.57 (td, J=8.5, 5.3 Hz, 2H), 1.51-1.31 (m, 8H), 1.25 (dtt, J=13.8, 10.4, 5.2 Hz, 2H). $^{13}$C NMR: (126 MHz, DMSO-d$_6$) 146.31, 143.20, 143.13, 136.22, 134.62, 134.24, 130.86, 130.76, 129.21, 127.16, 126.40. $^{31}$P NMR: (161.97 MHz, DMSO-d$_6$) –0.59 (s, 1P). HRMS: (ESI$^+$, TOF) calcd for C$_{44}$H$_{50}$O$_4$P$^+$: 673.3447, found: 673.3447.

Purification of (11bR)-2,6-Bis(3-(naphthalen-2-yl)phenyl)-4-hydroxy-dinaphtho[2,1-d:1',2'-f][1,3,2]dioxaphosphepine 4-Oxide (4)

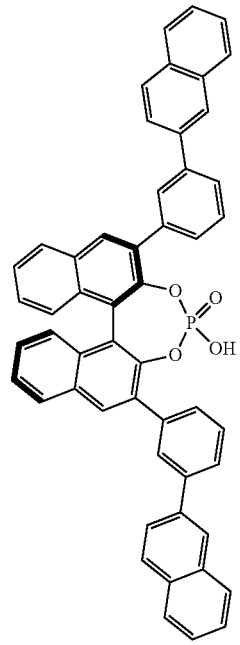

Synthesized on a 0.16 mmol scale (112 mg) following General Procedure 2. Compound 4 (98 mg crude mass). The yellow solid was purified by chromatography (silica gel, 2 cm×7 cm, dry load on Celite, 10 mL fractions, dichloromethane/methanol gradient elution: 100:0 (100 mL) to 99:1 (100 mL) to 98:2 (100 mL) to 97:3 (100 mL)) (R$_f$=0.60 (dichloromethane/methanol, 8:2) [UV]). The purified compound was taken up in dichloromethane (10 mL) and washed with aq. 6 N HCl (5×10 mL). The combined aqueous layers were then extracted with dichloromethane (30 mL) and the combined organic layers concentrated (30° C., 15 mm Hg) without drying. The concentrate was then dried under high vacuum (24 h, 80° C. at 0.5 mm Hg) to yield 0.067 g (55%) of 4 a as beige solid.

Data for 4: ¹H NMR: (500 MHz, DMSO-$d_6$) 8.47-8.43 (m, 2H), 8.39 (s, 2H), 8.33 (s, 2H), 8.16 (d, J=8.4 Hz, 2H), 8.06-7.98 (m, 6H), 7.96-7.89 (m, 6H), 7.65 (t, J=7.7 Hz, 2H), 7.57-7.49 (m, 6H), 7.38 (t, J=8.3 Hz, 2H), 7.19 (d, J=8.5 Hz, 2H). ¹³C NMR: (126 MHz, DMSO-$d_6$) 146.23, 146.15, 140.37, 138.59, 138.01, 134.31, 134.04, 132.97, 132.25, 131.93, 131.46, 129.81, 129.62, 129.43, 129.32, 129.12, 128.92, 128.16, 127.50, 127.04, 126.80, 126.36, 126.15, 122.95. ³¹P NMR: (161.97 MHz, DMSO-$d_6$) 2.64 (s, 1P). HRMS: (ESI-, TOF) calcd for $C_{52}H_{32}O_4P$ ([M]⁻¹) 751.2038, found: 751.2033. TLC: $R_f$=0.60 (dichloromethane/methanol, 8:2) [UV].

Purification of (11bR)-2,6-Bis(2-(naphthalen-2-yl)phenyl)-4-hydroxy-8,9,10,11,12,13,14,15-octahydrodinaphtho[2,1-d:1',2'-f][1,3,2]dioxaphosphepine 4-Oxide (18)

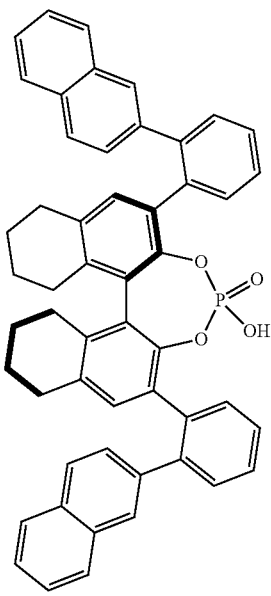

Synthesized on a 0.38 mmol scale (230 mg) following General Procedure 2. Compound 18 (209 mg crude mass). To the yellow solid was added boiling ethanol (2 mL, insoluble), and boiling dichloromethane (0.5 mL) was added dropwise until a homogenous solution was formed, concentrated to ~1 mL of volume. Solution was cooled to room temperature for 3 h yielding a small amount of crystals growth, the solution was transferred to a –20° C. freezer for 48 h. The crystals were collected by vacuum filtration, washed with ice cold Ethanol (2 mL), yielding 18 as a yellow solid (0.181 g, 72% yield).

Data for 18: ¹H NMR: (500 MHz, DMSO-$d_6$) 7.81-7.75 (m, 2H), 7.66-7.55 (m, 9H), 7.51-7.38 (m, 11H), 7.28 (d, J=8.4 Hz, 1H), 6.80 (s, 2H), 2.63-2.52 (m, 2H), 2.28-2.16 (m, 2H), 1.63-1.45 (m, 8H), 1.19-1.07 (m, 2H). ¹³C NMR: (126 MHz, DMSO-$d_6$) 144.18, 144.11, 141.65, 139.35, 136.97, 136.75, 134.09, 133.27, 132.29, 132.10, 131.94, 131.38, 131.35, 130.18, 128.41, 128.38, 128.16, 127.86, 127.52, 127.40, 127.17, 126.42, 126.32, 28.83, 27.25, 22.61, 22.60. ³¹P NMR: (161.97 MHz, DMSO-$d_6$) –1.00 (s, 1P). HRMS: (ESI⁺, TOF) calcd for $C_{52}H_{42}O_4P$ ([M]⁺¹) 761.2821, found: 761.2837. TLC: $R_f$=0.55 (8:2 dichloromethane/methanol, 8:2) [UV].

Purification of (R)-2,6-Bis(3-(methoxymethyl)phenyl)-4-hydroxy-8,9,10,11,12,13,14,15-octahydrodinaphtho[2,1-d:1',2'-t][1,3,2]dioxaphosphepine 4-Oxide (65)

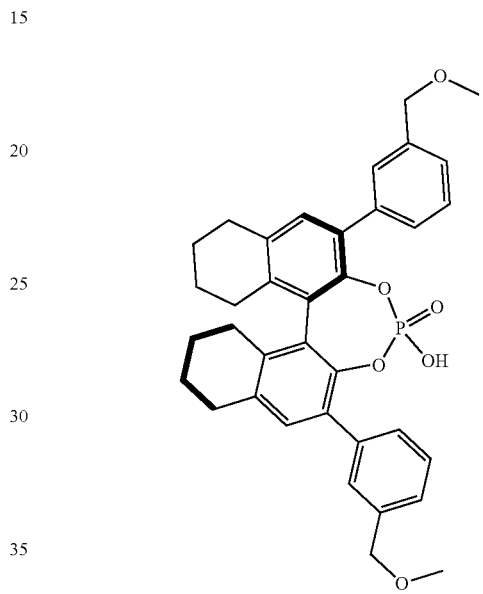

Synthesized on a 0.38 mmol scale (205 mg) following General Procedure 2. Compound 65 (201 mg crude mass). The product was purified by chromatography (silica gel, 2 cm×8 cm, dry load on Celite, 10 mL fractions, dichloromethane/methanol gradient elution: 100:0 (100 mL) to 95:5 (100 mL) to 90:10 (100 mL) to 85:15 (300 mL)) ($R_f$=0.53 (dichloromethane/methanol, 8:2) [UV]) to afford a beige solid. The purified compound was taken up in dichloromethane (10 mL) and washed with aq. 6 N HCl (5×10 mL). The combined aqueous layers were then extracted with dichloromethane (30 mL) and the combined organic layers concentrated (30° C., 15 mm Hg) without drying. The concentrate was then dried under high vacuum (24 h, 80° C. at 0.5 mm Hg) to yield 0.189 g (83%) of 65 as a yellow solid.

Data for 65: ¹H NMR: (500 MHz, DMSO-$d_6$) 7.58 (d, J=7.8 Hz, 2H), 7.53 (s, 2H), 7.39 (t, J=7.6 Hz, 2H), 7.28 (d, J=7.7 Hz, 2H), 7.21 (s, 2H), 4.44 (s, 4H), 3.29 (s, 6H), 2.95-2.76 (m, 4H), 2.74-2.60 (m, 2H), 2.29-2.16 (m, 2H), 1.83-1.71 (m, 6H), 1.64-1.50 (m, 2H). ¹³C NMR: (126 MHz, DMSO-$d_6$) 143.22, 143.14, 138.04, 137.05, 136.69, 134.45, 130.89, 130.87, 130.78, 128.56, 128.46, 128.04, 127.20, 126.35, 73.62, 57.52, 28.50, 27.36, 22.16, 22.14. ³¹P NMR: (161.97 MHz, DMSO-$d_6$) –0.61 (s, 1P). HRMS: (ESI⁺, TOF) calcd for $C_{36}H_{38}O_6P$ ([M]⁺¹) 597.2406, found: 597.2417. TLC: $R_f$=0.53 (dichloromethane/methanol, 8:2) [UV].

Purification of (11bR)-2,6-Bis(3-(methoxymethyl) phenyl)-4-hydroxydinaphtho[2,1-d:1',2'-t][1,3,2] dioxaphosphepine 4-Oxide (7)

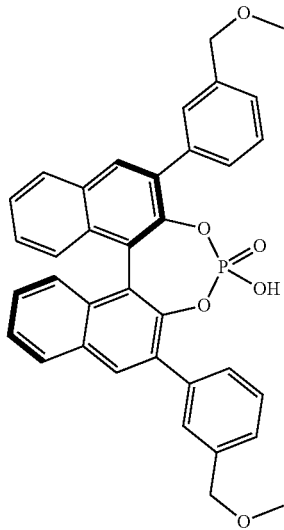

Synthesized on a 0.34 mmol scale (238 mg) following General Procedure 2. Compound 7 (216 mg crude mass) was recrystallized from a mixture of 4:1 acetone/water (4 mL) by dissolving the compound in the refluxing solvent mixture followed by cooling to room temperature. The product was allowed to crystallize overnight at room temperature, then was filtered and washed with water (10 mL). The product was dried under high vacuum (23° C., 0.1 mm Hg) for 24 h to afford 114 mg (41%) of 7 as colorless cubes.

Data for 7: $^1$H NMR: (500 MHz, DMSO-d$_6$) 8.21 (s, 2H), 8.15 (d, J=8.2 Hz, 2H), 7.78 (d, J=7.7 Hz, 2H), 7.72 (s, 2H), 7.54 (t, J=7.5 Hz, 2H), 7.48 (t, J=7.7 Hz, 2H), 7.41-7.33 (m, 4H), 7.17 (d, J=8.5 Hz, 2H), 4.49 (s, 4H), 3.32 (s, 6H). $^{13}$C NMR: (126 MHz, DMSO-d$_6$) 145.20, 145.12, 138.14, 137.01, 133.57, 131.42, 131.00, 130.75, 129.04, 128.95, 128.89, 128.68, 128.20, 128.10, 126.82, 126.74, 126.01, 125.71, 122.20, 73.59, 57.56. $^{31}$P NMR: (161.97 MHz, DMSO-d$_6$) 2.11 (s, 1P). HRMS: (ESI$^+$, TOF) calcd for C$_{36}$H$_{30}$O$_6$P: 589.1780, found: 589.1782.

Purification of (11bR)-2,6-Bis(anthracen-9-ylm-ethyl)-4-hydroxydinaphtho[2,1-d:1',2'-t][1,3,2]dioxa-phosphepine 4-Oxide (10)

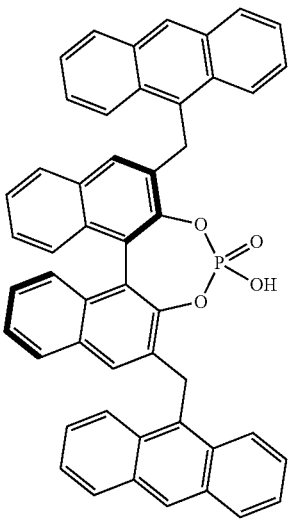

An oven-dried, 20-mL, scintillation vial equipped with an oven-dried, 0.75-cm×1.5-cm stir bar was charged with the corresponding diol (133 mg, 0.2 mmol) and pyridine (0.05 M, 4 mL). The mixture was stirred, and to the mixture was added POCl$_3$ (306 mg, 2 mmol, 10 equiv). The mixture was the capped, and the cap secured with electrical tape. The vial was then wrapped in aluminum foil and stirred at room temperature for 48 h. The mixture was cooled to 0° C. and quenched with water (2 mL), followed by 6 N HCl (3 mL). The mixture was then diluted with dichloromethane (3 mL). A yellow precipitate formed, which was filtered off. This yellow solid was washed with aq. 6 N HCl (10 mL), water (50 mL), dichloromethane (20 mL), and pentane (20 mL). The product was then dried under high-vacuum (23° C., 0.1 mm Hg) for Ca. 120 h to afford 74 mg (51%) of 10 as a yellow solid.

Data for 10: $^1$H NMR: (500 MHz, DMSO-d$_6$) 8.70 (s, 2H), 8.41 (d, J=8.7 Hz, 4H), 8.30-8.09 (m, 4H), 7.64-7.47 (m, 8H), 7.43 (d, J=7.4 Hz, 2H), 7.22 (d, J=9.4 Hz, 6H), 6.75 (s, 2H), 5.62 (d, J=18.0 Hz, 2H), 5.24 (d, J=18.0 Hz, 2H). $^{13}$C NMR: (126 MHz, DMSO-de) 148.31, 148.24, 133.99, 132.01, 131.18, 131.10, 131.05, 129.79, 128.59, 128.47, 127.42, 126.97, 126.53, 125.97, 125.83, 125.60, 122.46, 28.96. $^{31}$P NMR: (161.97 MHz, DMSO-d$_6$) 5.66 (s, 1P). HRMS:(ESI$^+$, TOF) calcd for C$_{50}$H$_{34}$O$_4$P$^+$: 729.2195, found: 729.2194.

Purification of (11bR)-2,6-Bis(2-(trifluoromethoxy) phenyl)-4-hydroxydinaphtho[2,1-d:1',2'-f][1,3,2] dioxaphosphepine 4-Oxide (58)

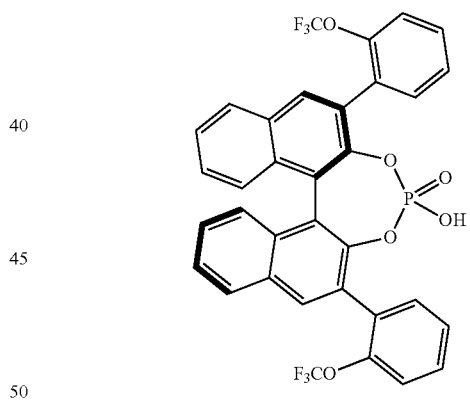

Synthesized on a 0.42 mmol scale (268 mg) following General Procedure 2. Compound 58 (241 mg crude mass) was triturated from pentane (10 mL) affording 0.219 g (74%) of 58 as a white solid.

Data for 58: $^1$H NMR: (500 MHz, DMSO-d$_6$) 8.21-8.10 (m, 4H), 7.76 (dd, J=7.4, 1.7 Hz, 2H), 7.62-7.41 (m, 10H), 7.21 (d, J=8.6 Hz, 2H). $^{13}$C NMR: (126 MHz, DMSO-d$_6$) 146.21, 145.11, 145.03, 132.88, 131.80, 131.76, 130.53, 130.02, 128.90, 128.80, 127.42, 127.30, 125.95, 125.55, 121.49, 120.46, 120.00 (q, J=259.17 Hz). $^{31}$P NMR: (161.97 MHz, DMSO-d$_6$) 1.82 (s, 1P). $^{19}$F NMR: (376.5 MHz, DMSO-d$_6$) −56.55 (s, 6F). HRMS: (ESI+, TOF) calcd for C34H20O6F6P ([M]+1) 669.0902, found: 669.0909. TLC: R$_f$ =0.42 (dichloromethane/methanol, 8:2) [UV].

Synthesis of Racemic Standards

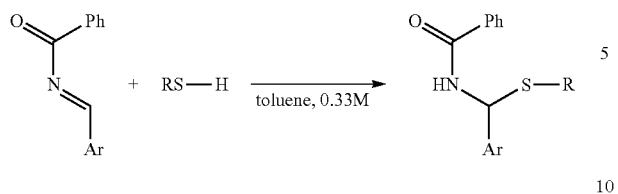

An oven-dried, 20-mL, scintillation vial equipped with an oven-dried, 0.75-cm×1.5-cm football-shaped stir bar was charged with acyl imine (1 mmol), and toluene (3 mL). To this solution was added the appropriate thiol (1.1 mmol, 1.1 equiv) in one portion. This mixture was heated at reflux while open to air for 2 min (caution: perform this in a well ventilated fume hood with the doors closed, the volatilized thiols produce a strong odor if precautions are not taken). The vial was removed from the stir plate and allowed to cool to room temperature. Upon cooling, white crystals formed. The crystals were filtered, pulverized on the filter paper, and rinsed with cold toluene to afford the products as white solids. To remove trace impurities, the materials were recrystallized (information listed separately for every compound), filtered, triturated with diethyl ether, and dried under high vacuum (25° C. at 0.1 mm Hg).

Purification of N-(Phenyl(phenylthio)methyl)benzamide (27)

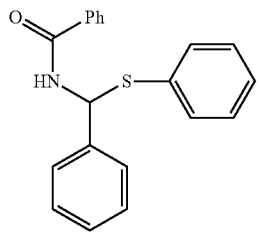 [SMILES: O=C(NC(Sc1ccccc1)c1ccccc1)c1ccccc1]

Compound 27 (280 mg) was recrystallized from a mixture of 1:1 EtOAc/TBME (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and filtered again. The product was dried under high vacuum (23° C., 0.1 mm Hg) for 24 h to afford 258 mg (81%) of 27 as a white solid.

Data for 27: mp: 172-174° C. (EtOAc/TBME) $^1$H NMR: (500 MHz, CDCl$_3$) 7.64 (m, 2H), 7.52 (m, 5H), 7.38 (m, 8H), 6.76 (d, J=9.2 Hz 1H, HC(8)), 6.66 (d, J=9.7 Hz, 1H). $^{13}$C NMR: (126 MHz, CDCl$_3$) 166.45 (s, 1C), 138.82 (s, 1C), 134.06 (s, 1C), 133.09 (s, 1C), 132.61 (s, 2C), 132.01 (s, 1C), 129.33 (s, 2C), 129.00 (s, 2C), 128.83 (s, 2C), 128.63 (s, 1C), 128.20 (s, 2 C(7)), 127.06 (s, 2C), 126.83 (s, 2C), 59.83 (s, 1C). HRMS: calcd for C$_{20}$H$_{17}$NONaS$^+$: 342.0929, found: 342.0916. SFC: t$_R$ 14.75 min (50%); t$_R$ 15.98 min (50%) (Chiralpak OD, Program: sCO$_2$/MeOH, gradient, 99:1 to 90:10 over 10 min; isocratic, 90:10 for 22 min, 3 mL/min, 220 nm, 40° C.).

Purification of N-((Cyclohexylthio)(phenyl)methyl)benzamide (28)

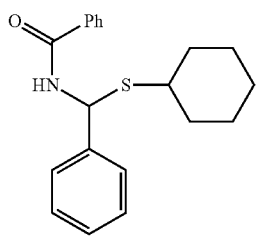 [SMILES: O=C(NC(SC1CCCCC1)c1ccccc1)c1ccccc1]

Compound 28 (311 mg) was recrystallized from a mixture of 5:1 TBME/EtOAc (5 mL), by dissolving the compound in the refluxing solvent mixture followed by cooling to room temperature. The product was allowed to crystallize overnight at room temperature. The crystals were filtered, pulverized and washed with a mixture of diethyl ether/hexanes, 1:1 (20 mL). The crystals were then collected, suspended in pentane (10 mL), sonicated for ca. 5 min., and filtered again. The compound dried under high vacuum (23° C. at 0.1 mm Hg) for 24 h to afford 197 mg (60%) of 28 as a white solid.

Data for 28: mp: 102-105° C. (pentane). $^1$H NMR: (500 MHz, CDCl$_3$) 7.81 (d, J=7.0 Hz, 2H), 7.53 (m, 1H), 7.47 (m, 4H), 7.35 (t, J=7.5 Hz, 2H), 7.28 (m, 1H), 6.65 (d, J=9.2 Hz, 1H), 6.52 (d, J=9.1 Hz, 1H), 2.92 (tt, J=10.5, 3.7 Hz, 1H), 2.21 (m, 1H), 1.93 (m, 1H), 1.76 (m, 2H), 1.59 (m, 1H), 1.48 (m, 2H), 1.28 (m, 3H). $^{13}$C NMR: (126 MHz, CDCl$_3$) 166.28 (s, 1C), 139.90 (s, 1C), 134.085 (s, 1C), 132.07 (s, 1C), 128.929 (s, 2C), 128.296 (s, 1C), 127.171 (s, 2C), 126.655 (s, 2C), 55.981 (s, 1C), 44.261 (s, 1C), 34.177 (s, 1C), 33.630 (s. 1C), 26.254 (s, 1C), 26.005 (s, 1C), 25.910 (s, 1C). HRMS: calcd for C$_{20}$H$_{23}$NO NaS$^+$: 348.1398, found: 348.1390. SFC: t$_R$ 11.39 min (50%); t$_R$ 12.63 min (50%) (Chiralpak OD, Program: sCO$_2$/MeOH, gradient, 99:1 to 90:10 over 10 min; isocratic, 90:10 for 12 min, 2.5 mL/min, 220 nm, 40° C.).

Purification of (N-((Ethylthio)(phenyl)methyl)benzamide (29)

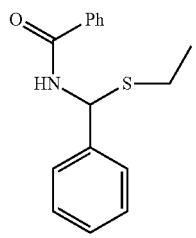 [SMILES: CCSC(NC(=O)c1ccccc1)c1ccccc1]

Compound 29 (251 mg) was recrystallized from a mixture of 4:1 TBME/EtOAc (5 mL), by dissolving the compound in the refluxing solvent mixture followed by cooling to room temperature. The product was allowed to crystallize overnight at room temperature. The crystals were filtered, pulverized and washed with a mixture of diethyl ether/hexanes (20 mL). The crystals were then collected, suspended in pentane (10 mL), sonicated for ca. 5 min, and filtered again. The compound dried under high vacuum (23° C. at 0.1 mm Hg) for 24 h to afford 169 mg (62%) of 29 as a white solid.

Data for 29: $^1$H NMR: (500 MHz, CDCl$_3$) 7.81 (d, J=7.0 Hz, 2H), 7.54 (dt, J=1.3, 7.4 Hz, 1H), 7.49 (m, 4H), 7.40-7.34 (m, 2H), 7.30 (m, 1H), 6.61 (d, J=9.5 Hz, 1H), 6.54 (d, J=9.4 Hz, 1H), 2.79 (dq, J=12.8, 7.3 Hz, 1H), 2.66 (dq, J=12.8, 7.5 Hz, 1H), 1.35 (t, J=7.4 Hz, 3H). $^{13}$C NMR:(126 MHz, CDCl$_3$) 166.91, 164.90 (d, $^1$J(F-C)=241 Hz, 1 C(1)), 140.73 (s, 2 C(5)), 138.3 (s, 2 C(6)), 137.76, 137.70 (d, $^3$J(F-C)=8 Hz, 2 C(3)), 115.76, 155.59 (d, $^2$J(F-C)=21 Hz, 2 C(2)), 106.94 (s, 2 C(7)), 57.05 (s, 2 C(8)). HRMS: calcd for C$_{16}$H$_{17}$NONaS$^+$: 294.0929, found: 294.0918. SFC: $t_R$ 8.14 min (50%); $t_R$ 8.85 min (50%) (Chiralpak AD, Program: sCO$_2$/MeOH, gradient, 95:5 to 82:18 over 18 min; 2.5 mL/min, 220 nm, 40° C.).

Purification of N-(((4-Methoxyphenyl)thio(phenyl)methyl)benzamide (30)

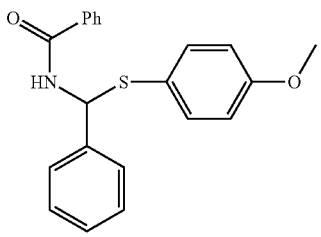 [SMILES: COc1ccc(SC(NC(=O)c2ccccc2)c2ccccc2)cc1]

Compound 30 (327 mg) was recrystallized from EtOAc (7 mL) by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and filtered again. The product was dried under high vacuum (23° C., 0.1 mm Hg) for 24 h to afford 282 mg (81%) of 30 as a white solid.

Data for 30: $^1$H NMR: (500 MHz, CDCl$_3$) 7.66 (d, J=8.2 Hz, 2H), 7.50 (m, 1H), 7.43 (m, 6H), 7.36 (td, J=7.5, 1.3 Hz, 2H), 7.34-7.28 (m, 1H), 6.80 (dd, J=8.9, 1.0 Hz, 2H), 6.64 (d, J=9.3 Hz, 1H), 6.59 (d, J=9.2 Hz, 1H), 3.77 (s, 3H). $^{13}$C NMR: (126 MHz, CDCl$_3$) 166.09, 160.22, 138.87, 136.05, 133.99, 131.77, 128.72, 128.64, 128.28, 126.86, 126.62, 122.83, 114.67, 60.62, 55.31. HRMS: calcd for C$_{21}$H$_{19}$NO$_2$NaS$^+$: 372.1034, found: 372.1027. SFC: $t_R$ 9.90 min (50%); $t_R$10.33 min (50%) (Chiralpak OD, Program: sCO$_2$/MeOH, gradient, 95:5 to 80:20 over 15 min; isocratic, 80:20 for 15 min, 2.5 mL/min, 220 nm, 40° C.).

Purification of N-(Phenyl(2-tolylthio)methyl)benzamide (31)

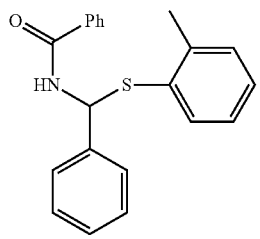 [SMILES: Cc1ccccc1SC(NC(=O)c1ccccc1)c1ccccc1]

Compound 31 (304 mg) was recrystallized from a mixture of EtOAc/TBME, 1:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 276 mg (83%) of 31 as a white solid.

Data for 31: $^1$H NMR: (500 MHz, CDCl$_3$) 7.64 (d, J=7.0 Hz, 1H), 7.49 (m, 4H), 7.38 (m, 4H), 7.32 (m, 1H), 7.18 (m, 2H), 7.10 (td, J=7.6, 1.6 Hz, 1H), 6.70 (d, J=9.0 Hz, 1H), 6.66 (d, J=9.2 Hz, 1H), 2.45 (s, 3H). $^{13}$C NMR: (126 MHz, CDCl$_3$) 140.11, 138.82, 133.86, 132.66, 132.21, 131.81, 130.56, 128.82, 128.64, 128.44, 128.10, 126.86, 126.61, 126.58, 58.70, 20.67. HRMS: calcd for C$_{21}$H$_{19}$NONaS$^+$: 356.1085, found: 356.1079. SFC: $t_R$ 16.61 min (50%); $t_R$ 18.49 min (50%) (Chiralpak OD, Program: sCO$_2$/MeOH, gradient, 99:1 to 80:20 over 20 min; isocratic, 80:20 for 2 min, 2.5 mL/min, 220 nm, 40° C.).

Purification of N-((Phenylthio)(4-(trifluoromethyl)phenyl)methyl)benzamide (32)

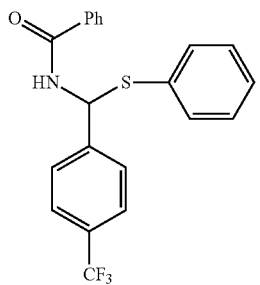 [SMILES: O=C(NC(Sc1ccccc1)c1ccc(C(F)(F)F)cc1)c1ccccc1]

Compound 32 (352 mg) was recrystallized from a mixture of ethyl actate/TBME, 1:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 315 mg (81%) of 32 as a white solid.

Data for 32: $^1$H NMR: (500 MHz, CDCl$_3$) 7.63 (m, 6H), 7.53 (m, 1H), 7.47 (m, 2H), 7.42 (dd, J=8.3, 7.1 Hz, 2H), 7.31 (m, 3H), 6.74 (d, J=8.6 Hz, 1H), 6.68 (d, J=8.8 Hz, 1H). $^{13}$C NMR: (126 MHz, CDCl$_3$) 166.44 (s, 1C), 142.61 (s, 1C), 133.45 (s, 1C), 132.58 (s, 2C), 132.12 (s, 1C), 132.08 (s, 1C), 130.56 (q, J=32.4 Hz), 129.34 (s, 2C), 128.74 (s, 2C), 128.45 (s, 1C), 127.10 (s, 2C), 126.89 (s, 2C), 125.78 (q, J=3.7 Hz), 59.29 (s, 1C). $^{19}$F NMR: (471 MHz, CDCl$_3$) −62.66 (s, 3F). HRMS:calcd for C$_{21}$H$_{16}$NOF$_3$NaS$^+$: 410.0802, found: 410.0788. SFC: $t_R$ 13.58 min (50%); $t_R$15.37 min (50%) (Chiralpak OD, Program: sCO$_2$/MeOH, gradient, 99:1 to 80:20 over 20 min; isocratic, 80:20 for 2 min, 2.5 mL/min, 220 nm, 40° C.).

Purification of N-((Cyclohexylthio)(4-(trifluoromethyl)phenyl)methyl)benzamide (33)

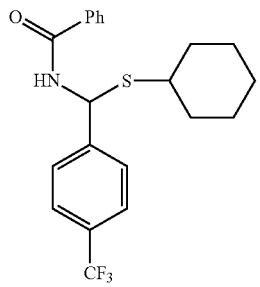 [SMILES: O=C(NC(SC1CCCCC1)c1ccc(C(F)(F)F)cc1)c1ccccc1]

Compound 33 (341 mg) was recrystallized from a mixture of TBME/EtOAc, 5:1 (5 mL), by dissolving the compound in the refluxing solvent mixture followed by cooling to room temperature. The product was allowed to crystallize overnight at room temperature. The crystals were filtered, pulverized and washed with a mixture of diethyl ether/hexanes, 1:1 (20 mL). The crystals were then collected, suspended in pentane (10 mL), sonicated for ca. 5 min, and filtered again. The compound dried under high vacuum (23° C. at 0.1 mm Hg) for 24 h to afford 266 mg (68%) of 33 as a white solid.

Data for 33: $^1$H NMR: (500 MHz, CDCl$_3$) 7.84 (dd, J=8.3, 1.3 Hz, 2H), 7.59 (m, 5H), 7.50 (dd, J=8.2, 6.8 Hz, 2H), 6.70 (d, J=8.7 Hz, 1H), 6.53 (d, J=8.6 Hz, 1H), 2.96 (tt, J=10.5, 3.7 Hz, 1H), 2.20 (m, 1H), 1.94 (m, 1H), 1.74 (m, 2H), 1.63 (m, 1H), 1.49 (m, 2H), 1.35 (m, 3H). $^{13}$C NMR:(126 MHz, CDCl$_3$) 166.285 (s, 1C), 143.706 (s, 1C), 133.464 (s, 1C), 132.137 (s, 1C), 130.096 (q, J=32.4 Hz), 128.834 (s, 2C), 126.996 (s, 2C), 126.916 (s, 1C), 125.719 (s, 2C), 125.689 (s, 2C), 125.017 (s, 1C), 122.855 (s, 1C), 55.474 (s, 1C), 44.423 (s, 1C), 33.920 (s, 1C), 33.410 (s, 1C), 26.021 (s, 1C), 25.775 (s, 1C), 25.636 (s, 1C). $^{19}$F NMR:(471 MHz, CDCl$_3$) −62.639 (s, 3F). HRMS: calcd for C$_{21}$H$_{21}$NOSF$_3^+$: 392.1296, found: 392.1294. SFC:t$_R$ 13.13 min (50%); t$_R$13.96 min (50%) (Chiralpak OD, Program: sCO$_2$/MeOH, gradient, 99:1 to 90:10 over 10 min; isocratic, 90:10 for 22 min, 3 mL/min, 220 nm, 40° C.).

Purification of N-((Ethylthio)(4-(trifluoromethyl)phenyl)methyl)benzamide (34)

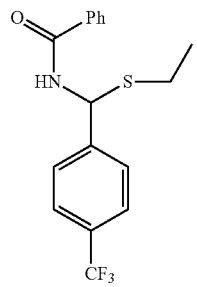 [SMILES: CCSC(NC(=O)c1ccccc1)c1ccc(C(F)(F)F)cc1]

Compound 34 (298 mg) was recrystallized from a mixture of TBME/ethyl actate, 4:1 (5 mL), by dissolving the compound in the refluxing solvent mixture followed by cooling to room temperature. The product was allowed to crystallize overnight at room temperature. The crystals were filtered, pulverized and washed with a mixture of diethyl ether/ hexanes, 1:1 (20 mL). The crystals were then collected, suspended in pentane (10 mL), sonicated for ca. 5 min, and filtered again. The compound dried under high vacuum (23° C. at 0.1 mm Hg) for 24 h to afford 217 mg (64%) of 34 as a white solid.

Data for 34: $^1$H NMR: (500 MHz, CDCl$_3$) 7.85 (d, J=7.0 Hz, 2H), 7.64 (m, 4H), 7.57 (m, 1H), 7.50 (ddt, J=8.2, 6.6, 1.2 Hz, 2H), 6.66 (d, J=9.0 Hz, 1H), 6.54 (d, J=9.0 Hz, 1H), 2.83 (dq, J=12.8, 7.3 Hz, 1H), 2.70 (dq, J=12.8, 7.5 Hz, 1H), 1.39 (t, J=7.4 Hz, 3H). $^{13}$C NMR: (126 MHz, CDCl$_3$) 166.51 (s, 1C), 143.24 (s, 1C), 133.36 (s, 1C), 132.20 (s, 1C), 130.41 (q, J=32.6 Hz, 1C), 128.83 (s, 2C), 127.01 (s, 2C), 126.69 (s, 2C), 125.77 (q, J=3.8 Hz, 1C), 125.74 (q, J=3.8 Hz, 1C), 56.28 (s, 1C), 26.08 (s, 1C), 14.78 (s, 1C). $^{19}$F NMR: (471 MHz, CDCl$_3$) −62.664 (s, 3F). HRMS: calcd for C$_{17}$H$_{15}$NOF$_3$S$^+$: 338.0826, found: 338.0823. SFC: t$_R$ 9.81 min (50%); t$_R$ 10.36 min (50%) (Chiralpak AD, Program: sCO$_2$/MeOH, gradient, 99:1 to 90:10 over 10 min; isocratic, 90:10 for 22 min, 3 mL/min, 220 nm, 40° C.).

Purification of N-(((4-Methoxyphenyl)thio)(4-(trifluoromethyl)phenyl)methyl)benzamide (35)

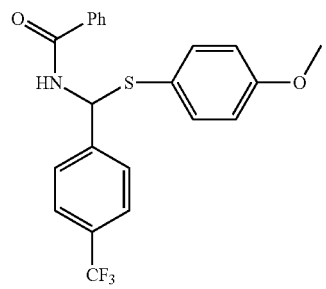 [SMILES: COc1ccc(SC(NC(=O)c2ccccc2)c2ccc(C(F)(F)F)cc2)cc1]

Compound 35 (390 mg) was recrystallized from EtOAc (4 mL) by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 341 mg (82%) of 35 as a white solid.

Data for 35: $^1$H NMR: (500 MHz, CDCl$_3$) 7.69 (d, J=7.1 Hz, 2H), 7.64 (d, J=8.2 Hz, 2H), 7.58 (d, J=8.2 Hz, 2H), 7.57-7.52 (m, 1H), 7.46 (t, J=7.7 Hz, 2H), 7.44-7.39 (m, 2H), 6.87-6.82 (m, 2H), 6.67 (d, J=8.8 Hz, 1H), 6.59 (d, J=8.7 Hz, 1H), 3.80 (s, 3H). $^{13}$C NMR: (126 MHz, CDCl$_3$) 166.25 (s, 1C), 160.51 (s, 1C), 142.88 (s, 1C), 136.16 (s, 2C), 132.03 (s, 1C), 130.51 (q, J=32.6 Hz, 1C), 128.74 (s, 2C), 127.05 (s, 2C), 126.88 (s, 2C), 125.67 (q, J=3.8 Hz, 1C), 121.96 (s, 1C), 114.87 (s, 2C), 60.17 (s, 1C), 55.35 (s, 1C). $^{19}$F NMR: (471 MHz, CDCl$_3$) −62.62 (s, 3F). HRMS: calcd for C$_{22}$H$_{18}$NO$_2$NaSF$_3^+$: 440.0908, found: 440.0905. SFC: t$_R$ 8.10 min (50%); t$_R$ 8.51 min (50%) (Chiralpak OD, Program: sCO$_2$/MeOH, gradient, 95:5 to 80:20 over 15 min; isocratic, 80:20 for 15 min, 2.5 mL/min, 220 nm, 40° C.).

Purification of N-((2-Tolylthio)(4-(trifluoromethyl)phenyl)methyl)benzamide (36)

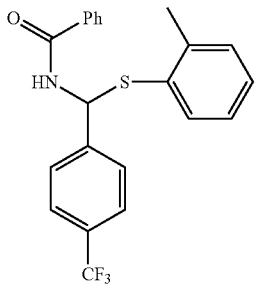 [SMILES: Cc1ccccc1SC(NC(=O)c1ccccc1)c1ccc(C(F)(F)F)cc1]

Compound 36 (374 mg) was recrystallized from a mixture of EtOAc/TBME, 1:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 338 mg (84%) of 36 as a white solid.

Data for 36: $^1$H NMR: (500 MHz, CDCl$_3$) 7.68-7.58 (m, 6H), 7.55-7.49 (m, 1H), 7.46-7.38 (m, 3H), 7.25-7.17 (m, 2H), 7.12 (td, J=7.5, 1.7 Hz, 1H), 6.67 (m, 2H), 2.45 (s, 3H). 13C NMR:(126 MHz, CDCl$_3$) 166.63 (s, 1C), 142.99 (s, 1C), 140.38 (s, 1C), 133.63 (s, 1C), 132.87 (s, 1C), 132.25 (s, 1C), 131.71 (s, 1C), 130.97 (s, 1C), 130.76 (q, J=32.6 Hz, 1C), 128.92 (s, 2C), 128.69 (s, 1C), 127.22 (s, 2C), 127.07 (s, 2C), 126.98 (s, 1C), 125.99 (q, J=3.8 Hz, 1C), 58.52 (s, 1C), 20.84 (s, 1C). $^{19}$F NMR: (471 MHz, CDCl$_3$) −62.66 (s, 3F). HRMS: calcd for C$_{22}$H$_{18}$NOF$_3$SNa$^+$: 424.0959, found: 424.0944. SFC: t$_R$ 11.51 min (50%); t$_R$ 12.35 min (50%) (Chiralpak OD, Program: sCO$_2$/MeOH, gradient, 99:1 to 90:10 over 10 min; isocratic, 90:10 for 12 min, 2.5 mL/min, 220 nm, 40° C.).

Purification of N-((4-Methoxyphenyl)(phenylthio)methyl)benzamide (37)

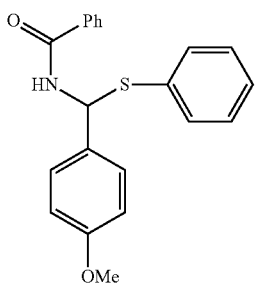 [SMILES: COc1ccc(C(NC(=O)c2ccccc2)Sc2ccccc2)cc1]

Compound 37 (314 mg) was recrystallized from a mixture of EtOAc/TBME, 2:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 261 mg (75%) of 37 as a white solid.

Data for 37: $^1$H NMR: (500 MHz, CDCl$_3$) 7.63 (m, 2H), 7.44 (m, 7H), 7.29 (m, 2H), 6.90 (d, J=8.7 Hz, 2H), 6.72 (d, J=9.0 Hz, 1H), 6.62 (d, J=9.1 Hz, 1H), 3.81 (s, 3H). $^{13}$C NMR: (126 MHz, CDCl$_3$) 166.39 (s, 1C), 159.78 (s, 1C), 134.11 (s, 1C), 133.30 (s, 1C), 132.47 (s, 2C), 131.96 (s, 1C), 130.98 (s, 1C), 129.30 (s, 2C), 128.81 (s, 2C), 128.09 (s, 2C), 127.05 (s, 2C), 114.35 (s, 2C), 59.39 (s, 1C), 55.54 (s, 1C). HRMS: calcd for C$_{21}$H$_{19}$NO$_2$NaS$^+$: 372.1034, found: 372.1044. SFC: t$_R$ 14.67 min (50%); t$_R$ 15.81 min (50%) (Chiralpak OD, Program: sCO$_2$/MeOH, gradient, 99:1 to 90:10 over 15 min; isocratic, 90:10 for 7 min, 3.0 mL/min, 220 nm, 40° C.).

Purification of N-((Cyclohexylthio)(4-methoxyphenyl)methyl)benzamide (38)

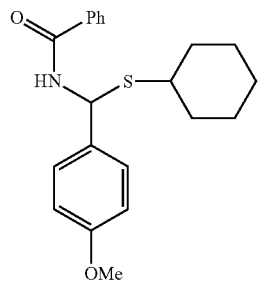 [SMILES: COc1ccc(C(NC(=O)c2ccccc2)SC2CCCCC2)cc1]

Compound 38 (302 mg) was recrystallized from a mixture of EtOAc/TBME, 2:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 187 mg (50%) of 38 as a white solid.

Data for 38: $^1$H NMR: (500 MHz, CDCl$_3$) 7.80 (dt, J=7.0, 1.4 Hz, 2H), 7.56-7.50 (m, 1H), 7.46 (tt, J=6.6, 1.3 Hz, 2H), 7.43-7.37 (m, 2H), 6.87 (d, J=8.7 Hz, 2H), 6.61 (d, J=9.1 Hz, 1H), 6.48 (d, J=9.1 Hz, 1H), 3.79 (s, 3H), 2.89 (tt, J=10.4, 3.7 Hz, 1H), 2.26-2.15 (m, 1H), 1.97-1.88 (m, 1H), 1.83-1.71 (m, 2H), 1.64-1.57 (m, 1H), 1.52-1.36 (m, 2H), 1.36-1.17 (m, 3H). $^{13}$C NMR: (126 MHz, CDCl$_3$) 166.01, 159.34, 133.96, 131.93, 131.82, 128.71, 127.69, 126.96, 114.11, 55.33, 44.00, 33.98, 33.45, 26.06, 25.82, 25.73. HRMS: calcd for C$_{21}$H$_{25}$NO$_2$SNa$^+$: 378.1504, found: 378.1499. SFC: t$_R$ 11.56 min (50%); t$_R$ 13.19 min (50%) (Chiralpak OD, Program: sCO$_2$/MeOH, gradient, 99:1 to 90:10 over 15 min; isocratic, 90:10 for 7 min, 3.0 mL/min, 220.

Purification of N-((Ethylthio)(4-methoxyphenyl)methyl)benzamide (39)

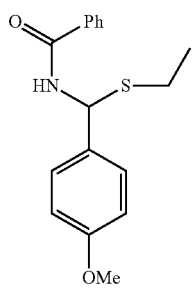 [SMILES: CCSC(NC(=O)c1ccccc1)c1ccc(OC)cc1]

Compound 39 (257 mg) was recrystallized from a mixture of EtOAc/TBME, 2:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 201 mg (68%) of 39 as a white solid.

Data for 39: $^1$H NMR: (500 MHz, CDCl$_3$) 7.85 (d, J=8.4 Hz, 2H), 7.57-7.39 (m, 5H), 6.89 (d, J=8.6 Hz, 2H), 6.57 (d, J=9.3 Hz, 2H), 6.49 (d, J=9.4 Hz, 2H), 3.80 (s, 3H), 2.77 (dq, J=12.7, 7.4 Hz, 1H), 2.63 (dq, J=12.8, 7.4 Hz, 1H), 1.34 (t, J=7.4 Hz, 2H). $^{13}$C NMR: (126 MHz, CDCl$_3$) 166.22, 159.45, 159.42, 132.03, 131.90, 128.71, 128.69, 128.64, 127.74, 127.34, 127.20, 126.98, 114.15, 114.12, 56.15, 55.34, 25.90, 14.80. HRMS: calcd for C$_{17}$H$_{19}$NO$_2$NaS$^+$: 324.1034, found: 324.1030. SFC: $t_R$ 10.27 min (50%); $t_R$ 11.09 min (50%) (Chiralpak OD, Program: sCO$_2$/MeOH, gradient, 99:1 to 90:10 over 15 min; isocratic, 90:10 for 7 min, 3.0 mL/min, 220.

Purification of N-((4-Methoxyphenyl)((4-methoxyphenyl)thio)methyl)benzamide (40)

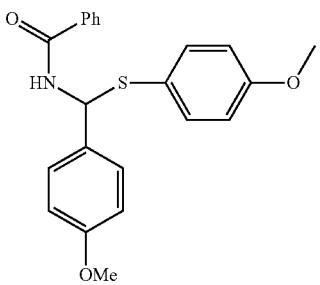 [SMILES: COc1ccc(SC(NC(=O)c2ccccc2)c2ccc(OC)cc2)cc1]

Compound 40 (351 mg) was recrystallized from toluene (10 mL) by dissolving the compound in the refluxing solvent followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 333 mg (88%) of 40 as a white solid.

Data for 40: $^1$H NMR: (500 MHz, CDCl$_3$) 7.84-7.79 (m, 2H), 7.68-7.60 (m, 2H), 7.57-7.35 (m, 5H), 6.91-6.84 (m, 2H), 6.83-6.77 (m, 2H), 6.61 (d, J=9.4 Hz, 1H), 6.55 (d, J=9.2 Hz, 1H), 3.81 (s, 3H), 3.76 (s, 3H). $^{13}$C NMR: (126 MHz, CDCl$_3$) 166.03, 160.13, 159.48, 135.93, 134.05, 132.03, 131.72, 131.05, 128.64, 128.61, 127.88, 127.34, 126.86, 123.06, 114.64, 114.07, 60.22, 55.35, 55.31. HRMS: calcd for C$_{22}$H$_{21}$NO$_3$NaS$^+$: 402.1140, found: 402.1131. SFC: $t_R$ 16.67 min (50%); $t_R$ 17.46 min (50%) (Chiralpak OD, Program: sCO$_2$/MeOH, gradient, 99:1 to 90:10 over 15 min; isocratic, 90:10 for 7 min, 3.0 mL/min, 220.

Purification of N-((4-Methoxyphenyl)(2-tolylthio)methyl)benzamide (41)

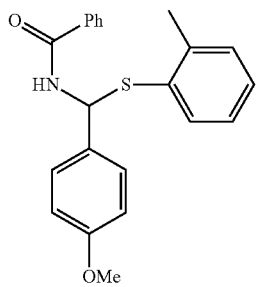 [SMILES: COc1ccc(C(NC(=O)c2ccccc2)Sc2ccccc2C)cc1]

Compound 41 (332 mg) was recrystallized from a mixture of EtOAc/TBME, 2:1 (8 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 290 mg (79%) of 41 as a white solid.

Data for 41: $^1$H NMR: (500 MHz, CDCl$_3$) 7.67-7.61 (m, 2H), 7.50-7.39 (m, 6H), 7.22-7.13 (m, 2H), 7.10 (td, J=7.5, 1.7 Hz, 1H), 6.93-6.86 (m, 2H), 6.65 (d, J=8.9 Hz, 1H), 6.60 (d, J=9.1 Hz, 1H), 3.81 (d, J=1.2 Hz, 3H), 2.45 (s, 3H). $^{13}$C NMR: (126 MHz, CDCl$_3$) 166.19, 159.61, 139.92, 133.93, 132.46, 132.44, 131.76, 131.00, 130.51, 128.61, 127.95, 127.85, 126.85, 126.59, 114.18, 58.26, 55.36, 29.71, 20.67. HRMS: calcd for C$_{22}$H$_{21}$NO$_2$NaS$^+$: 386.1191, found: 386.1189. SFC: $t_R$ 14.14 min (50%); $t_R$ 15.37 min (50%) (Chiralpak OD, Program: sCO$_2$/MeOH, gradient, 99:1 to 90:10 over 15 min; isocratic, 90:10 for 15 min, 3.0 mL/min, 220.

Purification of N-(Naphthalen-1-yl(phenylthio)methyl)benzamide (41)

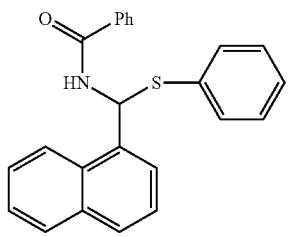 [SMILES: O=C(NC(Sc1ccccc1)c1cccc2ccccc12)c1ccccc1]

Compound 41 (351 mg) was recrystallized from a mixture of EtOAc/TBME, 3:1 (7 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 287 mg (78%) of 41 as a white solid.

Data for 41: $^1$H NMR: (500 MHz, CDCl$_3$) 8.40 (dd, J=8.7, 1.1 Hz, 1H), 7.93 (m, 1H), 7.87 (d, J=8.1 Hz, 1H), 7.70 (ddd, J=7.0, 4.8, 1.2 Hz, 3H), 7.64 (ddd, J=8.5, 6.8, 1.4 Hz, 1H), 7.51 (m, 8H), 7.31 (m, 3H), 6.90 (d, J=9.0 Hz, 1H). $^{13}$C NMR: (126 MHz, CDCl$_3$) 166.26 (s, 1C), 134.45 (s, 1C), 134.19 (s, 1C), 134.02 (s, 1C), 133.50 (s, 1C), 132.57 (s, 2C), 132.02 (s, 1C), 130.34 (s, 1C), 129.57 (s, 1C), 129.36 (s, 2C), 129.08 (s, 1C), 128.83 (s, 2C), 128.21 (s, 1C), 127.11 (s, 2C), 127.01 (s, 1C), 126.33 (s, 1C), 125.27 (s, 1C), 124.33 (s, 1C), 123.61 (s, 1C), 57.25 (s, 1C). HRMS: calcd for C$_{24}$H$_{19}$NONaS$^+$: 392.1085, found: 392.1094. SFC: $t_R$ 19.02 min (50%); $t_R$ 19.91 min (50%) (Chiralpak OD, Program: sCO$_2$/MeOH, gradient, 99:1 to 85:15 over 20 min; isocratic, 80:20 for min, 2.5 mL/min, 220 nm, 40° C.).

Purification of N-((Cyclohexylthio)(naphthalen-1-yl)methyl)benzamide (42)

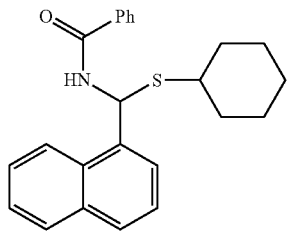 [SMILES: O=C(NC(SC1CCCCC1)c1cccc2ccccc12)c1ccccc1]

Compound 42 (321 mg) was recrystallized from a mixture of EtOAc/TBME, 1:1 (7 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 239 mg (64%) of 42 as a white solid.

Data for 42: $^1$H NMR: (500 MHz, CDCl$_3$) 8.35 (dd, J=8.6, 1.0 Hz, 1H), 7.87 (m, 1H), 7.81 (dd, J=8.3, 1.5 Hz, 3H), 7.72 (dt, J=7.1, 0.9 Hz, 1H), 7.60 (ddd, J=8.4, 6.8, 1.4 Hz, 1H), 7.52 (dddd, J=8.0, 6.6, 5.2, 1.2 Hz, 2H), 7.45 (m, 3H), 7.26 (d, 2H), 6.84 (d, J=9.1 Hz, 1H), 3.06 (tt, J=10.5, 3.7 Hz, 1H), 2.28 (m, 1H), 1.89 (m, 1H), 1.83 (m, 1H), 1.75 (dddd, J=12.8, 4.9, 3.2, 1.4 Hz, 1H), 1.61 (dtd, J=10.5, 4.9, 2.2 Hz, 2H), 1.40 (m, 4H). $^{13}$C NMR: (126 MHz, CDCl$_3$) 166.01 (s, 1C), 135.45 (s, 1C), 134.00 (s, 1C), 133.88 (s, 1C), 131.87 (s, 1C), 130.07 (s, 1C), 129.06 (s, 1C), 128.87 (s, 2C), 128.72 (s, 1C), 127.01 (s, 2C), 126.71 (s, 1C), 126.02 (s, 1C), 125.18 (s, 1C), 123.98 (s, 1C), 123.40 (s, 1C), 52.80 (s, 1C), 44.41 (s, 1C), 34.06, 33.45 (s, 1C), 26.11 (s, 1C), 25.89 (s, 1C), 25.76 (s, 1C). HRMS: calcd for C$_{24}$H$_{25}$NONaS$^+$: 398.1555, found: 398.1553. SFC: $t_R$ 4.93 min (50%); $t_R$ 7.41 min (50%) (Chiralpak AS, Program: sCO$_2$/MeOH, isocratic, 80:20 for 8.2 min, 2.5 mL/min, 220 nm, 40° C.).

Purification of N-((Ethylthio)(naphthalen-1-yl)methyl)benzamide (43)

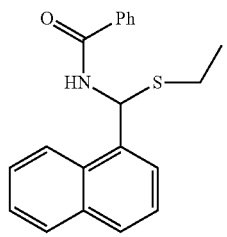 [SMILES: CCSC(NC(=O)c1ccccc1)c1cccc2ccccc12]

Compound 43 (298 mg) was recrystallized from a mixture of EtOAc/TBME, 1:1 (7 mL) by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 243 mg (76%) of 43 as a white solid.

Data for 43: $^1$H NMR: (500 MHz, CDCl$_3$) δ 8.38 (dd, J=8.6, 1.0 Hz, 1H), 7.90 (dt, J=8.1, 0.9 Hz, 1H), 7.84 (m, 3H), 7.77 (d, J=7.1 Hz, 0H), 7.63 (ddd, J=8.4, 6.8, 1.4 Hz, 1H), 7.54 (ddd, J=7.9, 6.8, 1.2 Hz, 2H), 7.48 (ddd, J=12.1, 8.4, 7.2 Hz, 3H), 7.28 (m, 2H), 6.82 (d, J=9.4 Hz, 1H), 2.94 (dq, J=12.7, 7.3 Hz, 1H), 2.78 (dq, J=12.8, 7.5 Hz, 1H), 1.44 (t, J=7.4 Hz, 3H). $^{13}$C NMR:(126 MHz, CDCl$_3$) δ 166.40 (s, 1C), 135.24 (s, 1C), 134.17 (s, 1C), 133.90 (s, 1C), 132.12 (s, 1C), 130.39 (s, 1C), 129.40 (s, 1C), 129.05 (s, 1C), 128.89 (s, 2C), 127.21 (s, 2C), 126.99 (s, 1C), 126.28 (s, 1C), 125.35 (s, 1C), 124.25 (s, 1C), 123.58 (s, 1C), 53.87 (s, 1C), 26.46 (s, 1C), 15.00 (s, 1C). HRMS: calcd for C$_{20}$H$_{19}$NONaS$^+$: 344.1085, found: 344.1092. SFC: $t_R$ 19.36 min (50%); $t_R$ 20.04 min (50%) (Chiralpak OD, Program: sCO$_2$/MeOH, gradient, 99:1 to 85:15 over 20 min; isocratic, 80:20 for 1 min, 2.5 mL/min, 220 nm, 40° C.).

Purification of N-(((4-Methoxyphenyl)thio)(naphthalen-1-yl)methyl)benzamide (44)

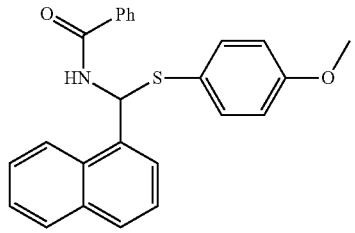 [SMILES: COc1ccc(SC(NC(=O)c2ccccc2)c2cccc3ccccc23)cc1]

Compound 44 (374 mg) was recrystallized from toluene (10 mL) by dissolving the compound in the refluxing solvent followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 355 mg (89%) of 44 as a white solid.

Data for 44: $^1$H NMR: (500 MHz, CDCl$_3$) 8.38 (dd, J=8.6, 1.1 Hz, 1H), 7.88 (m, 1H), 7.83 (dt, J=8.3, 1.0 Hz, 1H), 7.68 (m, 2H), 7.61 (m, 2H), 7.44 (m, 7H), 7.28 (d, J=9.2 Hz, 1H), 6.86 (d, J=9.1 Hz, 1H), 6.82 (m, 2H), 3.78 (s, 3H). $^{13}$C NMR: (126 MHz, CDCl$_3$) 166.09 (s, 1C), 160.45 (s, 1C), 136.27 (s, 2C), 134.70 (s, 1C), 134.18 (s, 1C), 134.16 (s, 1C), 131.96 (s, 1C), 130.35 (s, 1C), 129.40 (s, 1C), 129.05 (s, 2C), 128.82 (s, 1C), 127.09 (s, 2C), 126.93 (s, 1C), 126.28 (s, 1C), 125.20 (s, 1C), 124.19 (s, 1C), 123.72 (s, 1C), 123.40 (s, 1C), 114.88 (s, 2C), 58.22 (s, 1C), 55.51 (s, 1C). HRMS: calcd for $C_{25}H_{21}NO_2NaS^+$: 422.1191, found: 422.1194. SFC: $t_R$ 11.24 min (50%); $t_R$ 16.57 min (50%) (Chiralpak AD, Program: sCO$_2$/MeOH, isocratic, 80:20 for 25 min, 2.5 mL/min, 220 nm, 40° C.).

Purification of N-(Naphthalen-1-yl(2-tolylthio)methyl)benzamide (45)

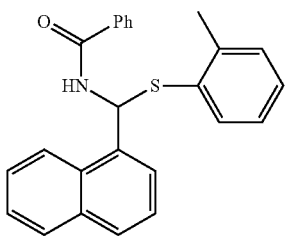 [SMILES: Cc1ccccc1SC(NC(=O)c1ccccc1)c1cccc2ccccc12]

Compound 45 (366 mg) was recrystallized from a mixture of EtOAc/toluene, 3:1 (7 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 321 mg (84%) of 45 as a white solid.

Data for 45: $^1$H NMR: (500 MHz, CDCl$_3$) 8.36 (dd, J=8.5, 1.0 Hz, 1H), 7.90 (m, 1H), 7.85 (d, J=8.3 Hz, 1H), 7.71 (d, J=7.1 Hz, 1H), 7.66 (m, 2H), 7.61 (ddd, J=8.5, 6.8, 1.4 Hz, 1H), 7.45 (m, 7H), 7.16 (m, 3H), 6.84 (d, J=9.0 Hz, 1H), 2.42 (s, 3H). $^{13}$C NMR: (126 MHz, CDCl$_3$) 166.25 (s, 1C), 140.07 (s, 1C), 134.64 (s, 1C), 134.18 (s, 1C), 134.01 (s, 1C), 132.85 (s, 1C), 132.45 (s, 1C), 132.01 (s, 1C), 130.72 (s, 1C), 130.42 (s, 1C), 129.55 (s, 1C), 129.09 (s, 1C), 128.82 (s, 2C), 128.12 (s, 1C), 127.09 (s, 2C), 127.03 (s, 1C), 126.87 (s, 1C), 126.32 (s, 1C), 125.32 (s, 1C), 124.35 (s, 1C), 123.52 (s, 1C), 55.93 (s, 1C), 20.88 (s, 1C). HRMS: calcd for $C_{25}H_{21}NONaS^+$: 406.1242, found: 406.1233. SFC: $t_R$ 21.81 min (50%); $t_R$ 22.70 min (50%) (Chiralpak OD, Program: sCO$_2$/MeOH, gradient, 99:1 to 80:20 over 20 min; isocratic, 80:20 for 10 min, 2.5 mL/min, 220 nm, 40° C.).

Purification of N-((2,4-Dichlorophenyl)(phenylthio)methyl)benzamide (46)

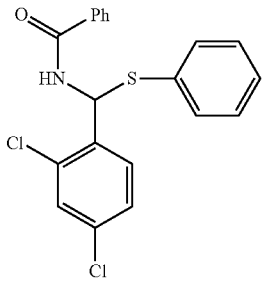 [SMILES: O=C(NC(Sc1ccccc1)c1ccc(Cl)cc1Cl)c1ccccc1]

Compound 46 (360 mg) was recrystallized from a mixture of EtOAc/TBME, 1:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 301 mg (78%) of 46 as a white solid.

Data for 46: $^1$H NMR: (500 MHz, CDCl$_3$) 7.68 (d, J=6.9 Hz, 1H), 7.47 (m, 6H), 7.32 (m, 4H), 7.22 (dd, J=8.4, 2.1 Hz, 1H), 6.93 (d, J=8.2 Hz, 1H), 6.81 (d, J=8.2 Hz, 1H). $^{13}$C NMR: (126 MHz, CDCl$_3$) 166.26 (s, 1C), 135.25 (s, 1C), 134.93 (s, 1C), 133.81 (s, 1C), 133.60 (s, 1C), 132.95 (s, 2C), 132.57 (s, 1C), 132.25 (s, 1C), 130.36 (s, 1C), 129.52 (s, 2C), 128.97 (s, 1C), 128.92 (s, 2C), 128.70 (s, 1C), 127.57 (s, 1C), 127.12 (s, 2C), 58.12 (s, 1C). HRMS: calcd for $C_{20}H_{15}NONaSCl_2^+$: 410.0149, found: 410.0145. SFC: $t_R$ 10.43 min (50%); $t_R$ 12.26 min (50%) (Chiralpak OD, Program: sCO$_2$/MeOH, gradient, 95:5 to 80:20 over 10 min; isocratic, 80:20 for 8 min, 2.5 mL/min, 220 nm, 40° C.).

Purification of N-((Cyclohexylthio)(2,4-dichlorophenyl)methyl)benzamide (47)

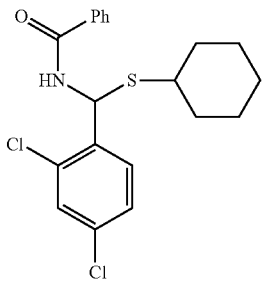 [SMILES: O=C(NC(SC1CCCCC1)c1ccc(Cl)cc1Cl)c1ccccc1]

Compound 47 (344 mg) was recrystallized from a mixture of TBME/ethyl acetate, 5:1 (4 mL), by dissolving the compound in the refluxing solvent mixture followed by cooling to room temperature. The product was allowed to crystallize overnight at room temperature. The crystals were filtered, pulverized and washed with a mixture of diethyl ether/hexanes, 1:1 (20 mL). The crystals were then collected, suspended in pentane (10 mL), sonicated for ca. 5 min, and filtered again. The compound dried under high vacuum (23° C. at 0.1 mm Hg) for 24 h to afford 251 mg (64%) of 47 as a white solid.

Data for 47: $^1$H NMR: (500 MHz, CDCl$_3$) 7.74 (d, J=7.1 Hz, 2H), 7.47 (m, 1H), 7.41 (dd, J=8.1, 6.9 Hz, 2H), 7.34 (m, 2H), 7.16 (dd, J=8.4, 2.1 Hz, 1H), 6.80 (d, J=8.2 Hz, 1H), 6.52 (d, J=8.1 Hz, 1H), 2.90 (tt, J=10.5, 3.7 Hz, 1H), 2.12 (m, 1H), 1.88 (m, 1H), 1.69 (m, 2H), 1.53 (m, 2H), 1.27 (m, 4H). $^{13}$C NMR: (126 MHz, CDCl$_3$) 166.16 (s, 1C), 136.47 (s, 1C), 134.53 (s, 1C), 133.64 (s, 1C), 133.42 (s, 1C), 132.26 (s, 1C), 130.24 (s, 1C), 128.98 (s, 2C), 128.84 (s, 1C), 128.60 (s, 1C), 127.68 (s, 1C), 127.53 (s, 1C), 127.19 (s, 2C), 53.89 (s, 1C), 45.18 (s, 1C), 33.89 (s, 1C), 33.68 (s, 1C), 26.21 (s, 1C), 25.97 (s, 1C), 25.83 (s, 1C). HRMS: calcd for C$_{20}$H$_{21}$NONaSCl$_2^+$: 416.0619, found: 416.0620. SFC: t$_R$ 8.57 min (50%); t$_R$ 10.64 min (50%) (Chiralpak OD, Program: sCO$_2$/MeOH, gradient, 95:5 to 80:20 over 15 min; isocratic, 80:20 for 10 min, 2.5 mL/min, 220 nm, 40° C.).

Purification of N-((2,4-Dichlorophenyl)(ethylthio)methyl)benzamide (48)

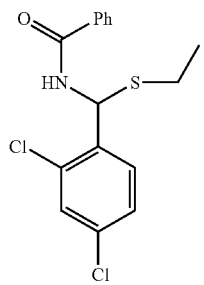 [SMILES: CCSC(NC(=O)c1ccccc1)c1ccc(Cl)cc1Cl]

Compound 48 (294 mg) was recrystallized from a mixture of TBME/EtOAc, 4:1 (2 mL), by dissolving the compound in the refluxing solvent mixture followed by cooling to room temperature. The product was allowed to crystallize overnight at room temperature. The crystals were filtered, pulverized and washed with a mixture of diethyl ether/hexanes, 1:1 (20 mL). The crystals were then collected, suspended in pentane (10 mL), sonicated for ca. 5 min, and filtered again. The compound dried under high vacuum (23° C. at 0.1 mm Hg) for 24 h to afford 264 mg (78%) of 48 as a white solid.

Data for 48: $^1$H NMR: (500 MHz, CDCl$_3$) 7.81 (d, J=7.0 Hz, 2H), 7.58-7.51 (m, 1H), 7.46 (m, 2H), 7.42 (m, 2H), 7.25 (m, 1H), 6.86 (d, J=8.5 Hz, 1H), 6.62 (d, J=8.6 Hz, 1H), 2.82 (dq, J=12.9, 7.3 Hz, 1H), 2.70 (dq, J=12.9, 7.4 Hz, 1H), 1.37 (t, J=7.4 Hz, 3H). 13C NMR: (126 MHz, CDCl$_3$) 166.38 (s, 1C), 135.96 (s, 1C), 134.74 (s, 1C), 133.61 (s, 1C), 133.57 (s, 1C), 132.30 (s, 1C), 130.32 (s, 1C), 128.97 (s, 2C), 128.84 (s, 1C), 127.71 (s, 1C), 127.20 (s, 2C), 54.68 (s, 1C), 26.81 (s, 1C), 14.98 (s, 1C). HRMS: calcd for C$_{16}$H$_{15}$NONaSCl$_2^+$: 362.0149, found: 362.0159. SFC: t$_R$ 11.63 min (50%); t$_R$ 12.91 min (50%) (Chiralpak OD, Program: sCO$_2$/MeOH, gradient, 99:1 to 90:10 over 10 min; isocratic, 90:10 for 12 min, 3.0 mL/min, 220 nm, 40° C.)

Purification of N-((2,4-Dichlorophenyl)((4-methoxyphenyl)thio)methyl)benzamide (49)

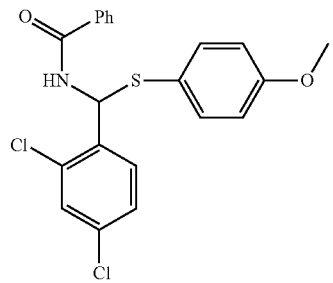 [SMILES: COc1ccc(SC(NC(=O)c2ccccc2)c2ccc(Cl)cc2Cl)cc1]

Compound 49 (388 mg) was recrystallized from a mixture of EtOAc/TBME, 2:1 (5 mL), by dissolving the compound in the refluxing solvent mixture followed by cooling to room temperature. The product was allowed to crystallize overnight at room temperature, then was filtered, and washed with diethyl ether (20 mL). The compound was then collected, suspended in diethyl ether (10 mL), sonicated for ca. 5 min, and was filtered again. The product was dried under high vacuum (23° C., 0.1 mm Hg) for 24 h to afford 314 mg (75%) of 49 as a white solid.

Data for 49: $^1$H NMR: (500 MHz, CDCl$_3$) 7.70 (d, J=7.0 Hz, 1H), 7.52 (m, 1H), 7.43 (m, 5H), 7.20 (m, 2H), 6.91 (d, J=8.3 Hz, 1H), 6.83 (d, J=8.7 Hz, 2H), 6.65 (d, J=8.3 Hz, 1H), 3.79 (s, 2H). $^{13}$C NMR: (126 MHz, CDCl$_3$) 166.11 (s, 1C), 160.73 (s, 1C), 136.45 (s, 2C), 135.46 (s, 1C), 134.72 (s, 1C), 133.75 (s, 1C), 133.73 (s, 1C), 132.19 (s, 1C), 130.31 (s, 1C), 128.92 (s, 2C), 128.86 (s, 1C), 127.42 (s, 1C), 127.10 (s, 2C), 122.47 (s, 1C), 115.05 (s, 2C), 58.89 (s, 1C), 55.55 (s, 1C). HRMS: calcd for C$_{21}$H$_{17}$NO$_2$NaSCl$_2^+$: 440.0255, found: 440.0239. SFC: t$_R$ 21.14 min (50%); t$_R$ 22.09 min (50%) (Chiralpak AD, Program: sCO$_2$/MeOH, gradient, 99:1 to 80:20 over 20 min; isocratic, 80:20 for 10 min, 2.5 mL/min, 220 nm, 40° C.).

Purification of N-((2,4-Dichlorophenyl)(2-tolylthio)methyl)benzamide (50)

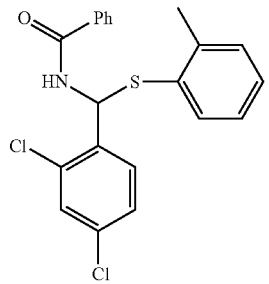 [SMILES: Cc1ccccc1SC(NC(=O)c1ccccc1)c1ccc(Cl)cc1Cl]

Compound 50 (371 mg) was recrystallized from a mixture of EtOAc/TBME, 1:1 (5 mL), by dissolving the compound in the refluxing solvent mixture followed by cooling to room temperature. The product was allowed to crystallize overnight at room temperature, was filtered, and was washed with diethyl ether (20 mL). The compound was collected, suspended in diethyl ether (10 mL), sonicated for ca. 5 min, and was filtered again. The product was dried under high vacuum (23° C., 0.1 mm Hg) for 24 h to afford 321 mg (80%) of 50 as a white solid.

Data for 50: $^1$H NMR: (500 MHz, CDCl$_3$) 7.67 (d, J=7.0 Hz, 2H), 7.51 (m, 1H), 7.44 (m, 4H), 7.32 (d, J=8.4 Hz, 1H), 7.22 (m, 3H), 7.13 (m, 1H), 6.91 (d, J=8.4 Hz, 1H), 6.80 (d, J=8.3 Hz, 1H), 2.44 (s, 3H). $^{13}$C NMR: (126 MHz, CDCl$_3$) 166.22 (s, 1C), 140.81 (s, 1C), 135.39 (s, 1C), 134.92 (s, 1C), 133.84 (s, 1C), 133.62 (s, 1C), 133.32 (s, 1C), 132.21 (s, 1C), 131.74 (s, 1C), 130.93 (s, 1C), 130.33 (s, 1C), 129.09 (s, 1C), 128.91 (s, 2C), 128.78 (s, 1C), 127.61 (s, 1C), 127.09 (s, 2C), 126.96 (s, 1C), 56.88 (s, 1C), 20.88 (s, 1C). HRMS: calcd for C$_{21}$H$_{17}$NONaSCl$_2$$^+$: 424.0306, found: 424.0316. SFC: $t_R$ 17.02 min (50%); $t_R$ 19.05 min (50%) (Chiralpak OD, Program: sCO$_2$/MeOH, gradient, 95:5 to 80:20 over 15 min; isocratic, 80:20 for 7 min, 2.5 mL/min, 220 nm, 40° C.).

Summary of Enantioselective Reactions

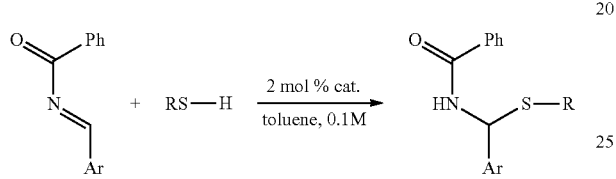

Screens for asymmetric reactions were set up via the following method: Reactions were set up on a 0.1 mmol scale using stock solutions of all reagents. To a 1-dram sized vial, under air, without a stir bar was added 0.1 mmol of the requisite imine (as a 0.20 M solution in toluene). Then, 2 mol % catalyst was added (as a 0.2 M solution in toluene). Finally, 1.2 equiv thiol was added (as a 0.25 M solution in toluene). The mixture was allowed to rest for 10 min, at which point the mixtures were diluted with 2 mL EtOAc and filtered through 0.5 g silica gel into GC vials. The vials were analyzed directly without further purification.

Enantioselectivity data was organized via the following nomenclature: each catalyst is designated a serial number based off the identity of substituents at the 3,3'-positions, the backbone, and groups decorating the phosphorus. Serial numbers for each catalyst tested are given in Table 5. Each imine is given a number designation and each thiol a letter designation, given in Table 4. The reaction serial number is the concatenation of the catalyst serial number, imine number designation, and thiol letter designation. For example, catalyst 1_i with imine 1 and thiol A is denoted as reaction 1_i_1_A. Enantioselectivities are taken as the average of duplicate runs, summarized in Table 6. Averages calculated with all decimal points before rounding.

TABLE 4

Reactant Designations

1

TABLE 4-continued

Reactant Designations

2

3

4

5

A

B

C

D

TABLE 4-continued
Reactant Designations
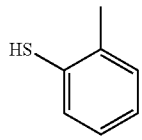
E
TABLE 5
Catalysts with serial numbers
242_i
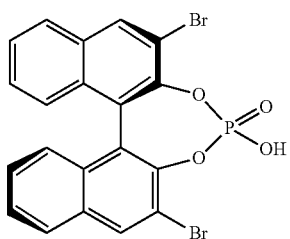
246_vi
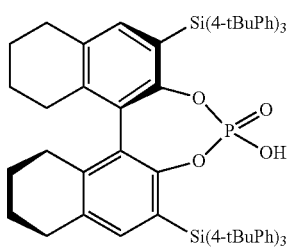
76_vi
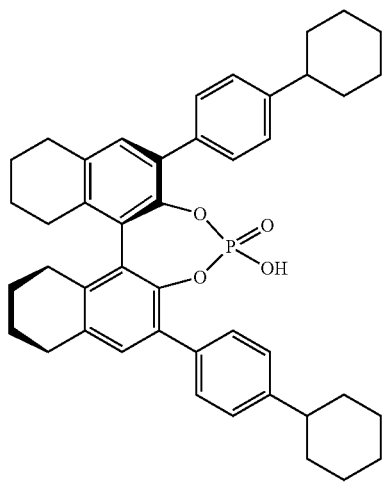
TABLE 5-continued
Catalysts with serial numbers
72_i
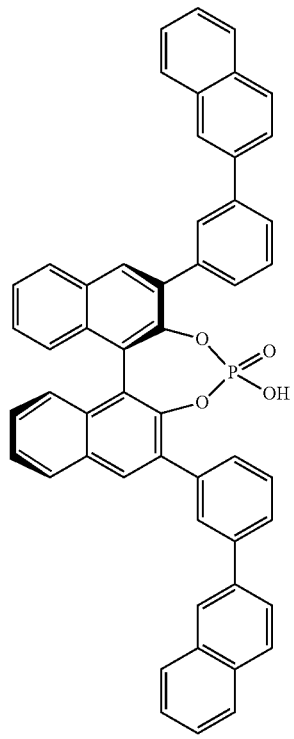
249_i
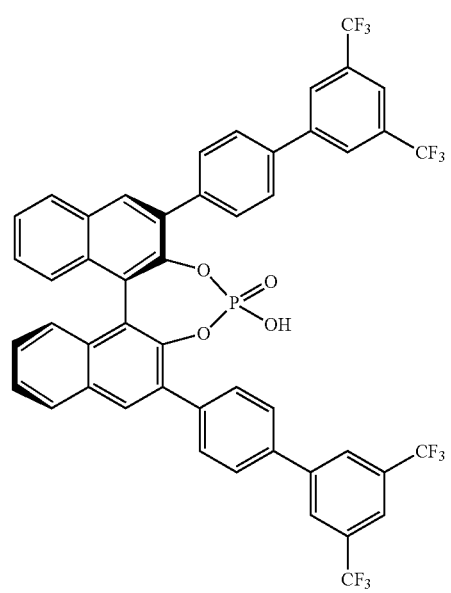

TABLE 5-continued
Catalysts with serial numbers
206_vi
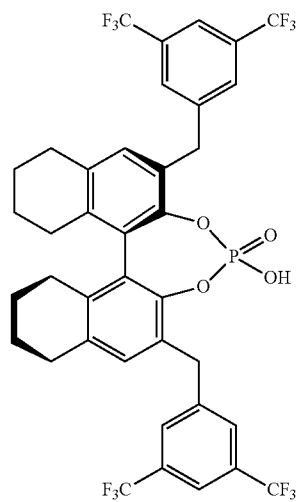
365_i
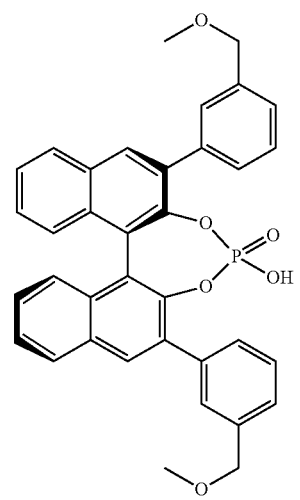
157_i
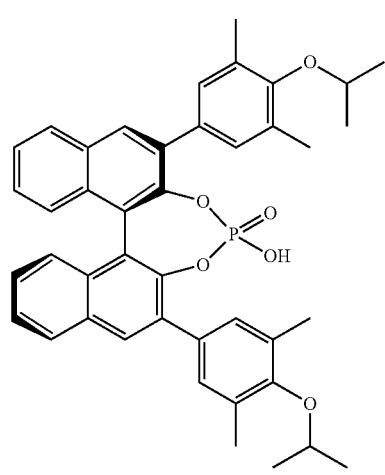
TABLE 5-continued
Catalysts with serial numbers
251_vi
207_i
253_i
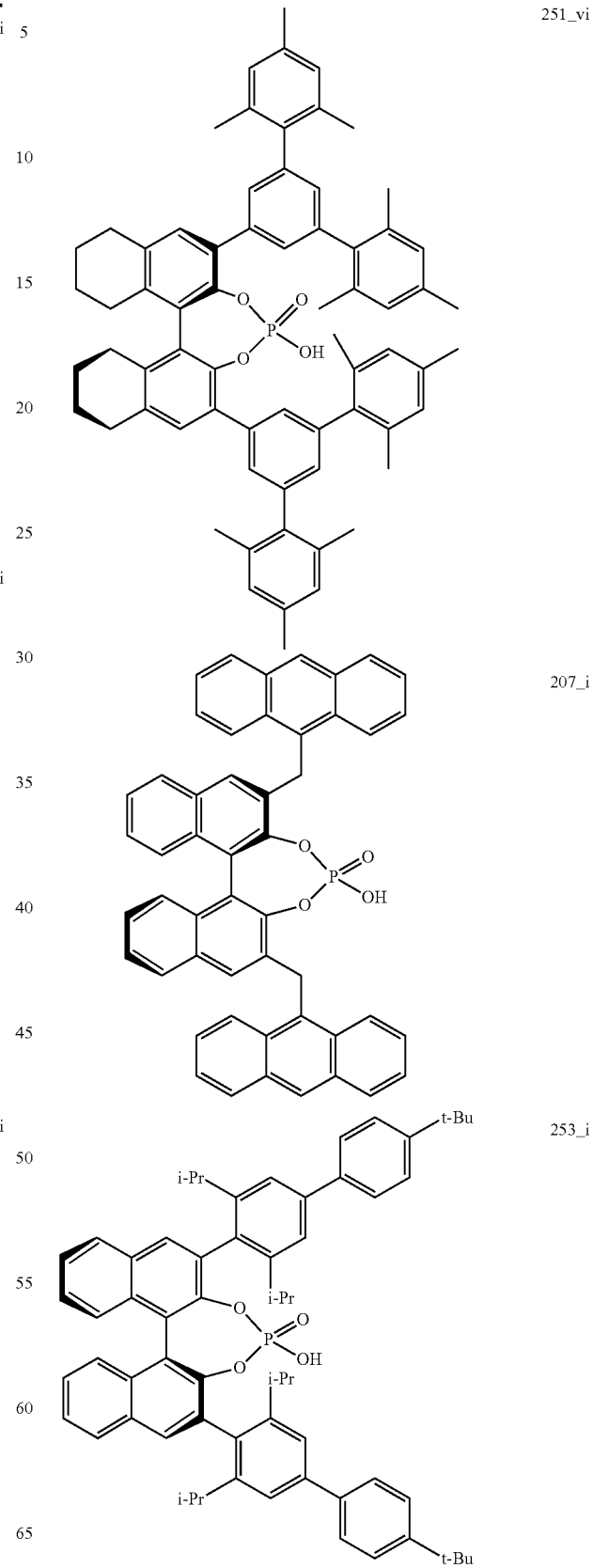

TABLE 5-continued
Catalysts with serial numbers
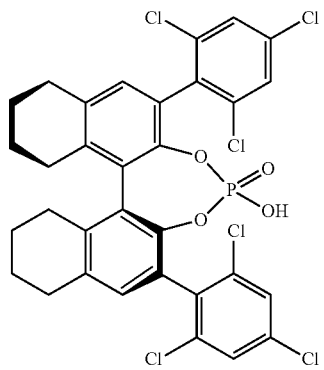
286_vi
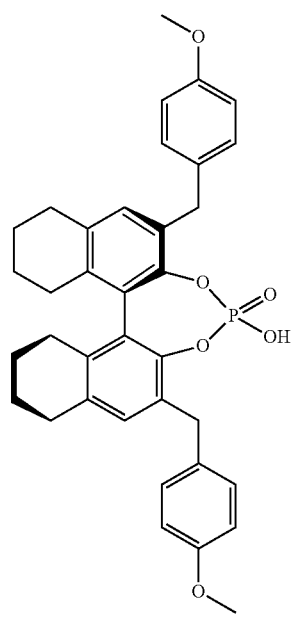
202_vi
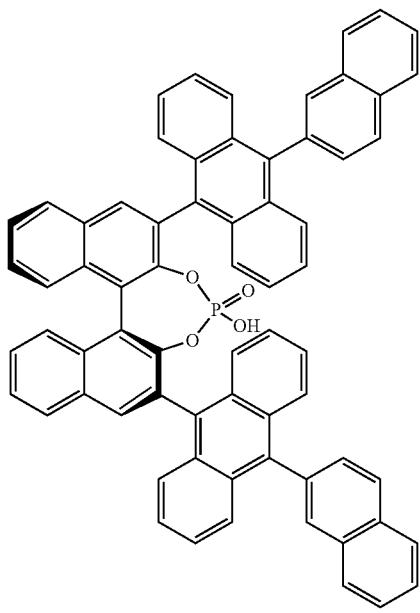
276_i
TABLE 5-continued
Catalysts with serial numbers
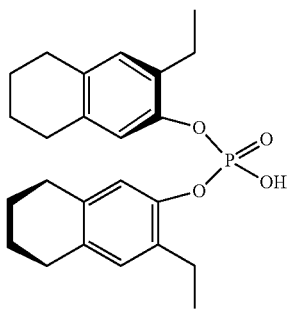
262_i
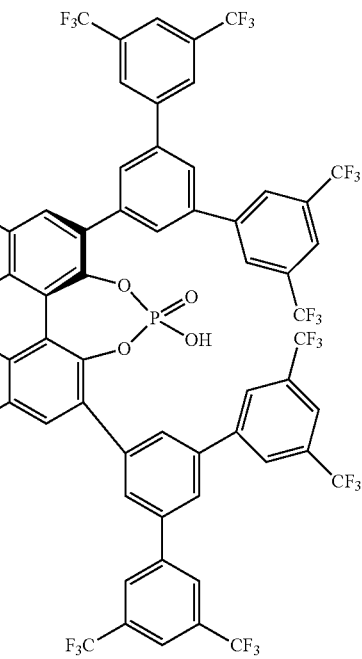
182_i
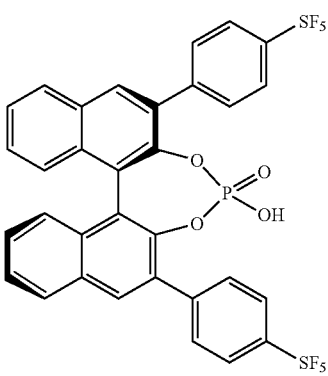
181_i TABLE 5-continued
Catalysts with serial numbers
71_vi
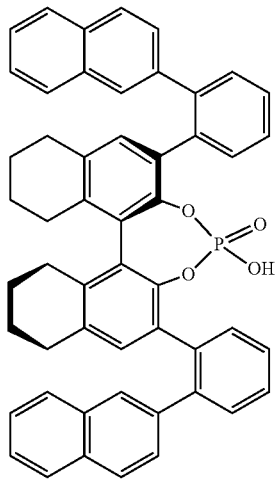
99_vi
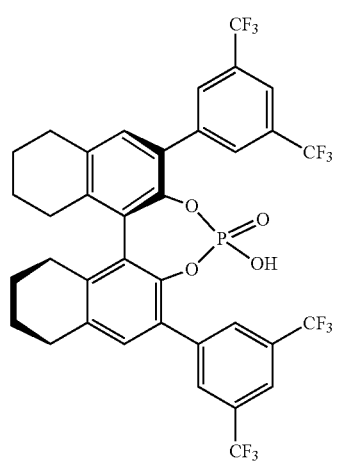
321_vi
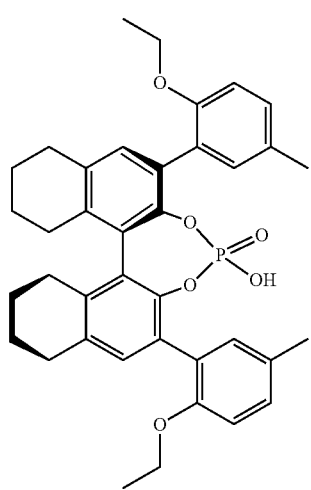
99_i
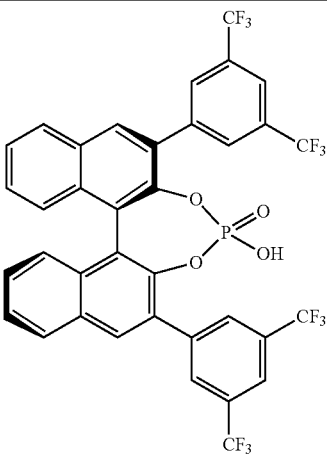
144_i
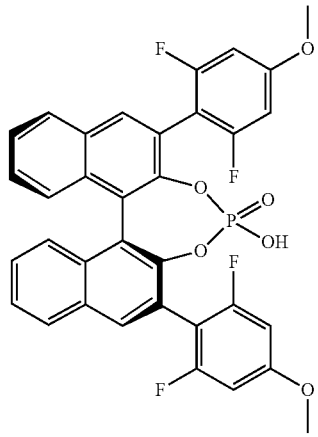
230_i TABLE 5-continued Catalysts with serial numbers 245_vi 166_i 147_i 87_i 145_i 5_i 7_i TABLE 5-continued
Catalysts with serial numbers
382_i
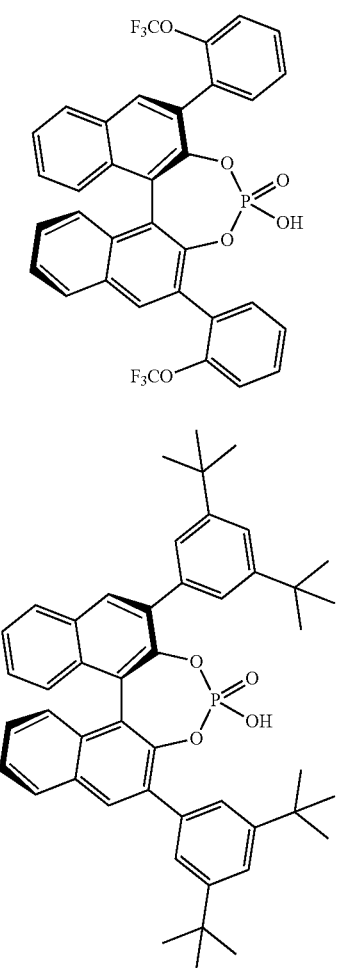
229_i
229_vi
TABLE 5-continued
Catalysts with serial numbers
371_i
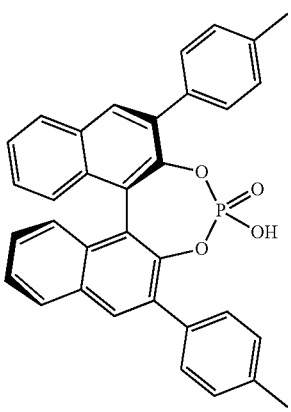
61_i
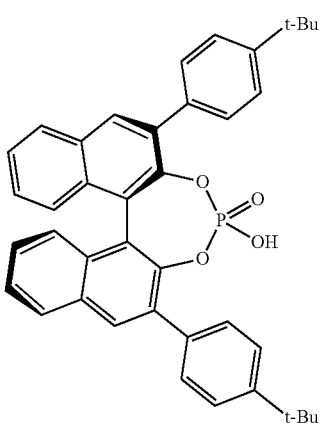
73_i
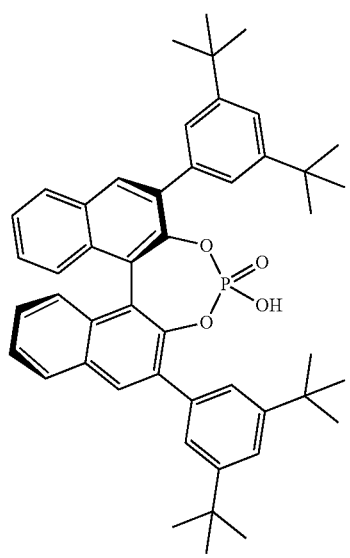
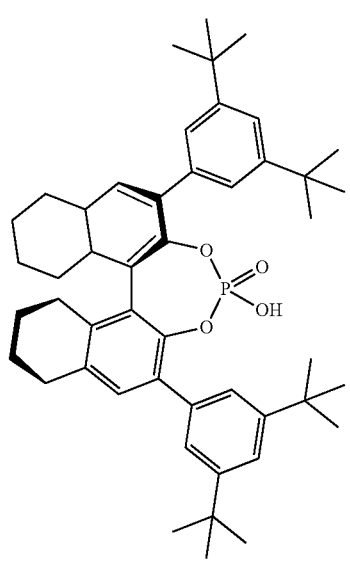
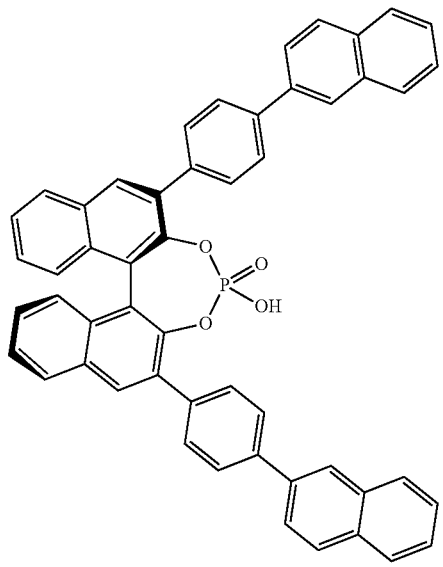

TABLE 5-continued
Catalysts with serial numbers
29_i
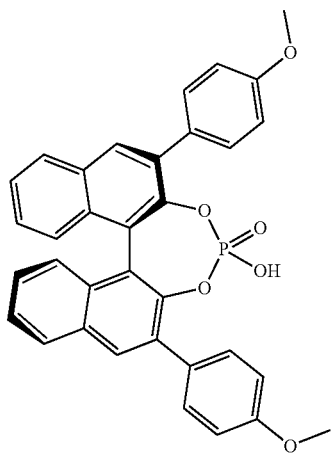
365_vi
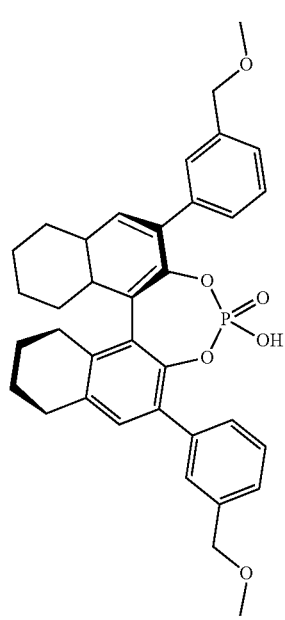
1_i
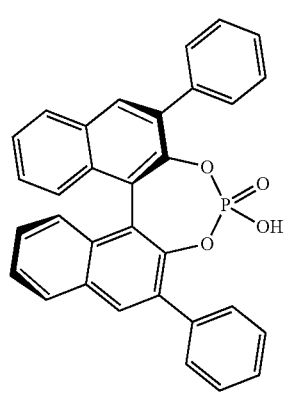
TABLE 5-continued
Catalysts with serial numbers
223_i
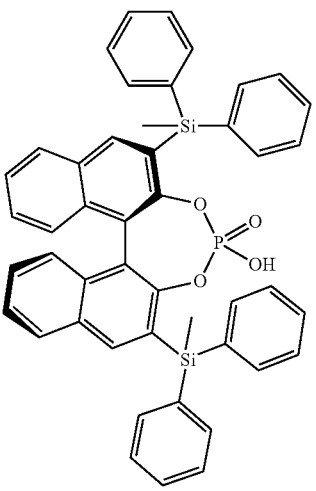
242_vi
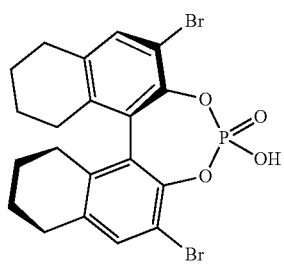
245_i
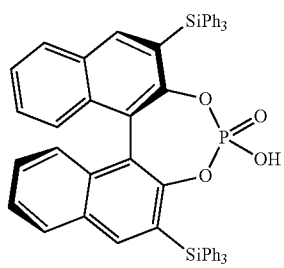

TABLE 5-continued

Catalysts with serial numbers

210_i (structure: F3C-substituted binaphthyl phosphoric acid catalyst)

TABLE 6

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 1_i_1_A | 89 | 11 | 87 | 13 | 88 | 12 | 76 |
| 1_i_1_B | 70 | 30 | 70 | 30 | 70 | 30 | 40 |
| 1_i_1_C | 77 | 23 | 73 | 27 | 75 | 25 | 50 |
| 1_i_1_D | 90 | 10 | 88 | 12 | 89 | 11 | 78 |
| 1_i_1_E | 90 | 10 | 90 | 10 | 90 | 10 | 80 |
| 1_i_2_A | 90 | 10 | 86 | 14 | 88 | 12 | 76 |
| 1_i_2_B | 70 | 30 | 70 | 30 | 70 | 30 | 40 |
| 1_i_2_C | 78 | 22 | 76 | 24 | 77 | 23 | 54 |
| 1_i_2_D | 88 | 12 | 86 | 14 | 87 | 13 | 74 |
| 1_i_2_E | 88 | 12 | 90 | 10 | 89 | 11 | 78 |
| 1_i_3_A | 87 | 13 | 87 | 13 | 87 | 13 | 74 |
| 1_i_3_B | 70 | 30 | 68 | 32 | 69 | 31 | 38 |
| 1_i_3_C | 73 | 27 | 75 | 25 | 74 | 26 | 48 |
| 1_i_3_D | 88 | 12 | 86 | 14 | 87 | 13 | 74 |
| 1_i_3_E | 85 | 15 | 89 | 11 | 87 | 13 | 74 |
| 1_i_4_A | 88 | 12 | 90 | 10 | 89 | 11 | 78 |
| 1_i_4_B | 60 | 40 | 60 | 40 | 60 | 40 | 20 |
| 1_i_4_C | 72 | 28 | 72 | 28 | 72 | 28 | 44 |
| 1_i_4_D | 84 | 16 | 88 | 12 | 86 | 14 | 72 |
| 1_i_4_E | 85 | 15 | 89 | 11 | 87 | 13 | 74 |
| 1_i_5_A | 89 | 11 | 87 | 13 | 88 | 12 | 76 |
| 1_i_5_B | 67 | 33 | 65 | 35 | 66 | 34 | 32 |
| 1_i_5_C | 74 | 26 | 70 | 30 | 72 | 28 | 44 |
| 1_i_5_D | 91 | 9 | 89 | 11 | 90 | 10 | 80 |
| 1_i_5_E | 85 | 15 | 85 | 15 | 85 | 15 | 70 |
| 144_i_1_A | 94 | 6 | 92 | 8 | 93 | 7 | 86 |
| 144_i_1_B | 84 | 16 | 84 | 16 | 84 | 16 | 68 |
| 144_i_1_C | 88 | 12 | 84 | 16 | 86 | 14 | 72 |
| 144_i_1_D | 92 | 8 | 90 | 10 | 91 | 9 | 82 |
| 144_i_1_E | 95 | 5 | 94 | 6 | 94 | 6 | 88 |
| 144_i_2_A | 95 | 5 | 90 | 10 | 92 | 8 | 84 |
| 144_i_2_B | 86 | 14 | 86 | 14 | 86 | 14 | 72 |
| 144_i_2_C | 81 | 19 | 79 | 21 | 80 | 20 | 60 |
| 144_i_2_D | 92 | 8 | 90 | 10 | 91 | 9 | 82 |
| 144_i_2_E | 91 | 9 | 93 | 7 | 92 | 8 | 84 |
| 144_i_3_A | 89 | 11 | 89 | 11 | 89 | 11 | 78 |
| 144_i_3_B | 81 | 19 | 79 | 21 | 80 | 20 | 60 |
| 144_i_3_C | 81 | 19 | 83 | 17 | 82 | 18 | 64 |
| 144_i_3_D | 94 | 6 | 92 | 8 | 93 | 7 | 86 |
| 144_i_3_E | 92 | 8 | 96 | 4 | 94 | 6 | 88 |
| 144_i_4_A | 94 | 6 | 96 | 4 | 95 | 5 | 90 |
| 144_i_4_B | 82 | 18 | 81 | 19 | 81 | 19 | 62 |
| 144_i_4_C | 86 | 14 | 85 | 15 | 85 | 15 | 70 |
| 144_i_4_D | 89 | 11 | 93 | 7 | 91 | 9 | 82 |
| 144_i_4_E | 90 | 10 | 94 | 6 | 92 | 8 | 84 |
| 144_i_5_A | 95 | 5 | 93 | 7 | 94 | 6 | 88 |
| 144_i_5_B | 80 | 20 | 80 | 20 | 80 | 20 | 60 |
| 144_i_5_C | 84 | 16 | 80 | 20 | 82 | 18 | 64 |
| 144_i_5_D | 93 | 7 | 91 | 9 | 92 | 8 | 84 |
| 144_i_5_E | 94 | 6 | 92 | 8 | 93 | 7 | 86 |
| 145_i_1_A | 94 | 6 | 96 | 4 | 95 | 5 | 90 |
| 145_i_1_B | 90 | 10 | 88 | 12 | 89 | 11 | 78 |
| 145_i_1_C | 83 | 17 | 87 | 13 | 85 | 15 | 70 |
| 145_i_1_D | 96 | 4 | 98 | 2 | 97 | 3 | 94 |
| 145_i_1_E | 97 | 3 | 97 | 3 | 97 | 3 | 94 |
| 145_i_2_A | 93 | 7 | 92 | 8 | 93 | 7 | 86 |
| 145_i_2_B | 86 | 14 | 90 | 10 | 88 | 12 | 76 |
| 145_i_2_C | 90 | 10 | 94 | 6 | 92 | 8 | 84 |
| 145_i_2_D | 99 | 1 | 97 | 3 | 98 | 2 | 96 |
| 145_i_2_E | 94 | 6 | 94 | 6 | 94 | 6 | 88 |
| 145_i_3_A | 93 | 7 | 89 | 11 | 91 | 9 | 82 |
| 145_i_3_B | 81 | 19 | 79 | 21 | 80 | 20 | 60 |
| 145_i_3_C | 91 | 9 | 91 | 9 | 91 | 9 | 82 |
| 145_i_3_D | 93 | 7 | 91 | 9 | 92 | 8 | 84 |
| 145_i_3_E | 90 | 10 | 90 | 10 | 90 | 10 | 80 |
| 145_i_4_A | 93 | 7 | 97 | 3 | 95 | 5 | 90 |
| 145_i_4_B | 77 | 23 | 79 | 21 | 78 | 22 | 56 |
| 145_i_4_C | 86 | 14 | 86 | 14 | 86 | 14 | 72 |
| 145_i_4_D | 96 | 4 | 96 | 4 | 96 | 4 | 92 |
| 145_i_4_E | 95 | 5 | 99 | 1 | 97 | 3 | 94 |
| 145_i_5_A | 93 | 7 | 97 | 3 | 95 | 5 | 90 |
| 145_i_5_B | 86 | 14 | 84 | 16 | 85 | 15 | 70 |
| 145_i_5_C | 93 | 7 | 93 | 7 | 93 | 7 | 86 |
| 145_i_5_D | 98 | 2 | 94 | 6 | 96 | 4 | 92 |
| 145_i_5_E | 97 | 3 | 95 | 5 | 96 | 4 | 92 |
| 147_i_1_A | 100 | 0 | 99 | 1 | 100 | 0 | 99 |
| 147_i_1_B | 96 | 4 | 94 | 6 | 95 | 5 | 90 |
| 147_i_1_C | 96 | 4 | 96 | 4 | 96 | 4 | 92 |
| 147_i_1_D | 100 | 0 | 100 | 0 | 100 | 0 | 99 |
| 147_i_1_E | 100 | 0 | 100 | 0 | 100 | 0 | 99 |
| 147_i_2_A | 98 | 2 | 96 | 4 | 97 | 3 | 94 |
| 147_i_2_B | 93 | 7 | 93 | 7 | 93 | 7 | 86 |
| 147_i_2_C | 95 | 5 | 91 | 9 | 93 | 7 | 86 |
| 147_i_2_D | 96 | 4 | 94 | 6 | 95 | 5 | 90 |
| 147_i_2_E | 97 | 3 | 97 | 3 | 97 | 3 | 94 |
| 147_i_3_A | 100 | 0 | 100 | 0 | 100 | 0 | 99 |
| 147_i_3_B | 93 | 7 | 95 | 5 | 94 | 6 | 88 |
| 147_i_3_C | 95 | 5 | 95 | 5 | 95 | 5 | 90 |
| 147_i_3_D | 99 | 1 | 95 | 5 | 97 | 3 | 94 |
| 147_i_3_E | 99 | 1 | 97 | 3 | 98 | 2 | 96 |
| 147_i_4_A | 100 | 0 | 98 | 2 | 99 | 1 | 98 |
| 147_i_4_B | 91 | 9 | 90 | 10 | 90 | 10 | 80 |
| 147_i_4_C | 93 | 7 | 97 | 3 | 95 | 5 | 90 |
| 147_i_4_D | 98 | 2 | 99 | 1 | 99 | 1 | 99 |
| 147_i_4_E | 99 | 1 | 97 | 3 | 98 | 2 | 96 |
| 147_i_5_A | 99 | 1 | 98 | 2 | 98 | 2 | 96 |
| 147_i_5_B | 92 | 8 | 88 | 12 | 90 | 10 | 80 |
| 147_i_5_C | 96 | 4 | 94 | 6 | 95 | 5 | 90 |
| 147_i_5_D | 100 | 0 | 100 | 0 | 100 | 0 | 99 |
| 147_i_5_E | 97 | 3 | 99 | 1 | 98 | 2 | 96 |
| 157_i_1_A | 89 | 11 | 87 | 13 | 88 | 12 | 76 |
| 157_i_1_B | 74 | 26 | 78 | 22 | 76 | 24 | 52 |
| 157_i_1_C | 75 | 25 | 77 | 23 | 76 | 24 | 52 |
| 157_i_1_D | 92 | 8 | 90 | 10 | 91 | 9 | 82 |
| 157_i_1_E | 88 | 12 | 86 | 14 | 87 | 13 | 74 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 157_i_2_A | 89 | 11 | 93 | 7 | 91 | 9 | 82 |
| 157_i_2_B | 66 | 34 | 70 | 30 | 68 | 32 | 36 |
| 157_i_2_C | 69 | 31 | 67 | 33 | 68 | 32 | 36 |
| 157_i_2_D | 92 | 8 | 91 | 9 | 91 | 9 | 82 |
| 157_i_2_E | 92 | 8 | 88 | 12 | 90 | 10 | 80 |
| 157_i_3_A | 92 | 8 | 90 | 10 | 91 | 9 | 82 |
| 157_i_3_B | 66 | 34 | 66 | 34 | 66 | 34 | 32 |
| 157_i_3_C | 72 | 28 | 70 | 30 | 71 | 29 | 42 |
| 157_i_3_D | 90 | 10 | 90 | 10 | 90 | 10 | 80 |
| 157_i_3_E | 85 | 15 | 89 | 11 | 87 | 13 | 74 |
| 157_i_4_A | 89 | 11 | 91 | 9 | 90 | 10 | 80 |
| 157_i_4_B | 68 | 32 | 67 | 33 | 67 | 33 | 34 |
| 157_i_4_C | 73 | 27 | 72 | 28 | 72 | 28 | 44 |
| 157_i_4_D | 86 | 14 | 90 | 10 | 88 | 12 | 76 |
| 157_i_4_E | 85 | 15 | 89 | 11 | 87 | 13 | 74 |
| 157_i_5_A | 87 | 13 | 85 | 15 | 86 | 14 | 72 |
| 157_i_5_B | 64 | 36 | 62 | 38 | 63 | 37 | 26 |
| 157_i_5_C | 73 | 27 | 69 | 31 | 71 | 29 | 42 |
| 157_i_5_D | 87 | 14 | 86 | 14 | 86 | 14 | 72 |
| 157_i_5_E | 84 | 16 | 88 | 12 | 86 | 14 | 72 |
| 166_i_1_A | 100 | 0 | 100 | 0 | 100 | 0 | 99 |
| 166_i_1_B | 97 | 3 | 95 | 5 | 96 | 4 | 92 |
| 166_i_1_C | 94 | 6 | 93 | 7 | 93 | 7 | 86 |
| 166_i_1_D | 99 | 1 | 95 | 5 | 97 | 3 | 94 |
| 166_i_1_E | 99 | 1 | 97 | 3 | 98 | 2 | 96 |
| 166_i_2_A | 100 | 0 | 100 | 0 | 100 | 0 | 99 |
| 166_i_2_B | 92 | 8 | 94 | 6 | 93 | 7 | 86 |
| 166_i_2_C | 99 | 1 | 97 | 3 | 98 | 2 | 96 |
| 166_i_2_D | 100 | 0 | 100 | 0 | 100 | 0 | 99 |
| 166_i_2_E | 96 | 4 | 98 | 2 | 97 | 3 | 94 |
| 166_i_3_A | 98 | 2 | 97 | 3 | 97 | 3 | 94 |
| 166_i_3_B | 95 | 5 | 94 | 6 | 94 | 6 | 88 |
| 166_i_3_C | 93 | 7 | 97 | 3 | 95 | 5 | 90 |
| 166_i_3_D | 100 | 0 | 100 | 0 | 100 | 0 | 99 |
| 166_i_3_E | 100 | 0 | 100 | 0 | 100 | 0 | 99 |
| 166_i_4_A | 100 | 0 | 99 | 1 | 100 | 0 | 99 |
| 166_i_4_B | 92 | 8 | 88 | 12 | 90 | 10 | 80 |
| 166_i_4_C | 96 | 4 | 94 | 6 | 95 | 5 | 90 |
| 166_i_4_D | 100 | 0 | 99 | 1 | 100 | 0 | 99 |
| 166_i_4_E | 100 | 0 | 100 | 0 | 100 | 0 | 99 |
| 166_i_5_A | 100 | 0 | 100 | 0 | 100 | 0 | 99 |
| 166_i_5_B | 86 | 14 | 90 | 10 | 88 | 12 | 76 |
| 166_i_5_C | 96 | 4 | 98 | 2 | 97 | 3 | 94 |
| 166_i_5_D | 100 | 0 | 99 | 1 | 100 | 0 | 99 |
| 166_i_5_E | 100 | 0 | 99 | 1 | 100 | 0 | 99 |
| 181_i_1_A | 82 | 18 | 86 | 14 | 84 | 16 | 68 |
| 181_i_1_B | 71 | 29 | 75 | 25 | 73 | 27 | 46 |
| 181_i_1_C | 73 | 27 | 71 | 29 | 72 | 28 | 44 |
| 181_i_1_D | 88 | 12 | 88 | 12 | 88 | 12 | 76 |
| 181_i_1_E | 88 | 12 | 84 | 16 | 86 | 14 | 72 |
| 181_i_2_A | 90 | 10 | 84 | 16 | 87 | 13 | 74 |
| 181_i_2_B | 72 | 28 | 70 | 30 | 71 | 29 | 42 |
| 181_i_2_C | 74 | 26 | 72 | 28 | 73 | 27 | 46 |
| 181_i_2_D | 82 | 18 | 86 | 14 | 84 | 16 | 68 |
| 181_i_2_E | 88 | 12 | 92 | 8 | 90 | 10 | 80 |
| 181_i_3_A | 90 | 10 | 88 | 12 | 89 | 11 | 78 |
| 181_i_3_B | 69 | 31 | 68 | 32 | 68 | 32 | 36 |
| 181_i_3_C | 78 | 22 | 74 | 26 | 76 | 24 | 52 |
| 181_i_3_D | 89 | 11 | 87 | 13 | 88 | 12 | 76 |
| 181_i_3_E | 89 | 11 | 88 | 12 | 88 | 12 | 76 |
| 181_i_4_A | 89 | 11 | 87 | 13 | 88 | 12 | 76 |
| 181_i_4_B | 67 | 33 | 67 | 33 | 67 | 33 | 34 |
| 181_i_4_C | 71 | 29 | 75 | 25 | 73 | 27 | 46 |
| 181_i_4_D | 86 | 14 | 88 | 12 | 87 | 13 | 74 |
| 181_i_4_E | 88 | 12 | 87 | 13 | 87 | 13 | 74 |
| 181_i_5_A | 87 | 13 | 85 | 15 | 86 | 14 | 72 |
| 181_i_5_B | 65 | 35 | 63 | 37 | 64 | 36 | 28 |
| 181_i_5_C | 71 | 29 | 70 | 30 | 70 | 30 | 40 |
| 181_i_5_D | 84 | 16 | 88 | 12 | 86 | 14 | 72 |
| 181_i_5_E | 86 | 14 | 90 | 10 | 88 | 12 | 76 |
| 182_i_1_A | 93 | 7 | 91 | 9 | 92 | 8 | 84 |
| 182_i_1_B | 70 | 30 | 70 | 30 | 70 | 30 | 40 |
| 182_i_1_C | 73 | 27 | 69 | 31 | 71 | 29 | 42 |
| 182_i_1_D | 91 | 9 | 89 | 11 | 90 | 10 | 80 |
| 182_i_1_E | 91 | 10 | 90 | 11 | 90 | 10 | 80 |
| 182_i_2_A | 93 | 7 | 91 | 9 | 92 | 8 | 84 |
| 182_i_2_B | 80 | 20 | 76 | 24 | 78 | 22 | 56 |
| 182_i_2_C | 81 | 19 | 79 | 21 | 80 | 20 | 60 |
| 182_i_2_D | 92 | 8 | 90 | 10 | 91 | 9 | 82 |
| 182_i_2_E | 94 | 6 | 92 | 8 | 93 | 7 | 86 |
| 182_i_3_A | 93 | 7 | 93 | 7 | 93 | 7 | 86 |
| 182_i_3_B | 78 | 22 | 82 | 18 | 80 | 20 | 60 |
| 182_i_3_C | 80 | 20 | 82 | 18 | 81 | 19 | 62 |
| 182_i_3_D | 93 | 7 | 92 | 8 | 92 | 8 | 84 |
| 182_i_3_E | 90 | 10 | 90 | 10 | 90 | 10 | 80 |
| 182_i_4_A | 92 | 8 | 92 | 8 | 92 | 8 | 84 |
| 182_i_4_B | 68 | 32 | 68 | 32 | 68 | 32 | 36 |
| 182_i_4_C | 78 | 22 | 82 | 18 | 80 | 20 | 60 |
| 182_i_4_D | 89 | 11 | 93 | 7 | 91 | 9 | 82 |
| 182_i_4_E | 93 | 7 | 91 | 9 | 92 | 8 | 84 |
| 182_i_5_A | 91 | 9 | 87 | 13 | 89 | 11 | 78 |
| 182_i_5_B | 75 | 25 | 73 | 27 | 74 | 26 | 48 |
| 182_i_5_C | 78 | 22 | 76 | 24 | 77 | 23 | 54 |
| 182_i_5_D | 92 | 8 | 90 | 10 | 91 | 9 | 82 |
| 182_i_5_E | 91 | 9 | 91 | 9 | 91 | 9 | 82 |
| 202_i_1_A | 64 | 36 | 68 | 32 | 66 | 34 | 32 |
| 202_i_1_B | 43 | 57 | 45 | 55 | 44 | 56 | −12 |
| 202_i_1_C | 45 | 55 | 43 | 57 | 44 | 56 | −12 |
| 202_i_1_D | 65 | 35 | 65 | 35 | 65 | 35 | 30 |
| 202_i_1_E | 60 | 40 | 60 | 40 | 60 | 40 | 20 |
| 202_i_2_A | 71 | 29 | 69 | 31 | 70 | 30 | 40 |
| 202_i_2_B | 41 | 59 | 37 | 63 | 39 | 61 | −22 |
| 202_i_2_C | 46 | 54 | 44 | 56 | 45 | 55 | −10 |
| 202_i_2_D | 61 | 39 | 60 | 40 | 61 | 39 | 22 |
| 202_i_2_E | 63 | 37 | 61 | 39 | 62 | 38 | 24 |
| 202_i_3_A | 57 | 43 | 57 | 43 | 57 | 43 | 14 |
| 202_i_3_B | 40 | 60 | 44 | 56 | 42 | 58 | −16 |
| 202_i_3_C | 77 | 23 | 79 | 21 | 78 | 22 | 56 |
| 202_i_3_D | 60 | 40 | 60 | 40 | 60 | 40 | 20 |
| 202_i_3_E | 58 | 42 | 58 | 42 | 58 | 42 | 16 |
| 202_i_4_A | 72 | 28 | 70 | 30 | 71 | 29 | 42 |
| 202_i_4_B | 38 | 62 | 42 | 58 | 40 | 60 | −20 |
| 202_i_4_C | 49 | 51 | 53 | 47 | 51 | 49 | 2 |
| 202_i_4_D | 59 | 41 | 57 | 43 | 58 | 42 | 16 |
| 202_i_4_E | 59 | 41 | 55 | 45 | 57 | 43 | 14 |
| 202_i_5_A | 66 | 34 | 64 | 36 | 65 | 35 | 30 |
| 202_i_5_B | 35 | 65 | 31 | 69 | 33 | 67 | −34 |
| 202_i_5_C | 41 | 59 | 39 | 61 | 40 | 60 | −20 |
| 202_i_5_D | 68 | 32 | 68 | 32 | 68 | 32 | 36 |
| 202_i_5_E | 60 | 40 | 58 | 42 | 59 | 41 | 18 |
| 205_i_1_A | 72 | 28 | 72 | 28 | 72 | 28 | 44 |
| 205_i_1_B | 33 | 67 | 37 | 63 | 35 | 65 | −30 |
| 205_i_1_C | 44 | 56 | 46 | 54 | 45 | 55 | −10 |
| 205_i_1_D | 72 | 28 | 72 | 28 | 72 | 28 | 44 |
| 205_i_1_E | 65 | 35 | 64 | 36 | 64 | 36 | 28 |
| 205_i_2_A | 77 | 23 | 75 | 25 | 76 | 24 | 52 |
| 205_i_2_B | 40 | 60 | 40 | 60 | 40 | 60 | −20 |
| 205_i_2_C | 45 | 55 | 49 | 51 | 47 | 53 | −6 |
| 205_i_2_D | 63 | 37 | 67 | 33 | 65 | 35 | 30 |
| 205_i_2_E | 71 | 29 | 73 | 27 | 72 | 28 | 44 |
| 205_i_3_A | 75 | 25 | 75 | 25 | 75 | 25 | 50 |
| 205_i_3_B | 38 | 62 | 38 | 62 | 38 | 62 | −24 |
| 205_i_3_C | 42 | 58 | 40 | 60 | 41 | 59 | −18 |
| 205_i_3_D | 75 | 25 | 75 | 26 | 75 | 25 | 50 |
| 205_i_3_E | 69 | 31 | 73 | 27 | 71 | 29 | 42 |
| 205_i_4_A | 72 | 28 | 76 | 24 | 74 | 26 | 48 |
| 205_i_4_B | 43 | 57 | 42 | 58 | 43 | 57 | −14 |
| 205_i_4_C | 37 | 63 | 38 | 64 | 37 | 63 | −26 |
| 205_i_4_D | 73 | 27 | 72 | 28 | 73 | 27 | 46 |
| 205_i_4_E | 62 | 38 | 60 | 40 | 61 | 39 | 22 |
| 205_i_5_A | 71 | 29 | 75 | 25 | 73 | 27 | 46 |
| 205_i_5_B | 38 | 62 | 42 | 58 | 40 | 60 | −20 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 205_i_5_C | 41 | 59 | 43 | 57 | 42 | 58 | −16 |
| 205_i_5_D | 70 | 30 | 69 | 31 | 69 | 31 | 38 |
| 205_i_5_E | 75 | 25 | 74 | 26 | 74 | 26 | 48 |
| 207_i_1_A | 70 | 30 | 70 | 30 | 70 | 30 | 40 |
| 207_i_1_B | 62 | 38 | 62 | 38 | 62 | 38 | 24 |
| 207_i_1_C | 64 | 36 | 68 | 32 | 66 | 34 | 32 |
| 207_i_1_D | 70 | 30 | 74 | 26 | 72 | 28 | 44 |
| 207_i_1_E | 74 | 23 | 73 | 27 | 73 | 27 | 46 |
| 207_i_2_A | 80 | 20 | 80 | 20 | 80 | 20 | 60 |
| 207_i_2_B | 62 | 38 | 60 | 40 | 61 | 39 | 22 |
| 207_i_2_C | 65 | 35 | 65 | 35 | 65 | 35 | 30 |
| 207_i_2_D | 73 | 27 | 77 | 23 | 75 | 25 | 50 |
| 207_i_2_E | 78 | 22 | 82 | 18 | 80 | 20 | 60 |
| 207_i_3_A | 77 | 23 | 79 | 21 | 78 | 22 | 56 |
| 207_i_3_B | 62 | 38 | 62 | 38 | 62 | 38 | 24 |
| 207_i_3_C | 66 | 34 | 66 | 34 | 66 | 34 | 32 |
| 207_i_3_D | 75 | 25 | 75 | 25 | 75 | 25 | 50 |
| 207_i_3_E | 78 | 22 | 78 | 22 | 78 | 22 | 56 |
| 207_i_4_A | 77 | 23 | 81 | 19 | 79 | 21 | 58 |
| 207_i_4_B | 57 | 43 | 61 | 39 | 59 | 41 | 18 |
| 207_i_4_C | 70 | 30 | 68 | 32 | 69 | 31 | 38 |
| 207_i_4_D | 76 | 24 | 80 | 20 | 78 | 22 | 56 |
| 207_i_4_E | 75 | 25 | 79 | 21 | 77 | 23 | 54 |
| 207_i_5_A | 79 | 21 | 77 | 23 | 78 | 22 | 56 |
| 207_i_5_B | 62 | 38 | 58 | 42 | 60 | 40 | 20 |
| 207_i_5_C | 66 | 34 | 62 | 38 | 64 | 36 | 28 |
| 207_i_5_D | 74 | 26 | 72 | 28 | 73 | 27 | 46 |
| 207_i_5_E | 76 | 24 | 76 | 24 | 76 | 24 | 52 |
| 210_i_1_A | 67 | 33 | 63 | 37 | 65 | 35 | 30 |
| 210_i_1_B | 46 | 54 | 44 | 56 | 45 | 55 | −10 |
| 210_i_1_C | 44 | 56 | 44 | 56 | 44 | 56 | −12 |
| 210_i_1_D | 67 | 33 | 63 | 37 | 65 | 35 | 30 |
| 210_i_1_E | 63 | 37 | 63 | 37 | 63 | 38 | 25 |
| 210_i_2_A | 72 | 28 | 70 | 30 | 71 | 29 | 41 |
| 210_i_2_B | 42 | 58 | 40 | 60 | 41 | 59 | −18 |
| 210_i_2_C | 45 | 55 | 48 | 52 | 47 | 54 | −7 |
| 210_i_2_D | 60 | 40 | 60 | 40 | 60 | 40 | 20 |
| 210_i_2_E | 62 | 38 | 60 | 40 | 61 | 39 | 22 |
| 210_i_3_A | 57 | 43 | 59 | 41 | 58 | 42 | 16 |
| 210_i_3_B | 43 | 57 | 41 | 59 | 42 | 58 | −16 |
| 210_i_3_C | 46 | 54 | 50 | 50 | 48 | 52 | −4 |
| 210_i_3_D | 60 | 40 | 62 | 38 | 61 | 39 | 22 |
| 210_i_3_E | 57 | 43 | 56 | 44 | 57 | 43 | 14 |
| 210_i_4_A | 71 | 29 | 71 | 29 | 71 | 29 | 42 |
| 210_i_4_B | 40 | 60 | 44 | 56 | 42 | 58 | −16 |
| 210_i_4_C | 49 | 51 | 53 | 47 | 51 | 49 | 2 |
| 210_i_4_D | 57 | 43 | 55 | 45 | 56 | 44 | 12 |
| 210_i_4_E | 56 | 44 | 54 | 46 | 55 | 45 | 10 |
| 210_i_5_A | 65 | 35 | 61 | 39 | 63 | 37 | 26 |
| 210_i_5_B | 40 | 60 | 38 | 62 | 39 | 61 | −22 |
| 210_i_5_C | 43 | 57 | 43 | 57 | 43 | 57 | −14 |
| 210_i_5_D | 67 | 33 | 65 | 35 | 66 | 34 | 32 |
| 210_i_5_E | 60 | 40 | 60 | 40 | 60 | 40 | 20 |
| 223_i_1_A | 82 | 18 | 78 | 22 | 80 | 20 | 60 |
| 223_i_1_B | 68 | 32 | 66 | 34 | 67 | 33 | 34 |
| 223_i_1_C | 68 | 32 | 68 | 32 | 68 | 32 | 36 |
| 223_i_1_D | 80 | 20 | 76 | 24 | 78 | 22 | 56 |
| 223_i_1_E | 80 | 20 | 80 | 20 | 80 | 20 | 60 |
| 223_i_2_A | 79 | 21 | 77 | 23 | 78 | 22 | 56 |
| 223_i_2_B | 63 | 37 | 61 | 39 | 62 | 38 | 24 |
| 223_i_2_C | 64 | 36 | 66 | 34 | 65 | 35 | 30 |
| 223_i_2_D | 81 | 19 | 81 | 19 | 81 | 19 | 62 |
| 223_i_2_E | 81 | 19 | 79 | 21 | 80 | 20 | 60 |
| 223_i_3_A | 74 | 26 | 76 | 24 | 75 | 25 | 50 |
| 223_i_3_B | 68 | 32 | 66 | 34 | 67 | 33 | 34 |
| 223_i_3_C | 62 | 38 | 66 | 34 | 64 | 36 | 28 |
| 223_i_3_D | 79 | 21 | 81 | 19 | 80 | 20 | 60 |
| 223_i_3_E | 81 | 19 | 80 | 20 | 81 | 19 | 62 |
| 223_i_4_A | 75 | 25 | 75 | 25 | 75 | 25 | 50 |
| 223_i_4_B | 59 | 41 | 63 | 37 | 61 | 39 | 22 |
| 223_i_4_C | 58 | 42 | 62 | 38 | 60 | 40 | 20 |
| 223_i_4_D | 82 | 18 | 80 | 20 | 81 | 19 | 62 |
| 223_i_4_E | 80 | 20 | 80 | 20 | 80 | 20 | 60 |
| 223_i_5_A | 87 | 13 | 83 | 17 | 85 | 15 | 70 |
| 223_i_5_B | 60 | 40 | 58 | 42 | 59 | 41 | 18 |
| 223_i_5_C | 61 | 39 | 59 | 41 | 60 | 40 | 20 |
| 223_i_5_D | 81 | 19 | 83 | 17 | 82 | 18 | 64 |
| 223_i_5_E | 84 | 16 | 82 | 18 | 83 | 17 | 66 |
| 229_i_1_A | 91 | 9 | 95 | 5 | 93 | 7 | 86 |
| 229_i_1_B | 69 | 31 | 71 | 29 | 70 | 30 | 40 |
| 229_i_1_C | 72 | 28 | 70 | 30 | 71 | 29 | 42 |
| 229_i_1_D | 86 | 14 | 85 | 15 | 86 | 14 | 72 |
| 229_i_1_E | 87 | 13 | 91 | 9 | 89 | 11 | 78 |
| 229_i_2_A | 89 | 11 | 93 | 7 | 91 | 9 | 82 |
| 229_i_2_B | 92 | 8 | 90 | 10 | 91 | 9 | 82 |
| 229_i_2_C | 73 | 27 | 73 | 27 | 73 | 27 | 46 |
| 229_i_2_D | 77 | 23 | 73 | 27 | 75 | 25 | 50 |
| 229_i_2_E | 92 | 8 | 90 | 10 | 91 | 9 | 82 |
| 229_i_3_A | 92 | 8 | 91 | 9 | 91 | 9 | 82 |
| 229_i_3_B | 73 | 27 | 71 | 29 | 72 | 28 | 44 |
| 229_i_3_C | 75 | 25 | 75 | 25 | 75 | 25 | 50 |
| 229_i_3_D | 86 | 14 | 90 | 10 | 88 | 12 | 76 |
| 229_i_3_E | 87 | 13 | 89 | 11 | 88 | 12 | 76 |
| 229_i_4_A | 93 | 7 | 92 | 8 | 93 | 7 | 86 |
| 229_i_4_B | 70 | 30 | 70 | 30 | 70 | 30 | 40 |
| 229_i_4_C | 72 | 28 | 76 | 24 | 74 | 26 | 48 |
| 229_i_4_D | 90 | 10 | 94 | 6 | 92 | 8 | 84 |
| 229_i_4_E | 92 | 8 | 90 | 10 | 91 | 9 | 82 |
| 229_i_5_A | 90 | 10 | 88 | 12 | 89 | 11 | 78 |
| 229_i_5_B | 73 | 27 | 69 | 31 | 71 | 29 | 42 |
| 229_i_5_C | 73 | 27 | 71 | 29 | 72 | 28 | 44 |
| 229_i_5_D | 88 | 12 | 88 | 12 | 88 | 12 | 76 |
| 229_i_5_E | 91 | 9 | 89 | 11 | 90 | 10 | 80 |
| 229_vi_1_A | 91 | 9 | 91 | 9 | 91 | 9 | 82 |
| 229_vi_1_B | 74 | 26 | 70 | 30 | 72 | 28 | 44 |
| 229_vi_1_C | 70 | 30 | 74 | 26 | 72 | 28 | 44 |
| 229_vi_1_D | 89 | 11 | 87 | 13 | 88 | 12 | 76 |
| 229_vi_1_E | 88 | 12 | 87 | 13 | 88 | 12 | 76 |
| 229_vi_2_A | 92 | 8 | 88 | 12 | 90 | 10 | 80 |
| 229_vi_2_B | 91 | 9 | 89 | 11 | 90 | 10 | 80 |
| 229_vi_2_C | 70 | 30 | 70 | 30 | 70 | 30 | 40 |
| 229_vi_2_D | 75 | 25 | 73 | 27 | 74 | 26 | 48 |
| 229_vi_2_E | 89 | 11 | 91 | 9 | 90 | 10 | 80 |
| 229_vi_3_A | 92 | 8 | 90 | 10 | 91 | 9 | 82 |
| 229_vi_3_B | 75 | 25 | 71 | 29 | 73 | 27 | 46 |
| 229_vi_3_C | 78 | 22 | 76 | 24 | 77 | 23 | 54 |
| 229_vi_3_D | 90 | 10 | 88 | 12 | 89 | 11 | 78 |
| 229_vi_3_E | 88 | 12 | 86 | 14 | 87 | 13 | 74 |
| 229_vi_4_A | 90 | 10 | 94 | 6 | 92 | 8 | 84 |
| 229_vi_4_B | 67 | 33 | 71 | 29 | 69 | 31 | 38 |
| 229_vi_4_C | 75 | 25 | 73 | 27 | 74 | 26 | 48 |
| 229_vi_4_D | 92 | 8 | 92 | 8 | 92 | 8 | 84 |
| 229_vi_4_E | 93 | 7 | 89 | 11 | 91 | 9 | 82 |
| 229_vi_5_A | 91 | 9 | 89 | 11 | 90 | 10 | 80 |
| 229_vi_5_B | 71 | 29 | 69 | 31 | 70 | 30 | 40 |
| 229_vi_5_C | 71 | 29 | 73 | 27 | 72 | 28 | 44 |
| 229_vi_5_D | 90 | 10 | 88 | 12 | 89 | 11 | 78 |
| 229_vi_5_E | 89 | 11 | 93 | 7 | 91 | 9 | 82 |
| 230_i_i_A | 89 | 11 | 91 | 9 | 90 | 10 | 80 |
| 230_i_i_B | 68 | 32 | 67 | 33 | 68 | 32 | 36 |
| 230_i_i_C | 72 | 28 | 72 | 28 | 72 | 28 | 44 |
| 230_i_i_D | 86 | 14 | 90 | 10 | 88 | 12 | 76 |
| 230_i_i_E | 87 | 13 | 91 | 9 | 89 | 11 | 78 |
| 230_i_2_A | 93 | 7 | 91 | 9 | 92 | 8 | 84 |
| 230_i_2_B | 82 | 18 | 78 | 22 | 80 | 20 | 60 |
| 230_i_2_C | 82 | 18 | 78 | 22 | 80 | 20 | 60 |
| 230_i_2_D | 94 | 6 | 92 | 8 | 93 | 7 | 86 |
| 230_i_2_E | 95 | 5 | 95 | 5 | 95 | 5 | 90 |
| 230_i_3_A | 94 | 6 | 92 | 8 | 93 | 7 | 86 |
| 230_i_3_B | 81 | 19 | 81 | 19 | 81 | 19 | 62 |
| 230_i_3_C | 78 | 22 | 82 | 18 | 80 | 20 | 60 |
| 230_i_3_D | 89 | 11 | 91 | 9 | 90 | 10 | 80 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 230_i_3_E | 90 | 10 | 90 | 10 | 90 | 10 | 80 |
| 230_i_4_A | 93 | 7 | 93 | 7 | 93 | 7 | 86 |
| 230_i_4_B | 68 | 32 | 72 | 28 | 70 | 30 | 40 |
| 230_i_4_C | 81 | 19 | 85 | 15 | 83 | 17 | 66 |
| 230_i_4_D | 93 | 7 | 91 | 9 | 92 | 8 | 84 |
| 230_i_4_E | 94 | 6 | 92 | 8 | 93 | 7 | 86 |
| 230_i_5_A | 91 | 9 | 87 | 13 | 89 | 11 | 78 |
| 230_i_5_B | 72 | 28 | 72 | 28 | 72 | 28 | 44 |
| 230_i_5_C | 75 | 25 | 79 | 21 | 77 | 23 | 54 |
| 230_i_5_D | 91 | 9 | 95 | 5 | 93 | 7 | 86 |
| 230_i_5_E | 93 | 7 | 91 | 9 | 92 | 8 | 84 |
| 242_i_1_A | 67 | 33 | 66 | 34 | 67 | 33 | 34 |
| 242_i_1_B | 67 | 33 | 63 | 37 | 65 | 35 | 30 |
| 242_i_1_C | 67 | 33 | 65 | 35 | 66 | 34 | 32 |
| 242_i_1_D | 73 | 27 | 71 | 29 | 72 | 28 | 44 |
| 242_i_1_E | 63 | 37 | 65 | 35 | 64 | 36 | 28 |
| 242_i_2_A | 66 | 34 | 64 | 36 | 65 | 35 | 30 |
| 242_i_2_B | 42 | 58 | 46 | 54 | 44 | 56 | -12 |
| 242_i_2_C | 54 | 46 | 56 | 44 | 55 | 45 | 10 |
| 242_i_2_D | 61 | 39 | 60 | 40 | 61 | 39 | 22 |
| 242_i_2_E | 62 | 38 | 62 | 38 | 62 | 38 | 24 |
| 242_i_3_A | 55 | 45 | 59 | 41 | 57 | 43 | 14 |
| 242_i_3_B | 45 | 55 | 49 | 51 | 47 | 53 | -6 |
| 242_i_3_C | 79 | 21 | 77 | 23 | 78 | 22 | 56 |
| 242_i_3_D | 60 | 40 | 60 | 40 | 60 | 40 | 20 |
| 242_i_3_E | 60 | 40 | 56 | 44 | 58 | 42 | 16 |
| 242_i_4_A | 72 | 28 | 70 | 30 | 71 | 29 | 42 |
| 242_i_4_B | 40 | 60 | 40 | 60 | 40 | 60 | -20 |
| 242_i_4_C | 52 | 48 | 50 | 50 | 51 | 49 | 2 |
| 242_i_4_D | 58 | 42 | 58 | 42 | 58 | 42 | 16 |
| 242_i_4_E | 55 | 45 | 59 | 41 | 57 | 43 | 14 |
| 242_i_5_A | 62 | 38 | 64 | 36 | 63 | 37 | 26 |
| 242_i_5_B | 52 | 48 | 52 | 48 | 52 | 48 | 4 |
| 242_i_5_C | 50 | 50 | 50 | 50 | 50 | 50 | 0 |
| 242_i_5_D | 68 | 32 | 72 | 28 | 70 | 30 | 40 |
| 242_i_5_E | 57 | 43 | 61 | 39 | 59 | 41 | 18 |
| 242_vi_1_A | 67 | 33 | 65 | 35 | 66 | 34 | 32 |
| 242_vi_1_B | 65 | 35 | 65 | 35 | 65 | 35 | 30 |
| 242_vi_1_C | 69 | 31 | 65 | 35 | 67 | 33 | 34 |
| 242_vi_1_D | 73 | 27 | 67 | 33 | 70 | 30 | 40 |
| 242_vi_1_E | 65 | 35 | 65 | 35 | 65 | 35 | 30 |
| 242_vi_2_A | 65 | 35 | 64 | 36 | 64 | 36 | 28 |
| 242_vi_2_B | 43 | 57 | 47 | 53 | 45 | 55 | -10 |
| 242_vi_2_C | 53 | 47 | 57 | 43 | 55 | 45 | 10 |
| 242_vi_2_D | 61 | 39 | 59 | 41 | 60 | 40 | 20 |
| 242_vi_2_E | 62 | 38 | 62 | 38 | 62 | 38 | 24 |
| 242_vi_3_A | 59 | 41 | 55 | 45 | 57 | 43 | 14 |
| 242_vi_3_B | 47 | 53 | 45 | 55 | 46 | 54 | -8 |
| 242_vi_3_C | 72 | 28 | 71 | 29 | 71 | 29 | 42 |
| 242_vi_3_D | 64 | 36 | 62 | 38 | 63 | 37 | 26 |
| 242_vi_3_E | 60 | 40 | 60 | 40 | 60 | 40 | 20 |
| 242_vi_4_A | 68 | 32 | 72 | 28 | 70 | 30 | 40 |
| 242_vi_4_B | 38 | 62 | 40 | 60 | 39 | 61 | -22 |
| 242_vi_4_C | 51 | 49 | 50 | 50 | 50 | 50 | 0 |
| 242_vi_4_D | 58 | 40 | 56 | 44 | 57 | 43 | 14 |
| 242_vi_4_E | 58 | 40 | 57 | 43 | 57 | 43 | 14 |
| 242_vi_5_A | 64 | 37 | 63 | 38 | 63 | 37 | 26 |
| 242_vi_5_B | 48 | 52 | 52 | 48 | 50 | 50 | 0 |
| 242_vi_5_C | 48 | 52 | 52 | 48 | 50 | 50 | 0 |
| 242_vi_5_D | 70 | 30 | 68 | 32 | 69 | 31 | 38 |
| 242_vi_5_E | 61 | 40 | 60 | 41 | 60 | 40 | 20 |
| 245_i_1_A | 62 | 38 | 58 | 42 | 60 | 40 | 20 |
| 245_i_1_B | 51 | 49 | 49 | 51 | 50 | 50 | 0 |
| 245_i_1_C | 51 | 49 | 51 | 59 | 51 | 49 | 2 |
| 245_i_1_D | 62 | 38 | 60 | 40 | 61 | 39 | 22 |
| 245_i_1_E | 58 | 42 | 54 | 46 | 56 | 44 | 12 |
| 245_i_2_A | 57 | 43 | 55 | 45 | 56 | 44 | 12 |
| 245_i_2_B | 51 | 49 | 49 | 51 | 50 | 50 | 0 |
| 245_i_2_C | 52 | 48 | 50 | 50 | 51 | 49 | 2 |
| 245_i_2_D | 57 | 43 | 57 | 43 | 57 | 43 | 14 |
| 245_i_2_E | 56 | 44 | 60 | 40 | 58 | 42 | 16 |
| 245_i_3_A | 59 | 41 | 61 | 39 | 60 | 40 | 20 |
| 245_i_3_B | 53 | 47 | 51 | 49 | 52 | 48 | 4 |
| 245_i_3_C | 49 | 51 | 47 | 53 | 48 | 52 | -4 |
| 245_i_3_D | 60 | 40 | 58 | 42 | 59 | 41 | 18 |
| 245_i_3_E | 59 | 41 | 57 | 43 | 58 | 42 | 16 |
| 245_i_4_A | 56 | 44 | 60 | 40 | 58 | 42 | 16 |
| 245_i_4_B | 49 | 51 | 53 | 47 | 51 | 49 | 2 |
| 245_i_4_C | 53 | 47 | 51 | 49 | 52 | 48 | 4 |
| 245_i_4_D | 59 | 41 | 55 | 45 | 57 | 43 | 14 |
| 245_i_4_E | 57 | 43 | 55 | 45 | 56 | 44 | 12 |
| 245_i_5_A | 58 | 42 | 57 | 43 | 58 | 42 | 16 |
| 245_i_5_B | 52 | 48 | 50 | 50 | 51 | 49 | 2 |
| 245_i_5_C | 50 | 50 | 50 | 50 | 50 | 50 | 0 |
| 245_i_5_D | 57 | 43 | 61 | 39 | 59 | 41 | 18 |
| 245_i_5_E | 55 | 45 | 57 | 43 | 56 | 44 | 12 |
| 245_vi_1_A | 58 | 42 | 58 | 43 | 58 | 42 | 16 |
| 245_vi_1_B | 53 | 47 | 51 | 49 | 52 | 48 | 4 |
| 245_vi_1_C | 53 | 47 | 51 | 49 | 52 | 48 | 4 |
| 245_vi_1_D | 61 | 39 | 59 | 41 | 60 | 40 | 20 |
| 245_vi_1_E | 57 | 43 | 53 | 47 | 55 | 45 | 10 |
| 245_vi_2_A | 57 | 43 | 55 | 45 | 56 | 44 | 12 |
| 245_vi_2_B | 51 | 49 | 50 | 50 | 50 | 50 | 0 |
| 245_vi_2_C | 52 | 48 | 50 | 50 | 51 | 49 | 2 |
| 245_vi_2_D | 55 | 45 | 55 | 45 | 55 | 45 | 10 |
| 245_vi_2_E | 54 | 46 | 58 | 42 | 56 | 44 | 12 |
| 245_vi_3_A | 59 | 41 | 61 | 39 | 60 | 40 | 20 |
| 245_vi_3_B | 49 | 51 | 49 | 51 | 49 | 51 | -2 |
| 245_vi_3_C | 50 | 50 | 50 | 50 | 50 | 50 | 0 |
| 245_vi_3_D | 58 | 42 | 58 | 42 | 58 | 42 | 16 |
| 245_vi_3_E | 55 | 45 | 59 | 41 | 57 | 43 | 14 |
| 245_vi_4_A | 56 | 44 | 60 | 40 | 58 | 42 | 16 |
| 245_vi_4_B | 52 | 48 | 50 | 50 | 51 | 49 | 2 |
| 245_vi_4_C | 54 | 46 | 50 | 50 | 52 | 48 | 4 |
| 245_vi_4_D | 56 | 44 | 54 | 46 | 55 | 45 | 10 |
| 245_vi_4_E | 58 | 42 | 54 | 46 | 56 | 44 | 12 |
| 245_vi_5_A | 55 | 45 | 53 | 47 | 54 | 46 | 8 |
| 245_vi_5_B | 52 | 48 | 50 | 50 | 51 | 49 | 2 |
| 245_vi_5_C | 50 | 50 | 48 | 52 | 49 | 51 | -2 |
| 245_vi_5_D | 55 | 45 | 55 | 45 | 55 | 45 | 10 |
| 245_vi_5_E | 53 | 47 | 57 | 43 | 55 | 45 | 10 |
| 246_vi_1_A | 51 | 49 | 53 | 47 | 52 | 48 | 4 |
| 246_vi_1_B | 50 | 50 | 50 | 50 | 50 | 50 | 0 |
| 246_vi_1_C | 52 | 48 | 50 | 50 | 51 | 49 | 2 |
| 246_vi_1_D | 55 | 45 | 55 | 45 | 55 | 45 | 10 |
| 246_vi_1_E | 48 | 52 | 48 | 52 | 48 | 52 | -4 |
| 246_vi_2_A | 47 | 53 | 51 | 49 | 49 | 51 | -2 |
| 246_vi_2_B | 49 | 51 | 53 | 47 | 51 | 49 | 2 |
| 246_vi_2_C | 51 | 49 | 53 | 47 | 52 | 48 | 4 |
| 246_vi_2_D | 50 | 50 | 50 | 50 | 50 | 50 | 0 |
| 246_vi_2_E | 50 | 50 | 50 | 50 | 50 | 50 | 0 |
| 246_vi_3_A | 48 | 52 | 48 | 52 | 48 | 52 | -4 |
| 246_vi_3_B | 56 | 44 | 56 | 44 | 56 | 44 | 12 |
| 246_vi_3_C | 46 | 54 | 50 | 50 | 48 | 52 | -4 |
| 246_vi_3_D | 56 | 44 | 60 | 40 | 58 | 42 | 16 |
| 246_vi_3_E | 52 | 48 | 52 | 48 | 52 | 48 | 4 |
| 246_vi_4_A | 55 | 45 | 55 | 45 | 55 | 45 | 10 |
| 246_vi_4_B | 48 | 52 | 46 | 54 | 47 | 53 | -6 |
| 246_vi_4_C | 50 | 50 | 48 | 52 | 49 | 51 | -2 |
| 246_vi_4_D | 48 | 52 | 48 | 52 | 50 | 50 | 0 |
| 246_vi_4_E | 51 | 49 | 55 | 45 | 53 | 47 | 6 |
| 246_vi_5_A | 53 | 47 | 55 | 45 | 54 | 46 | 8 |
| 246_vi_5_B | 50 | 50 | 50 | 50 | 50 | 50 | 0 |
| 246_vi_5_C | 52 | 48 | 51 | 59 | 51 | 49 | 2 |
| 246_vi_5_D | 55 | 45 | 55 | 45 | 55 | 45 | 10 |
| 246_vi_5_E | 55 | 45 | 55 | 45 | 55 | 45 | 10 |
| 249_i_1_A | 90 | 10 | 94 | 6 | 92 | 8 | 84 |
| 249_i_1_B | 72 | 28 | 76 | 24 | 74 | 26 | 48 |
| 249_i_1_C | 76 | 24 | 74 | 26 | 75 | 25 | 50 |
| 249_i_1_D | 85 | 15 | 84 | 16 | 85 | 15 | 70 |
| 249_i_1_E | 92 | 8 | 90 | 10 | 91 | 9 | 82 |
| 249_i_2_A | 92 | 8 | 90 | 10 | 91 | 9 | 82 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 249_i_2_B | 88 | 12 | 92 | 8 | 90 | 10 | 80 |
| 249_i_2_C | 69 | 31 | 73 | 27 | 71 | 29 | 42 |
| 249_i_2_D | 76 | 24 | 78 | 22 | 77 | 23 | 54 |
| 249_i_2_E | 91 | 9 | 89 | 11 | 90 | 10 | 80 |
| 249_i_3_A | 91 | 11 | 89 | 11 | 89 | 11 | 78 |
| 249_i_3_B | 70 | 30 | 70 | 30 | 70 | 30 | 40 |
| 249_i_3_C | 73 | 27 | 73 | 27 | 73 | 27 | 46 |
| 249_i_3_D | 85 | 15 | 89 | 11 | 87 | 13 | 74 |
| 249_i_3_E | 87 | 13 | 91 | 9 | 89 | 11 | 78 |
| 249_i_4_A | 92 | 8 | 90 | 10 | 91 | 9 | 82 |
| 249_i_4_B | 69 | 31 | 73 | 27 | 71 | 29 | 42 |
| 249_i_4_C | 71 | 29 | 75 | 25 | 73 | 27 | 46 |
| 249_i_4_D | 92 | 8 | 90 | 10 | 91 | 9 | 82 |
| 249_i_4_E | 91 | 9 | 87 | 13 | 89 | 11 | 78 |
| 249_i_5_A | 90 | 10 | 86 | 14 | 88 | 12 | 76 |
| 249_i_5_B | 67 | 33 | 71 | 29 | 69 | 31 | 38 |
| 249_i_5_C | 68 | 32 | 72 | 28 | 70 | 30 | 40 |
| 249_i_5_D | 88 | 12 | 86 | 14 | 87 | 13 | 74 |
| 249_i_5_E | 90 | 10 | 89 | 11 | 89 | 11 | 78 |
| 251_vi_1_A | 96 | 4 | 92 | 8 | 94 | 6 | 88 |
| 251_vi_1_B | 74 | 26 | 72 | 28 | 73 | 27 | 46 |
| 251_vi_1_C | 73 | 27 | 71 | 29 | 72 | 28 | 44 |
| 251_vi_1_D | 94 | 6 | 96 | 4 | 95 | 5 | 90 |
| 251_vi_1_E | 92 | 8 | 90 | 10 | 91 | 9 | 82 |
| 251_vi_2_A | 95 | 5 | 91 | 9 | 93 | 7 | 86 |
| 251_vi_2_B | 81 | 19 | 79 | 21 | 80 | 20 | 60 |
| 251_vi_2_C | 82 | 18 | 80 | 20 | 81 | 19 | 62 |
| 251_vi_2_D | 92 | 8 | 94 | 6 | 93 | 7 | 86 |
| 251_vi_2_E | 95 | 5 | 93 | 7 | 94 | 6 | 88 |
| 251_vi_3_A | 92 | 8 | 94 | 6 | 93 | 7 | 86 |
| 251_vi_3_B | 79 | 21 | 77 | 23 | 78 | 22 | 56 |
| 251_vi_3_C | 79 | 21 | 83 | 17 | 81 | 19 | 62 |
| 251_vi_3_D | 91 | 9 | 95 | 5 | 93 | 7 | 86 |
| 251_vi_3_E | 90 | 10 | 90 | 10 | 90 | 10 | 80 |
| 251_vi_4_A | 95 | 5 | 94 | 6 | 94 | 6 | 88 |
| 251_vi_4_B | 77 | 27 | 73 | 27 | 73 | 27 | 46 |
| 251_vi_4_C | 79 | 21 | 78 | 22 | 79 | 21 | 58 |
| 251_vi_4_D | 90 | 10 | 94 | 6 | 92 | 8 | 84 |
| 251_vi_4_E | 90 | 10 | 94 | 6 | 92 | 8 | 84 |
| 251_vi_5_A | 89 | 11 | 91 | 9 | 90 | 10 | 80 |
| 251_vi_5_B | 76 | 24 | 76 | 24 | 76 | 24 | 52 |
| 251_vi_5_C | 77 | 23 | 75 | 25 | 76 | 24 | 52 |
| 251_vi_5_D | 95 | 5 | 94 | 6 | 94 | 6 | 88 |
| 251_vi_5_E | 90 | 10 | 89 | 11 | 90 | 10 | 80 |
| 253_i_1_A | 98 | 2 | 100 | 0 | 99 | 1 | 99 |
| 253_i_1_B | 90 | 10 | 94 | 6 | 92 | 8 | 84 |
| 253_i_1_C | 91 | 9 | 93 | 7 | 92 | 8 | 84 |
| 253_i_1_D | 100 | 0 | 98 | 2 | 99 | 1 | 98 |
| 253_i_1_E | 99 | 1 | 98 | 2 | 98 | 2 | 96 |
| 253_i_2_A | 100 | 0 | 99 | 1 | 99 | 1 | 98 |
| 253_i_2_B | 89 | 12 | 88 | 12 | 88 | 12 | 76 |
| 253_i_2_C | 87 | 13 | 91 | 9 | 89 | 11 | 78 |
| 253_i_2_D | 97 | 3 | 100 | 0 | 99 | 1 | 98 |
| 253_i_2_E | 100 | 0 | 100 | 0 | 100 | 0 | 99 |
| 253_i_3_A | 98 | 2 | 100 | 0 | 99 | 1 | 99 |
| 253_i_3_B | 87 | 13 | 91 | 9 | 89 | 11 | 78 |
| 253_i_3_C | 91 | 9 | 89 | 11 | 90 | 10 | 80 |
| 253_i_3_D | 99 | 1 | 99 | 1 | 99 | 1 | 99 |
| 253_i_3_E | 100 | 0 | 100 | 0 | 100 | 0 | 99 |
| 253_i_4_A | 100 | 0 | 100 | 0 | 100 | 0 | 99 |
| 253_i_4_B | 88 | 12 | 92 | 8 | 90 | 10 | 80 |
| 253_i_4_C | 93 | 7 | 91 | 9 | 92 | 8 | 84 |
| 253_i_4_D | 100 | 0 | 100 | 0 | 100 | 0 | 99 |
| 253_i_4_E | 99 | 1 | 99 | 1 | 99 | 1 | 98 |
| 253_i_5_A | 99 | 1 | 99 | 1 | 99 | 1 | 98 |
| 253_i_5_B | 89 | 11 | 87 | 13 | 88 | 12 | 76 |
| 253_i_5_C | 88 | 12 | 90 | 10 | 89 | 11 | 78 |
| 253_i_5_D | 99 | 1 | 97 | 3 | 98 | 2 | 96 |
| 253_i_5_E | 99 | 1 | 99 | 1 | 99 | 1 | 98 |
| 262_vi_1_A | 62 | 38 | 60 | 40 | 61 | 39 | 22 |
| 262_vi_1_B | 46 | 54 | 44 | 56 | 45 | 55 | −10 |
| 262_vi_1_C | 49 | 51 | 51 | 49 | 50 | 50 | 0 |
| 262_vi_1_D | 56 | 44 | 54 | 46 | 55 | 45 | 10 |
| 262_vi_1_E | 54 | 46 | 56 | 44 | 55 | 45 | 10 |
| 262_vi_2_A | 61 | 39 | 59 | 41 | 60 | 40 | 20 |
| 262_vi_2_B | 43 | 57 | 47 | 53 | 45 | 55 | −10 |
| 262_vi_2_C | 49 | 51 | 53 | 47 | 51 | 49 | 2 |
| 262_vi_2_D | 62 | 38 | 61 | 39 | 61 | 39 | 22 |
| 262_vi_2_E | 63 | 37 | 63 | 37 | 63 | 37 | 26 |
| 262_vi_3_A | 60 | 40 | 60 | 40 | 60 | 40 | 20 |
| 262_vi_3_B | 47 | 53 | 45 | 55 | 46 | 54 | −8 |
| 262_vi_3_C | 46 | 54 | 50 | 50 | 48 | 52 | −4 |
| 262_vi_3_D | 60 | 40 | 64 | 36 | 62 | 38 | 24 |
| 262_vi_3_E | 56 | 44 | 60 | 40 | 58 | 42 | 16 |
| 262_vi_4_A | 76 | 24 | 76 | 24 | 76 | 24 | 52 |
| 262_vi_4_B | 48 | 52 | 46 | 54 | 47 | 53 | −6 |
| 262_vi_4_C | 57 | 43 | 55 | 45 | 56 | 44 | 12 |
| 262_vi_4_D | 65 | 35 | 63 | 37 | 64 | 36 | 28 |
| 262_vi_4_E | 63 | 37 | 61 | 39 | 62 | 38 | 24 |
| 262_vi_5_A | 65 | 35 | 69 | 31 | 67 | 33 | 34 |
| 262_vi_5_B | 38 | 62 | 42 | 58 | 40 | 60 | −20 |
| 262_vi_5_C | 51 | 49 | 53 | 47 | 52 | 48 | 4 |
| 262_vi_5_D | 59 | 41 | 57 | 43 | 58 | 42 | 16 |
| 262_vi_5_E | 63 | 37 | 61 | 39 | 62 | 38 | 24 |
| 276_i_1_A | 99 | 1 | 98 | 2 | 98 | 2 | 96 |
| 276_i_1_B | 88 | 12 | 86 | 14 | 87 | 13 | 74 |
| 276_i_1_C | 85 | 15 | 89 | 11 | 87 | 13 | 74 |
| 276_i_1_D | 95 | 5 | 99 | 1 | 97 | 3 | 94 |
| 276_i_1_E | 99 | 1 | 97 | 3 | 98 | 2 | 96 |
| 276_i_2_A | 95 | 5 | 99 | 1 | 97 | 3 | 94 |
| 276_i_2_B | 90 | 10 | 94 | 6 | 92 | 8 | 84 |
| 276_i_2_C | 91 | 9 | 89 | 11 | 90 | 10 | 80 |
| 276_i_2_D | 98 | 2 | 98 | 2 | 98 | 2 | 96 |
| 276_i_2_E | 99 | 1 | 99 | 1 | 99 | 1 | 98 |
| 276_i_3_A | 98 | 2 | 98 | 2 | 98 | 2 | 96 |
| 276_i_3_B | 86 | 14 | 90 | 10 | 88 | 12 | 76 |
| 276_i_3_C | 91 | 9 | 89 | 11 | 90 | 10 | 80 |
| 276_i_3_D | 99 | 1 | 98 | 2 | 98 | 2 | 96 |
| 276_i_3_E | 100 | 0 | 100 | 0 | 100 | 0 | 99 |
| 276_i_4_A | 100 | 0 | 100 | 0 | 100 | 0 | 99 |
| 276_i_4_B | 87 | 13 | 85 | 15 | 86 | 14 | 72 |
| 276_i_4_C | 87 | 13 | 89 | 11 | 88 | 12 | 76 |
| 276_i_4_D | 100 | 0 | 100 | 0 | 100 | 0 | 99 |
| 276_i_4_E | 98 | 2 | 98 | 2 | 98 | 2 | 96 |
| 276_i_5_A | 97 | 3 | 95 | 5 | 96 | 4 | 92 |
| 276_i_5_B | 88 | 12 | 86 | 14 | 87 | 13 | 74 |
| 276_i_5_C | 83 | 17 | 85 | 15 | 84 | 16 | 68 |
| 276_i_5_D | 99 | 1 | 97 | 3 | 98 | 2 | 96 |
| 276_i_5_E | 99 | 1 | 99 | 1 | 99 | 1 | 98 |
| 286_vi_1_A | 96 | 4 | 93 | 7 | 95 | 6 | 89 |
| 286_vi_1_B | 87 | 13 | 91 | 9 | 89 | 12 | 77 |
| 286_vi_1_C | 85 | 15 | 89 | 11 | 87 | 14 | 73 |
| 286_vi_1_D | 97 | 3 | 96 | 4 | 97 | 4 | 93 |
| 286_vi_1_E | 97 | 3 | 95 | 5 | 96 | 4 | 92 |
| 286_vi_2_A | 94 | 6 | 93 | 7 | 94 | 7 | 87 |
| 286_vi_2_B | 88 | 12 | 87 | 13 | 88 | 13 | 75 |
| 286_vi_2_C | 90 | 10 | 95 | 5 | 93 | 8 | 85 |
| 286_vi_2_D | 99 | 1 | 99 | 1 | 99 | 1 | 97 |
| 286_vi_2_E | 94 | 6 | 96 | 4 | 95 | 5 | 89 |
| 286_vi_3_A | 94 | 6 | 90 | 10 | 92 | 8 | 84 |
| 286_vi_3_B | 84 | 16 | 82 | 18 | 83 | 17 | 66 |
| 286_vi_3_C | 92 | 8 | 90 | 10 | 91 | 9 | 82 |
| 286_vi_3_D | 94 | 6 | 91 | 9 | 93 | 7 | 85 |
| 286_vi_3_E | 91 | 9 | 91 | 9 | 91 | 9 | 81 |
| 286_vi_4_A | 93 | 7 | 97 | 3 | 95 | 5 | 90 |
| 286_vi_4_B | 80 | 20 | 81 | 19 | 81 | 19 | 61 |
| 286_vi_4_C | 88 | 12 | 86 | 14 | 87 | 13 | 74 |
| 286_vi_4_D | 98 | 2 | 96 | 4 | 97 | 3 | 94 |
| 286_vi_4_E | 98 | 2 | 96 | 4 | 97 | 3 | 94 |
| 286_vi_5_A | 98 | 2 | 96 | 4 | 97 | 3 | 93 |
| 286_vi_5_B | 88 | 12 | 85 | 15 | 87 | 13 | 73 |
| 286_vi_5_C | 94 | 6 | 92 | 8 | 93 | 7 | 86 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 286_vi_5_D | 98 | 2 | 96 | 4 | 97 | 3 | 94 |
| 286_vi_5_E | 98 | 2 | 94 | 6 | 96 | 4 | 92 |
| 29_i_1_A | 88 | 12 | 86 | 14 | 87 | 13 | 74 |
| 29_i_1_B | 75 | 25 | 75 | 25 | 75 | 25 | 50 |
| 29_i_1_C | 72 | 28 | 72 | 28 | 72 | 28 | 44 |
| 29_i_1_D | 90 | 10 | 88 | 12 | 89 | 11 | 78 |
| 29_i_1_E | 86 | 14 | 84 | 16 | 85 | 15 | 70 |
| 29_i_2_A | 91 | 9 | 89 | 11 | 90 | 10 | 80 |
| 29_i_2_B | 67 | 33 | 65 | 35 | 66 | 34 | 32 |
| 29_i_2_C | 67 | 33 | 65 | 35 | 66 | 34 | 32 |
| 29_i_2_D | 91 | 9 | 89 | 11 | 90 | 10 | 80 |
| 29_i_2_E | 91 | 9 | 89 | 11 | 90 | 10 | 80 |
| 29_i_3_A | 89 | 11 | 91 | 9 | 90 | 10 | 80 |
| 29_i_3_B | 69 | 31 | 67 | 33 | 68 | 32 | 36 |
| 29_i_3_C | 72 | 28 | 70 | 30 | 71 | 29 | 42 |
| 29_i_3_D | 90 | 10 | 88 | 12 | 89 | 11 | 78 |
| 29_i_3_E | 88 | 12 | 86 | 14 | 87 | 13 | 74 |
| 29_i_4_A | 90 | 10 | 88 | 12 | 89 | 11 | 78 |
| 29_i_4_B | 67 | 33 | 65 | 35 | 66 | 34 | 32 |
| 29_i_4_C | 70 | 30 | 70 | 30 | 70 | 30 | 40 |
| 29_i_4_D | 88 | 12 | 86 | 14 | 87 | 13 | 74 |
| 29_i_4_E | 86 | 14 | 84 | 16 | 85 | 15 | 70 |
| 29_i_5_A | 87 | 13 | 85 | 15 | 86 | 14 | 72 |
| 29_i_5_B | 65 | 35 | 63 | 37 | 64 | 36 | 28 |
| 29_i_5_C | 71 | 29 | 69 | 31 | 70 | 30 | 40 |
| 29_i_5_D | 86 | 14 | 84 | 16 | 85 | 15 | 70 |
| 29_i_5_E | 87 | 13 | 85 | 15 | 86 | 14 | 72 |
| 328_i_1_A | 94 | 6 | 96 | 4 | 95 | 5 | 90 |
| 328_i_1_B | 79 | 21 | 77 | 23 | 78 | 22 | 56 |
| 328_i_1_C | 82 | 18 | 80 | 20 | 81 | 19 | 62 |
| 328_i_1_D | 88 | 12 | 86 | 14 | 87 | 13 | 74 |
| 328_i_1_E | 97 | 3 | 95 | 5 | 96 | 4 | 92 |
| 328_i_2_A | 92 | 8 | 90 | 10 | 91 | 9 | 82 |
| 328_i_2_B | 82 | 18 | 80 | 20 | 81 | 19 | 62 |
| 328_i_2_C | 92 | 8 | 92 | 8 | 92 | 8 | 84 |
| 328_i_2_D | 91 | 9 | 89 | 11 | 90 | 10 | 80 |
| 328_i_2_E | 90 | 10 | 88 | 12 | 89 | 11 | 78 |
| 328_i_3_A | 94 | 6 | 92 | 8 | 93 | 7 | 86 |
| 328_i_3_B | 81 | 19 | 79 | 21 | 80 | 20 | 60 |
| 328_i_3_C | 96 | 4 | 94 | 6 | 95 | 5 | 90 |
| 328_i_3_D | 96 | 4 | 94 | 6 | 95 | 5 | 90 |
| 328_i_3_E | 98 | 2 | 96 | 4 | 97 | 3 | 94 |
| 328_i_4_A | 91 | 9 | 93 | 7 | 92 | 8 | 84 |
| 328_i_4_B | 78 | 22 | 76 | 24 | 77 | 23 | 54 |
| 328_i_4_C | 85 | 15 | 83 | 17 | 84 | 16 | 68 |
| 328_i_4_D | 91 | 9 | 89 | 11 | 90 | 10 | 80 |
| 328_i_4_E | 87 | 13 | 85 | 15 | 86 | 14 | 72 |
| 328_i_5_A | 95 | 5 | 93 | 7 | 94 | 6 | 88 |
| 328_i_5_B | 89 | 11 | 87 | 13 | 88 | 12 | 76 |
| 328_i_5_C | 89 | 11 | 87 | 13 | 88 | 12 | 76 |
| 328_i_5_D | 88 | 12 | 86 | 14 | 87 | 13 | 74 |
| 328_i_5_E | 91 | 9 | 89 | 11 | 90 | 10 | 80 |
| 365_i_1_A | 88 | 12 | 90 | 10 | 89 | 11 | 78 |
| 365_i_1_B | 69 | 31 | 67 | 33 | 68 | 32 | 36 |
| 365_i_1_C | 73 | 27 | 71 | 29 | 72 | 28 | 44 |
| 365_i_1_D | 92 | 8 | 90 | 10 | 91 | 9 | 82 |
| 365_i_1_E | 93 | 7 | 91 | 9 | 92 | 8 | 84 |
| 365_i_2_A | 89 | 11 | 87 | 13 | 88 | 12 | 76 |
| 365_i_2_B | 73 | 27 | 71 | 29 | 72 | 28 | 44 |
| 365_i_2_C | 77 | 23 | 75 | 25 | 76 | 24 | 52 |
| 365_i_2_D | 91 | 9 | 89 | 11 | 90 | 10 | 80 |
| 365_i_2_E | 92 | 8 | 90 | 10 | 91 | 9 | 82 |
| 365_i_3_A | 93 | 7 | 91 | 9 | 92 | 8 | 84 |
| 365_i_3_B | 80 | 20 | 78 | 22 | 79 | 21 | 58 |
| 365_i_3_C | 78 | 22 | 76 | 24 | 77 | 23 | 54 |
| 365_i_3_D | 93 | 7 | 91 | 9 | 92 | 8 | 84 |
| 365_i_3_E | 93 | 7 | 91 | 9 | 92 | 8 | 84 |
| 365_i_4_A | 90 | 10 | 88 | 12 | 89 | 11 | 78 |
| 365_i_4_B | 71 | 29 | 69 | 31 | 70 | 30 | 40 |
| 365_i_4_C | 74 | 26 | 72 | 28 | 73 | 27 | 46 |
| 365_i_4_D | 94 | 6 | 92 | 8 | 93 | 7 | 86 |
| 365_i_4_E | 92 | 8 | 90 | 10 | 91 | 9 | 82 |
| 365_i_5_A | 89 | 11 | 87 | 13 | 88 | 12 | 76 |
| 365_i_5_B | 69 | 31 | 69 | 31 | 69 | 31 | 38 |
| 365_i_5_C | 71 | 29 | 75 | 25 | 73 | 27 | 46 |
| 365_i_5_D | 88 | 12 | 90 | 10 | 89 | 11 | 78 |
| 365_i_5_E | 92 | 8 | 90 | 10 | 91 | 9 | 82 |
| 365_vi_1_A | 88 | 12 | 88 | 12 | 88 | 12 | 76 |
| 365_vi_1_B | 66 | 34 | 70 | 30 | 68 | 32 | 36 |
| 365_vi_1_C | 69 | 31 | 73 | 27 | 71 | 29 | 42 |
| 365_vi_1_D | 90 | 10 | 88 | 12 | 89 | 11 | 78 |
| 365_vi_1_E | 90 | 10 | 90 | 10 | 90 | 10 | 80 |
| 365_vi_2_A | 91 | 9 | 87 | 13 | 89 | 11 | 78 |
| 365_vi_2_B | 72 | 28 | 70 | 30 | 71 | 29 | 42 |
| 365_vi_2_C | 74 | 26 | 72 | 28 | 73 | 27 | 46 |
| 365_vi_2_D | 86 | 14 | 84 | 16 | 85 | 15 | 70 |
| 365_vi_2_E | 87 | 13 | 87 | 13 | 87 | 13 | 74 |
| 365_vi_3_A | 93 | 7 | 89 | 11 | 91 | 9 | 82 |
| 365_vi_3_B | 72 | 28 | 76 | 24 | 74 | 26 | 48 |
| 365_vi_3_C | 78 | 22 | 76 | 24 | 77 | 23 | 54 |
| 365_vi_3_D | 88 | 12 | 86 | 14 | 87 | 13 | 74 |
| 365_vi_3_E | 92 | 8 | 88 | 12 | 90 | 10 | 80 |
| 365_vi_4_A | 89 | 11 | 87 | 13 | 88 | 12 | 76 |
| 365_vi_4_B | 71 | 31 | 68 | 32 | 69 | 31 | 38 |
| 365_vi_4_C | 71 | 29 | 69 | 31 | 70 | 30 | 40 |
| 365_vi_4_D | 89 | 11 | 91 | 9 | 90 | 10 | 80 |
| 365_vi_4_E | 88 | 12 | 88 | 12 | 88 | 12 | 76 |
| 365_vi_5_A | 90 | 10 | 86 | 14 | 88 | 12 | 76 |
| 365_vi_5_B | 70 | 30 | 68 | 32 | 69 | 31 | 38 |
| 365_vi_5_C | 72 | 28 | 72 | 28 | 72 | 28 | 44 |
| 365_vi_5_D | 88 | 12 | 88 | 12 | 88 | 12 | 76 |
| 365_vi_5_E | 87 | 13 | 91 | 9 | 89 | 11 | 78 |
| 371_i_1_A | 87 | 13 | 91 | 9 | 89 | 11 | 78 |
| 371_i_1_B | 76 | 24 | 74 | 26 | 75 | 25 | 50 |
| 371_i_1_C | 81 | 19 | 79 | 21 | 80 | 20 | 60 |
| 371_i_1_D | 92 | 8 | 88 | 12 | 90 | 10 | 80 |
| 371_i_1_E | 93 | 7 | 91 | 9 | 92 | 8 | 84 |
| 371_i_2_A | 85 | 15 | 83 | 17 | 84 | 16 | 68 |
| 371_i_2_B | 69 | 31 | 71 | 29 | 70 | 30 | 40 |
| 371_i_2_C | 81 | 19 | 79 | 21 | 80 | 20 | 60 |
| 371_i_2_D | 85 | 15 | 89 | 11 | 87 | 13 | 74 |
| 371_i_2_E | 89 | 11 | 91 | 9 | 90 | 10 | 80 |
| 371_i_3_A | 88 | 12 | 86 | 14 | 87 | 13 | 74 |
| 371_i_3_B | 85 | 15 | 83 | 17 | 84 | 16 | 68 |
| 371_i_3_C | 84 | 16 | 88 | 12 | 86 | 14 | 72 |
| 371_i_3_D | 85 | 15 | 89 | 11 | 87 | 13 | 74 |
| 371_i_3_E | 88 | 12 | 86 | 14 | 87 | 13 | 74 |
| 371_i_4_A | 93 | 7 | 92 | 8 | 92 | 8 | 84 |
| 371_i_4_B | 62 | 38 | 58 | 42 | 60 | 40 | 20 |
| 371_i_4_C | 73 | 27 | 71 | 29 | 72 | 28 | 44 |
| 371_i_4_D | 82 | 18 | 80 | 20 | 81 | 19 | 62 |
| 371_i_4_E | 88 | 12 | 86 | 14 | 87 | 13 | 74 |
| 371_i_5_A | 88 | 12 | 88 | 12 | 88 | 12 | 76 |
| 371_i_5_B | 73 | 27 | 77 | 23 | 75 | 25 | 50 |
| 371_i_5_C | 78 | 22 | 80 | 20 | 79 | 21 | 58 |
| 371_i_5_D | 90 | 10 | 89 | 11 | 90 | 10 | 80 |
| 371_i_5_E | 85 | 15 | 85 | 15 | 85 | 15 | 70 |
| 382_i_1_A | 91 | 9 | 95 | 5 | 93 | 7 | 86 |
| 382_i_1_B | 69 | 31 | 73 | 27 | 71 | 29 | 42 |
| 382_i_1_C | 81 | 19 | 79 | 21 | 80 | 20 | 60 |
| 382_i_1_D | 93 | 7 | 92 | 8 | 92 | 8 | 84 |
| 382_i_1_E | 91 | 9 | 87 | 13 | 89 | 11 | 78 |
| 382_i_2_A | 95 | 5 | 93 | 7 | 94 | 6 | 88 |
| 382_i_2_B | 71 | 29 | 75 | 25 | 73 | 27 | 46 |
| 382_i_2_C | 76 | 24 | 80 | 20 | 78 | 22 | 56 |
| 382_i_2_D | 97 | 3 | 95 | 5 | 96 | 4 | 92 |
| 382_i_2_E | 90 | 10 | 88 | 12 | 89 | 11 | 78 |
| 382_i_3_A | 90 | 10 | 86 | 14 | 88 | 12 | 76 |
| 382_i_3_B | 76 | 24 | 74 | 26 | 75 | 25 | 50 |
| 382_i_3_C | 80 | 20 | 78 | 22 | 79 | 21 | 58 |
| 382_i_3_D | 89 | 11 | 91 | 9 | 90 | 10 | 80 |
| 382_i_3_E | 91 | 9 | 89 | 11 | 90 | 10 | 80 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 382_i_4_A | 93 | 7 | 97 | 3 | 95 | 5 | 90 |
| 382_i_4_B | 71 | 29 | 73 | 27 | 72 | 28 | 44 |
| 382_i_4_C | 71 | 29 | 69 | 31 | 70 | 30 | 40 |
| 382_i_4_D | 91 | 9 | 91 | 9 | 91 | 9 | 82 |
| 382_i_4_E | 90 | 10 | 94 | 6 | 92 | 8 | 84 |
| 382_i_5_A | 90 | 10 | 94 | 6 | 92 | 8 | 84 |
| 382_i_5_B | 70 | 30 | 68 | 32 | 69 | 31 | 38 |
| 382_i_5_C | 72 | 28 | 72 | 28 | 72 | 28 | 44 |
| 382_i_5_D | 91 | 9 | 87 | 13 | 89 | 11 | 78 |
| 382_i_5_E | 91 | 9 | 89 | 11 | 90 | 10 | 80 |
| 5_i_1_A | 97 | 3 | 96 | 4 | 96 | 4 | 92 |
| 5_i_1_B | 89 | 11 | 87 | 13 | 88 | 12 | 76 |
| 5_i_1_C | 90 | 10 | 90 | 10 | 90 | 10 | 80 |
| 5_i_1_D | 91 | 9 | 95 | 5 | 93 | 7 | 86 |
| 5_i_1_E | 92 | 8 | 94 | 6 | 93 | 7 | 86 |
| 5_i_2_A | 94 | 6 | 94 | 6 | 94 | 6 | 88 |
| 5_i_2_B | 88 | 12 | 87 | 13 | 87 | 13 | 74 |
| 5_i_2_C | 87 | 13 | 91 | 9 | 89 | 11 | 78 |
| 5_i_2_D | 90 | 10 | 94 | 6 | 92 | 8 | 84 |
| 5_i_2_E | 97 | 3 | 95 | 5 | 96 | 4 | 92 |
| 5_i_3_A | 92 | 8 | 92 | 8 | 92 | 8 | 84 |
| 5_i_3_B | 74 | 26 | 70 | 30 | 72 | 28 | 44 |
| 5_i_3_C | 88 | 12 | 82 | 18 | 85 | 15 | 70 |
| 5_i_3_D | 98 | 2 | 96 | 4 | 97 | 3 | 94 |
| 5_i_3_E | 97 | 3 | 95 | 5 | 96 | 4 | 92 |
| 5_i_4_A | 98 | 2 | 98 | 2 | 98 | 2 | 96 |
| 5_i_4_B | 88 | 12 | 92 | 8 | 90 | 10 | 80 |
| 5_i_4_C | 87 | 13 | 85 | 15 | 86 | 14 | 72 |
| 5_i_4_D | 97 | 3 | 95 | 5 | 96 | 4 | 92 |
| 5_i_4_E | 98 | 2 | 98 | 2 | 98 | 2 | 96 |
| 5_i_5_A | 91 | 9 | 89 | 11 | 90 | 10 | 80 |
| 5_i_5_B | 87 | 13 | 85 | 15 | 86 | 14 | 72 |
| 5_i_5_C | 77 | 23 | 75 | 25 | 76 | 24 | 52 |
| 5_i_5_D | 95 | 5 | 95 | 5 | 95 | 5 | 90 |
| 5_i_5_E | 93 | 7 | 97 | 3 | 95 | 5 | 90 |
| 61_i_1_A | 90 | 10 | 92 | 8 | 91 | 9 | 82 |
| 61_i_1_B | 69 | 31 | 68 | 32 | 68 | 32 | 36 |
| 61_i_1_C | 72 | 28 | 72 | 28 | 72 | 28 | 44 |
| 61_i_1_D | 92 | 8 | 90 | 10 | 91 | 9 | 82 |
| 61_i_1_E | 93 | 7 | 91 | 9 | 92 | 8 | 84 |
| 61_i_2_A | 88 | 12 | 92 | 8 | 90 | 10 | 80 |
| 61_i_2_B | 69 | 31 | 73 | 27 | 71 | 29 | 42 |
| 61_i_2_C | 72 | 28 | 70 | 30 | 71 | 29 | 42 |
| 61_i_2_D | 92 | 8 | 90 | 10 | 91 | 9 | 82 |
| 61_i_2_E | 95 | 5 | 91 | 9 | 93 | 7 | 86 |
| 61_i_3_A | 81 | 19 | 79 | 21 | 80 | 20 | 60 |
| 61_i_3_B | 73 | 27 | 71 | 29 | 72 | 28 | 44 |
| 61_i_3_C | 76 | 24 | 74 | 26 | 75 | 25 | 50 |
| 61_i_3_D | 93 | 7 | 89 | 11 | 91 | 9 | 82 |
| 61_i_3_E | 91 | 9 | 89 | 11 | 90 | 10 | 80 |
| 61_i_4_A | 85 | 15 | 85 | 16 | 85 | 15 | 70 |
| 61_i_4_B | 68 | 32 | 66 | 34 | 67 | 34 | 33 |
| 61_i_4_C | 68 | 32 | 68 | 32 | 68 | 32 | 36 |
| 61_i_4_D | 86 | 14 | 90 | 10 | 88 | 12 | 76 |
| 61_i_4_E | 88 | 12 | 90 | 10 | 89 | 11 | 78 |
| 61_i_5_A | 92 | 8 | 91 | 9 | 91 | 9 | 82 |
| 61_i_5_B | 78 | 22 | 77 | 23 | 77 | 23 | 54 |
| 61_i_5_C | 77 | 23 | 75 | 25 | 76 | 24 | 52 |
| 61_i_5_D | 90 | 10 | 88 | 12 | 89 | 11 | 78 |
| 61_i_5_E | 88 | 12 | 92 | 8 | 90 | 10 | 80 |
| 7_i_1_A | 85 | 15 | 89 | 11 | 87 | 13 | 74 |
| 7_i_1_B | 73 | 27 | 71 | 29 | 72 | 28 | 44 |
| 7_i_1_C | 88 | 12 | 84 | 16 | 86 | 14 | 72 |
| 7_i_1_D | 93 | 7 | 91 | 9 | 92 | 8 | 84 |
| 7_i_1_E | 94 | 6 | 92 | 8 | 93 | 7 | 86 |
| 7_i_2_A | 96 | 4 | 94 | 6 | 95 | 5 | 90 |
| 7_i_2_B | 75 | 25 | 75 | 25 | 75 | 25 | 50 |
| 7_i_2_C | 85 | 15 | 89 | 11 | 87 | 13 | 74 |
| 7_i_2_D | 97 | 3 | 99 | 1 | 98 | 2 | 96 |
| 7_i_2_E | 100 | 0 | 98 | 2 | 99 | 1 | 98 |
| 7_i_3_A | 88 | 12 | 86 | 14 | 87 | 13 | 74 |
| 7_i_3_B | 57 | 43 | 56 | 44 | 57 | 43 | 14 |
| 7_i_3_C | 79 | 21 | 77 | 23 | 78 | 22 | 56 |
| 7_i_3_D | 91 | 9 | 87 | 13 | 89 | 11 | 78 |
| 7_i_3_E | 92 | 8 | 90 | 10 | 91 | 9 | 82 |
| 7_i_4_A | 96 | 4 | 94 | 6 | 95 | 5 | 90 |
| 7_i_4_B | 76 | 24 | 74 | 26 | 75 | 25 | 50 |
| 7_i_4_C | 95 | 5 | 95 | 5 | 95 | 5 | 90 |
| 7_i_4_D | 98 | 2 | 98 | 2 | 98 | 2 | 96 |
| 7_i_4_E | 99 | 1 | 99 | 1 | 99 | 1 | 98 |
| 7_i_5_A | 96 | 4 | 95 | 5 | 95 | 5 | 90 |
| 7_i_5_B | 68 | 32 | 68 | 32 | 68 | 32 | 36 |
| 7_i_5_C | 80 | 20 | 80 | 20 | 80 | 20 | 60 |
| 7_i_5_D | 90 | 10 | 94 | 6 | 92 | 8 | 84 |
| 7_i_5_E | 98 | 2 | 98 | 2 | 98 | 2 | 96 |
| 71_vi_1_A | 96 | 4 | 94 | 6 | 95 | 5 | 90 |
| 71_vi_1_B | 82 | 18 | 78 | 22 | 80 | 20 | 60 |
| 71_vi_1_C | 81 | 19 | 79 | 21 | 80 | 20 | 60 |
| 71_vi_1_D | 94 | 6 | 90 | 10 | 92 | 8 | 84 |
| 71_vi_1_E | 89 | 11 | 87 | 13 | 88 | 12 | 76 |
| 71_vi_2_A | 96 | 4 | 95 | 5 | 95 | 5 | 90 |
| 71_vi_2_B | 79 | 21 | 77 | 23 | 78 | 22 | 56 |
| 71_vi_2_C | 81 | 19 | 81 | 19 | 81 | 19 | 62 |
| 71_vi_2_D | 93 | 7 | 97 | 3 | 95 | 5 | 90 |
| 71_vi_2_E | 88 | 12 | 90 | 10 | 89 | 11 | 78 |
| 71_vi_3_A | 90 | 10 | 89 | 11 | 89 | 11 | 78 |
| 71_vi_3_B | 80 | 20 | 79 | 21 | 79 | 21 | 58 |
| 71_vi_3_C | 80 | 20 | 80 | 20 | 80 | 20 | 60 |
| 71_vi_3_D | 94 | 6 | 93 | 7 | 93 | 7 | 86 |
| 71_vi_3_E | 88 | 12 | 92 | 8 | 90 | 10 | 80 |
| 71_vi_4_A | 95 | 5 | 99 | 1 | 97 | 3 | 94 |
| 71_vi_4_B | 71 | 29 | 73 | 27 | 72 | 28 | 44 |
| 71_vi_4_C | 76 | 24 | 74 | 26 | 75 | 25 | 50 |
| 71_vi_4_D | 96 | 4 | 94 | 6 | 95 | 5 | 90 |
| 71_vi_4_E | 95 | 5 | 93 | 7 | 94 | 6 | 88 |
| 71_vi_5_A | 93 | 7 | 91 | 9 | 92 | 8 | 84 |
| 71_vi_5_B | 68 | 32 | 72 | 28 | 70 | 30 | 40 |
| 71_vi_5_C | 73 | 27 | 77 | 23 | 75 | 25 | 50 |
| 71_vi_5_D | 93 | 7 | 91 | 9 | 92 | 8 | 84 |
| 71_vi_5_E | 92 | 8 | 90 | 10 | 91 | 9 | 82 |
| 72_i_1_A | 87 | 13 | 85 | 15 | 86 | 14 | 72 |
| 72_i_1_B | 73 | 27 | 71 | 29 | 72 | 28 | 44 |
| 72_i_1_C | 71 | 29 | 75 | 25 | 73 | 27 | 46 |
| 72_i_1_D | 87 | 13 | 91 | 9 | 89 | 11 | 78 |
| 72_i_1_E | 85 | 15 | 87 | 13 | 86 | 14 | 72 |
| 72_i_2_A | 92 | 8 | 90 | 10 | 91 | 9 | 82 |
| 72_i_2_B | 68 | 32 | 66 | 34 | 67 | 33 | 34 |
| 72_i_2_C | 68 | 32 | 66 | 34 | 67 | 33 | 34 |
| 72_i_2_D | 92 | 8 | 90 | 10 | 91 | 9 | 82 |
| 72_i_2_E | 88 | 12 | 92 | 8 | 90 | 10 | 80 |
| 72_i_3_A | 88 | 12 | 92 | 8 | 90 | 10 | 80 |
| 72_i_3_B | 67 | 33 | 65 | 35 | 66 | 34 | 32 |
| 72_i_3_C | 74 | 26 | 72 | 28 | 73 | 27 | 46 |
| 72_i_3_D | 88 | 12 | 86 | 14 | 87 | 13 | 74 |
| 72_i_3_E | 90 | 10 | 88 | 12 | 89 | 11 | 78 |
| 72_i_4_A | 88 | 12 | 92 | 8 | 90 | 10 | 80 |
| 72_i_4_B | 66 | 34 | 70 | 30 | 68 | 32 | 36 |
| 72_i_4_C | 72 | 28 | 74 | 26 | 73 | 27 | 46 |
| 72_i_4_D | 89 | 11 | 87 | 13 | 88 | 12 | 76 |
| 72_i_4_E | 90 | 10 | 88 | 12 | 89 | 11 | 78 |
| 72_i_5_A | 89 | 11 | 87 | 13 | 88 | 12 | 76 |
| 72_i_5_B | 66 | 34 | 64 | 36 | 65 | 35 | 30 |
| 72_i_5_C | 71 | 29 | 75 | 25 | 73 | 27 | 46 |
| 72_i_5_D | 84 | 16 | 88 | 12 | 86 | 14 | 72 |
| 72_i_5_E | 88 | 12 | 86 | 14 | 87 | 13 | 74 |
| 73_i_1_A | 90 | 10 | 94 | 6 | 92 | 8 | 84 |
| 73_i_1_B | 72 | 28 | 76 | 24 | 74 | 26 | 48 |
| 73_i_1_C | 76 | 24 | 74 | 26 | 75 | 25 | 50 |
| 73_i_1_D | 90 | 10 | 86 | 14 | 88 | 12 | 76 |
| 73_i_1_E | 92 | 8 | 88 | 12 | 90 | 10 | 80 |
| 73_i_2_A | 91 | 9 | 89 | 11 | 90 | 10 | 80 |
| 73_i_2_B | 68 | 32 | 68 | 32 | 68 | 32 | 36 |

TABLE 6-continued

Integrated Areas Rounded to the Nearest Integer.

| Reaction | Area Percent Peak 1, run 1 | Area Percent Peak 2, run 1 | Area Percent Peak 1, run 2 | Area Percent Peak 2, run 2 | Average Peak 1 | Average Peak 2 | % ee |
|---|---|---|---|---|---|---|---|
| 73_i_2_C | 79 | 21 | 75 | 25 | 77 | 23 | 54 |
| 73_i_2_D | 91 | 9 | 89 | 11 | 90 | 10 | 80 |
| 73_i_2_E | 91 | 9 | 89 | 11 | 90 | 10 | 80 |
| 73_i_3_A | 84 | 16 | 80 | 20 | 82 | 18 | 64 |
| 73_i_3_B | 74 | 26 | 74 | 26 | 74 | 26 | 48 |
| 73_i_3_C | 70 | 30 | 68 | 32 | 69 | 31 | 38 |
| 73_i_3_D | 88 | 12 | 86 | 14 | 87 | 13 | 74 |
| 73_i_3_E | 88 | 12 | 90 | 10 | 89 | 11 | 78 |
| 73_i_4_A | 87 | 13 | 87 | 13 | 87 | 13 | 74 |
| 73_i_4_B | 73 | 27 | 71 | 29 | 72 | 28 | 44 |
| 73_i_4_C | 69 | 31 | 71 | 29 | 70 | 30 | 40 |
| 73_i_4_D | 88 | 12 | 86 | 14 | 87 | 13 | 74 |
| 73_i_4_E | 87 | 13 | 91 | 9 | 89 | 11 | 78 |
| 73_i_5_A | 89 | 11 | 91 | 9 | 90 | 10 | 80 |
| 73_i_5_B | 71 | 29 | 69 | 31 | 70 | 30 | 40 |
| 73_i_5_C | 76 | 24 | 75 | 25 | 75 | 25 | 50 |
| 73_i_5_D | 87 | 13 | 91 | 9 | 89 | 11 | 78 |
| 73_i_5_E | 86 | 14 | 90 | 10 | 88 | 12 | 76 |
| 76_vi_1_A | 88 | 12 | 86 | 14 | 87 | 13 | 74 |
| 76_vi_1_B | 75 | 25 | 75 | 25 | 75 | 25 | 50 |
| 76_vi_1_C | 78 | 22 | 74 | 26 | 76 | 24 | 52 |
| 76_vi_1_D | 90 | 10 | 88 | 12 | 89 | 11 | 78 |
| 76_vi_1_E | 91 | 9 | 89 | 11 | 90 | 10 | 80 |
| 76_vi_2_A | 87 | 13 | 85 | 15 | 86 | 14 | 72 |
| 76_vi_2_B | 71 | 29 | 71 | 29 | 71 | 29 | 42 |
| 76_vi_2_C | 77 | 23 | 73 | 27 | 75 | 25 | 50 |
| 76_vi_2_D | 88 | 12 | 86 | 14 | 87 | 13 | 74 |
| 76_vi_2_E | 92 | 8 | 91 | 9 | 91 | 9 | 82 |
| 76_vi_3_A | 90 | 10 | 86 | 14 | 88 | 12 | 76 |
| 76_vi_3_B | 72 | 28 | 72 | 28 | 72 | 28 | 44 |
| 76_vi_3_C | 76 | 24 | 74 | 26 | 75 | 25 | 50 |
| 76_vi_3_D | 91 | 9 | 89 | 11 | 90 | 10 | 80 |
| 76_vi_3_E | 86 | 14 | 88 | 12 | 87 | 13 | 74 |
| 76_vi_4_A | 89 | 11 | 89 | 11 | 89 | 11 | 78 |
| 76_vi_4_B | 72 | 28 | 70 | 30 | 71 | 29 | 42 |
| 76_vi_4_C | 73 | 27 | 75 | 25 | 74 | 26 | 48 |
| 76_vi_4_D | 92 | 8 | 90 | 10 | 91 | 9 | 82 |
| 76_vi_4_E | 86 | 14 | 90 | 10 | 88 | 12 | 76 |
| 76_vi_5_A | 84 | 16 | 86 | 14 | 85 | 15 | 70 |
| 76_vi_5_B | 75 | 25 | 73 | 27 | 74 | 26 | 48 |
| 76_vi_5_C | 79 | 21 | 77 | 23 | 78 | 22 | 56 |
| 76_vi_5_D | 84 | 16 | 88 | 12 | 86 | 14 | 72 |
| 76_vi_5_E | 85 | 15 | 89 | 11 | 87 | 13 | 74 |
| 87_i_1_A | 95 | 5 | 93 | 7 | 94 | 6 | 88 |
| 87_i_1_B | 90 | 10 | 89 | 11 | 90 | 11 | 79 |
| 87_i_1_C | 90 | 10 | 86 | 14 | 88 | 13 | 75 |
| 87_i_1_D | 97 | 3 | 95 | 5 | 96 | 4 | 92 |
| 87_i_1_E | 97 | 3 | 95 | 5 | 96 | 4 | 91 |
| 87_i_2_A | 93 | 7 | 95 | 5 | 94 | 6 | 88 |
| 87_i_2_B | 90 | 10 | 87 | 13 | 89 | 11 | 77 |
| 87_i_2_C | 91 | 9 | 95 | 5 | 93 | 7 | 85 |
| 87_i_2_D | 98 | 2 | 99 | 1 | 98 | 2 | 97 |
| 87_i_2_E | 95 | 5 | 95 | 55 | 95 | 5 | 90 |
| 87_i_3_A | 94 | 6 | 93 | 7 | 93 | 7 | 86 |
| 87_i_3_B | 84 | 16 | 88 | 12 | 85 | 15 | 71 |
| 87_i_3_C | 89 | 11 | 93 | 7 | 91 | 9 | 82 |
| 87_i_3_D | 94 | 6 | 92 | 8 | 93 | 7 | 86 |
| 87_i_3_E | 91 | 9 | 90 | 10 | 91 | 10 | 81 |
| 87_i_4_A | 97 | 3 | 93 | 7 | 95 | 5 | 90 |
| 87_i_4_B | 82 | 18 | 80 | 20 | 81 | 19 | 62 |
| 87_i_4_C | 88 | 12 | 87 | 13 | 88 | 12 | 75 |
| 87_i_4_D | 98 | 2 | 96 | 4 | 97 | 3 | 94 |
| 87_i_4_E | 97 | 3 | 97 | 3 | 97 | 3 | 94 |
| 87_i_5_A | 95 | 5 | 99 | 1 | 97 | 3 | 93 |
| 87_i_5_B | 85 | 15 | 87 | 13 | 86 | 14 | 72 |
| 87_i_5_C | 94 | 6 | 93 | 7 | 93 | 7 | 86 |
| 87_i_5_D | 98 | 2 | 98 | 2 | 98 | 2 | 96 |
| 87_i_5_E | 94 | 6 | 98 | 2 | 96 | 4 | 92 |
| 99_i_1_A | 85 | 15 | 90 | 10 | 88 | 12 | 75 |
| 99_i_1_B | 71 | 29 | 69 | 31 | 70 | 30 | 40 |
| 99_i_1_C | 66 | 34 | 66 | 34 | 66 | 34 | 32 |
| 99_i_1_D | 93 | 7 | 90 | 10 | 92 | 8 | 83 |
| 99_i_1_E | 92 | 8 | 90 | 10 | 91 | 9 | 81 |
| 99_i_2_A | 92 | 8 | 91 | 9 | 92 | 8 | 83 |
| 99_i_2_B | 81 | 19 | 79 | 21 | 80 | 20 | 60 |
| 99_i_2_C | 76 | 24 | 76 | 24 | 76 | 24 | 52 |
| 99_i_2_D | 88 | 12 | 84 | 16 | 86 | 14 | 72 |
| 99_i_2_E | 88 | 12 | 92 | 10 | 90 | 10 | 79 |
| 99_i_3_A | 88 | 12 | 86 | 14 | 88 | 12 | 75 |
| 99_i_3_B | 69 | 31 | 68 | 32 | 69 | 32 | 37 |
| 99_i_3_C | 61 | 39 | 57 | 43 | 59 | 41 | 18 |
| 99_i_3_D | 92 | 8 | 90 | 10 | 90 | 10 | 81 |
| 99_i_3_E | 92 | 98 | 90 | 10 | 91 | 9 | 82 |
| 99_i_4_A | 87 | 13 | 85 | 15 | 86 | 14 | 72 |
| 99_i_4_B | 62 | 38 | 63 | 37 | 63 | 37 | 25 |
| 99_i_4_C | 67 | 33 | 66 | 34 | 67 | 33 | 33 |
| 99_i_4_D | 89 | 11 | 85 | 15 | 87 | 13 | 73 |
| 99_i_4_E | 88 | 12 | 85 | 15 | 87 | 13 | 73 |
| 99_i_5_A | 90 | 10 | 90 | 10 | 90 | 10 | 80 |
| 99_i_5_B | 61 | 39 | 60 | 40 | 60 | 40 | 21 |
| 99_i_5_C | 69 | 31 | 72 | 28 | 70 | 30 | 41 |
| 99_i_5_D | 80 | 20 | 83 | 17 | 82 | 18 | 63 |
| 99_i_5_E | 85 | 15 | 83 | 17 | 84 | 16 | 68 |
| 99_vi_1_A | 94 | 3 | 92 | 8 | 93 | 7 | 86 |
| 99_vi_1_B | 77 | 23 | 73 | 27 | 75 | 25 | 50 |
| 99_vi_1_C | 79 | 21 | 77 | 23 | 78 | 22 | 56 |
| 99_vi_1_D | 85 | 15 | 83 | 17 | 84 | 16 | 68 |
| 99_vi_1_E | 92 | 8 | 94 | 6 | 93 | 7 | 86 |
| 99_vi_2_A | 89 | 11 | 87 | 13 | 88 | 12 | 76 |
| 99_vi_2_B | 63 | 37 | 67 | 33 | 65 | 35 | 30 |
| 99_vi_2_C | 69 | 31 | 71 | 29 | 70 | 30 | 40 |
| 99_vi_2_D | 88 | 12 | 86 | 14 | 87 | 13 | 74 |
| 99_vi_2_E | 92 | 8 | 90 | 10 | 91 | 9 | 82 |
| 99_vi_3_A | 86 | 14 | 90 | 10 | 88 | 12 | 76 |
| 99_vi_3_B | 67 | 33 | 71 | 29 | 69 | 31 | 38 |
| 99_vi_3_C | 66 | 34 | 64 | 36 | 65 | 35 | 30 |
| 99_vi_3_D | 90 | 10 | 89 | 11 | 89 | 11 | 78 |
| 99_vi_3_E | 87 | 13 | 83 | 17 | 85 | 15 | 70 |
| 99_vi_4_A | 91 | 9 | 89 | 11 | 90 | 10 | 80 |
| 99_vi_4_B | 68 | 32 | 68 | 32 | 68 | 32 | 36 |
| 99_vi_4_C | 77 | 23 | 75 | 25 | 76 | 24 | 52 |
| 99_vi_4_D | 86 | 14 | 86 | 14 | 86 | 14 | 72 |
| 99_vi_4_E | 83 | 17 | 87 | 13 | 85 | 15 | 70 |
| 99_vi_5_A | 90 | 10 | 92 | 8 | 91 | 9 | 82 |
| 99_vi_5_B | 64 | 36 | 64 | 36 | 64 | 36 | 28 |
| 99_vi_5_C | 75 | 25 | 73 | 27 | 74 | 26 | 48 |
| 99_vi_5_D | 85 | 15 | 89 | 11 | 87 | 13 | 74 |
| 99_vi_5_E | 83 | 17 | 87 | 13 | 85 | 15 | 70 |

153 154
TABLE 7
Substituents on the BINOL and H8_BINOL cores for generation of an in-silico library
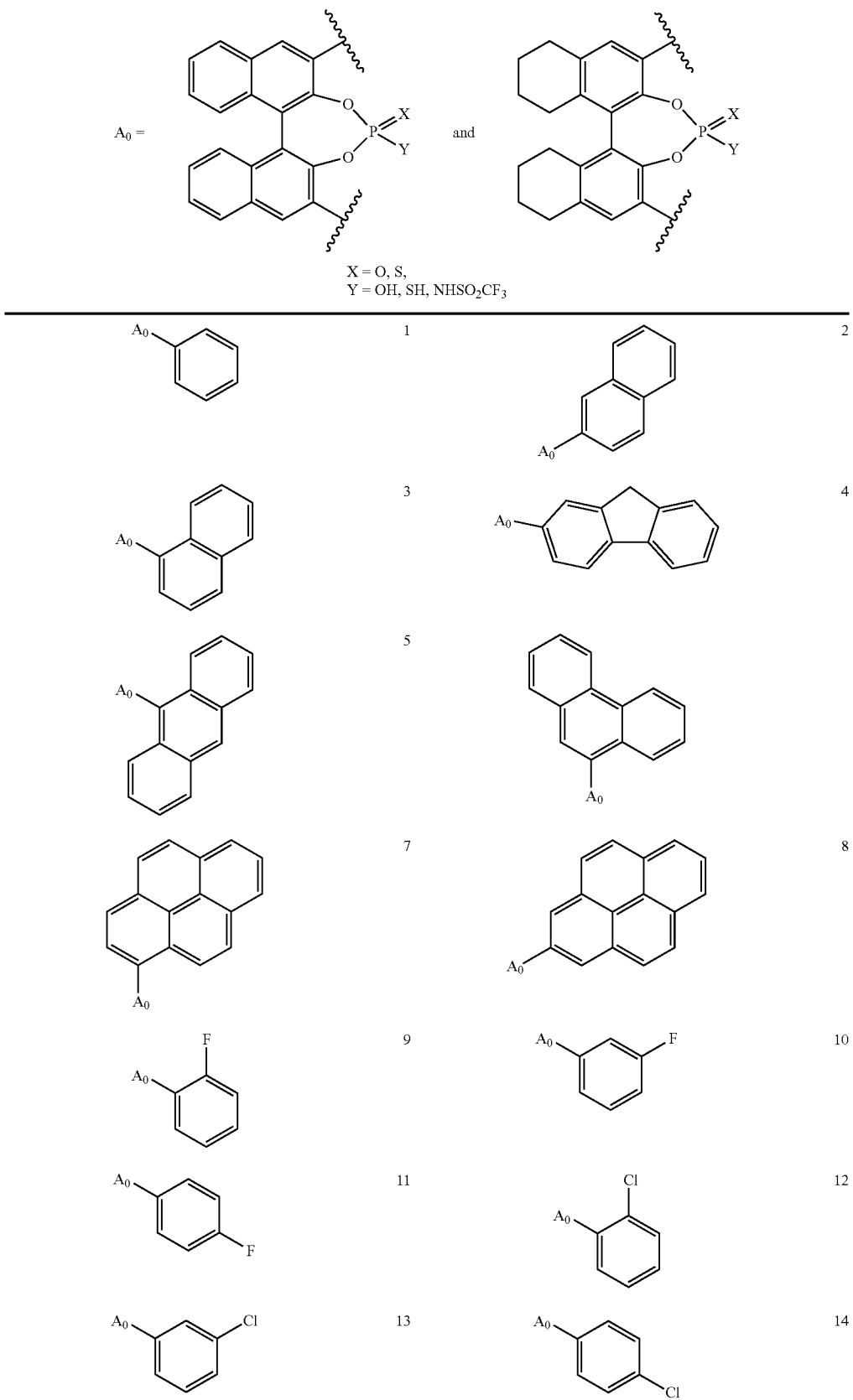

TABLE 7-continued
Substituents on the BINOL and H8_BINOL cores for generation of an in-silico library
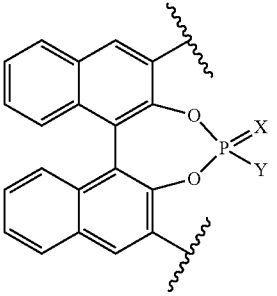
$A_0 =$ 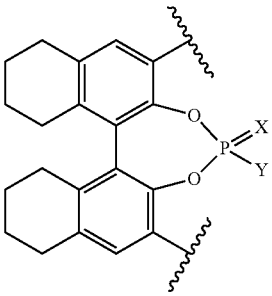 and 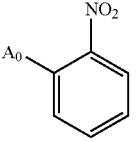
X = O, S,
Y = OH, SH, NHSO$_2$CF$_3$
| | | |
|---|---|---|
| 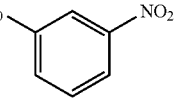 | 15 | 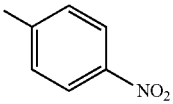 16 |
| 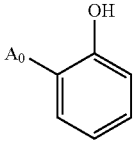 | 17 | 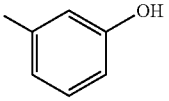 18 |
| 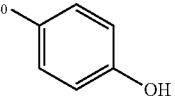 | 19 | 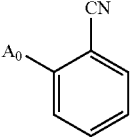 20 |
| 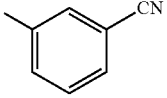 | 21 | 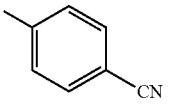 22 |
| 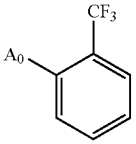 | 23 | 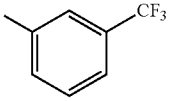 24 |
| 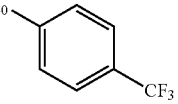 | 25 | 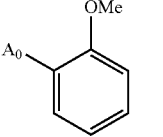 26 |
| 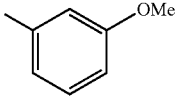 | 27 | 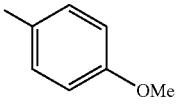 28 |
| 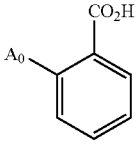 | 29 |  30 |

TABLE 7-continued

Substituents on the BINOL and H8_BINOL cores for generation of an in-silico library $A_0$ = [BINOL phosphate structure] and [H8_BINOL phosphate structure]

X = O, S,
Y = OH, SH, $NHSO_2CF_3$

| Structure | No. | Structure | No. |
|---|---|---|---|
| $A_0$—C6H4—$CO_2H$ (meta) | 31 | $A_0$—C6H4—$CO_2H$ (para) | 32 |
| $A_0$—C6H4—$CONH_2$ (ortho) | 33 | $A_0$—C6H4—$CONH_2$ (meta) | 34 |
| $A_0$—C6H4—$CONH_2$ (para) | 35 | $A_0$—C6H4—CONHMe (ortho) | 36 |
| $A_0$—C6H4—CONHMe (meta) | 37 | $A_0$—C6H4—CONHMe (para) | 38 |
| $A_0$—C6H4—$CONMe_2$ (ortho) | 39 | $A_0$—C6H4—$CONMe_2$ (meta) | 40 |
| $A_0$—C6H4—$CONMe_2$ (para) | 41 | $A_0$—C6H4—SMe (ortho) | 42 |
| $A_0$—C6H4—SMe (meta) | 43 | $A_0$—C6H4—SMe (para) | 44 |
| $A_0$—C6H4—$CH_2OH$ (para) | 45 | $A_0$—C6H4—$CH_2OH$ (meta) | 46 |

TABLE 7-continued
Substituents on the BINOL and H8_BINOL cores for generation of an in-silico library
$A_0 =$ 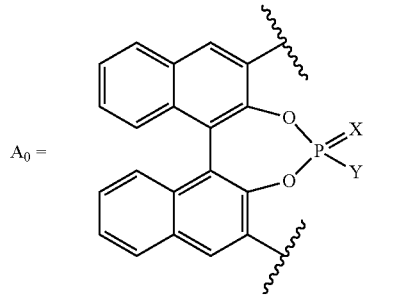 and 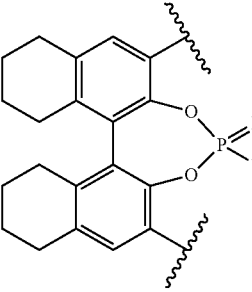
X = O, S,
Y = OH, SH, NHSO$_2$CF$_3$
| | | | | |
|---|---|---|---|---|
| 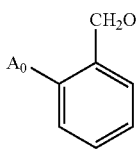 | 47 | 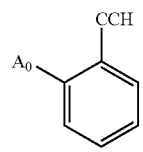 | 48 |
| 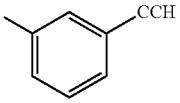 | 49 | 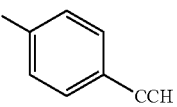 | 50 |
| 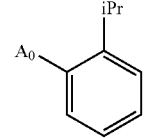 | 51 | 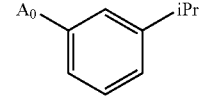 | 52 |
| 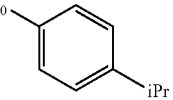 | 53 | 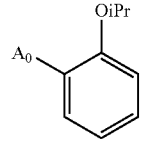 | 54 |
| 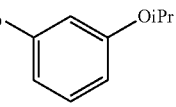 | 55 | 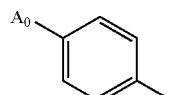 | 56 |
| 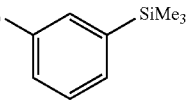 | 57 | 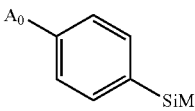 | 58 |
| 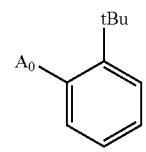 | 59 | 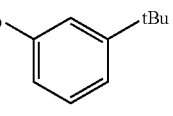 | 60 |
| 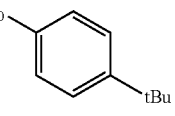 | 61 | 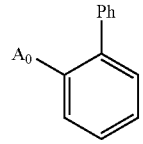 | 62 |

TABLE 7-continued
Substituents on the BINOL and H8_BINOL cores for generation of an in-silico library
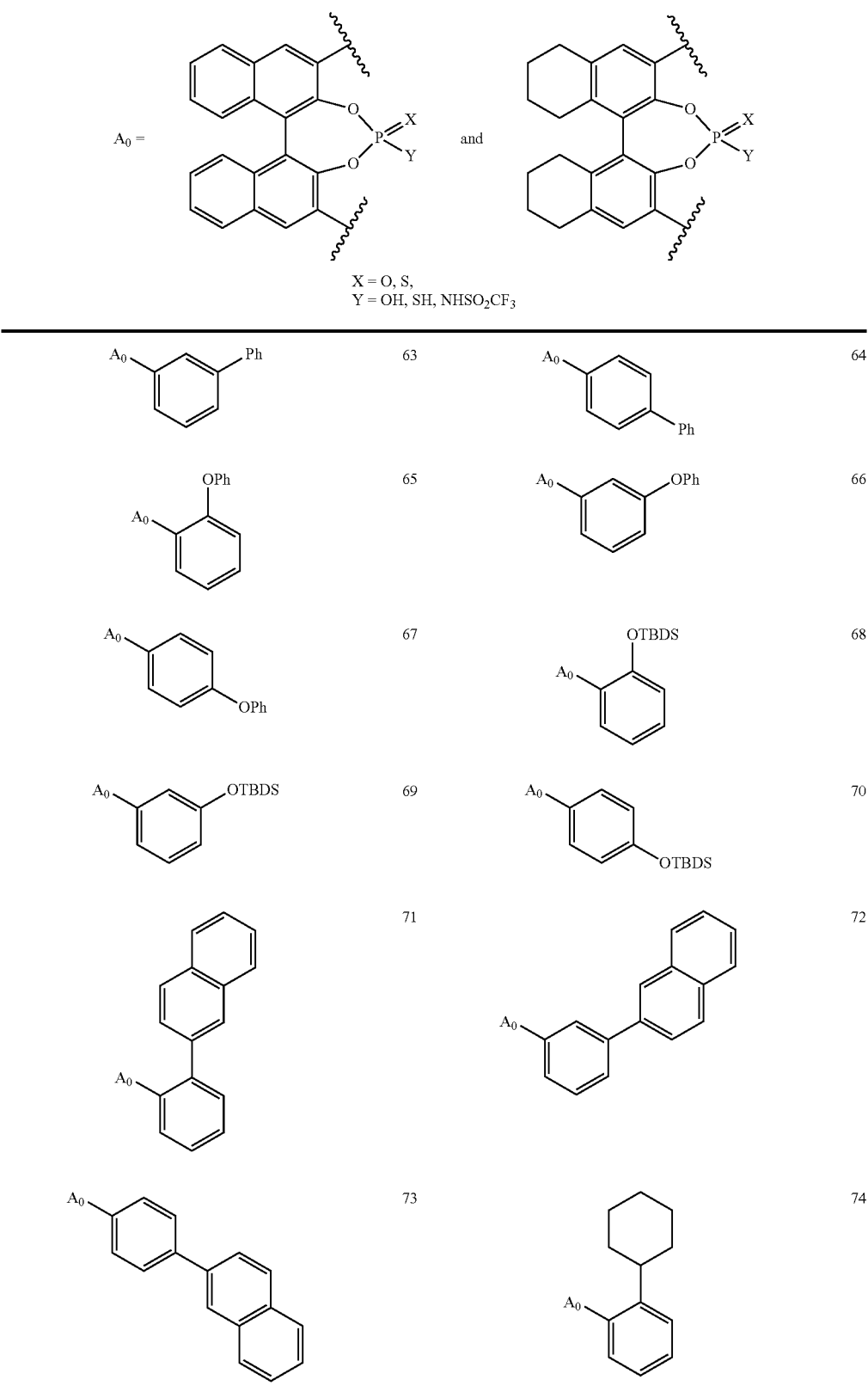
X = O, S,
Y = OH, SH, NHSO$_2$CF$_3$ TABLE 7-continued
Substituents on the BINOL and H8_BINOL cores for generation of an in-silico library
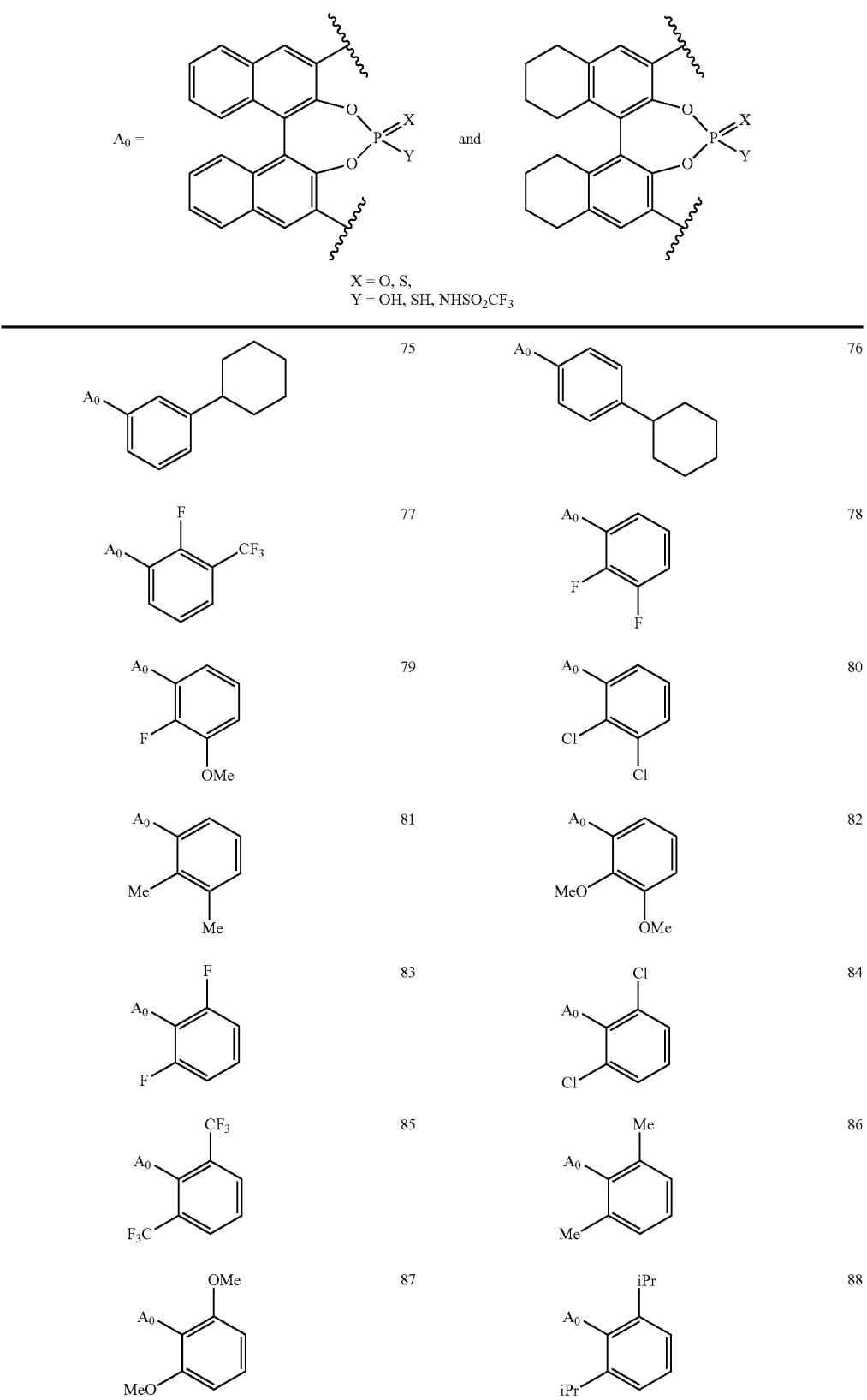

TABLE 7-continued

Substituents on the BINOL and H8_BINOL cores for generation of an in-silico library $A_0 =$ [BINOL phosphite structure] and [H8-BINOL phosphite structure]

X = O, S,
Y = OH, SH, NHSO$_2$CF$_3$

| # | Structure |
|---|---|
| 89 | $A_0$-phenyl with Ph (ortho), Ph (ortho) |
| 90 | $A_0$-phenyl with F (ortho), BuO (ortho) |
| 91 | $A_0$-phenyl with OMe (ortho), iPrO (ortho) |
| 92 | $A_0$-phenyl with OMe (ortho), tBuO (ortho) |
| 93 | $A_0$-phenyl with Me (para-like), F |
| 94 | $A_0$-phenyl with CF$_3$, F |
| 95 | $A_0$-phenyl with OEt, F |
| 96 | $A_0$-phenyl with Cl, Cl (3,5) |
| 97 | $A_0$-phenyl with F, F (3,5) |
| 98 | $A_0$-phenyl with OH, F (3,5) |
| 99 | $A_0$-phenyl with CF$_3$, CF$_3$ (3,5) |
| 100 | $A_0$-phenyl with Me, Me (3,5) |
| 101 | $A_0$-phenyl with OMe, OMe (3,5) |
| 102 | $A_0$-phenyl with tBu, Me (3,5) |

TABLE 7-continued
Substituents on the BINOL and H8_BINOL cores for generation of an in-silico library
$A_0 =$ 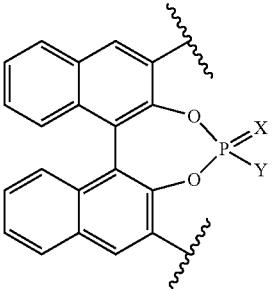 and 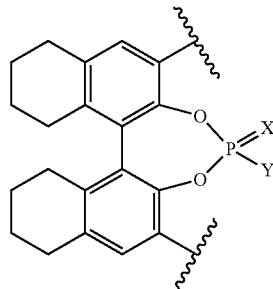
X = O, S,
Y = OH, SH, NHSO$_2$CF$_3$
| | | | | |
|---|---|---|---|---|
| 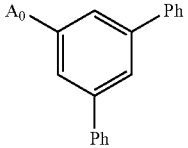 | 103 | 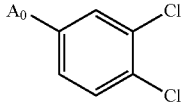 | 104 |
| 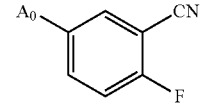 | 105 | 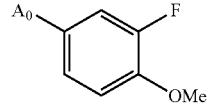 | 106 |
| 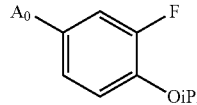 | 107 | 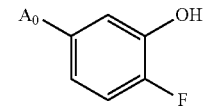 | 108 |
| 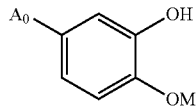 | 109 | 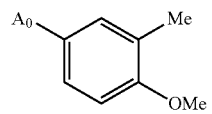 | 110 |
| 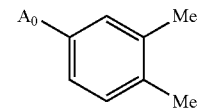 | 111 | 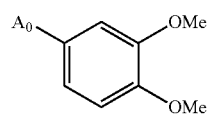 | 112 |
| 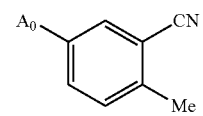 | 113 | 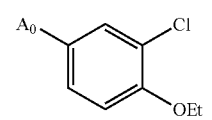 | 114 |
| 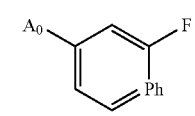 | 115 | 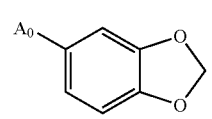 | 116 |
| 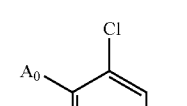 | 117 | 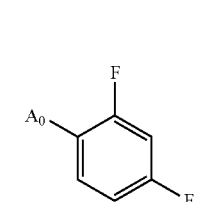 | 118 |
| 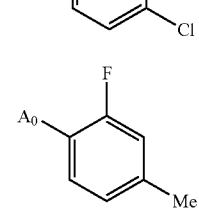 | 119 | | 120 |

TABLE 7-continued
Substituents on the BINOL and H8_BINOL cores for generation of an in-silico library
$A_0 =$ 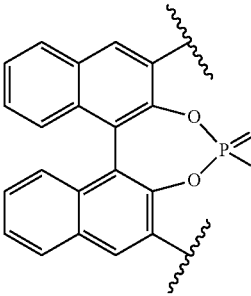 and 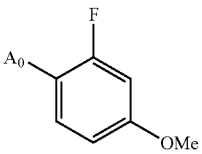
X = O, S,
Y = OH, SH, NHSO$_2$CF$_3$
| | | | | |
|---|---|---|---|---|
| 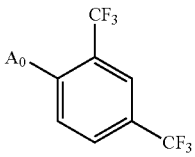 | 121 | 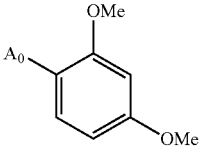 | 122 |
| 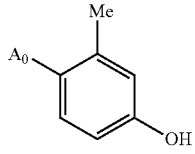 | 123 | 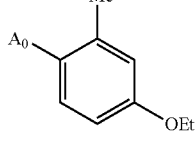 | 124 |
| 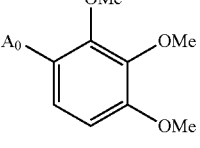 | 125 | 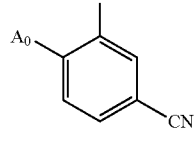 | 126 |
| 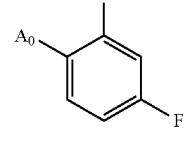 | 127 | 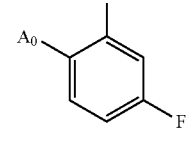 | 128 |
| 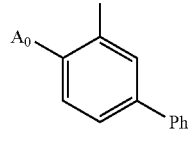 | 129 | 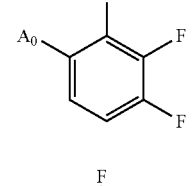 | 130 |
| 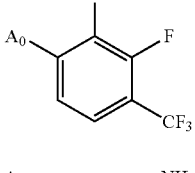 | 131 | 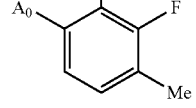 | 132 |
| 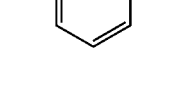 | 133 | | 134 |

TABLE 7-continued
Substituents on the BINOL and H8_BINOL cores for generation of an in-silico library
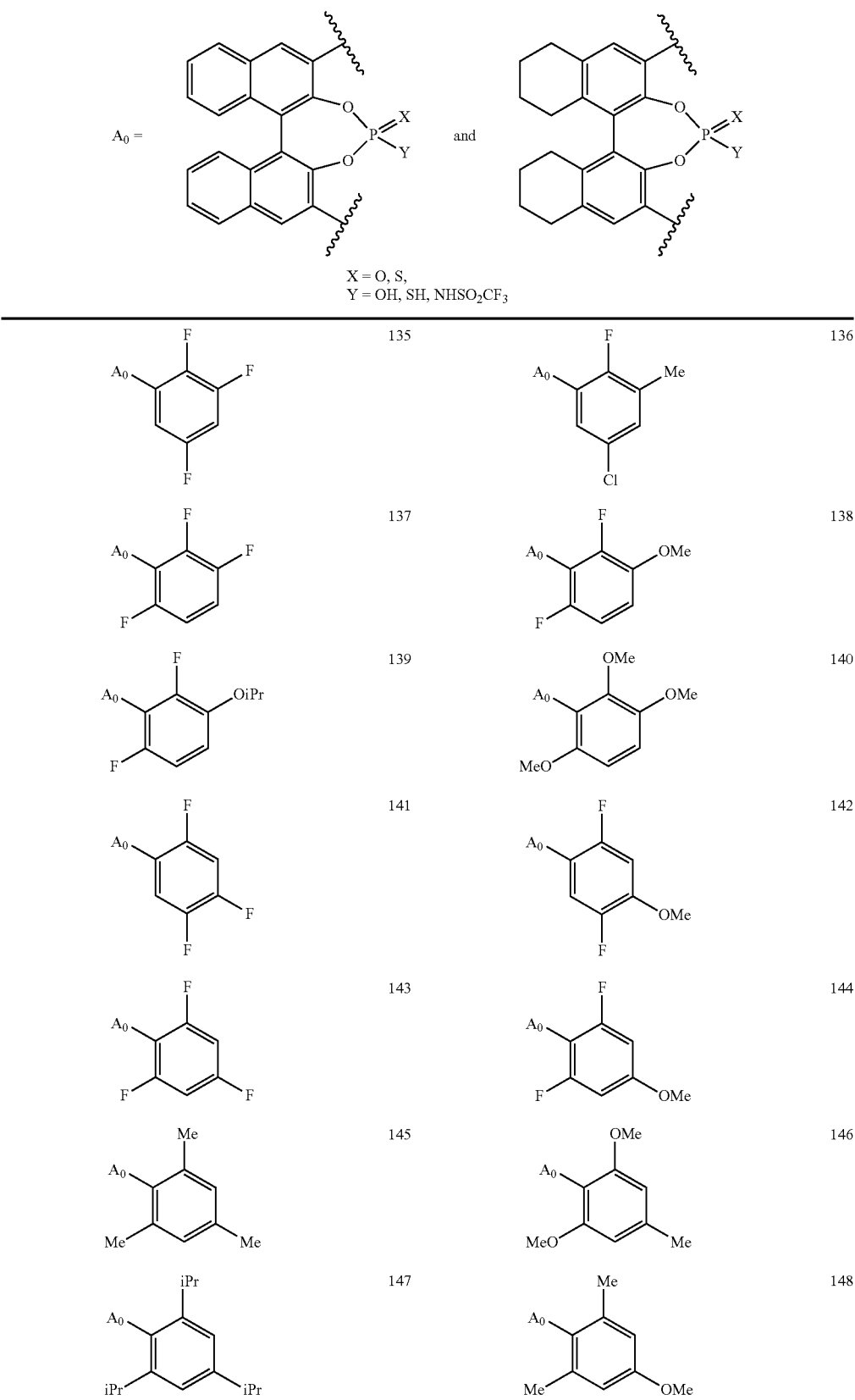

TABLE 7-continued
Substituents on the BINOL and H8_BINOL cores for generation of an in-silico library
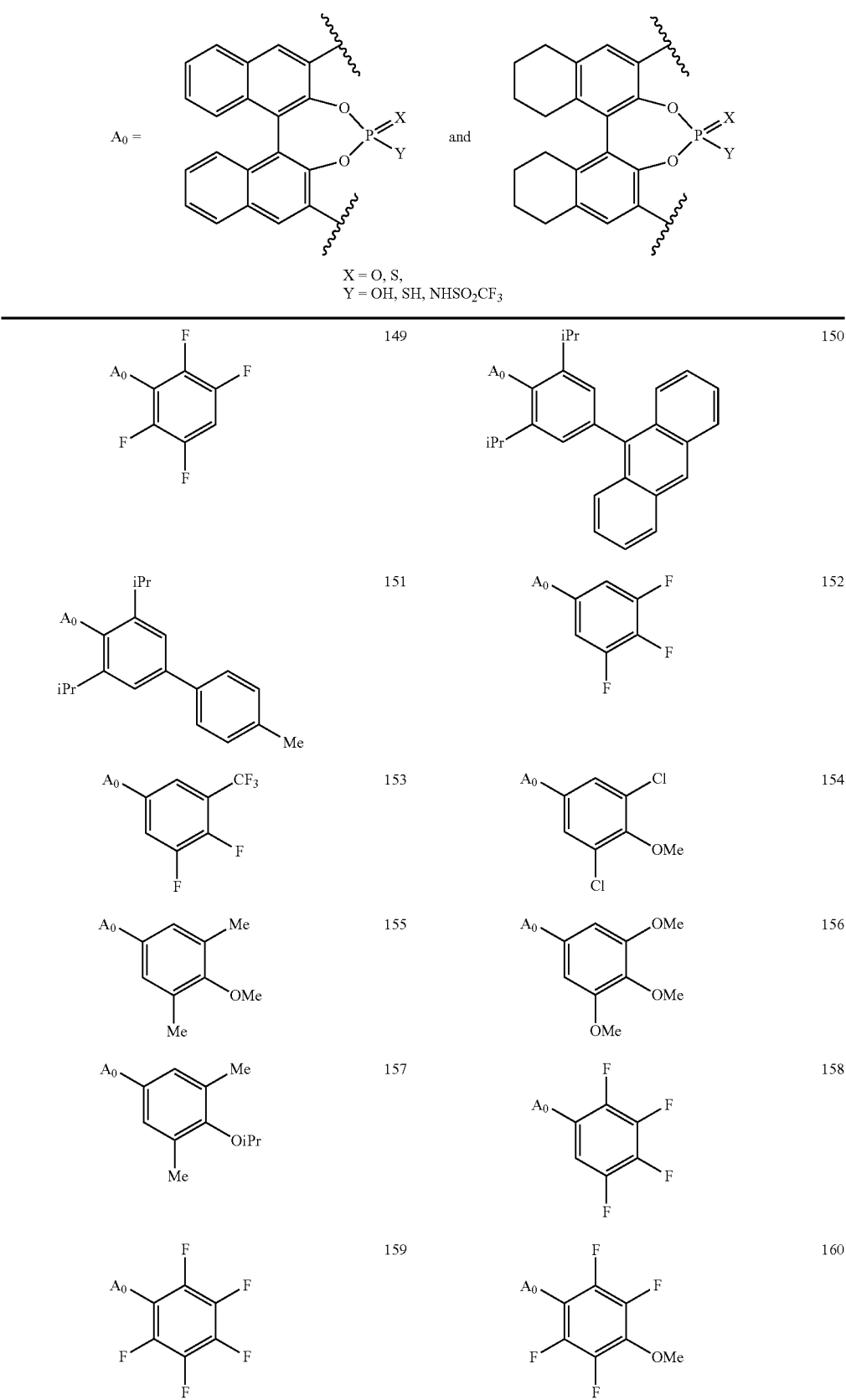
X = O, S,
Y = OH, SH, NHSO₂CF₃

TABLE 7-continued
Substituents on the BINOL and H8_BINOL cores for generation of an in-silico library
$A_0 =$ 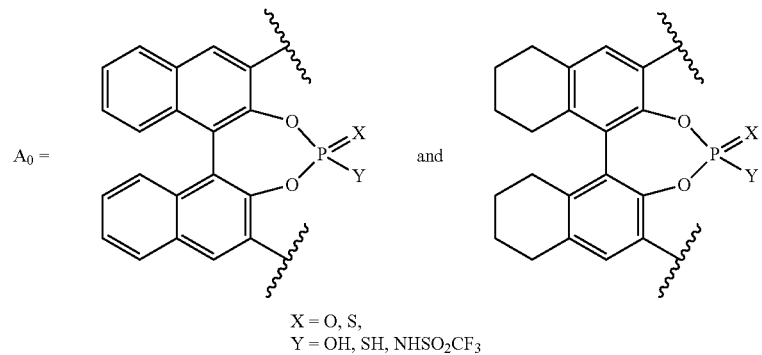 and
X = O, S,
Y = OH, SH, NHSO$_2$CF$_3$
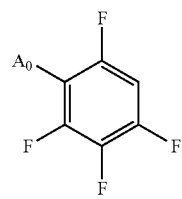 161
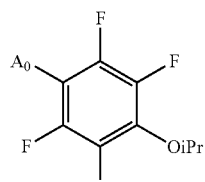 162
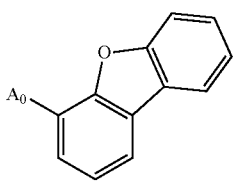 163
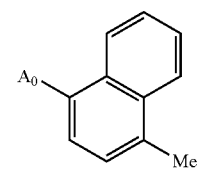 164
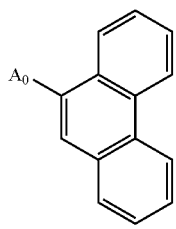 165
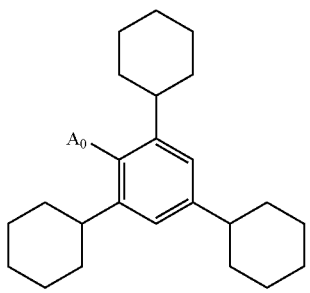 166
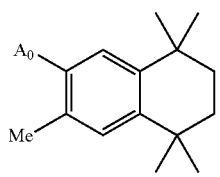 167
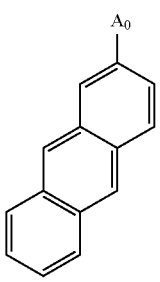 168
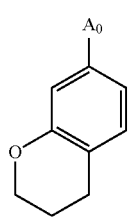 169
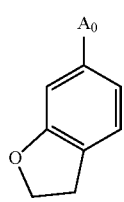 170

TABLE 7-continued
Substituents on the BINOL and H8_BINOL cores for generation of an in-silico library
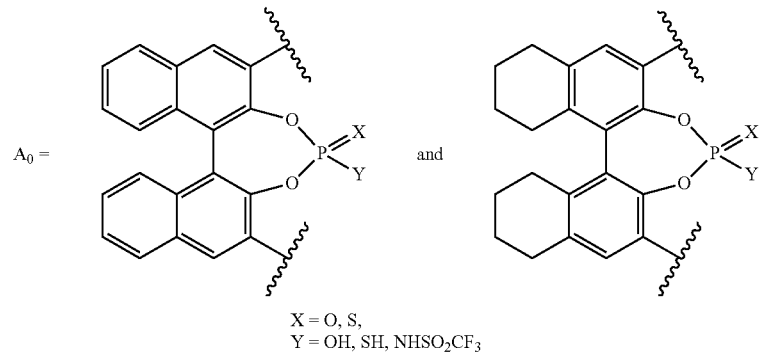
$A_0 = $ and
$X = O, S,$
$Y = OH, SH, NHSO_2CF_3$
| | |
|---|---|
| 171 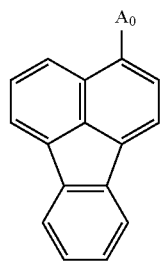 | 172 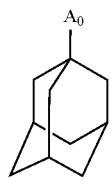 |
| 173 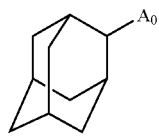 | 174 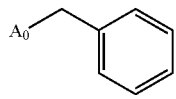 |
| 175 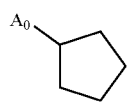 | 176 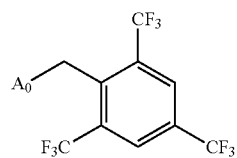 |
| 177 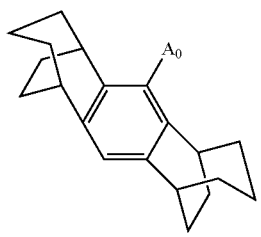 | 178 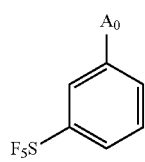 |
| 179 | 180 |

TABLE 7-continued
Substituents on the BINOL and H8_BINOL cores for generation of an in-silico library
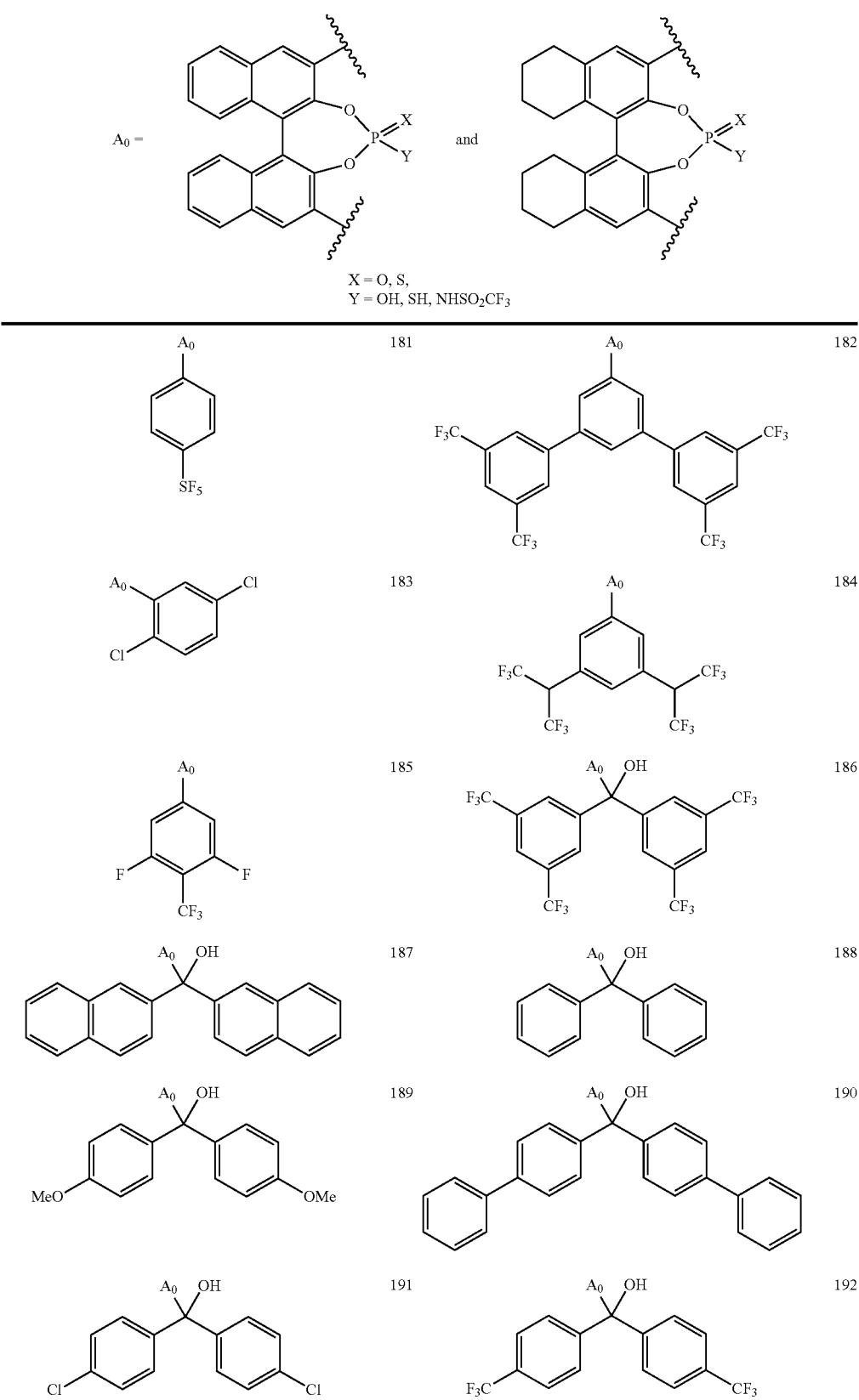

TABLE 7-continued
Substituents on the BINOL and H8_BINOL cores for generation of an in-silico library
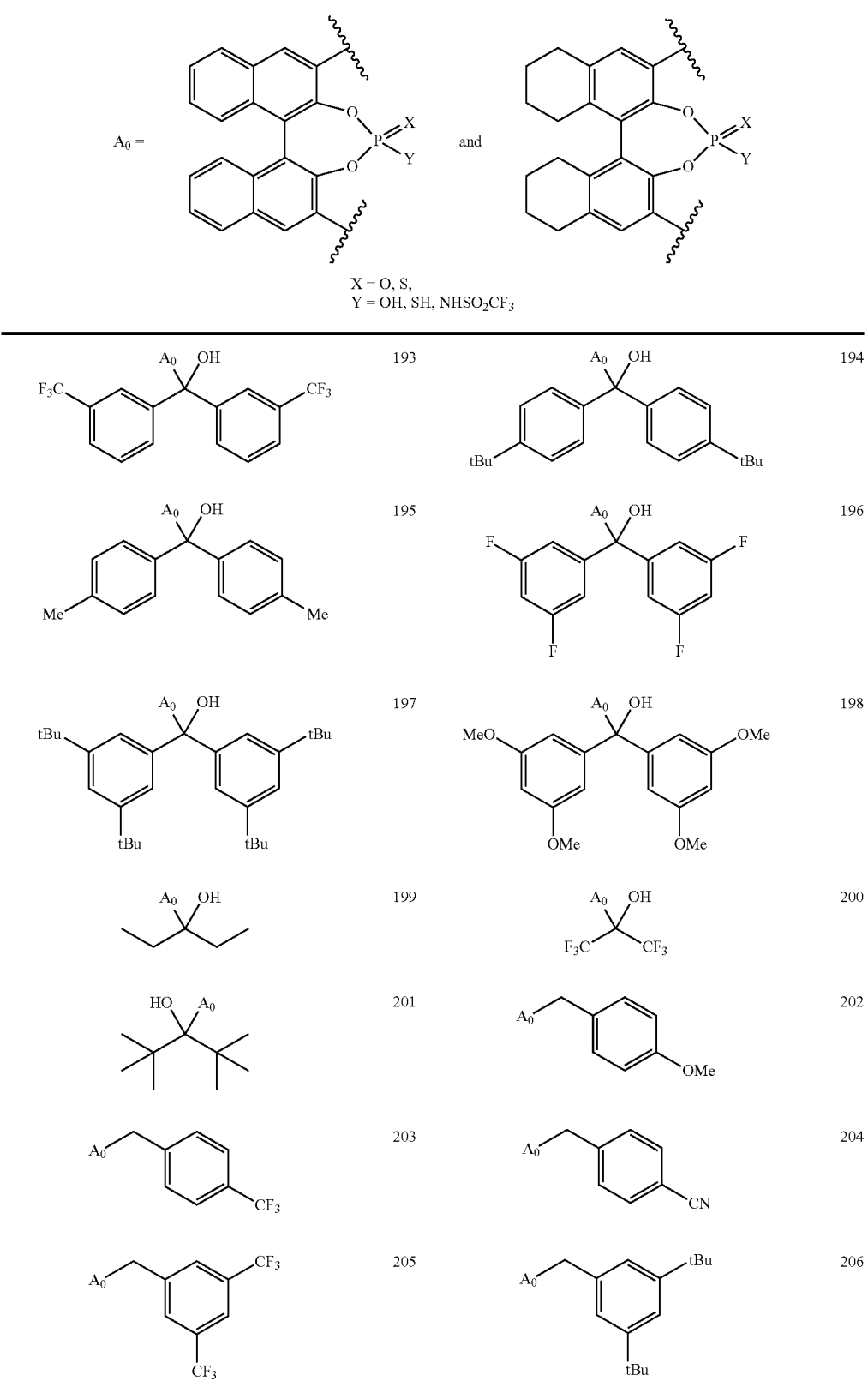

TABLE 7-continued

Substituents on the BINOL and H8_BINOL cores for generation of an in-silico library

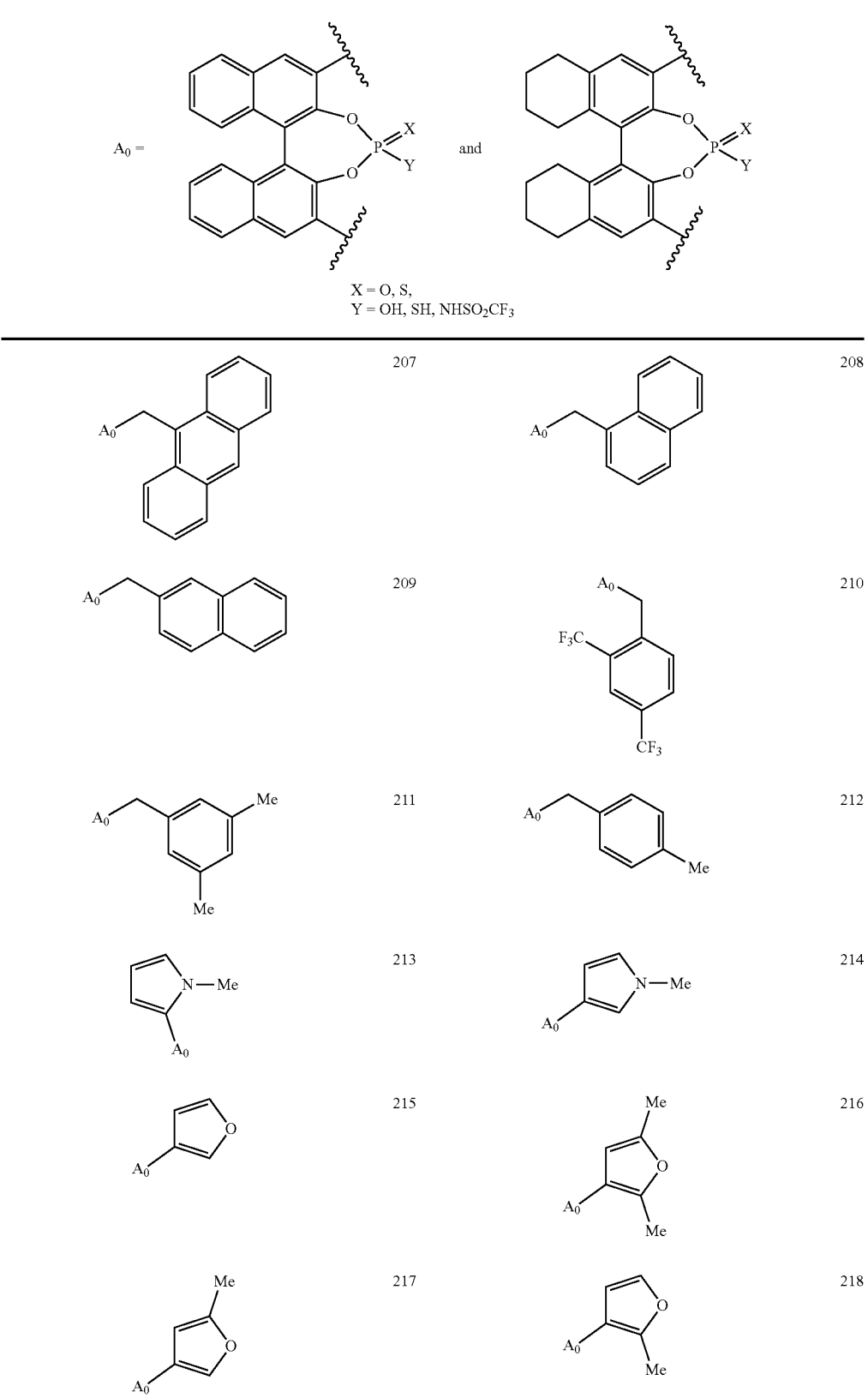

$A_0 = $ [BINOL phosphate structure] and [H8_BINOL phosphate structure]

$X = O, S,$
$Y = OH, SH, NHSO_2CF_3$

207: $A_0$—CH$_2$—(9-anthracenyl)

208: $A_0$—CH$_2$—(1-naphthyl)

209: $A_0$—CH$_2$—(2-naphthyl)

210: $A_0$—CH$_2$—(2,4-bis(trifluoromethyl)phenyl)

211: $A_0$—CH$_2$—(3,5-dimethylphenyl)

212: $A_0$—CH$_2$—(4-methylphenyl)

213: $A_0$—(N-methylpyrrol-2-yl)

214: $A_0$—(N-methylpyrrol-3-yl)

215: $A_0$—(furan-3-yl)

216: $A_0$—(2,5-dimethylfuran-3-yl)

217: $A_0$—(5-methylfuran-3-yl)

218: $A_0$—(2-methylfuran-3-yl)

US 11,664,093 B2
185                                                                                                                          186
TABLE 7-continued
Substituents on the BINOL and H8_BINOL cores for generation of an in-silico library
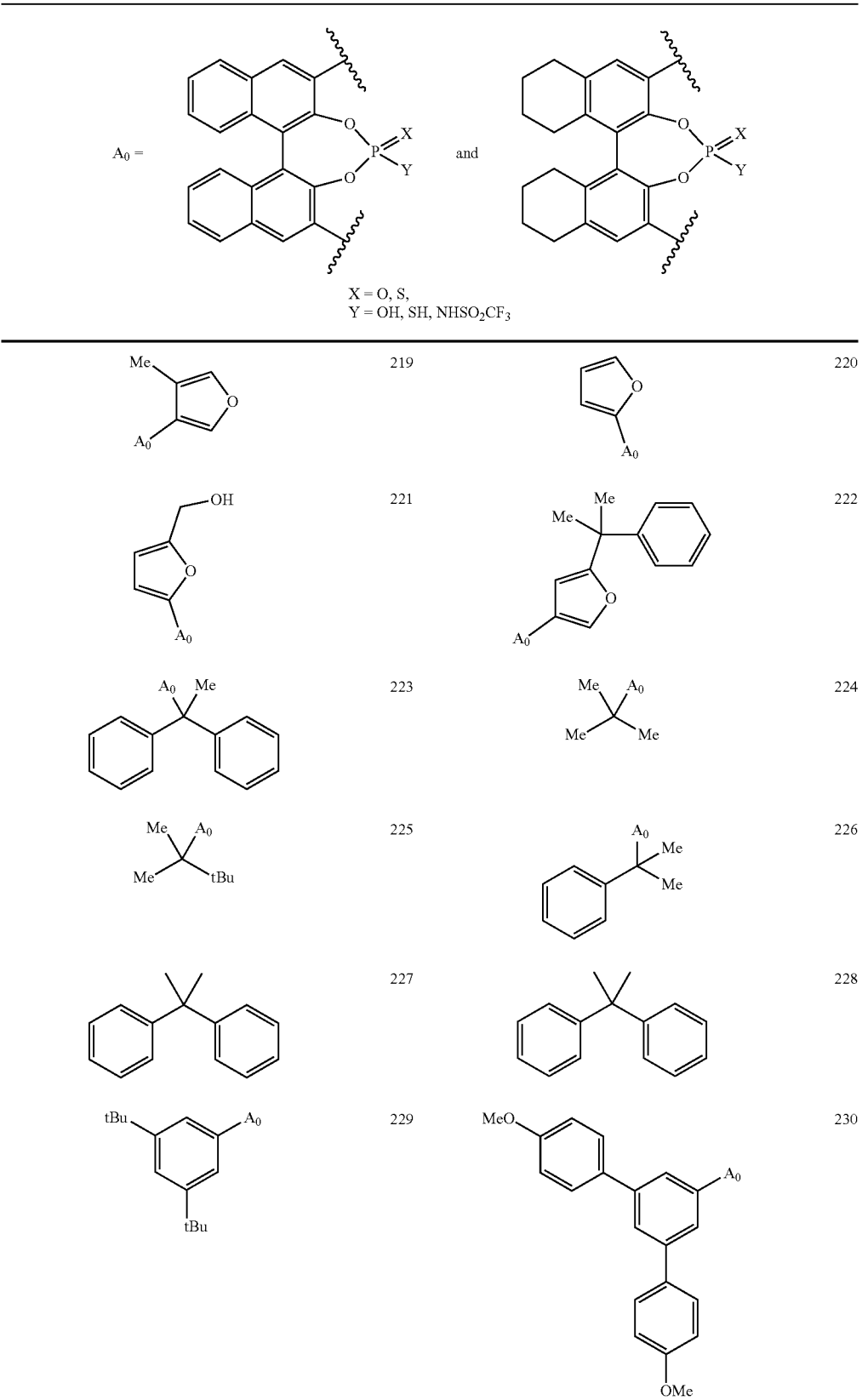

TABLE 7-continued
Substituents on the BINOL and H8_BINOL cores for generation of an in-silico library
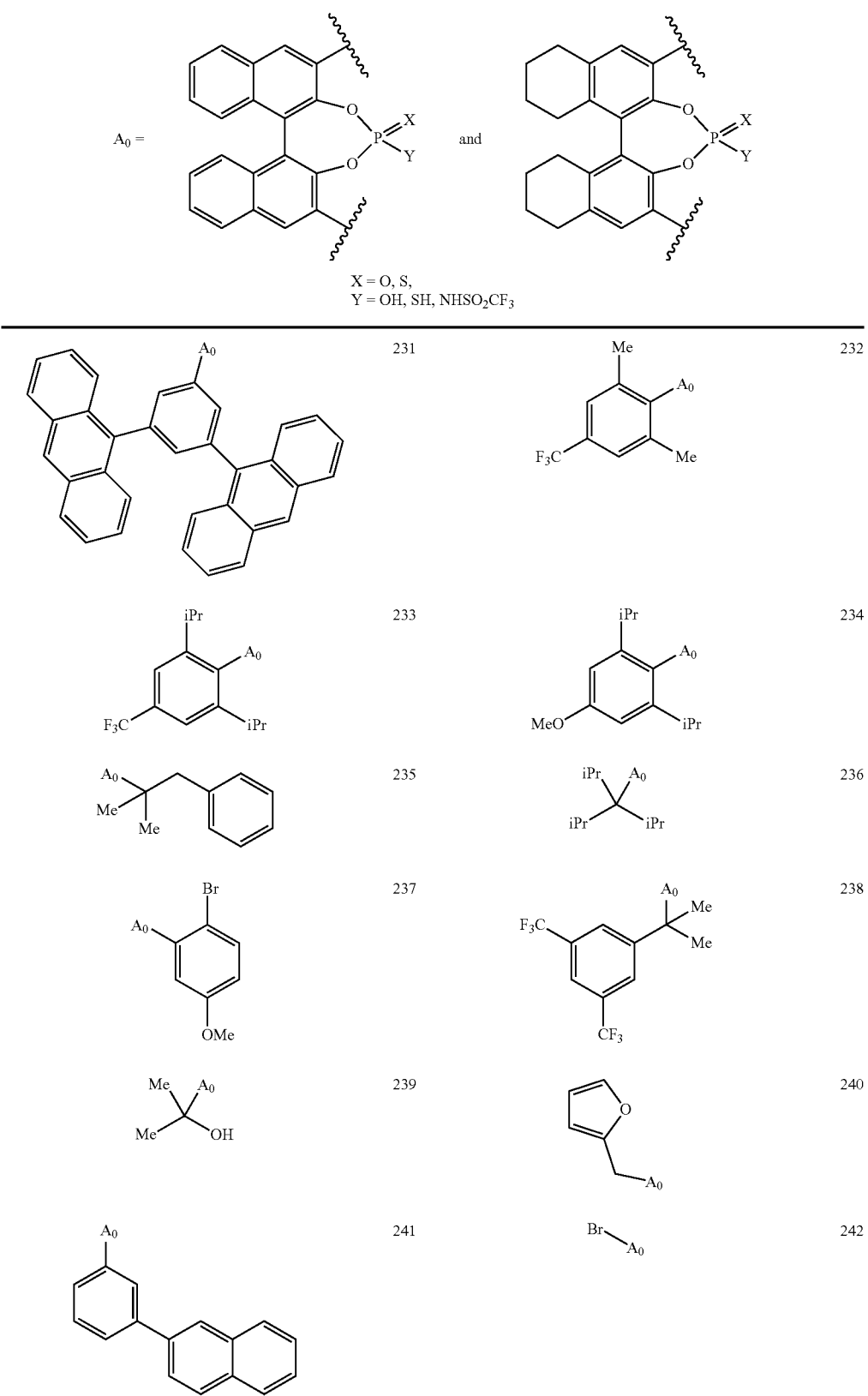
X = O, S,
Y = OH, SH, NHSO$_2$CF$_3$ TABLE 7-continued
Substituents on the BINOL and H8_BINOL cores for generation of an in-silico library
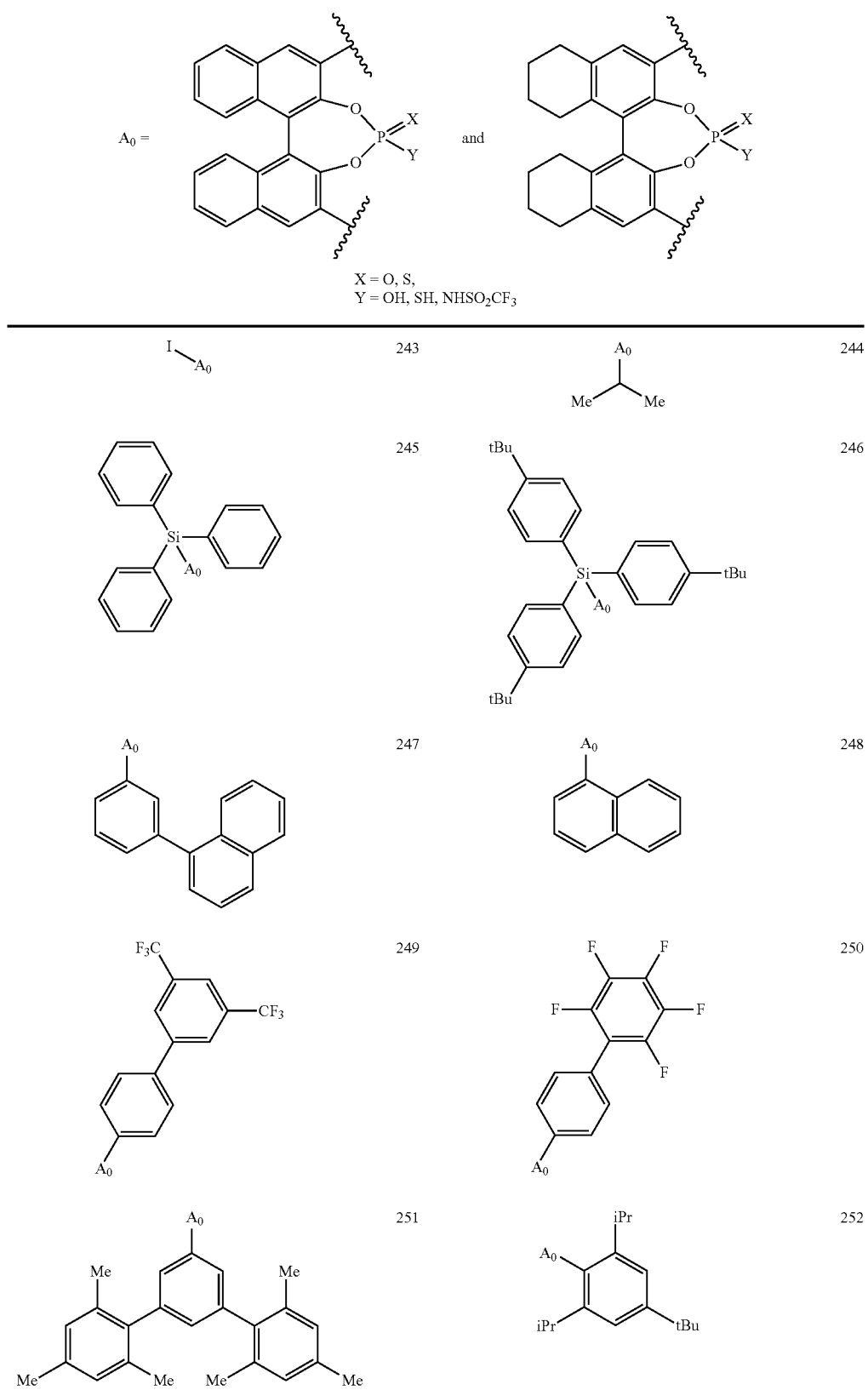
$A_0 =$ and
$X = O, S,$
$Y = OH, SH, NHSO_2CF_3$ TABLE 7-continued
Substituents on the BINOL and H8_BINOL cores for generation of an in-silico library
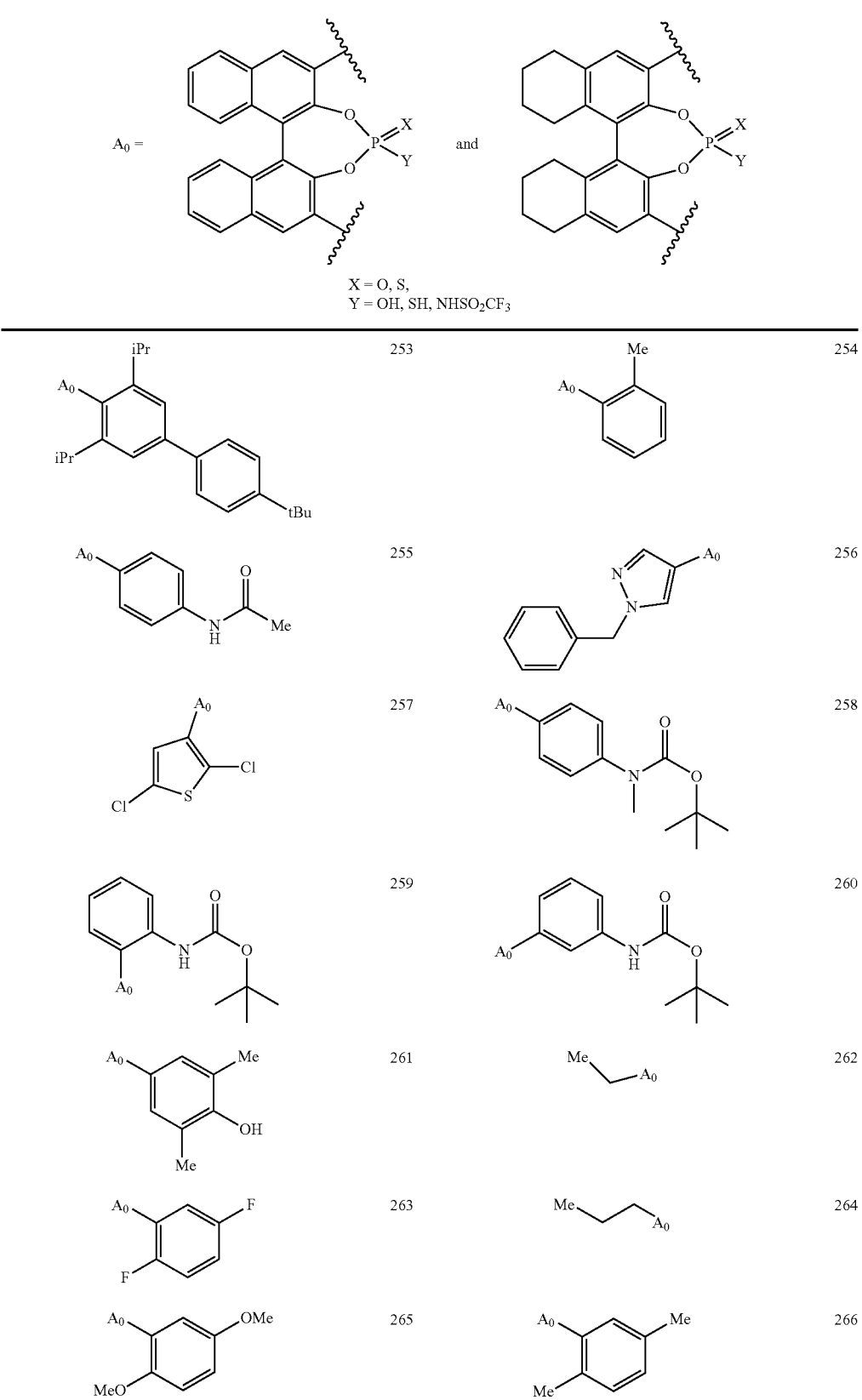

TABLE 7-continued
Substituents on the BINOL and H8_BINOL cores for generation of an in-silico library
$A_0 =$ 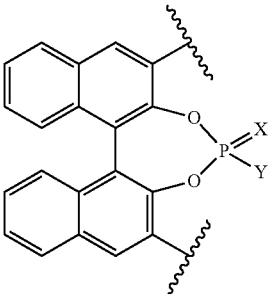 and 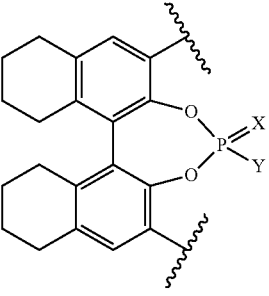
X = O, S,
Y = OH, SH, NHSO$_2$CF$_3$
| | | | |
|---|---|---|---|
| 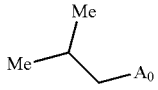 | 267 | 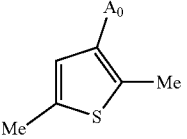 | 268 |
| 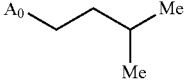 | 269 | 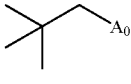 | 270 |
| 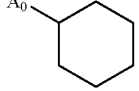 | 271 | 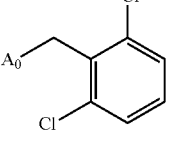 | 272 |
| 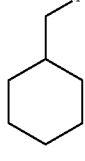 | 273 | 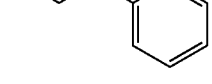 | 274 |
| 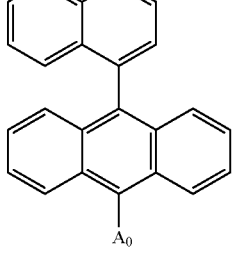 | 275 | 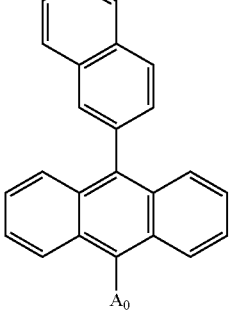 | 276 |
| 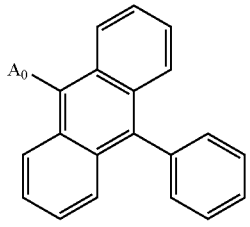 | 277 | 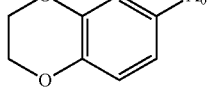 | 278 |

TABLE 7-continued
Substituents on the BINOL and H8_BINOL cores for generation of an in-silico library
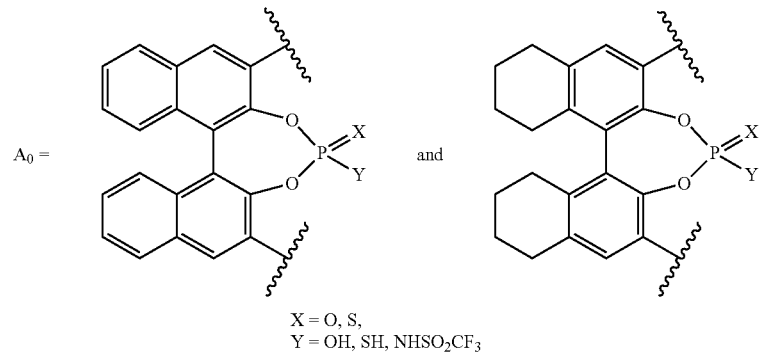
$A_0 =$ and
$X = O, S,$
$Y = OH, SH, NHSO_2CF_3$
| | | | |
|---|---|---|---|
| 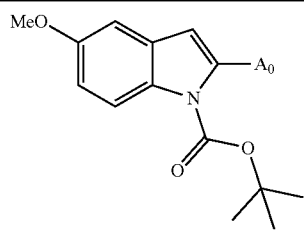 | 279 | 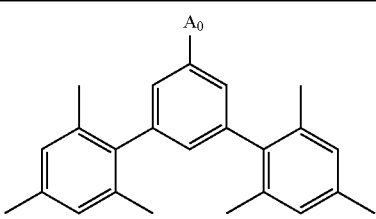 | 280 |
| 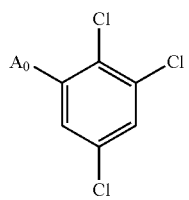 | 281 | 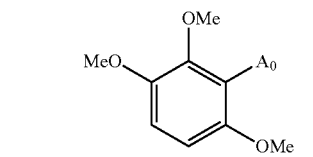 | 282 |
| 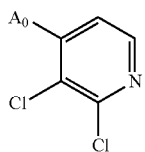 | 283 |  | 284 |
| 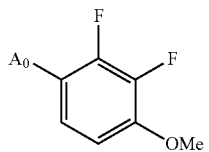 | 285 | 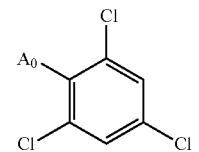 | 286 |
| 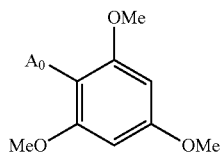 | 287 | 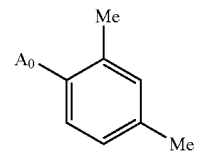 | 288 |
| 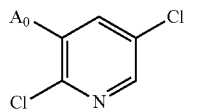 | 289 | 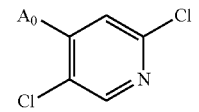 | 290 |
| 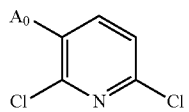 | 291 | 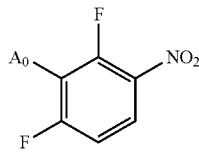 | 292 |

TABLE 7-continued
Substituents on the BINOL and H8_BINOL cores for generation of an in-silico library
$A_0 =$ 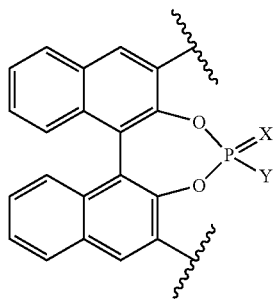 and 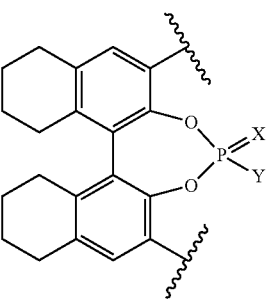
X = O, S,
Y = OH, SH, $NHSO_2CF_3$
| | | | |
|---|---|---|---|
| 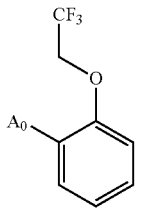 | 293 | 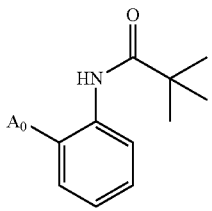 | 294 |
| 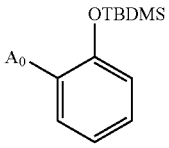 | 295 | 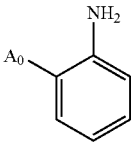 | 296 |
| 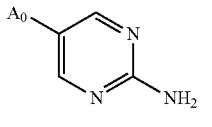 | 297 | 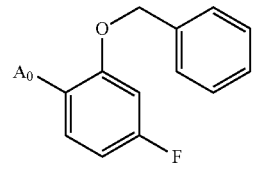 | 298 |
| 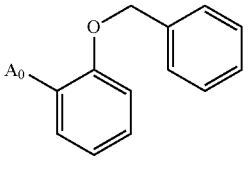 | 299 | 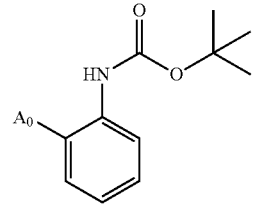 | 300 |
| 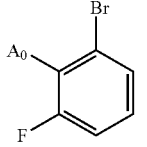 | 301 | 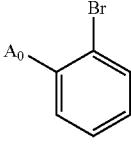 | 302 |
| 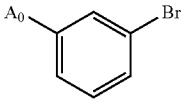 | 303 | 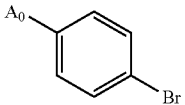 | 304 |
| 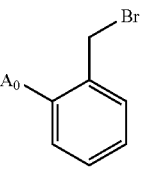 | 305 | 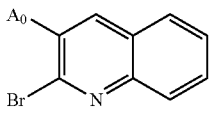 | 306 |

TABLE 7-continued
Substituents on the BINOL and H8_BINOL cores for generation of an in-silico library
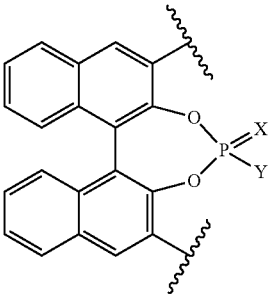
$A_0 = $ 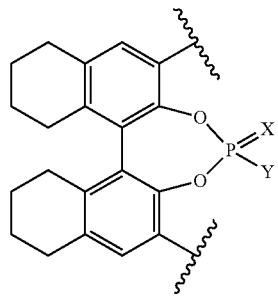 and 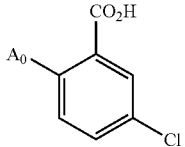
X = O, S,
Y = OH, SH, NHSO$_2$CF$_3$
| | | | |
|---|---|---|---|
| 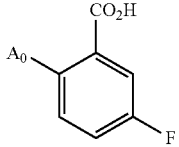 | 307 | 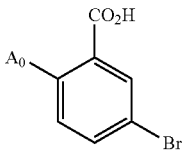 | 308 |
| 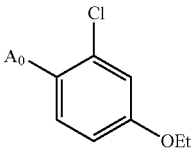 | 309 | 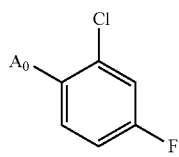 | 310 |
| 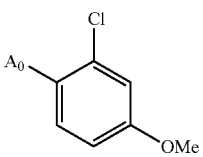 | 311 | 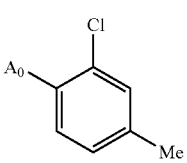 | 312 |
| 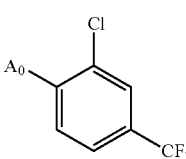 | 313 | 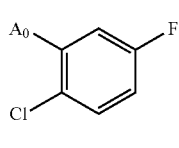 | 314 |
| 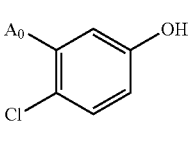 | 315 | 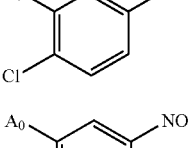 | 316 |
| 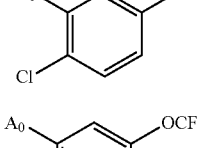 | 317 | 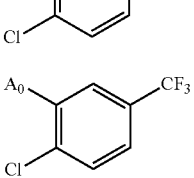 | 318 |
| 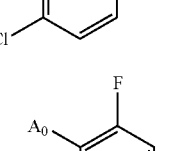 | 319 |  | 320 |
| 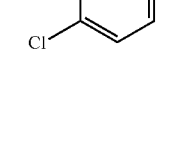 | 321 | | 322 |

TABLE 7-continued
Substituents on the BINOL and H8_BINOL cores for generation of an in-silico library
$A_0 =$ 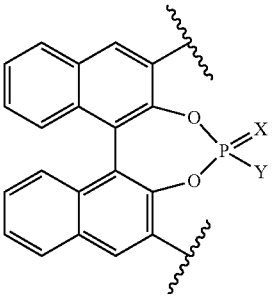 and 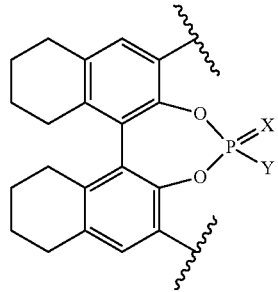
X = O, S,
Y = OH, SH, $NHSO_2CF_3$
| | | | | |
|---|---|---|---|---|
| 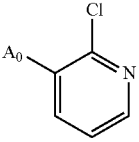 | 323 | 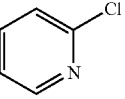 | 324 |
| 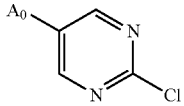 | 325 | 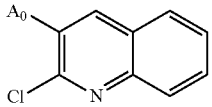 | 326 |
| 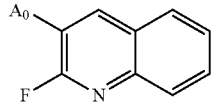 | 327 | 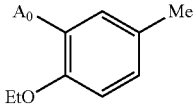 | 328 |
| 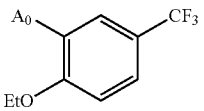 | 329 | 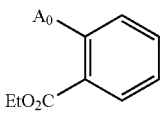 | 330 |
| 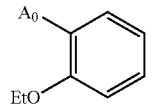 | 331 | 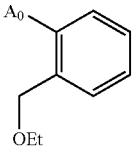 | 332 |
| 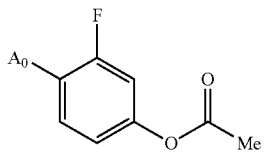 | 333 | 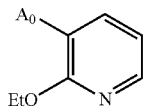 | 334 |
| 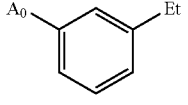 | 336 | 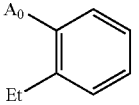 | 335 |
| 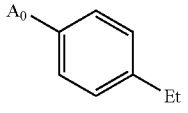 | 337 | 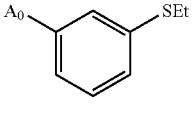 | 338 |

TABLE 7-continued

Substituents on the BINOL and H8_BINOL cores for generation of an in-silico library $A_0 =$ 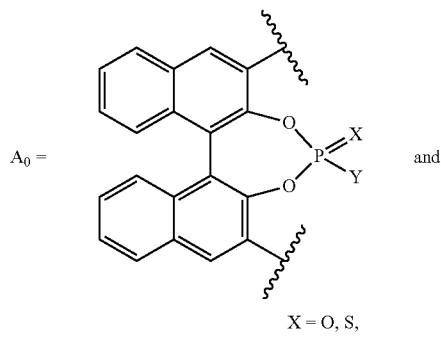 and 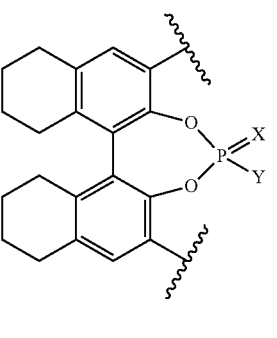

X = O, S,
Y = OH, SH, NHSO$_2$CF$_3$

| | | | | |
|---|---|---|---|---|
| 2-F, 3-A$_0$, N-Me benzamide | 339 | A$_0$-pyridine with Me and F | 340 |
| 3-A$_0$, 4-F benzaldehyde | 341 | 3-F, 4-A$_0$, methylsulfonyl benzene | 342 |
| 2-F, 4-CF$_3$, A$_0$ benzene | 343 | 3-A$_0$, 4-F benzoic acid | 344 |
| 3-A$_0$, 4-F, OCF$_3$ benzene | 345 | 3-A$_0$, 4-F, NO$_2$ benzene | 346 |
| 3-A$_0$, 4-F, N-phenyl benzamide | 347 | A$_0$, F-pyridine | 348 |
| 2-OMe, 3-A$_0$, 6-F benzene | 349 | 2-CF$_3$, 3-A$_0$, 6-F benzene | 350 |
| 3-A$_0$, 2-F pyridine | 351 | 4-A$_0$ benzaldehyde | 352 |

TABLE 7-continued
Substituents on the BINOL and H8_BINOL cores for generation of an in-silico library
$A_0 =$ 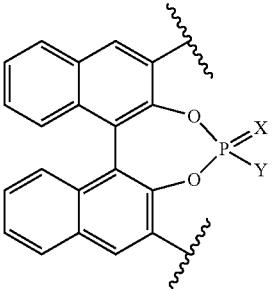 and 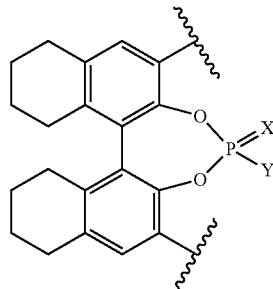
X = O, S,
Y = OH, SH, NHSO$_2$CF$_3$
| | | | |
|---|---|---|---|
| 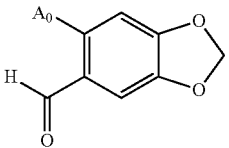 | 353 | 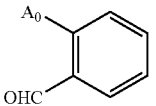 | 354 |
| 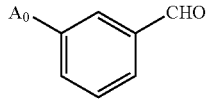 | 355 | 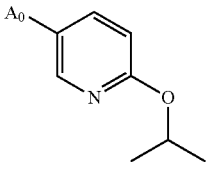 | 356 |
| 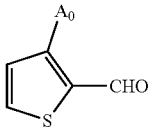 | 357 | 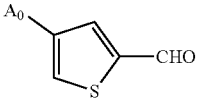 | 358 |
| 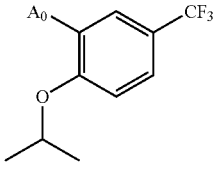 | 359 | 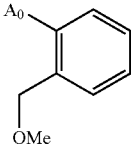 | 360 |
| 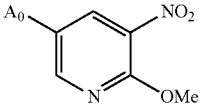 | 361 | 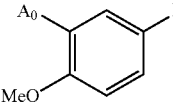 | 362 |
| 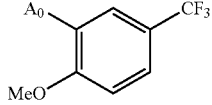 | 363 | 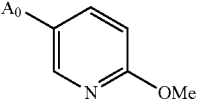 | 364 |
| 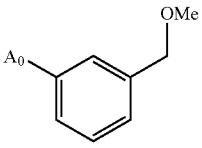 | 365 | 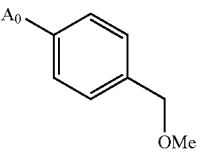 | 366 |
| 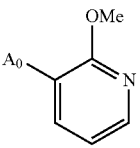 | 367 | 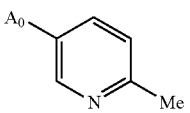 | 368 |

TABLE 7-continued
Substituents on the BINOL and H8_BINOL cores for generation of an in-silico library
$A_0 =$ 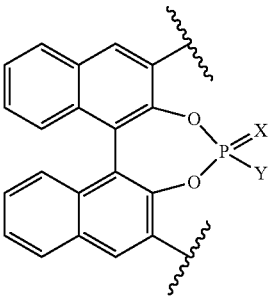 and 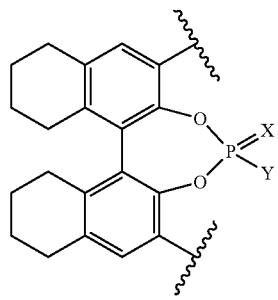
X = O, S,
Y = OH, SH, NHSO₂CF₃
| | | | |
|---|---|---|---|
| 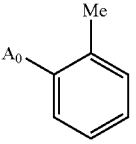 | 369 | 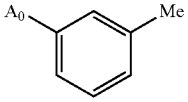 | 370 |
| 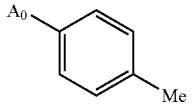 | 371 | 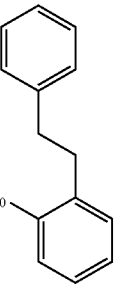 | 376 |
| 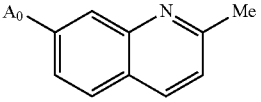 | 372 | 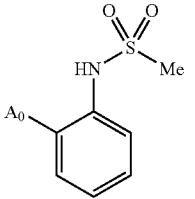 | 374 |
| 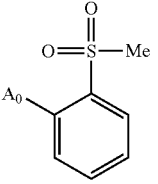 | 375 | 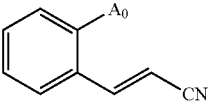 | 373 |
| 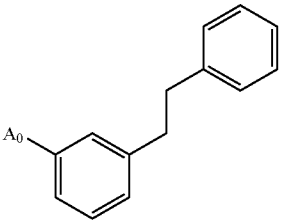 | 377 | 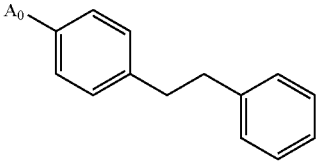 | 378 |
|  | 379 | 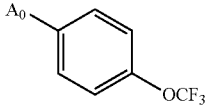 | 380 |

TABLE 7-continued

Substituents on the BINOL and H8_BINOL cores for generation of an in-silico library $A_0 =$ [BINOL phosphate structure] and [H8_BINOL phosphate structure]

X = O, S,
Y = OH, SH, $NHSO_2CF_3$

| # | Structure | # | Structure |
|---|---|---|---|
| 381 | $A_0$-phenyl-CH=CH-$CO_2Me$ (ortho) | 382 | $A_0$-phenyl-$OCF_3$ (ortho) |
| 383 | $A_0$-phenyl-$OCF_3$ (meta) | 384 | $A_0$-phenyl-$CH_2CH_2OH$ (meta) |
| 385 | $A_0$-pyridyl-$CF_3$ | 386 | $A_0$-phenyl-vinyl (ortho) |
| 387 | $A_0$-phenyl-$SO_2$-pyrrolidine (meta) | 388 | $A_0$-phenyl-(3-pyridyl) (meta) |
| 389 | $A_0$-phenyl-$CH_2CH_2CH_3$ (ortho) | 390 | $A_0$-phenyl-$CH_2CH_2OH$ (para) |
| 391 | $A_0$-phenyl-(2-methyl-1,3-dioxolan-2-yl) (meta) | 392 | $A_0$-phenyl-$SO_2$-morpholine (meta) |
| 393 | $A_0$-phenyl-3,4-diF | 394 | $A_0$-phenyl-(3-pyridyl) (meta) |

TABLE 7-continued

Substituents on the BINOL and H8_BINOL cores for generation of an in-silico library

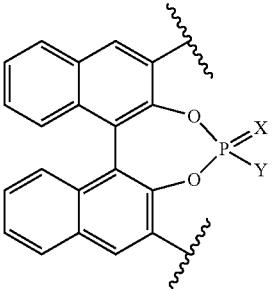

$A_0 =$ 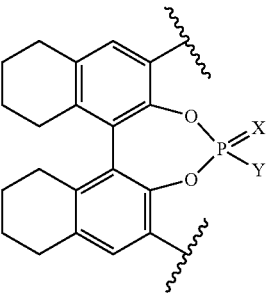 and 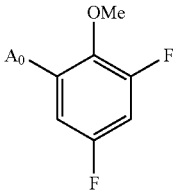

X = O, S,
Y = OH, SH, NHSO$_2$CF$_3$

| | | | | |
|---|---|---|---|---|
| 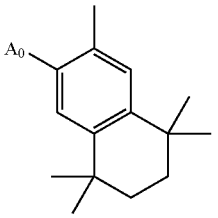 | 395 | 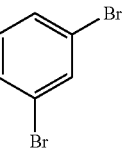 | 396 |
| 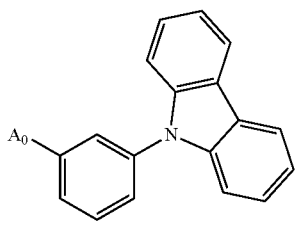 | 398 | 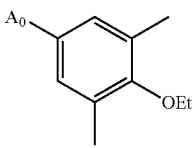 | 399 |
| 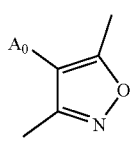 | 400 | (structure with OEt) | 401 |
| (isoxazole structure) | 402 | 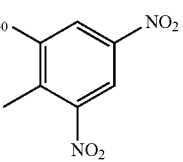 | 403 |
| | | 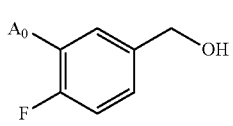 | 410 |

Computational Methods

To create a more user-friendly experience, an inclusive software package was created to help automate and standardize the process of generating and analyzing these large datasets. This python package, ccheminfolib, contains datatype definitions, construction code, and allows a user to use simple scripting code to go from a chemdraw file of core structures and substituents, through library generation and preparation, and through to descriptor calculation and modeling. Additionally, this code has also been optimized to work on parallel, high performance computing (HPC) clusters that can invoke different parallelization implementations. Parallelization of the code allows for shorter computation time by taking advantage of computers with multiple processing cores. This software package is still under development and does not constitute a finished product, but provides a significant advance in manipulating and calculating data for large in silico chemical libraries. The code can be downloaded from GitLab.

A Note on Data Logistics. While the descriptions may seem trivial, the sheer amount of data generated for this analysis cannot be ignored. A dataset of ~33,000 compounds (not an unreasonable number of molecules) takes just over 200 gigabytes (Gb) of hard drive space. Any movement or reading of the data requires specialized scripts and programs as it would be impractical to modify these files by hand. Automation of the process and development of a software package were essential to this process, both in terms of the ease of use and of the overall output of valid data. Validation was done on samples of the final data set, ensuring no loss of precision or introduction of random error bias. It should be noted that if there are any errors in the data, they must be caught early, or else entire data sets and models can be contaminated.

Combinatorial, in silico Library Generation. For a catalyst scaffold, a series of substituent databases were created from which the individual in silico library was to be constructed in a combinatorial manner. The structures were generally drawn by hand from catalogs of commercially available regents (although ccheminfolib has preliminary code allowing for direct transcription from chemdraws), with structures modified to contain a label for the proper attachment point.

For each catalyst scaffold, a base scaffold core was created in silico. At each attachment point, a representative substituent group was attached, and the equilibrium conformer of the core was located using molecular mechanics (MMFF94, Spartan'2016(85)). The resulting conformer structure was then minimized at a higher level of theory (DFT, B3LYP/6-31G*) to give a starting global minimum for the core structure. From this minimized structure, an unsubstituted structure was extracted and labeled with sequential attachment points, with each attachment point corresponding to a specific substituent data-base defined for a given library.

Library compounds were constructed using marked attachment points on the core scaffold and a database of substituent groups. Then, ccheminfolib's in silico library constructor constructed a 3D graph of each compound and determined if any interlocking rings were present, and if so, corrected the problems. The structures in the libraries were minimized using MOE's MFF94x67 batch minimization, implemented as a script of SVL written and executed dynamically with a Python2 script. After minimization, a conformer library of each catalyst was obtained with Macromodel and all compounds were aligned with Maestro. After alignment, a common grid was calculated with ccheminfolib, and ASO descriptors were calculated (example code available via GitLab). Additionally, substituent-based electronic descriptors were also calculated (more detail on ASO and electronic descriptor calculation is available below). This general procedure was repeated with the reactants and products of each reaction and the descriptors concatenated to give reaction profiles. Additionally, NBO charges, orbital energies, and occupancies for the the two highest energy orbitals on the sulfur in the thiol were used as descriptors (calculated at MP2/6-311++G** using Gaussian09).

Descriptor Calculations. To describe the steric environment around a given structure, the strategy taken in these laboratories returned to using grid point type descriptors. However, instead of utilizing van der Waals potential energy values at grid point locations, this novel descriptor incorporates steric data from a population of conformers of a given compound. The calculation process is as follows, and as illustrated in FIG. 2A, demonstrated using a BINOL-based phosphoric acid derivative scaffold. (1) For each base compound within an in silico library, a set of conformers within a given energy window (generally 7-10 kcal/mol) is generated. (2) The full set of compounds and associated conformer libraries are aligned to a common core. (3) A spherical grid of points is then calculated to encompass the entire set of aligned compounds to a depth of 3 angstroms. (4) For each conformer, an indicator field is created by determining which grid point locations are determined to be within the van der Waals radius of an atom. Locations determined to be within atoms are given a value of 1; those outside are given a value of 0. (5) The Average Steric Occupancy of a given catalyst is calculated as the average of the indicator fields for each conformer of that catalyst. This gives a descriptor value of $0 \leq ASO \leq 1$ at each grid point. When compiled, the descriptor set acts both to describe the shape of the molecule, but weight that shape with how often the molecule occupies different regions of space. The process of calculating the ASO descriptor set is completed for every catalyst in the in silico library. Specifically, for the phosphoric acid library, Macromodel from Schrodinger Suit was used to calculate the conformer distribution. The calculation was done with the OPLS3 force field, with no solvent. Maximum interations was set to 2500 and the convergence threshold 0.05. The search method used was mixed torsional/Low-mode sampling with maximum number of steps set to 1000, 100 steps per rotatable bond specified, and the energy cutoff set to 7 kcal/mol. Redundant conformers were identified using a maximum atom deviation cutoff of 0.5 Å. All other options were left as defaults. It is worth noting that the energy window was selected simply to exclude chemically unreasonable structures—the relative energies of conformers are not used at any point in the process because of the unreliable accuracy of force field energies.

When visualized in 3D, it is apparent how the ASO captures the catalyst structure (FIG. 2B). Blue regions in FIG. 2B (toward the center) are higher-ASO areas, where most conformers of the given compound share this space. Green, yellow, and orange regions are areas of decreasing occupancy, where the catalyst only occupies that region of space in a fraction of the conformers of the catalyst.

The ASO descriptor can be used to visually compare the shapes and sizes of different compounds by plotting the descriptor values as bar charts. Shown in FIG. 2D is a comparison between 3,3'-diphenyl substituted BINOL-phosphoramide 1_iv and the much larger catalysts 182_iv. As can be seen in the plots, the ASO descriptor values for 182_iv are much more varied, and non-zero ASO values can be seen for much more of the available descriptor range, indicating that this catalyst is much larger and covers more of the space available to the catalyst. This type of comparative analysis shows that the descriptors are capturing the shape of the molecule as well as seeing a difference between catalysts of different size and constitution.

To capture the electrostatic effects of substituents on the compounds of interest, a separate set of descriptors was considered. Electrostatic MIF descriptors have underperformed in the applications tested in these laboratories, and these 3D MIF-based electrostatic descriptors do not incorporate conformation dependent information. Additionally, most descriptor calculation methods based on electrostatic field determinations fail to distinguish between through-bond and through-space effects. Although others have used 1D and 2D descriptors, such as Hammett parameters to describe such changes, the substituent libraries utilized in these laboratories are too diverse to have these parameters derived for them. To that end, a novel electrostatic parameter that correlates well with known 1D parameters has been devised.

Figure 10:
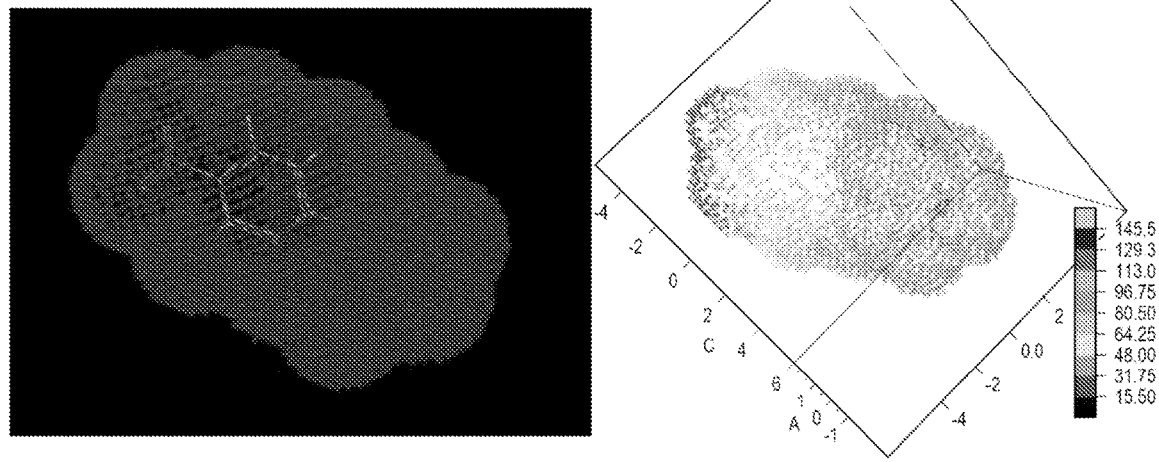
FIG. 10 is an example MIF calculated for 4-nitrobenzyltrimethylammonium cation.

This novel electrostatic parameter was calculated for individual substituents represented in the catalyst in silico library and is used to estimate the effect of the substituent's electronic effects on the core molecule. The calculation was performed by attaching the substituent group to a tetramethylammonium cation, generating a benzyl-trimethylammonium cation if the substituent is aryl, a homobenzyl-trimethylammonium cation if the substituent is benzyl, or an tetraalkylammonium ion if the substituent is alkyl. An electrostatic potential MIF is then calculated using NWCHEM(46) at the B3LYP/6-31G* level of theory, specifying a specific probe and range for the grid to give a single layer of grid points 0.025 Å apart. An example of the grid and calculated electrostatic potential for 4-nitrobenzyltrimethylammonium cation is shown in FIG. 10.

Figure 11:
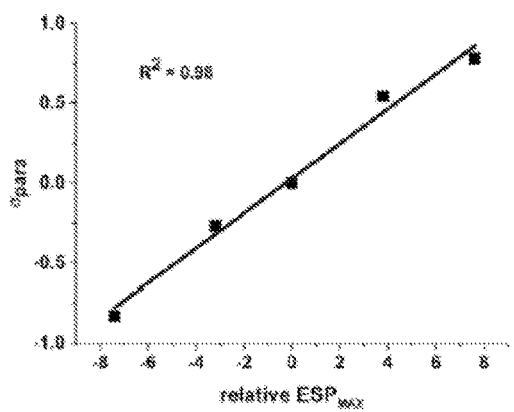
FIG. 11 illustrates test compounds to evaluate the correlation between ESPMAX and the Hammett $\sigma_{para}$ parameter, and linear correlation observed.

After the energies are calculated, the maximum and minimum energies calculated in the single layer MIF are saved, giving the Substituent ESP Minimum (ESPMIN) and Substituent ESP Maximum (ESPMAX) descriptors. The ESPMAX descriptors correlated well with known Hammett parameters, suggesting the descriptor was describing the electron-donating or withdrawing nature of the given substituents (FIG. 11).

Model Generation. All machine learning methods except deep neural networks were implemented with Python2 scripts using SciKitLearn, (47) a Python machine learning package. A collection of models was generated using a variety of feature selection methods with experimental ΔΔG as the observable. Prior to modeling, all data descriptors were scaled to a mean of zero and unit variance. A variety of feature selection or transform methods were screened (variance threshold method, mutual information, f-regression, and principle component analysis). For the feature selection methods, 100, 500, 1000, and 2000 features were selected. Additionally, using a percentile cutoff, the $10^{th}$, $25^{th}$, and $50^{th}$ percentiles were selected. Using principle component analysis, models were generated using 10, 20, 30, 50, and 100 principle components (64%, 78%, 84%, 89%, and 94% of variance, respectively). These methods were all performed separately on the scaled descriptor data (i.e. PCA and a feature selection method were never used together). The enantioselectivity data (expressed as the free energy differential between the diastereomeric transition structures leading to the different enantiomers) was highly skewed, so this data was transformed with the boxcox transformation using SciPy prior to model generation. Each set of preprocessed data (meaning one of the selection methods or PCA with the transformed or untransformed selectivity data) were then used to make a collection of models. Models generated include PLSn (n=2,4,6,8,10,14, 18 latent variables when n<number of principle components), Random Forest, LASSOCV, LASSOLARSCV, Elastic NetCV, RidgeCV, Kernal RidgeCV (kernel=rbf)(k=5), kNN, and Support Vector Machines with linear, rbf, and polynomial kernals ($2^{nd}$, $3^{rd}$ and $4^{th}$ order polynomials). Grid optimization of hyperparameters was performed (example code can be found on the GitLab site). For the first study, ten sets of 600 reactions were used to generate ten different models. For the sake of comparison, the descriptor data was preprocessed using mutual information regression, each time keeping the top 25% of features. Models compared were support vector machines with second order polynomial kernals. Different combinations of hyperparamemters were evaluated with the grid hyperparameter optimization methods in Sci-Kit learn (grid_param input as follows: "C": [0.001, 0.01, 0.1, 1, 10, 100, 1000, 10000], "gamma": [0.00001, 0.0001, 0.001, 0.01, 0.1, 1, 10, 100, 1000], "epsilon": [0.01, 0.1, 0.5, 1, 2, 4]). The results are summarized in FIG. 12, and the full results can be found in the supplement to "Prediction of higher-selectivity catalysts by computer-driven workflow and machine learning," by Zahrt et al. in Science, vol. 363, published on Jan. 18, 2019, in the file FIG. 4_ValidationData.xlsx, which is hereby incorporated by reference in its entirety.

Figures 12, 13:
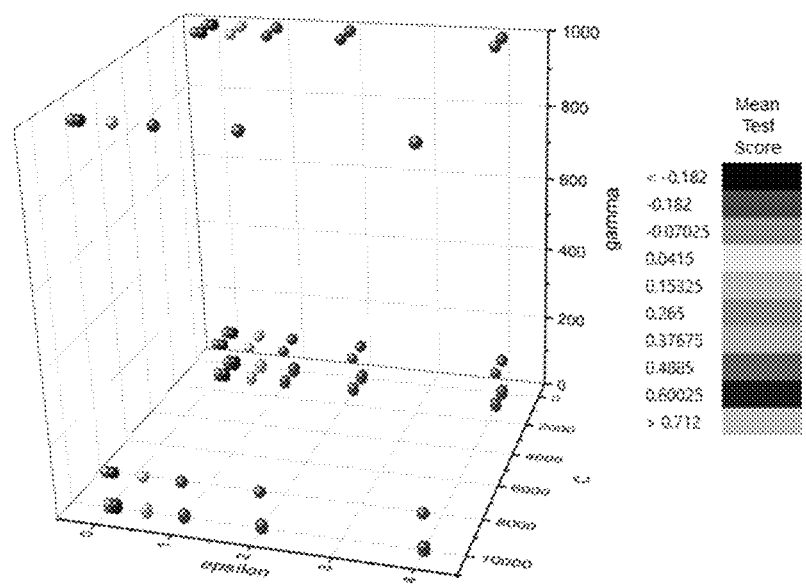
FIG. 12 is a visual summary of hyperparameter optimization.
FIG. 13 illustrates the division of data modeling with UTS.

For the second study, a pictoral representation of how the training data was separated is shown in FIG. 13. Here, the 24 UTS catalysts were used with 16 "train" substrate combinations. Then, the 9 substrate combinations left over were used with the UTS to evaluate the capability to predict new substrate combination outcomes, and the test set of catalysts was used with the 16 training substrates to evaluate the ability to predict new catalyst outcomes. To further challenge the transferability of the model, the 9 test substrate combinations were used with the test catalysts as a third external test set.

Figure 14:
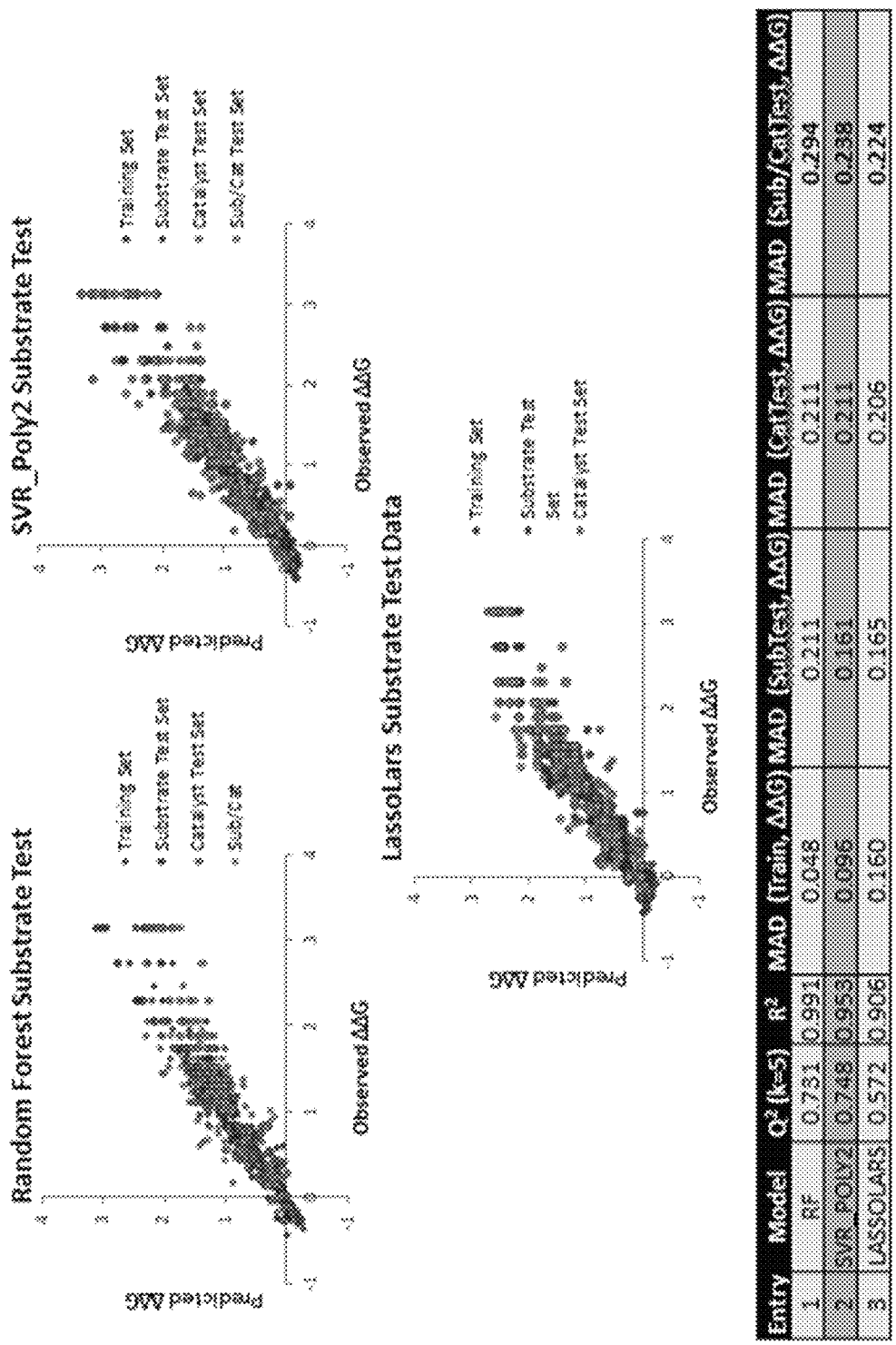
FIG. 14 is a graphical view illustrating the performance of interpolative models.

Hyperparameter optimization was performed with a five-fold train/validation split (e.g. in the case of the UTS data, the 384 "training reactions" were split—the three external test sets were not used at any time during model optimization). Models were evaluated via $q^2$, $R^2$, and mean absolute deviation (MAD) from an external test set (not used in hyperparameter optimization) of reactions. Three examples are given in FIG. 14. Each model used the transformed (boxcox) selectivity data and used the top 25% of features selected by mutual information regression. It is worth noting that SVR_poly2 (support vector regressor with second order polynomial kernel) was the only member of the best models accurately to predict the most selective test reactions.

For the third study FIG. 8, the training data was selected such that all reactions below 80% ee in Table 6 were used to train the model (718 reactions), and the remaining 357 reactions above 80% ee were withheld as an external test set. The eight high selectivity catalysts in FIG. 8B appeared in the training data as follows, cat (number of reactions in the training data): 52 (one), 11 (five), 53 (zero), 14 (seven), 54 (five), 12 (seven), 55 (seven), and 56 (five). It is noteworthy that despite the appearance of a single reaction of 52 in the training data, which is less selective than three of the five reactions with 11, it is still predicted to be the most selective catalyst.

Whereas SVR_poly2 qualitatively selected the correct relative selectivities, the models quantitatively under predicted these reactions. Using Keras(49) with the Theano backend, a python package that can facilitate deep learning, a deep feedforward network was generated. Grid based hyperparameter optimization was used with linear, relu, elu, and selu activation functions, 0.05, 0.1, and 0.2 dropouts on the layers, 4,40,400,4000 nodes per layer, and 0-6 hidden layers. Further, all optimizers available in keras were tested. The best network used the 'adam' optimizer, had a learning rate of 500, batch size of 32, three layers with 4, 40, and 40 nodes, respectively, and 0.0, 0.1, and 0.0 dropouts, respectively. Some networks with increased number of layers and either 40 or 400 nodes per layer also performed comparably, but the network with a smaller number of layers was selected. This method of hyperparameter optimization was extremely time intensive and it is strongly recommended that practitioners instead use a Bayesian optimization or random search optimization of hyperparameters. Attempts to use the former and use more modern deep learning methods are currently underway.

Control Experiments

Figure 7:
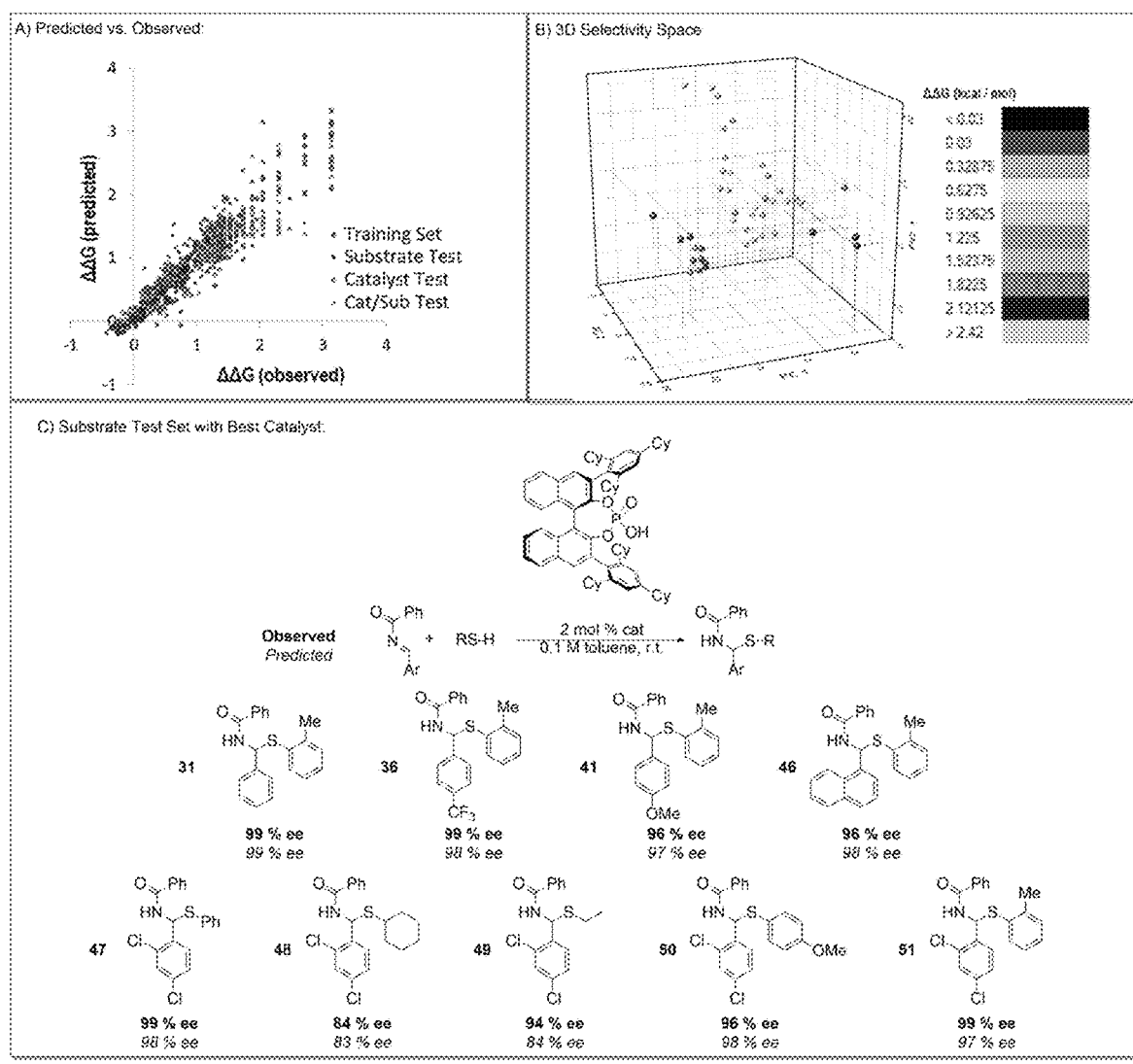
Figure 8:
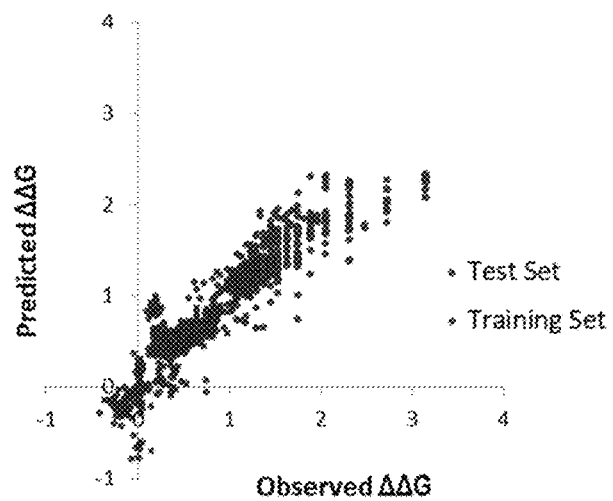
Figure 8:
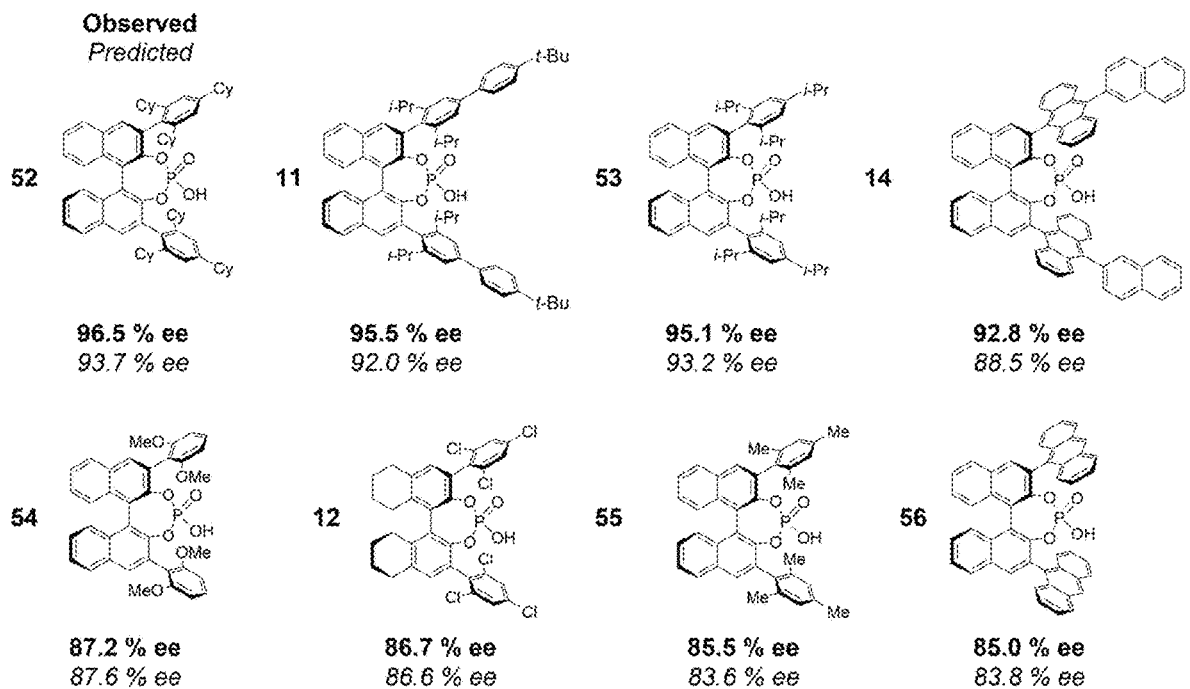

To further validate our chemical descriptors, control experiments for each of the studies in FIGS. 4, 7, and 8 were performed in which random features were used in place of our chemical descriptors. In each of these cases, the same protocol for sample division and modeling were used as in the original studies. The only difference is that random numbers, using a random number generator, were used rather than our chemical descriptors. For the study in FIG. 4, ten different divisions of train, validation, and test sets were selected randomly. The average values of the test sets were plotted against their experimental values, revealing the inability of the random descriptors to identify meaningful relations with respect to enantioselectivity. The MAD of the test set with random descriptors was found to be much greater than the MAD of the test set with chemical descriptors (0.53 kcal/mol vs. 0.15 kcal/mol, respectively). Further, the respective $q^2$ values also reflect the validity of the two datasets ($q^2=-0.17$ for random descriptors and $q^2=0.70$ or chemical descriptors). For the study in FIG. 7, similar results were observed. For the substrate test set, random descriptors gave a MAD value of 0.59 kcal/mol was calculated (for chemical descriptors MAD=0.161 kcal/mol). For the catalyst test set, a MAD value of 0.59 kcal/mol was calculated (for chemical descriptors MAD=0.211 kcal/mol). For the substrate/catalyst set, a MAD value of 0.68 was calculated (for chemical descriptors MAD=0.238 kcal/mol). This difference was also reflected in internal validation, wherein the $q^2$ for the random descriptors was −0.468 and the $q^2$ for chemical descriptors 0.748. For the study in FIG. 8, the randomized variables gave a MAD of ca. 0.54 kcal/mol for the test set.

Clauses

Clause 1. A compound of Formula (I) or Formula (II):

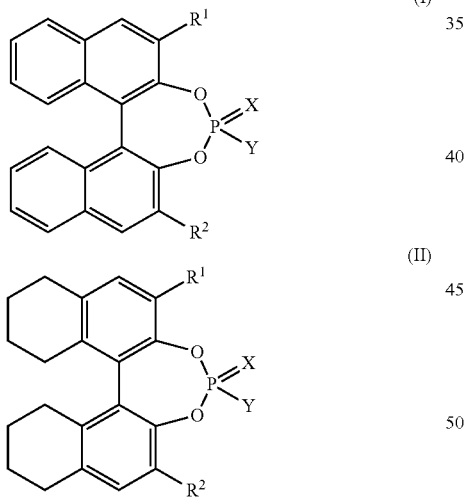

wherein:

X is O or S;

Y is OH, SH, or NHSO$_2$CF$_3$; and

R$^1$ and R$^2$ are independently selected from the group consisting of:
halogen;
unsubstituted phenyl;
C$_1$-C$_6$ alkyl, optionally substituted with phenyl, the phenyl being optionally substituted with 1-3 substituents independently selected from C$_1$-C$_6$ alkyl and C$_1$-C$_6$ haloalkyl;
phenyl substituted with 1-3 substituents independently selected from the group consisting of halogen, CN, SF$_5$, CH$_2$OCH$_3$, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, and C$_6$-C$_{10}$ aryl; and wherein each C$_1$-C$_6$ alkyl and C$_6$-C$_{10}$aryl may be unsubstituted or may be substituted with 1-3 substituents selected from the group consisting of C$_1$-C$_6$ alkyl, C$_1$-C$_6$ haloalkyl, and C$_1$-C$_6$ alkoxy;
C$_7$-C$_{16}$ aryl optionally substituted with 1-5 substituents selected from C$_1$-C$_6$ alkyl, C$_1$-C$_6$ haloalkyl, and C$_6$-C$_{14}$ aryl; and SiR$^3$R$^4$R$^5$, wherein R$^3$, R$^4$, and R$^5$, are each independently selected from phenyl and C$_1$-C$_6$ alkyl.

Clause 2. A compound of Formula (I) or Formula (II):

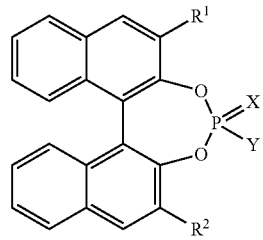

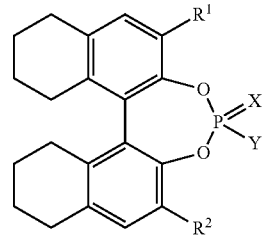

wherein:

X is O or S;

Y is OH, SH, or NHSO$_2$CF$_3$; and

R$^1$ and R$^2$ are independently selected from the group consisting of:
C$_1$-C$_6$ alkyl, optionally substituted with phenyl, the phenyl being optionally substituted with 1-3 substituents independently selected from C$_1$-C$_6$ alkyl and C$_1$-C$_6$ haloalkyl;
phenyl substituted with 1-3 substituents independently selected from the group consisting of halogen, CN, SF$_5$, CH$_2$OCH$_3$, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, and C$_6$-C$_{10}$ aryl; and wherein each C$_1$-C$_6$ alkyl and C$_6$-C$_{10}$ aryl may be unsubstituted or may be substituted with 1-3 substituents selected from the group consisting of C$_1$-C$_6$ alkyl, C$_1$-C$_6$ haloalkyl, and C$_1$-C$_6$ alkoxy;
C$_7$-C$_{16}$ aryl optionally substituted with 1-5 substituents selected from C$_1$-C$_6$ alkyl, C$_1$-C$_6$ haloalkyl, and C$_6$-C$_{14}$ aryl; and SiR$^3$R$^4$R$^5$, wherein R$^3$, R$^4$, and R$^5$, are each independently selected from phenyl and C$_1$-C$_6$ alkyl.

Clause 3. The compound of clause 1 or 2, wherein $R^1=R^2$.

Clause 4. The compound of any of clauses 1-3, wherein X=O and Y=OH.

Clause 5. The compound of any of clauses 1-4, wherein the compound is of Formula (II), and wherein: $R^1$ and $R^2$ are each selected from the group consisting of: $C_1$-$C_6$ alkyl, optionally substituted with phenyl substituted with 1-3 substituents independently selected from $C_1$-$C_6$ alkyl and $C_1$-$C_6$ haloalkyl; phenyl substituted with 1-3 substituents independently selected from the group consisting of halogen, $C_1$-$C_6$ haloalkyl, $C_1$-$C_6$ alkoxy, $CH_2OCH_3$, $C_3$-$C_6$ cycloalkyl, and $C_6$-$C_{10}$ aryl substituted with 1-3 substituents selected from the group consisting of $C_1$-$C_6$ alkyl, $C_1$-$C_6$ haloalkyl, and $C_1$-$C_6$ alkoxy; $SiR^3R^4R^5$, wherein $R^3$, $R^4$, and $R^5$, are each independently selected from 4 tert-butylphenyl and phenyl.

Clause 6. The compound of any of clauses 1-5, wherein $R^1$ and $R^2$ are selected from ethyl and —$CH_2$-Ph($CF_3$)$_2$.

Clause 7. The compound of any of clauses 1-5, wherein $R^1$ and $R^2$ are phenyl substituted with 1-3 substituents independently selected from the group consisting of Cl, $CF_3$, $OCH_3$, cyclohexane, napthyl, and phenyl substituted with 1-3 methyl groups.

Clause 8. The compound of any of clauses 1-4, wherein the compound is of Formula (I), and wherein $R^1$ and $R^2$ are each selected from the group consisting of: phenyl substituted with 1-3 substituents independently selected from the group consisting of halogen, CN, $SF_5$, $C_1$-$C_6$ alkyl, $C_1$-$C_6$ haloalkyl, $C_1$-$C_6$ haloalkoxy, $C_1$-$C_6$ alkoxy, and $C_6$-$C_{10}$ aryl; wherein each $C_6$-$C_{10}$ aryl may be unsubstituted or may be substituted with 1-3 substituents selected from the group consisting of $C_1$-$C_6$ alkyl, $C_1$-$C_6$ haloalkyl, and $C_1$-$C_6$ alkoxy; $C_7$-$C_{16}$ aryl optionally substituted with $C_6$-$C_{14}$ aryl; and $SiR^3R^4R^5$, wherein $R^3$, $R^4$, and $R^5$ are each independently selected from phenyl and methyl.

Clause 9. The compound of any of clauses 1-4 and 8, wherein $R^1$ and $R^2$ are each unsubstituted $C_{14}$ aryl, $C_{14}$ aryl substituted with $C_{10}$ aryl, or unsubstituted $C_{16}$ aryl.

Clause 10. The compound of any of clauses 1-4 and 8, wherein $R^1$ and $R^2$ are each phenyl substituted with 1-3 substituents independently selected from the group consisting of $CH_3$, F, $CF_3$, $OCF_3$, $C_1$-$C_6$ haloalkyl, $OCH_3$, $CH_2OCH_3$, isopropyl, naphthyl, and phenyl substituted with 1-3 substituents selected from the group consisting of $CF_3$, $OCH_3$, $OCH(CH_3)_2$, $CH_2OCH_3$, and tert-butyl.

Clause 11: The compound of any of clauses 1-10, selected from the group consisting of:

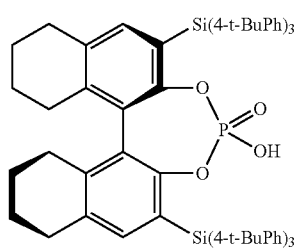

2

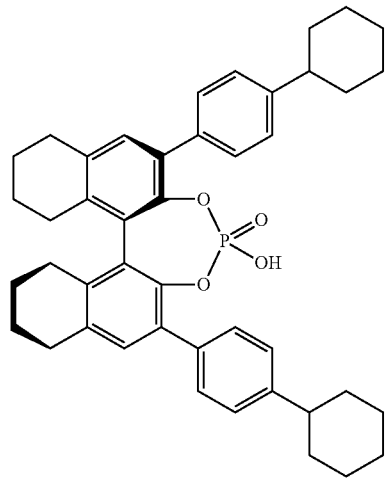

3

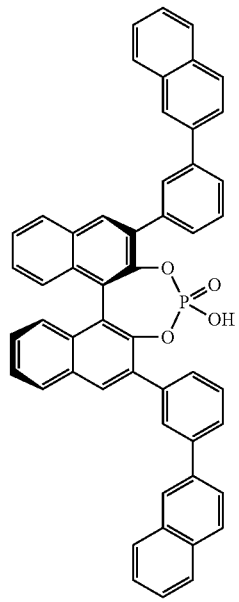

4

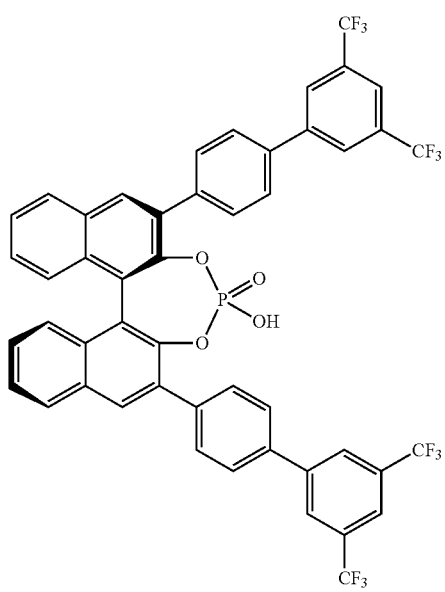

5

221
-continued
6
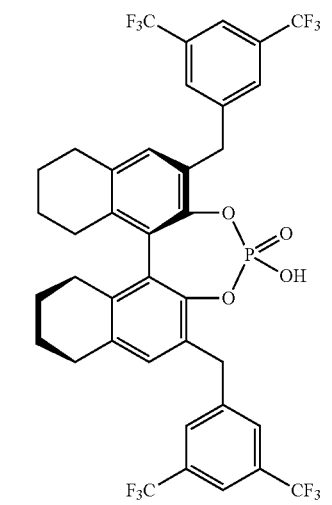
7
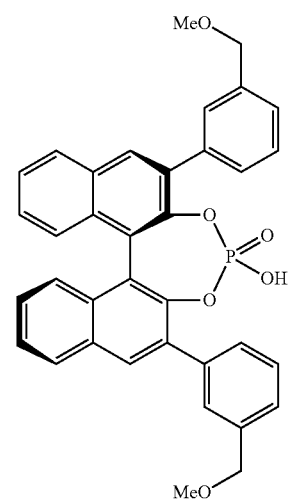
8
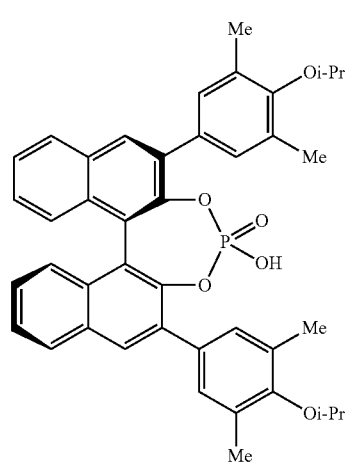
222
-continued
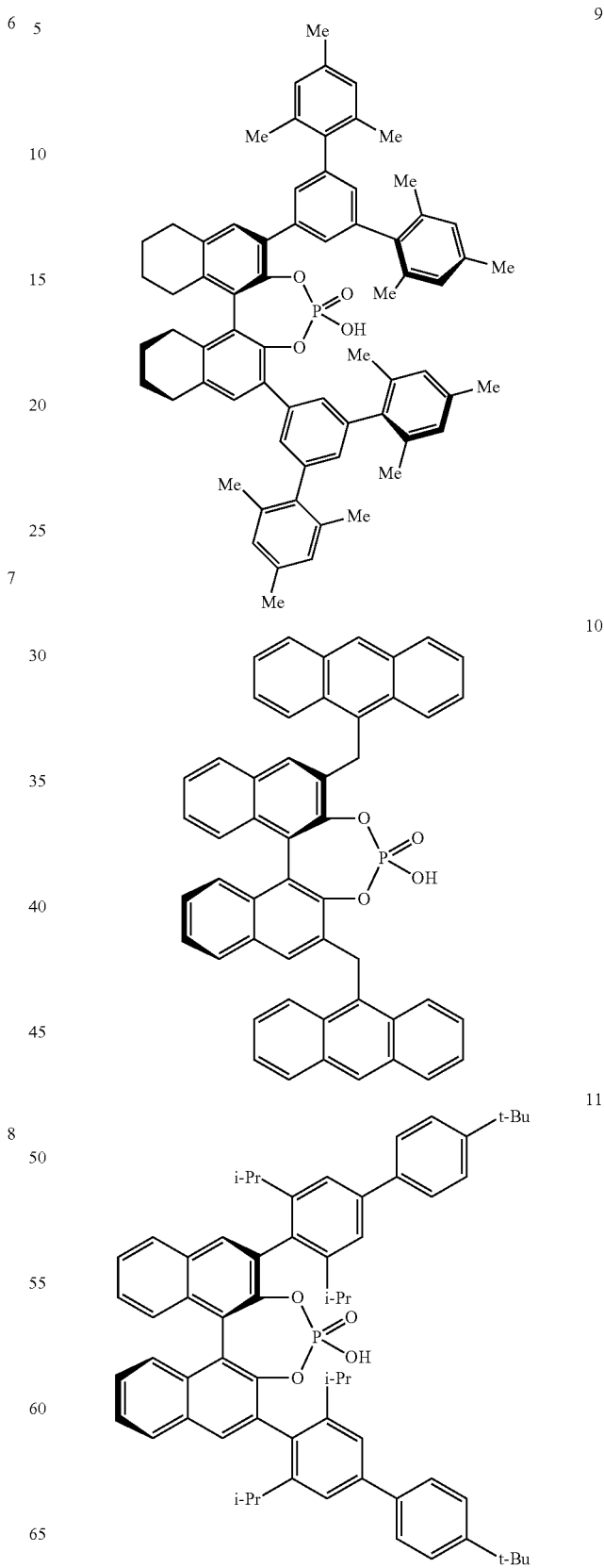

223
-continued
12
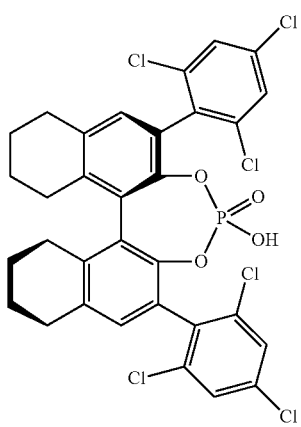
13
14
224
-continued
15
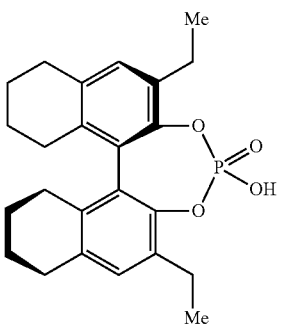
16
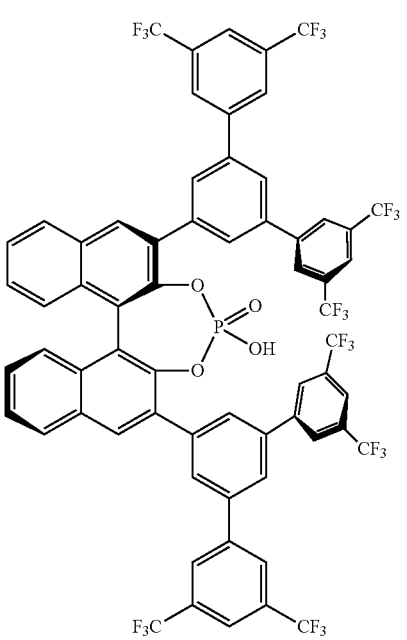
17
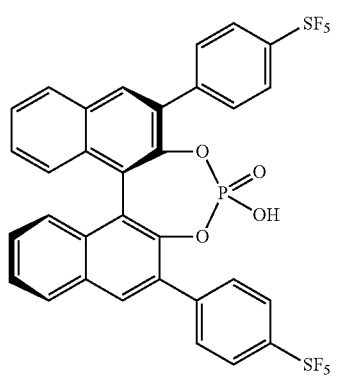

225
-continued
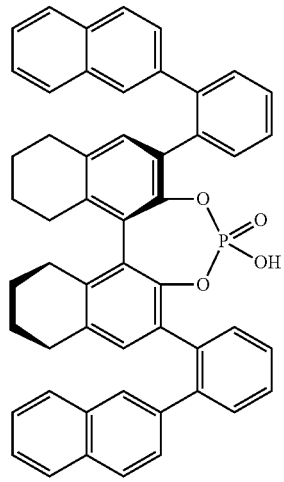
18
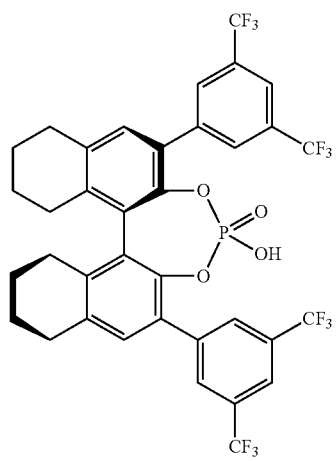
19
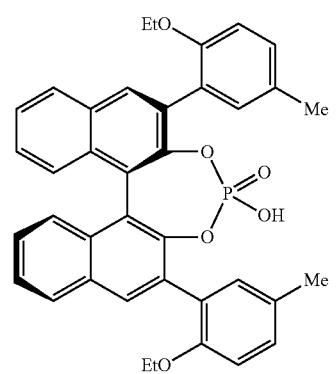
20
226
-continued
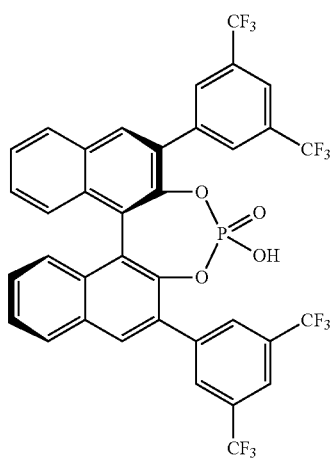
21
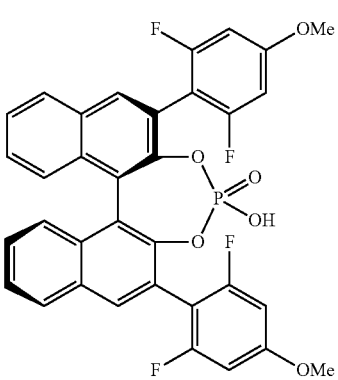
22
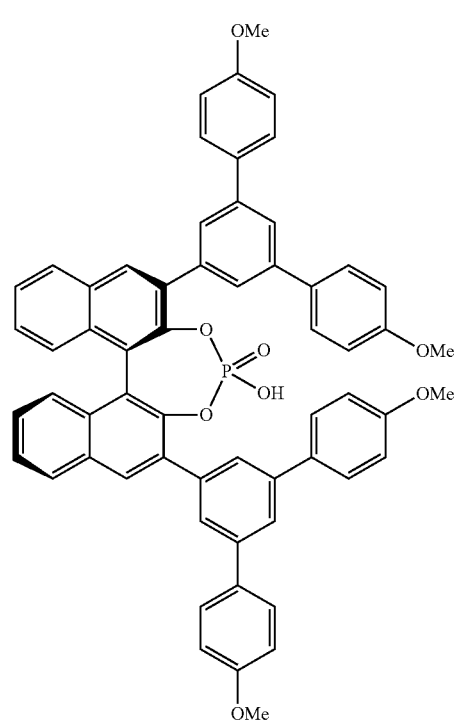
23

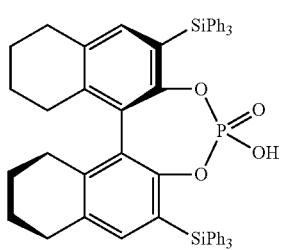

24

Clause 12. A kit comprising a compound of any of clauses 1-11.

Clause 13. The kit of clause 12, comprising at least two compounds of Formula (I) or Formula (II).

Clause 14. The kit of any of clauses 12-13, comprising at least three compounds of Formula (I) or Formula (II).

Clause 15. A kit comprising at least two compounds of clause 11.

Clause 16. A kit comprising at least three compounds of clause 11.

Clause 17. A kit of any of clauses 11-15, for use as a training set for a catalytic algorithm.

Clause 18. The compound of any of clauses 1-10, selected from the group consisting of:

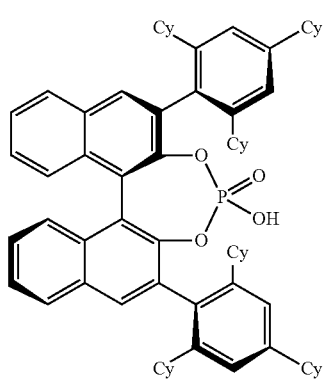

52

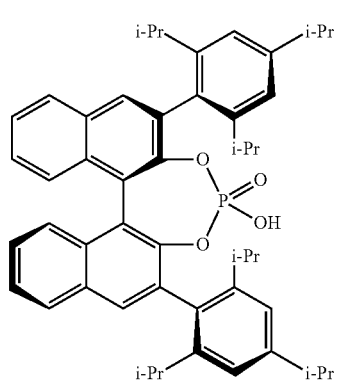

53

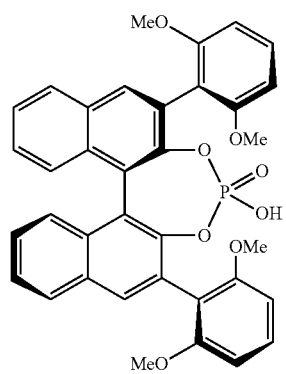

54

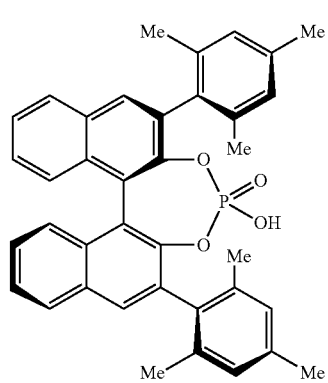

55

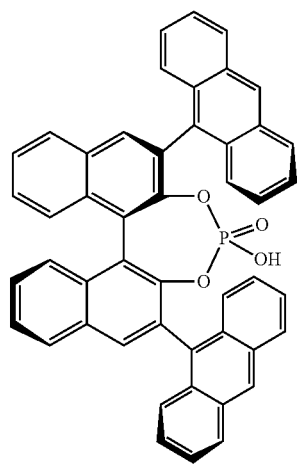

56

229
-continued
57
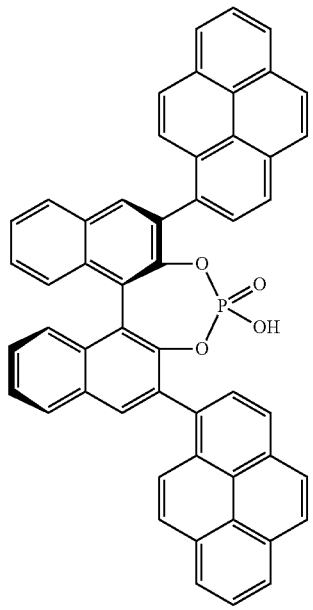
58
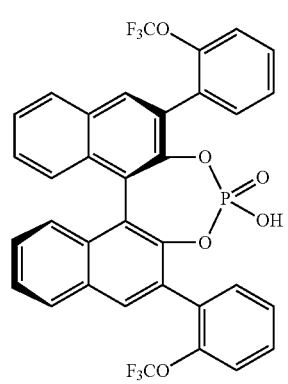
59
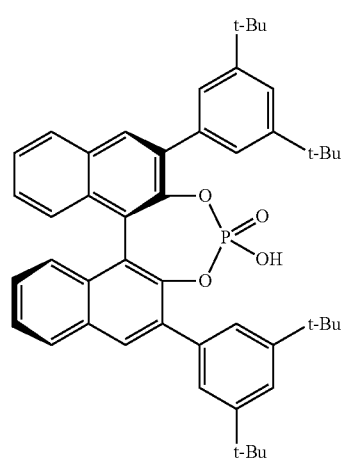
230
-continued
60
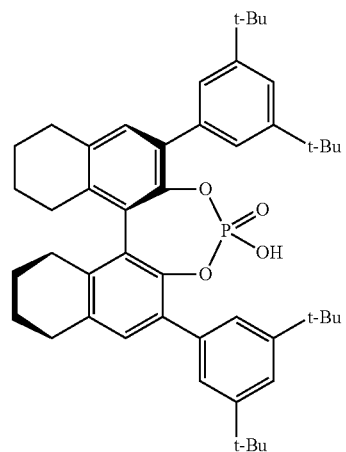
61
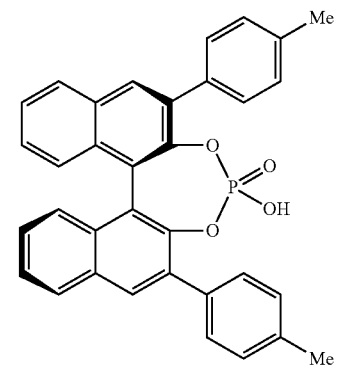
62
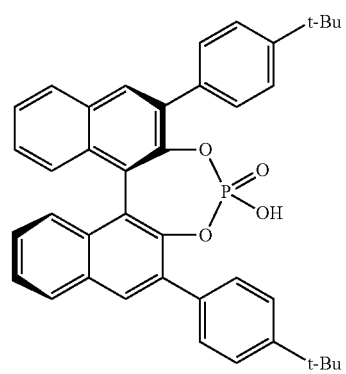

231
-continued
232
-continued
63
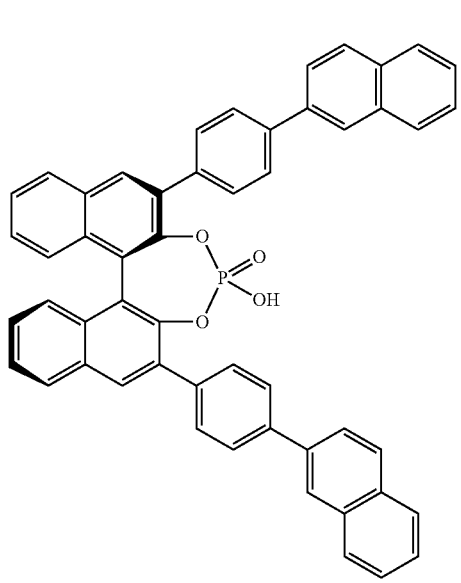
64
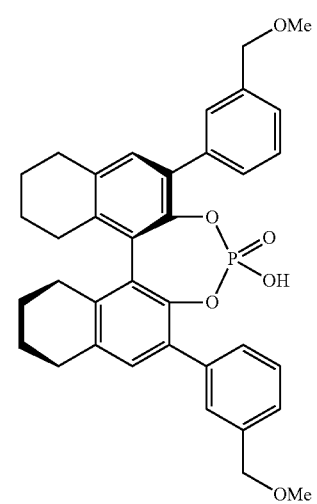
65
66
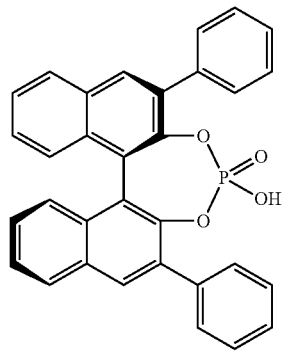
67
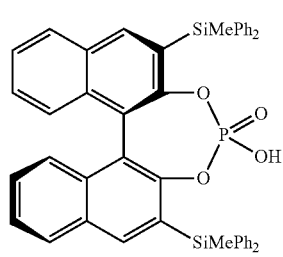
68
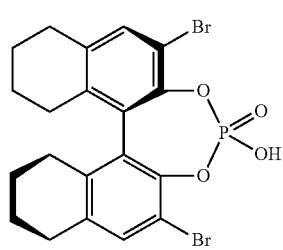
69
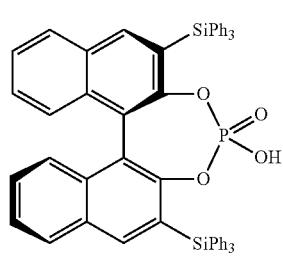

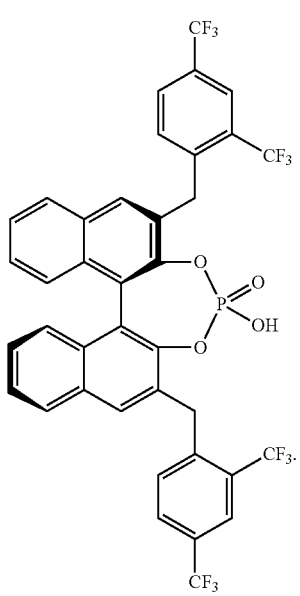

Clause 1D. A method including: accessing a library including chemical structures; via a model, determining a predicted behavior for a chemical metric for each of the chemical structures based on a level of a descriptor; selecting a sample of the chemical structures; characterizing each chemical structure of the sample to determine a measured behavior for the chemical metric; determining a difference between the predicted behavior and the measured behavior; and based on the difference, adjusting the model.

Clause 2D. The method of clause 1D, where the descriptor includes a descriptor characterizing a three-dimensional spatial distribution for a first one of the chemical structures.

Clause 3D. The method of either of clauses 1D or 2D, where the descriptor includes a descriptor generated based on an analysis of one or more conformers for a first one of the chemical structures.

Clause 4D. The method of any of clauses 1D-3D, where the descriptor includes a descriptor selected because: it is rapidly calculable for the chemical structures; it reflects three-dimensional information regarding the chemical structures; it is general for a scaffold used in the library; and captures subtle features responsible for the behavior of the chemical structures with regard to the chemical metric.

Clause 5D. The method of any of clauses 1D-4D, where the chemical metric includes catalyst selectivity.

Clause 6D. The method of any of clauses 1D-5D, where the chemical structures include a chemical class with differing substituents at specific structural locations.

Clause 7D. The method of clause 6D, where the chemical class includes Brønsted acid catalysts.

Clause 8D. The method of either of clauses 6D or 7D, where the chemical class includes chiral phosphoric acid catalysts.

Clause 9D. The method of any of clauses 1D-8D, where the library includes an in silico library.

Clause 10D. The method of any of clauses 1D-9D, where the descriptor includes a descriptor derived from a molecular interaction field.

Clause 11D. The method of any of clauses 1D-10D, where the descriptor includes a zero-dimensional, one-dimensional, two-dimensional, three-dimensional, or four-dimensional descriptor, where the dimensionality of the descriptor is determined by the dimensionality of the information used to derive the descriptor.

Clause 12D. The method of any of clauses 1D-11D, where the descriptor defines a dimension of a multi-dimensional descriptor space.

Clause 13D. The method of clause 12D, where the chemical structures are positioned within the descriptor space based on the predicted behavior of the chemical structures.

Clause 14D. The method of clause 13D, where the sample is selected from among the chemical structures to be distributed within the descriptor space.

Clause 15D. The method of any of clauses 1D-14D, where the sample is selected using a Kennard-Stone algorithm; or additionally where prior to selection using the Kennard-Stone selection, the dimensionality of the descriptor space is reduced by analyzing vector components of the space and selecting the K top-ranked components (e.g., judged from an informational loss analysis), where K is an integer less than the dimensionality of the descriptor space.

Clause 16D. The method of any of clauses 1D-15D, where the model includes a support vector machine model, a deep neural network, or both.

Clause 17D. The method of any of clauses 1D-16D, where the model includes a regression model where the chemical structures are mapped into a high-dimensional space.

Clause 18D. The method clause 17D, where the chemical structures are mapped on to a multidimensional plane within the high-dimensional space, the multidimensional plane providing larger distances between the mapped chemical structures than other mapped planes.

Clause 19D. The method of any of clauses 1D-18D, where the features and behavioral responses of the chemical structures are represented as a network of interconnected nodes where the nodes are activated in response to input of the chemical structures, where differing aspects of the chemical structures activate differing nodes.

Clause 20D. A method including: determining a chemical descriptor by analyzing the a population of conformers for a chemical structure versus a Van der Waals radius for the chemical structure.

Clause 21D. The method of clause 20D, where the descriptor includes an average steric occupancy for the chemical structure.

Clause 22D. A descriptor resulting from implementing the method of either of clauses 20D or 21D.

Clause 23D. A method including: determining a chemical descriptor by estimating an electrical effects of a substituent on a core molecule.

Clause 24D. The method of clause 23D, where estimating the effect includes calculating an electrostatic potential MIF (molecular interaction field).

Clause 25D. The method of clause 24D, where estimating the MIF include calculating the MIF using a single layer of grid points with a predetermined spacing.

Clause 26D. The method of clause 25D, where the spacing includes 0.025 angstroms.

Clause 27D. The method of any of clauses 23D-26D, where estimating the electrical effects of the substituent includes simulating attachment of the substituent group to a cation.

Clause 28D. The method of clause 27D, where the cation includes a tetramethylammonium cation.

Clause 29D. A descriptor resulting from implementing the method of any of clauses 23D-27D.

Clause 30D. A method including: selecting a sample from a library of chemical structures using a selection algorithm, the chemical structures characterized by a descriptor; providing physical specimens of the sample; and responsive to measured data obtained by interacting the physical specimens with a target system, determining predictive data describing interaction of the target system with a chemical structure in the library and not within the sample.

Clause 31D. The method of clause 30D, where the descriptor defines a dimension of a multi-dimensional descriptor space.

Clause 32D. The method of clause 31D, where the chemical structures are positioned within the descriptor space based on predicted behavior of the chemical structures.

Clause 33D. The method of clause 32D, where the sample is selected from among the chemical structures to be distributed within the descriptor space.

Clause 34D. The method of any of clauses 30D-33D, where the sample is selected using a Kennard-Stone algorithm; or additionally where prior to selection using the Kennard-Stone selection, the dimensionality of the descriptor space is reduced by analyzing vector components of the space and selecting the K top-ranked components (e.g., judged from an informational loss analysis), where K is an integer less than the dimensionality of the descriptor space.

Clause 35D. The method of any of clauses 30D-33D, where the descriptor includes a descriptor derived from a molecular interaction field.

Clause 36D. The method of any of clauses 30D-33D, where the descriptor includes a zero-dimensional, one-dimensional, two-dimensional, three-dimensional, or four-dimensional descriptor, where the dimensionality of the descriptor is determined by the dimensionality of the information used to derive the descriptor.

Clause 37D. The method of any of clauses 30D-33D, where the descriptor includes a descriptor characterizing a three-dimensional spatial distribution for a first one of the chemical structures.

Clause 38D. The method of any of clauses 30D-33D, where the descriptor includes a descriptor generated based on an analysis of one or more conformers for a first one of the chemical structures.

Clause 39D. The method of any of clauses 30D-33D, where the descriptor includes the descriptor of either of clause 22D or 29D.

Clause 40D. A system including circuitry configured to implement any of the methods of clauses 1D-21 D, 23D-28D, or 30-39D.

Clause 41D. A product including: machine-readable media other than a transitory signal; and instructions stored on the machine-readable media, the instructions configured to, when executed, cause a machine to implement any of the methods of clauses 1D-21D, 23D-28D, or 30-39D.

Clause A1 In an example, a method includes: accessing a library including chemical structures; at processing circuitry: determining a respective occupancy descriptor for each of the chemical structures, the respective occupancy descriptor based on a respective conformer population versus respective heteroatom Van der Waals radii for each of the chemical structures; via a model, determining a predicted behavior for a chemical metric for each of the chemical structures based on their respective occupancy descriptors; selecting a sample of the chemical structures; characterizing each chemical structure of the sample to determine a measured behavior for the chemical metric; determining a difference between the predicted behavior and the measured behavior; and based on the difference, adjusting the model.

Clause A2 The method of any of the preceding examples, where, for each of the chemical structures, the respective heteroatom Van der Waals radii includes a heteroatom Van der Waals radii around heteroatoms of an individual conformer of the respective conformer population.

Clause A3 The method of any of the preceding examples, where, determining a respective occupancy descriptor for each of the chemical structures includes: setting up grid points; for each individual conformer of the respective conformer population: when an individual grid point is within at least one of the heteroatom Van der Waals radii around the heteroatoms for the individual conformer of the respective conformer population, assigning an occupied value to the individual grid point for the individual conformer; and when an individual grid point is outside heteroatom Van der Waals radii for heteroatoms of the individual conformer of the respective conformer population, assigning an unoccupied value to the individual grid point for the individual conformer.

Clause A4 The method of any of the preceding examples, where, determining a respective occupancy descriptor for each of the chemical structures further includes averaging over values assigned to each of the grid points for each of the individual conformers of the respective conformer population.

Clause B1 In an example, a method includes: accessing a library including chemical structures; at processing circuitry: determining a respective occupancy descriptor for each of the chemical structures, the respective occupancy descriptor based on a respective conformer population versus respective Van der Waals radii for each of the chemical structures; via a model, determining a predicted behavior for a chemical metric for each of the chemical structures based on their respective occupancy descriptors; selecting a sample of the chemical structures; characterizing each chemical structure of the sample to determine a measured behavior for the chemical metric; determining a difference between the predicted behavior and the measured behavior; and based on the difference, adjusting the model.

Clause B2 The method of any of the preceding examples, where, for each of the chemical structures, the respective Van der Waals radii includes a Van der Waals radii around atoms of an individual conformer of the respective conformer population.

Clause B3 The method of any of the preceding examples, where, determining a respective occupancy descriptor for each of the chemical structures includes: setting up grid points; for each individual conformer of the respective conformer population: when an individual grid point is within at least one of the Van der Waals radii around the atoms for the individual conformer of the respective conformer population, assigning an occupied value to the individual grid point for the individual conformer; and when an individual grid point is outside Van der Waals radii for atoms of the individual conformer of the respective conformer population, assigning an unoccupied value to the individual grid point for the individual conformer.

Clause B4 The method of any of the preceding examples, where, determining a respective occupancy descriptor for each of the chemical structures further includes averaging over values assigned to each of the grid points for each of the individual conformers of the respective conformer population.

Clause B5 The method of any of the preceding examples, where assigned occupancy values are weighted according to the atom charge of the atom or atoms within the Van der Waals radius the grid point resides.

Clause C1 In an example, a method includes: accessing a library including chemical structures; at processing circuitry: determining a respective atomic-charge-weighted occupancy descriptor for each of the chemical structures, the respective atomic-charge-weighted occupancy descriptor based on a respective conformer population versus respective Van der Waals radii for each of the chemical structures; via a model, determining a predicted behavior for a chemical metric for each of the chemical structures based on their respective atomic-charge-weighted occupancy descriptors; selecting a sample of the chemical structures; characterizing each chemical structure of the sample to determine a measured behavior for the chemical metric; determining a difference between the predicted behavior and the measured behavior; and based on the difference, adjusting the model.

Clause J1 In an example, a method includes: accessing a library including chemical structures; via a model, determining a predicted behavior for a chemical metric for each of the chemical structures based on a level of a descriptor; selecting a sample of the chemical structures; characterizing each chemical structure of the sample to determine a measured behavior for the chemical metric; determining a difference between the predicted behavior and the measured behavior; and based on the difference, adjusting the model.

Clause J2 The method of any of the preceding examples, where the descriptor includes a descriptor characterizing a three-dimensional spatial distribution for a first one of the chemical structures.

Clause J3 The method of any of the preceding examples, where the descriptor includes a descriptor generated based on an analysis of one or more conformers for a first one of the chemical structures.

Clause J4 The method of any of the preceding examples, where the descriptor includes a descriptor selected because: it is rapidly calculable for the chemical structures; it reflects three-dimensional information regarding the chemical structures; it is general for a scaffold used in the library; and captures subtle features responsible for the behavior of the chemical structures with regard to the chemical metric.

Clause J5 The method of any of the preceding examples, where the chemical metric includes catalyst selectivity.

Clause J6 The method of any of the preceding examples, where the chemical structures include a chemical class with differing substituents at specific structural locations.

Clause J7 The method of any of the preceding examples, where the chemical class includes Brønsted acid catalysts.

Clause J8 The method of any of the preceding examples, where the chemical class includes chiral phosphoric acid catalysts.

Clause J9 The method of any of the preceding examples, where the library includes an in silico library.

Clause J10 The method of any of the preceding examples, where the descriptor includes a descriptor derived from a molecular indicator field.

Clause J11 The method of any of the preceding examples, where the descriptor includes a zero-dimensional, one-dimensional, two-dimensional, three-dimensional, or four-dimensional descriptor, where the dimensionality of the descriptor is determined by the dimensionality of the information used to derive the descriptor.

Clause J12 The method of any of the preceding examples, where the descriptor defines a dimension of a multi-dimensional descriptor space.

Clause J13 The method of any of the preceding examples, where the chemical structures are positioned within the descriptor space based on the predicted behavior of the chemical structures.

Clause J14 The method of any of the preceding examples, where the sample is selected from among the chemical structures to be distributed within the descriptor space.

Clause J15 The method of any of the preceding examples, where the sample is selected using a Kennard-Stone algorithm; or additionally where prior to selection using the Kennard-Stone selection, the dimensionality of the descriptor space is reduced by analyzing vector components of the space and selecting the K top-ranked components (e.g., judged from an informational loss analysis), where K is an integer less than the dimensionality of the descriptor space.

Clause J16 The method of any of the preceding examples, where the model includes a support vector machine model, a deep neural network, or both.

Clause J17 The method of any of the preceding examples, where the model includes a regression model where the chemical structures are mapped into a high-dimensional space.

Clause J18 The method of any of the preceding examples, where the chemical structures are mapped on to a multidimensional plane within the high-dimensional space, the multidimensional plane providing larger distances between the mapped chemical structures than other mapped planes.

Clause J19 The method of any of the preceding examples, where the features and behavioral responses of the chemical structures are represented as a network of interconnected nodes where the nodes are activated in response to input of the chemical structures, where differing aspects of the chemical structures activate differing nodes.

Clause E1 In an example, a method includes: determining a chemical descriptor by analyzing a population of conformers for a chemical structure versus a Van der Waals radius for the chemical structure.

Clause E2 The method of any of the preceding examples, where the descriptor includes an average steric occupancy for the chemical structure.

Clause E3 An occupancy descriptor resulting from implementing the method of any of the preceding examples.

Clause F1 In an example, a method includes: determining a chemical descriptor by estimating an electrical effects of a substituent on a core molecule.

Clause F2 The method of any of the preceding examples, where estimating the effect includes calculating an electrostatic potential MIF (molecular interaction field).

Clause F3 The method of any of the preceding examples, where estimating the MIF include calculating the MIF using a single layer of grid points with a predetermined spacing.

Clause F4 The method of any of the preceding examples, where the spacing includes 0.025 angstroms or 1 angstrom.

Clause F5 The method of any of the preceding examples, where estimating the electrical effects of the substituent includes simulating attachment of the substituent group to a cation.

Clause F6 The method of any of the preceding examples, where the cation includes a tetramethylammonium cation.

Clause F7 An electrical descriptor resulting from implementing the method of any of the preceding examples.

Clause G1 In an example, a method includes: selecting a sample from a library of chemical structures using a selection algorithm, the chemical structures characterized by a descriptor; providing physical specimens of the sample; and responsive to measured data obtained by interacting the physical specimens with a target system, determining predictive data describing interaction of the target system with a chemical structure in the library and not within the sample.

Clause G2 The method of any of the preceding examples, where the descriptor defines a dimension of a multi-dimensional descriptor space.

Clause G3 The method of any of the preceding examples, where the chemical structures are positioned within the descriptor space based on the respective descriptors for the chemical structures.

Clause G4 The method of any of the preceding examples, where the sample is selected from among the chemical structures to be distributed within the descriptor space.

Clause G5 The method of any of the preceding examples, where the sample is selected using a Kennard-Stone algorithm; or additionally where prior to selection using the Kennard-Stone selection, the dimensionality of the descriptor space is reduced by analyzing vector components of the space and selecting the K top-ranked components (e.g., judged from an informational loss analysis), where K is an integer less than the dimensionality of the descriptor space.

Clause G6 The method of any of the preceding examples, where the descriptor includes a descriptor derived from a molecular interaction field.

Clause G7 The method of any of the preceding examples, where the descriptor includes a zero-dimensional, one-dimensional, two-dimensional, three-dimensional, or four-dimensional descriptor, where the dimensionality of the descriptor is determined by the dimensionality of the information used to derive the descriptor.

Clause G8 The method of any of the preceding examples, where the descriptor includes a descriptor characterizing a three-dimensional spatial distribution for a first one of the chemical structures.

Clause G9 The method of any of the preceding examples, where the descriptor includes a descriptor generated based on an analysis of one or more conformers for a first one of the chemical structures.

Clause G10 The method of any of the preceding examples, where the descriptor includes the descriptor of either of the example from clause E3 or the example from clause F7.

Clause H1 in an example, a system includes circuitry configured to implement any of the methods of the preceding examples.

Clause 11 In an example, a product includes: machine-readable media other than a transitory signal; and instructions stored on the machine-readable media, the instructions configured to, when executed, cause a machine to implement any of the methods of the preceding examples.

What is claimed is:

1. A method including:
   accessing a library including chemical structures;
   at processing circuitry:
   determining a respective occupancy descriptor for each of the chemical structures, the respective occupancy descriptor based on a respective conformer population versus respective Van der Waals radii for each of the chemical structures;
   via a model, determining a predicted behavior for a chemical metric for each of the chemical structures based on their respective occupancy descriptors;
   selecting a sample of the chemical structures;
   characterizing each chemical structure of the sample to determine a measured behavior for the chemical metric;
   determining a difference between the predicted behavior and the measured behavior; and
   based on the difference, adjusting the model.

2. The method of claim 1, where, for each of the chemical structures, the respective Van der Waals radii includes a Van der Waals radii around atoms of an individual conformer of the respective conformer population.

3. The method of claim 2, where, determining a respective occupancy descriptor for each of the chemical structures includes:
   setting up grid points;
   for each individual conformer of the respective conformer population:
   when an individual grid point is within at least one of the Van der Waals radii around the atoms for the individual conformer of the respective conformer population, assigning an occupied value to the individual grid point for the individual conformer; and
   when an individual grid point is outside Van der Waals radii for atoms of the individual conformer of the respective conformer population, assigning an unoccupied value to the individual grid point for the individual conformer.

4. The method of claim 3, where, determining a respective occupancy descriptor for each of the chemical structures further includes averaging over values assigned to each of the grid points for the individual conformer of the respective conformer population.

5. The method of claim 1, where the chemical metric includes catalyst selectivity.

6. The method of claim 1, where the chemical structures include a chemical class with differing substituents at specific structural locations.

7. The method of claim 6, where the chemical class includes Brønsted acid catalysts.

8. The method of claim 6, where the chemical class includes chiral phosphoric acid catalysts.

9. The method of claim 1, where the library includes an in silico library.

* * * * *

UNITED STATES PATENT AND TRADEMARK OFFICE
CERTIFICATE OF CORRECTION

PATENT NO. : 11,664,093 B2  
APPLICATION NO. : 16/551007  
DATED : May 30, 2023  
INVENTOR(S) : Scott E. Denmark et al.

Page 1 of 3

It is certified that error appears in the above-identified patent and that said Letters Patent is hereby corrected as shown below:

In the Specification

Column 7, Line 67, delete "OD" and insert in its place --0D--.

Column 24, between Lines 50-65, delete compound "56" and insert in its place:

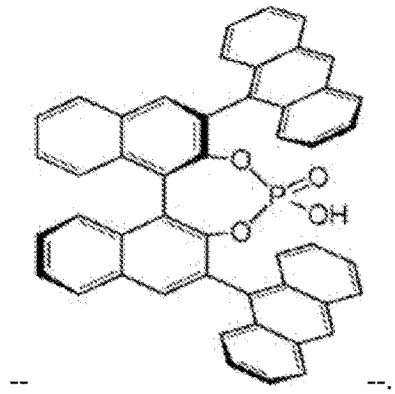

-- --.

Column 30, Line 46, delete "4-A" and insert in its place --4-Å--.

Column 32, Line 39, delete "MG" and insert in its place --ΔΔG--.

Column 37, Line 12, delete "-A6-" and insert in its place -- -λ6- --.

Column 37, Line 27, delete "-ciiol," and insert in its place -- -diol,--.

Column 40, Line 58, delete "THE" and insert in its place --THF--.

Column 44, Line 34, delete "icelisopropyl" and insert in its place --ice/isopropyl--.

Column 50, Line 17, delete "THE" and insert in its place --THF--.

Signed and Sealed this  
Eleventh Day of July, 2023

Katherine Kelly Vidal  
*Director of the United States Patent and Trademark Office*

CERTIFICATE OF CORRECTION (continued)
U.S. Pat. No. 11,664,093 B2

Column 55, first compound between Lines 5-20, approx. Line 12, delete "(2.1 equiv)" and insert in its place --(3.0 equiv)--.

Column 58, Line 50, delete "THE" and insert in its place --THF--.

Column 61, adjacent to the first compound between Lines 1-20, at approx. Line 10, delete "(2.5 equiv)".

Column 62, Line 17, delete "THE" and insert in its place --THF--.

Column 62, Line 34, delete "S13" and insert in its place --S14--.

Column 64, Line 19, delete "THE" and insert in its place --THF--.

Column 66, Line 38, delete "C34H23O4F4" and insert in its place --$C_{34}H_{23}O_4F_4$--.

Column 69, Line 40, delete "THE" and insert in its place --THF--.

Column 70, Line 15, delete "THE" and insert in its place --THF--.

Column 70, Line 40, delete "C36H31O6" and insert in its place --$C_{36}H_{31}O_6$--.

Column 76, Line 26, delete "(t-Bus)" and insert in its place --(t-Bu)$_3$--.

Column 77, Line 6, delete "C52H43O2" and insert in its place --$C_{52}H_{43}O_2$--.

Column 78, Line 66, delete "C36H38O4Na" and insert in its place --$C_{36}H_{38}O_4Na$--.

Column 82, Line 2, delete "THE" and insert in its place --THF--.

Column 87, Line 10, delete "13C" and insert in its place --$^{13}C$--.

Column 93, Line 3, delete "[2,1-d:1',2'-t]" and insert in its place --"[2,1-d:1'2'-f]--.

Column 97, Line 3, delete "[2,1-d:1',2'-t]" and insert in its place --"[2,1-d:1',2'-f]--.

Column 97, Line 60, delete "13C" and insert in its place --$^{13}C$--.

Column 97, Line 66, delete "$C_{84}H_{30}O_4F_{24}P^+$:" and insert in its place --$C_{64}H_{30}O_4F_{24}P^+$:--.

Column 98, Line 3, delete "2't]" and insert in its place --2'f]--.

Column 102, Line 9, delete "[2,1-d:1',2'-t]" and insert in its place --"[2,1-d:1',2'-f]--.

Column 103, Line 2, delete "[2,1-d:1',2'-t]" and insert in its place --"[2,1-d:1',2'-f]--.

CERTIFICATE OF CORRECTION (continued)
U.S. Pat. No. 11,664,093 B2

Column 104, Line 65, delete "C34H20O6F6P" and insert in its place --$C_{34}H_{20}O_6F_6P$--.

Column 106, Line 38, delete "$C_{20}H_{23}NO\ NaS^+$:" and insert in its place --$C_{20}H_{23}NONaS^+$:--.

Column 111, Line 34, delete "13C" and insert in its place --$^{13}C$--.

Column 119, Line 58, delete "13C" and insert in its place --$^{13}C$--.

Column 235, Line 45, delete "1D-21 D," and insert in its place --1D-21D--.

Column 239, Line 40, delete "in" and insert in its place --In--.

Column 239, Line 43, delete "11" and insert in its place --I1--.